United States Patent
Ammann

(10) Patent No.: US 10,939,992 B2
(45) Date of Patent: *Mar. 9, 2021

(54) APPARATUS AND METHOD FOR LIGAMENT RECONSTRUCTION

(71) Applicant: AnatomACL, LLC, Boulder, CO (US)

(72) Inventor: Kelly G. Ammann, Boulder, CO (US)

(73) Assignee: AnatomACL, LLC, Boulder, CO (US)

(*) Notice: Subject to any disclaimer, the term of this patent is extended or adjusted under 35 U.S.C. 154(b) by 504 days.

This patent is subject to a terminal disclaimer.

(21) Appl. No.: 14/397,370

(22) PCT Filed: Jan. 31, 2013

(86) PCT No.: PCT/US2013/024145
§ 371 (c)(1),
(2) Date: Oct. 27, 2014

(87) PCT Pub. No.: WO2013/162663
PCT Pub. Date: Oct. 31, 2013

(65) Prior Publication Data
US 2015/0173886 A1 Jun. 25, 2015

Related U.S. Application Data

(63) Continuation-in-part of application No. 13/528,680, filed on Jun. 20, 2012, now Pat. No. 9,089,416.
(Continued)

(51) Int. Cl.
*A61F 2/08* (2006.01)

(52) U.S. Cl.
CPC ..... *A61F 2/0811* (2013.01); *A61F 2002/0829* (2013.01); *A61F 2002/0858* (2013.01)

(58) Field of Classification Search
CPC .. A61F 2/08; A61F 2/0811; A61F 2002/0858; A61F 2002/0829;
(Continued)

(56) References Cited

U.S. PATENT DOCUMENTS 5,282,802 A 2/1994 Mahony, III
6,123,711 A 9/2000 Winters
(Continued)

FOREIGN PATENT DOCUMENTS

EP 1 297 794 4/2003
WO WO 2007/109280 9/2007
(Continued)

*Primary Examiner* — Jerrah Edwards
*Assistant Examiner* — Rokhaya Diop
(74) *Attorney, Agent, or Firm* — Pandiscio & Pandiscio

(57) ABSTRACT

Apparatus for reconstructing a ligament, the apparatus comprising a fixation device for maintaining a graft ligament in a bone hole, the fixation device comprising a fixation screw comprising a body having screw threads formed thereon; and a ligament spacer mounted to the fixation screw, the ligament spacer comprising a canted face disposed opposite the fixation screw; such that the fixation screw and ligament spacer may be advanced into the bone hole with the graft ligament so that the fixation screw and the ligament spacer maintain the graft ligament within the bone hole and the canted face of the ligament spacer is aligned with the adjacent surface of the bone.

14 Claims, 76 Drawing Sheets

Related U.S. Application Data

(60) Provisional application No. 61/498,663, filed on Jun. 20, 2011, provisional application No. 61/638,848, filed on Apr. 26, 2012.

(58) Field of Classification Search
CPC ...... A61F 2002/0817; A61F 2002/0882; A61F 2002/0888; A61F 2002/0864
See application file for complete search history.

(56) References Cited

U.S. PATENT DOCUMENTS

| | | | |
|---|---|---|---|
| 6,214,007 B1 | 4/2001 | Anderson | |
| 6,833,005 B1 | 12/2004 | Mantas et al. | |
| 7,235,078 B2 | 6/2007 | West, Jr. | |
| 2002/0156476 A1* | 10/2002 | Wilford | A61F 2/0805 606/232 |
| 2003/0040795 A1* | 2/2003 | Elson | A61F 2/08 623/13.12 |
| 2006/0052787 A1 | 3/2006 | Re et al. | |
| 2006/0095130 A1 | 5/2006 | Caborn et al. | |
| 2006/0189991 A1* | 8/2006 | Bickley | A61B 17/864 606/916 |
| 2006/0276789 A1* | 12/2006 | Jackson | A61B 17/7032 606/916 |
| 2007/0233071 A1 | 10/2007 | Dewey et al. | |
| 2009/0287259 A1 | 11/2009 | Trenhaile et al. | |
| 2009/0319043 A1 | 12/2009 | McDevitt et al. | |
| 2010/0069958 A1 | 3/2010 | Sullivan et al. | |
| 2011/0282449 A1 | 11/2011 | Montgomery et al. | |
| 2013/0030527 A1 | 1/2013 | Ammann | |
| 2013/0079780 A1 | 3/2013 | Wagner et al. | |

FOREIGN PATENT DOCUMENTS

| | | |
|---|---|---|
| WO | WO 2007/110863 | 10/2007 |
| WO | WO 2010/045207 | 4/2010 |
| WO | WO 2013/162663 | 10/2013 |

\* cited by examiner

AM & PL BUNDLES

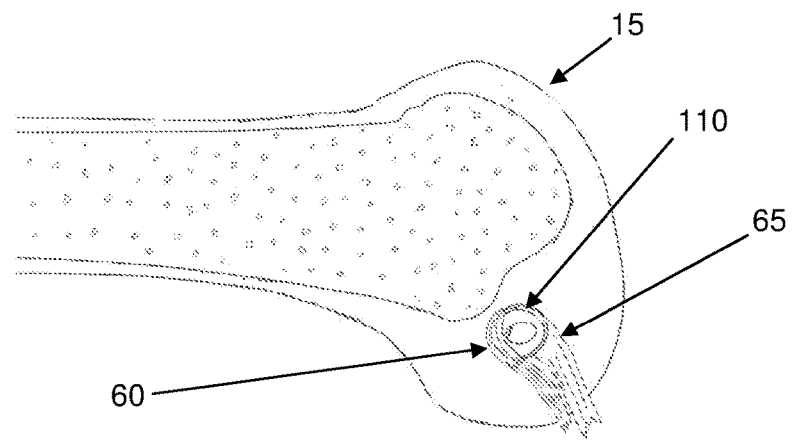
FIG. 30
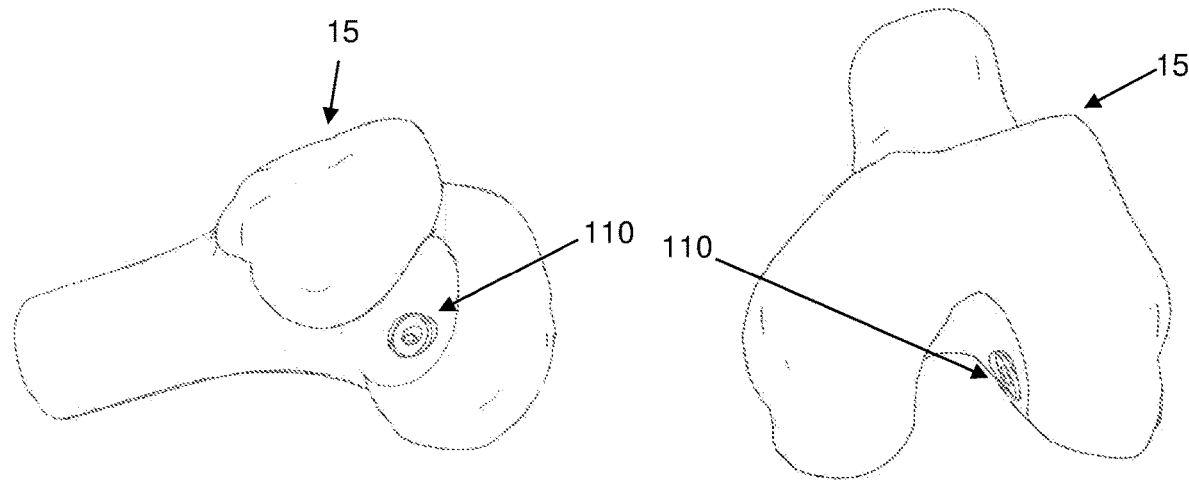
FIG. 31A
FIG. 31B

APPARATUS AND METHOD FOR LIGAMENT RECONSTRUCTION

REFERENCE TO PENDING PRIOR PATENT APPLICATIONS

This patent application is a continuation-in-part of pending prior U.S. patent application Ser. No. 13/528,680, filed Jun. 20, 2012 by Kelly G. Ammann for APPARATUS AND METHOD FOR LIGAMENT RECONSTRUCTION, which in turn claims benefit of (i) prior U.S. Provisional Patent Application Ser. No. 61/498,663, filed Jun. 20, 2011 by Kelly G. Ammann for APPARATUS AND METHOD FOR ANATOMIC ACL RECONSTRUCTION; and (ii) prior U.S. Provisional Patent Application Ser. No. 61/638,848, filed Apr. 26, 2012 by Kelly G. Ammann for APPARATUS AND METHOD FOR ANATOMIC ACL RECONSTRUCTION.

The three (3) above-identified patent applications are hereby incorporated herein by reference.

FIELD OF THE INVENTION

This invention relates to medical apparatus and methods in general, and more particularly to medical apparatus and methods for reconstructing a ligament.

BACKGROUND OF THE INVENTION

A ligament is a piece of soft, fibrous tissue that connects one bone to another bone in the skeletal system. Ligaments can often become damaged or injured. When injured, ligaments may tear, rupture or become detached from bone. The loss of a ligament can cause instability, pain and eventual increased wear on the joint surfaces, which can lead to osteoarthritis.

Various surgical techniques have been developed for ligament repair. The surgical technique that is used depends on the ligament that has been damaged and the extent of the injury.

A ligament that is commonly injured is the anterior cruciate ligament (ACL). As seen in FIG. 1, the ACL 5 traverses from the top of the tibia 10 to the bottom of the femur 15.

Trauma to the knee can cause injury to the anterior cruciate ligament (ACL). The ACL may become partially or completely torn. FIG. 2 depicts a diagram representation of a torn ACL 5 in the right knee.

A torn ACL reduces the stability of the knee joint and can result in pain, instability and additional wear on the cartilage surfaces of the knee, resulting in eventual osteoarthritis.

Several surgical techniques and ligament fixation devices are available for ACL repair. One of the most commonly used ACL repair techniques involves removal of the native ACL ligament remnants, drilling tunnels in both the femur and the tibia, inserting a tissue graft into the tunnels in place of the native ACL and securing the tissue graft in place with interference screws or other fixation devices.

Looking now at FIG. 3, after removal of the injured native ACL, currently available aiming instruments are aligned to the tibia and a guide pin is drilled into the tibia. FIG. 3 illustrates a typical aiming device 20 for locating a guide pin (or guide wire) 25 from the outside of the tibia 10 to an exit point inside the joint at the corresponding location of the tibial ACL insertion. Note that the guide pin 25 enters at an angle α to the tibia, and exits into the joint space at the angle α as measured from the upper surface of the tibia (also known as the tibial plateau).

The aiming device 20 is then removed from the tibia 10, leaving the guide wire 25 in place. A special cannulated drill 30 (i.e., a drill with a center hole through the length of the drill) is slid over the guide wire 25 and drilled from the front surface of the tibia 10 into the joint space of the knee. FIG. 4 shows the guide pin 25 and the cannulated drill 30 after drilling through the tibia.

A similar process is followed for drilling into the femur (FIG. 5). The guide pin 25 is inserted through the tibial tunnel 35 into the femur 15 near the femoral insertion site of the native ACL, and then the femoral tunnel 40 is drilled into femur 15, as shown in FIG. 5.

The method described above and shown in FIG. 5 is sometimes referred to as transtibial femoral tunnel drilling since the femoral tunnel 40 is drilled by access through the tibial tunnel 35. One problem with transtibial femoral tunnel drilling is that the femoral tunnel location ends up higher in the femoral notch than the normal anatomic femoral insertion of the ACL because access to the femur is limited by the size and location of the tibial tunnel 35. An alternative method that has been developed and is in current use is to create the femoral tunnel by drilling through the anteromedial portal 45 (FIG. 6). Anteromedial (AM) portal drilling of the femoral tunnel 40 involves drilling across the knee joint through the AM portal skin incision 45 such that the femoral tunnel location can be brought into a more anatomic position. In AM portal drilling, a guide pin 25 is first drilled into the anatomic location on the femur through the AM portal 45, followed by drilling with a cannulated drill 30 as shown in FIG. 6. The guide pin 25 and the cannulated drill 30 enter the AM portal 45 and traverse across the joint space. As shown in FIG. 6, it is clear that the guide pin 25 and drill 30 must pass in front of the adjacent femoral condyle to prevent damaging the condyle. The knee quite often must be put into a state of deep flexion in order to reach the anatomic ACL footprint on the femur and still safely pass by the adjacent condyle and the tibial plateau.

With the tibial tunnel 35 and the femoral tunnel 40 created, the tissue graft 50 (FIG. 7A) is prepared. The tissue graft 50 is typically harvested from the patient's own body tissue and may be hamstring tendons, quadriceps tendon, or patellar tendon. Alternatively, similar tissue grafts may be harvested from a donor and also include the Achilles tendon, anterior tibialis tendon or other graft sources. The graft 50 is first prepared by creating one long tissue graft strand, folding the graft over onto itself, and making measurements along the graft. See FIG. 7A. Example measurements for adults are 30 mm of graft length for the portion of the graft that is inserted into the femoral tunnel, 27 mm of graft length for the portion of the graft that is intra-articular (inside the knee joint) and 35 mm of graft length for the portion of the graft that is inserted inside the tibial tunnel. The tissue graft 50 is folded over into two bundles 60, 65 as shown in FIG. 7A. Sutures are applied at the areas of the graft 50 that will interface with the tunnel fixation to add additional strength. The folded section 55 will interface with the femoral tunnel 40 and the two opposite ends 60, 65 will be in the tibial tunnel 35.

Additional sutures are looped around the folded portion 55 of the graft 50, forming a strand of sutures 70 (or lead sutures) that can be used to pull the graft 50 into place (FIG. 7B). The lead sutures 70 are passed through the tibial tunnel 35 and femoral tunnel 40, with the assistance of a suture passing guide wire (not shown). FIG. 7B shows the folded over graft in position to be pulled through the tibial tunnel 35 and into the femoral tunnel 40. The lead sutures 70 (upper left in FIG. 7B) are grasped with a clamp 75 outside the femur and the graft construct is pulled through the tibial tunnel 35, through the interior of the knee joint, and into the femoral tunnel 40.

Once the tissue graft 50 is in place, the individual bundles 60, 65 making up the aggregate tissue graft may be manipulated to approximate their anatomic positions.

More particularly, advances in the research of ACL anatomy indicate that there are two primary bundles that make up the natural ACL, the anteromedial bundle 80 (FIG. 8) and the posterolateral bundle 85. The anteromedial bundle 80 and the posterolateral bundle 85 are also sometimes referred to as the AM bundle and the PL bundle. The name of the ligament refers to their point of origin on the tibial plateau, that is, the AM bundle originates anteromedially and the PL bundle originates posterolaterally (relative to each other on the tibial plateau). FIG. 8 illustrates the two bundles and their relative positions in the knee joint. Points A and B (FIG. 8) illustrate the ligament insertions on the tibial plateau as well as the ligament insertions on the femur. The AM and PL bundles cross each other during normal flexion of the knee joint. The AM and PL bundles are roughly parallel to each other when the knee is in full extension.

In the typical surgical technique, the tissue graft 50 is manipulated into positions (FIG. 9) such that the two graft strands 60, 65 (making up the aggregate tissue graft) approximate the locations of the AM and PL bundles and yield a reconstruction that approximates the native ACL anatomy. It has been demonstrated in biomechanical tests that this construct results in a more stable result. There are several techniques and devices which are used to approximate the footprint of the AM and PL bundles.

After the AM and PL bundles are manipulated into position, fixation screws 90 (also known as interference screws) are inserted (e.g., into the femoral tunnel 40 and then into the tibial tunnel 35). First the femoral portion of the graft is fixed into place by inserting an interference screw 90 through the AM portal 45 and into the femoral tunnel 40, as shown in FIG. 9. The interference screw 90 squeezes the ligament graft tightly up against the tunnel wall so as to secure the ligament graft in position within the tunnel. As the interference screw 90 is tightened into place, it creates an interference fit between the tunnel, the graft and the screw.

FIG. 10 shows the femoral fixation in place, with the AM bundle approximating its anatomic position and the PL bundle approximating its anatomic position.

Lastly, an interference screw 90 (FIG. 11) is inserted into the tibial tunnel 35, thereby completing the fixation of the tissue graft. FIG. 11 illustrates the final construct.

The foregoing technique has been used for many years for reconstruction of the ACL. This technique has been very successful, but it does have limitations. More particularly, a closer look at the current technique reveals limitations due to the geometry of the drilled holes and the use of currently available fixation devices.

More particularly, because the drill 30 enters the femoral notch at an angle, the entrance of the femoral tunnel 40 into the femur 15 is elliptical (FIG. 12). Note that this is not due to poorly manufactured drills, or poor surgical technique, etc.—it is simply the normal result of drilling a hole into a surface with the drill set at an angle to the surface. This becomes more evident when viewing the tunnel straight into (i.e., perpendicular to) the bone surface, as shown in FIG. 12.

Similarly, because the drill 30 exits the tibial tunnel 35 and enters the interior of the joint at an angle, the shape of the tibial tunnel 35 is elliptical at the entrance to the joint space (FIG. 13). This phenomenon has been documented in various biomechanical studies.

Typical interference screws 90 fixate the graft ligament 50 along the length of the screw and about the perimeter of the screw. However, the portion of the ligament disposed in the elliptical portion of a bone tunnel (i.e., that portion of the bone tunnel that does not form a complete circular cross-section) is not secured against bone, as shown in FIG. 14.

The fixation screw 90 and the ligament graft 50 are represented in FIG. 15. The AM and PL bundles are essentially free to reside wherever they may land around the perimeter of the interference screw and are not secured in the elliptical portion of the bone tunnel, because that elliptical portion of the bone tunnel does not form a complete circular cross-section.

On the tibial side, a similar geometric condition exists (FIG. 16). Furthermore, the taper of the typical interference screw 90 at its distal end, which is disposed near the joint side mouth of the tibial tunnel 35, adds additional laxity to the ligament fixation, as shown in the tibial cross-section of FIG. 16. This figure shows a standard interference screw 90 secured in the tibial tunnel 35. The AM and PL bundles are shown roughly in their anatomic positions. The area at the distal end of the interference screw 90 shows how the ligament 50 is not securely fixated in the area near the distal tip of the screw (i.e., where the ligament enters the joint space). This type of limited fixation may contribute to problems such as the so-called "windshield wiper effect" (where the graft ligament sweeps across the mouth of the bone tunnel, thereby causing abrasion to the graft ligament and to the mouth of the bone tunnel), and joint laxity (due to incomplete fixation of the ligament into its anatomic position).

As discussed above, there are potential problems with current interference screw fixation, i.e., there is a lack of complete fixation of the ligament graft at the entrance of the tunnel to the joint space. The unsecured ligament in the elliptical opening of the bone tunnel may contribute to the windshield wiper effect, biomechanical instability and tunnel widening. Furthermore, the rotational position of the ligament graft in the tunnel is not controlled, which can result in a biomechanical construct that does not reproduce the native anatomy, i.e., the ligament strands 60, 65 may not be properly disposed in the locations of the native AM and PM bundles.

Thus there is a need for new apparatus and method for reconstructing a ligament which addresses deficiencies in the prior art.

SUMMARY OF THE INVENTION

The present invention provides new apparatus and method for fixation of the ACL which addresses deficiencies in the prior art. The new apparatus secures the graft ligament along the entire periphery of the elliptical bone tunnel entrance so as to provide complete fixation of the ligament graft and to spread the ligament graft over the natural anatomic footprint of the ACL insertions of both the tibia and femur. As an additional benefit, the new apparatus substantially completely fills the bony defect resulting from the drilling process. The elliptical opening of the bone tunnel no longer becomes a detriment, but rather an asset, towards achieving a more accurate anatomic reconstruction.

In one preferred form of the invention, there is provided apparatus for reconstructing a ligament, the apparatus comprising:
- a fixation device for maintaining a graft ligament in a bone hole, the fixation device comprising:
  - a fixation screw comprising a body having screw threads formed thereon; and
  - a ligament spacer mounted to the fixation screw, the ligament spacer comprising a canted face disposed opposite the fixation screw;
  - such that when a graft ligament is disposed within a bone hole, the fixation screw and ligament spacer may be advanced into the bone hole alongside the graft ligament so that the fixation screw creates an interference fit between the graft ligament and the wall of the bone hole, and the ligament spacer creates an interference fit between the graft ligament and the wall of the bone hole, with the canted face of the ligament spacer being aligned with the adjacent surface of the bone.

In another preferred form of the invention, there is provided an apparatus for reconstructing a ligament, the apparatus comprising:
- a first fixation device for maintaining a graft ligament in a first bone hole, the first fixation device comprising:
  - a first fixation screw comprising a body having screw threads formed thereon; and
  - a first ligament spacer mounted to the first fixation screw, the first ligament spacer comprising a first canted face disposed opposite the first fixation screw;
  - such that when a graft ligament is disposed within the first bone hole, the first fixation screw and first ligament spacer may be advanced into the first bone hole alongside the graft ligament so that the first fixation screw creates an interference fit between the graft ligament and the wall of the first bone hole, and the first ligament spacer creates an interference fit between the graft ligament and the wall of the first bone hole, with the first canted face of the first ligament spacer being aligned with the adjacent surface of the first bone; and
- a second fixation device for maintaining the graft ligament in a second bone hole, the second fixation device comprising:
  - a second fixation screw comprising a body having screw threads formed thereon; and
  - a second ligament spacer mounted to the second fixation screw, the second ligament spacer comprising a second canted face disposed opposite the second fixation screw;
  - such that when the graft ligament is disposed within the second bone hole, the second fixation screw and second ligament spacer may be advanced into the second bone hole alongside the graft ligament so that the second fixation screw creates an interference fit between the graft ligament and the wall of the second bone hole, and the second ligament spacer creates an interference fit between the graft ligament and the wall of the second bone hole, with the second canted face of the second ligament spacer being aligned with the adjacent surface of the second bone.

In another preferred form of the invention, there is provided a method for reconstructing a ligament, the method comprising:
providing a fixation device for maintaining a graft ligament in a bone hole, the fixation device comprising:
- a fixation screw comprising a body having screw threads formed thereon; and
- a ligament spacer mounted to the fixation screw, the ligament spacer comprising a canted face disposed opposite the fixation screw;
- such that when a graft ligament is disposed within a bone hole, the fixation screw and ligament spacer may be advanced into the bone hole alongside the graft ligament so that the fixation screw creates an interference fit between the graft ligament and the wall of the bone hole, and the ligament spacer creates an interference fit between the graft ligament and the wall of the bone hole, with the canted face of the ligament spacer being aligned with the adjacent surface of the bone;

forming a bone hole in a bone;
extending a graft ligament along the bone hole;
advancing the fixation screw and the ligament spacer into the bone hole alongside the graft ligament so as to secure the graft ligament in the bone hole.

In another preferred form of the invention, there is provided apparatus for reconstructing a ligament, the apparatus comprising:
- a fixation device for maintaining a graft ligament in a bone hole, the fixation device comprising:
  - a fixation screw comprising a body having screw threads formed thereon; and
  - a ligament spacer comprising a distal end and a proximal end, the ligament spacer mounted to the fixation screw at its distal end and having a canted face disposed at its proximal end, the ligament spacer comprising at least one opening formed between the distal end and the proximal end;
  - such that the graft ligament may be disposed within the at least one opening in the ligament spacer, and when the fixation screw and ligament spacer are advanced into the bone hole, the screw threads of the fixation screw engage the wall of the bone hole and the canted face of the ligament spacer is aligned with the adjacent surface of the bone.

In another preferred form of the invention, there is provided apparatus for reconstructing a ligament, the apparatus comprising:
- a first fixation device for maintaining a graft ligament in a first bone hole, the first fixation device comprising:
  - a first fixation screw comprising a body having screw threads formed thereon; and
  - a first ligament spacer mounted to the first fixation screw, the first ligament spacer comprising a distal end and a proximal end, the first ligament spacer mounted to the fixation screw at its distal end and having a canted face disposed at its proximal end, the first ligament spacer comprising at least one opening formed between the distal end and the proximal end;
  - such that the graft ligament may be disposed within the at least one opening in the first ligament spacer, and when the first fixation screw and first ligament spacer are advanced into the first bone hole, the screw threads of the first fixation screw engage the wall of the first bone hole and the first canted face of the first ligament spacer is aligned with the adjacent surface of the first bone; and
- a second fixation device for maintaining the graft ligament in a second bone hole, the second fixation device comprising:
  - a second fixation screw comprising a body having screw threads formed thereon; and a second ligament spacer mounted to the second fixation screw, the second ligament spacer comprising a distal end and a proximal end, the second ligament spacer mounted to the fixation screw at its distal end and having a canted face disposed at its proximal end, the second ligament spacer comprising at least one opening formed between the distal end and the proximal end;

such that the graft ligament may be disposed within the at least one opening in the second ligament spacer, and when the second fixation screw and the second ligament spacer are advanced into the second bone hole, the screw threads of the second fixation screw engage the wall of the second bone hole and the second canted face of the second ligament spacer is aligned with the adjacent surface of the second bone.

In another preferred form of the invention, there is provided apparatus for reconstructing a ligament, the apparatus comprising:

a fixation device for maintaining a graft ligament in a bone hole, the fixation device comprising:
  a fixation screw comprising a body having screw threads formed thereon; and
  a ligament spacer mounted to the fixation screw, the ligament spacer comprising a canted face disposed opposite the fixation screw;
  such that the fixation screw and ligament spacer may be advanced into the bone hole with the graft ligament so that the fixation screw and the ligament spacer maintain the graft ligament within the bone hole and the canted face of the ligament spacer is aligned with the adjacent surface of the bone.

In another preferred form of the invention, there is provided a method for reconstructing a ligament, the method comprising:

providing a fixation device for maintaining a graft ligament in a bone hole, the fixation device comprising:
  a fixation screw comprising a body having screw threads formed thereon; and
  a ligament spacer mounted to the fixation screw, the ligament spacer comprising a canted face disposed opposite the fixation screw;
  such that the fixation screw and ligament spacer may be advanced into the bone hole with the graft ligament so that the fixation screw and the ligament spacer maintain the graft ligament within the bone hole and the canted face of the ligament spacer is aligned with the adjacent surface of the bone;
forming a bone hole in a bone;
advancing the fixation screw and the ligament spacer into the bone hole with the graft ligament so as to maintain the graft ligament in the bone hole.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 30 is a schematic view showing the femoral fixation device and ligament bundles;

FIG. 31A is a schematic view showing the femoral fixation device inserted, but with the graft ligament not shown, to illustrate the congruence of fixation to the femoral surface;

FIG. 31B is a view similar to that of FIG. 31A, but taken from a different angle of view;

FIG. 101B is a schematic view showing a tibial ligament spacer with angled lead-in;

FIG. 102A is a schematic view showing a tibial fixation device;

FIG. 102B is a schematic view showing a tibial fixation device and a ligament graft;

FIG. 103 is a schematic view showing a tibial fixation device disposed over a tibial alignment pin;

FIG. 104 is a schematic view showing a tibial fixation device, a guide pin, and hex wrench;

FIG. 105 is a schematic view showing a guide pin;

FIG. 106 is a schematic view showing a tibial alignment pin;

FIG. 107 is a schematic view showing a guide pin;

FIG. 108 is a schematic view showing a guide pin;

FIG. 109A is a schematic view showing a ligament tensioning bar disposed over a guide pin;

FIG. 109B is a schematic view showing a ligament tensioning bar disposed over the tibial alignment pin, and showing ligament graft sutures;

FIG. 110 is a schematic view showing a tibial fixation device, a wrench, and a tensioning bar disposed over a guide pin;

FIG. 111A is a schematic view showing a tibial fixation device and a hex wrench disposed over a guide pin;

Figure 111A:
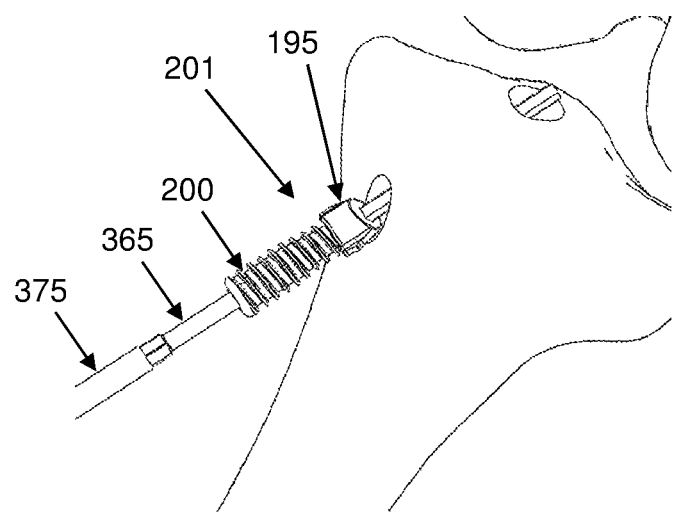
Figure 111B:
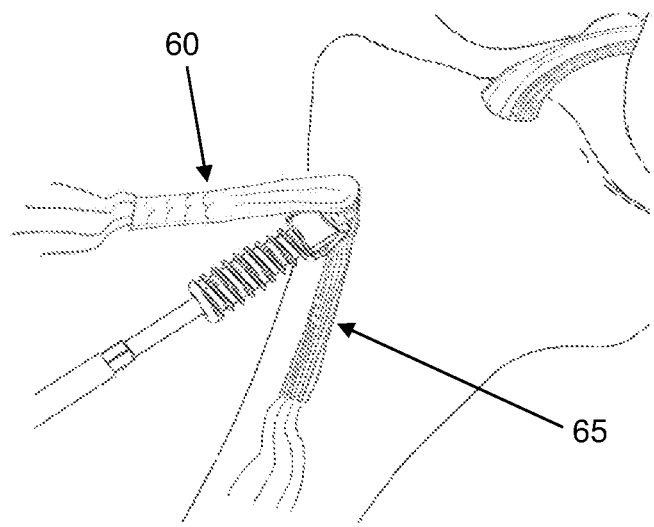
Figure 112:
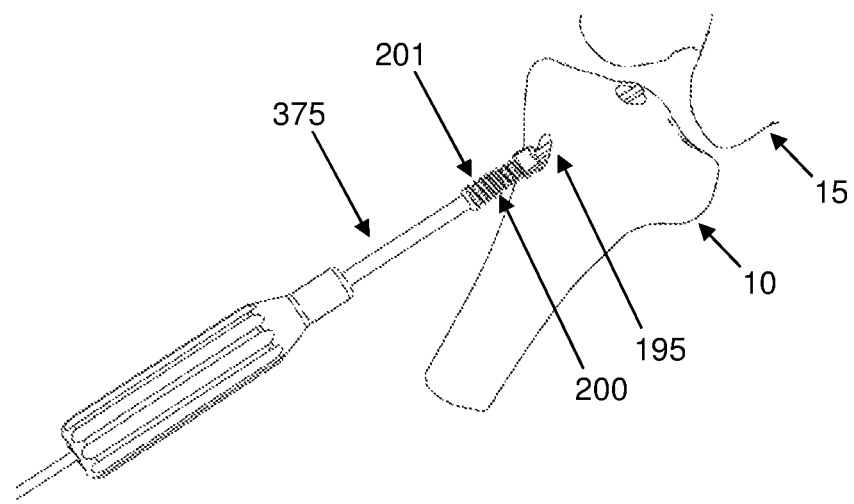
Figure 113A:
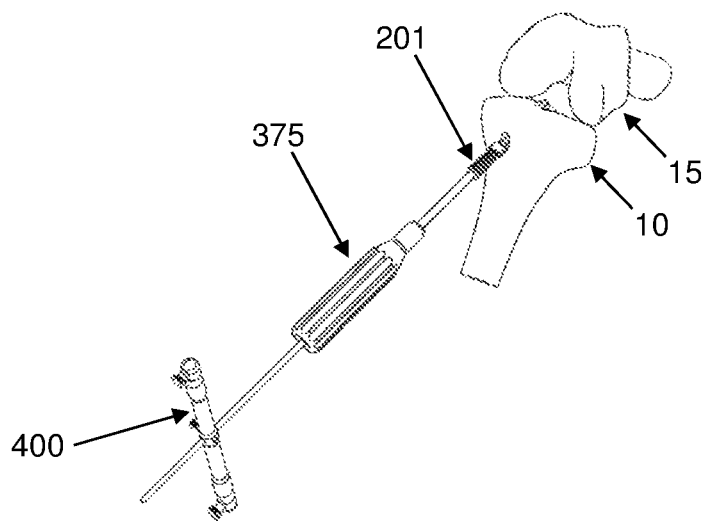
Figure 113B:
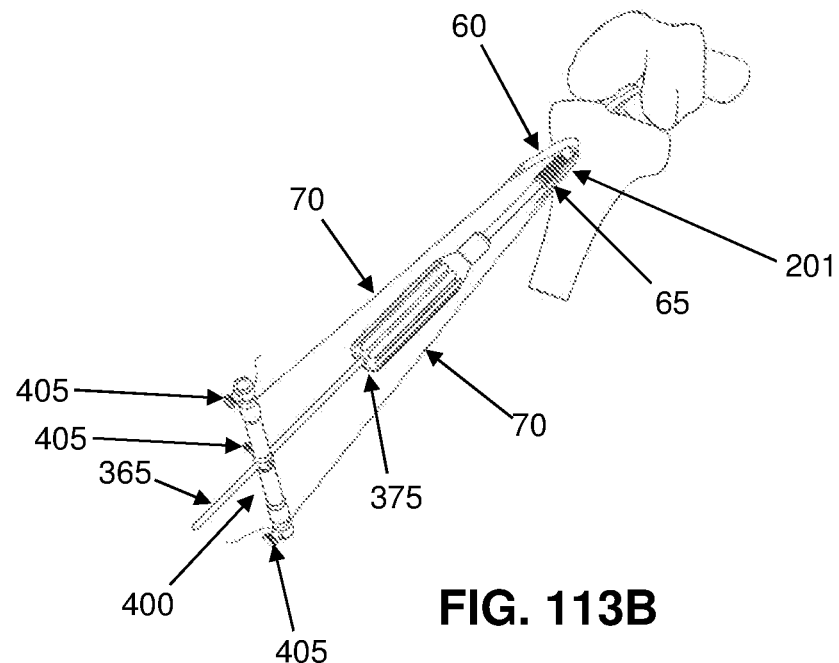
Figure 114:
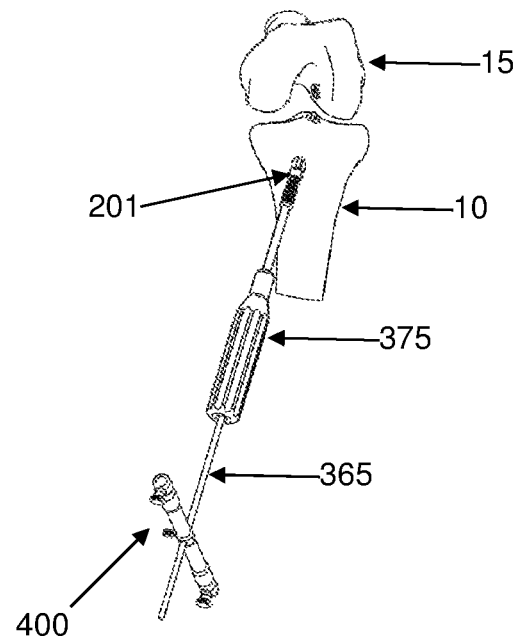
Figure 115:
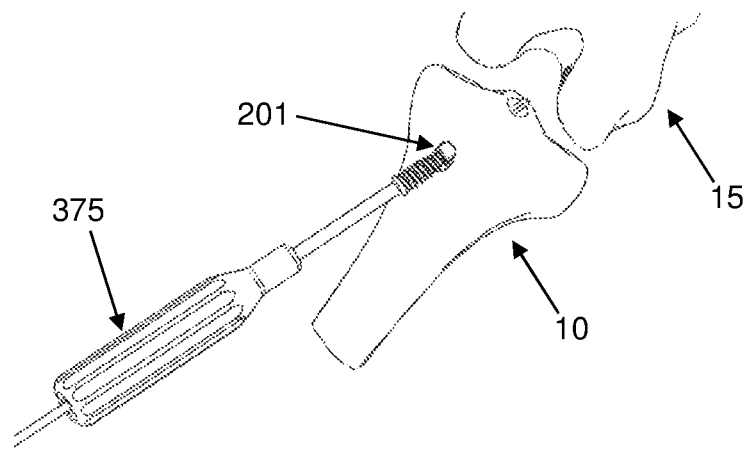
Figure 116:
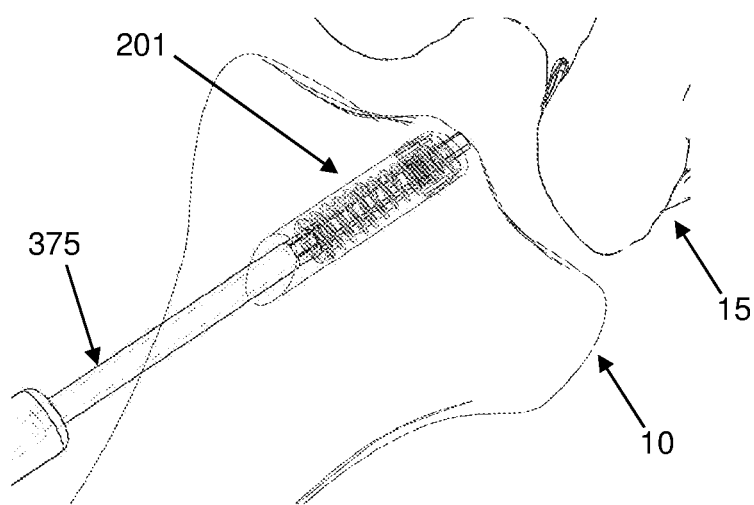
Figure 117:
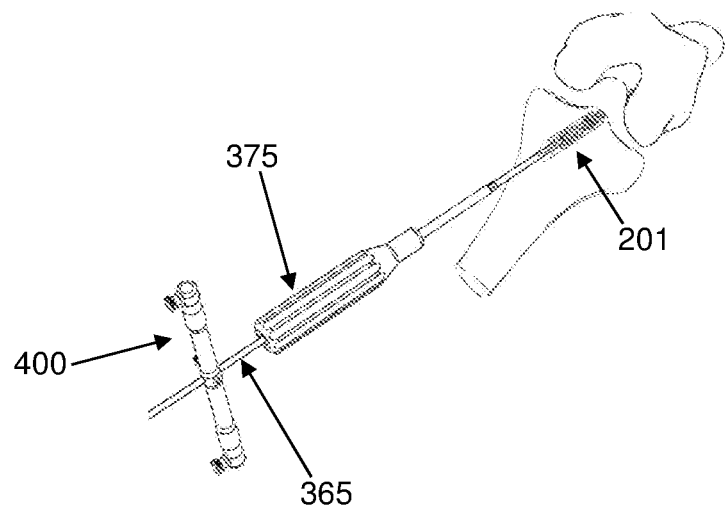
Figure 118:
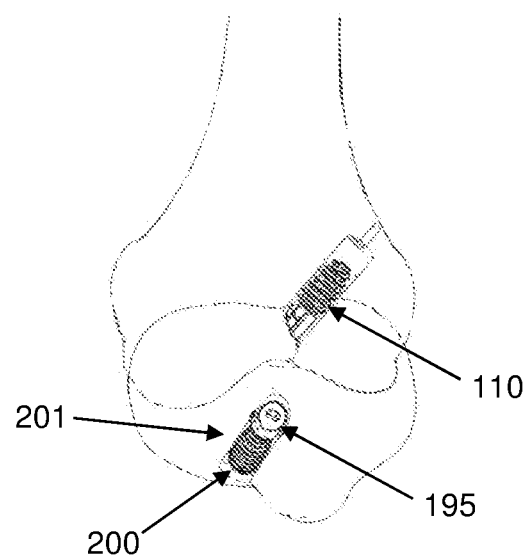
Figure 119A:
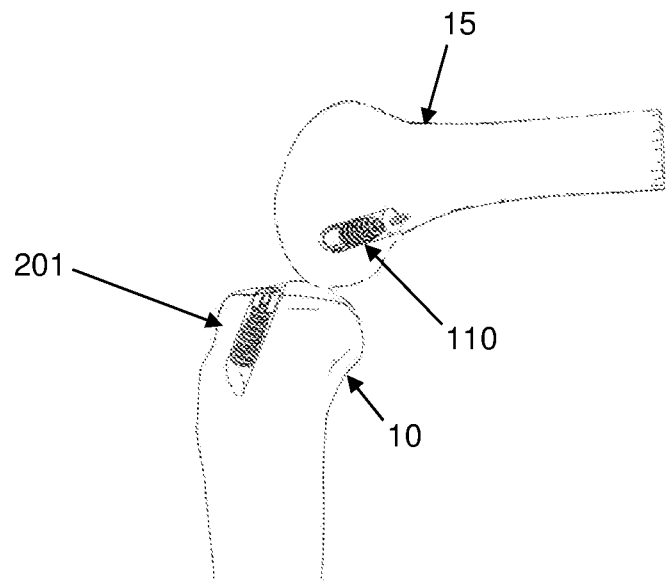
Figure 119B:
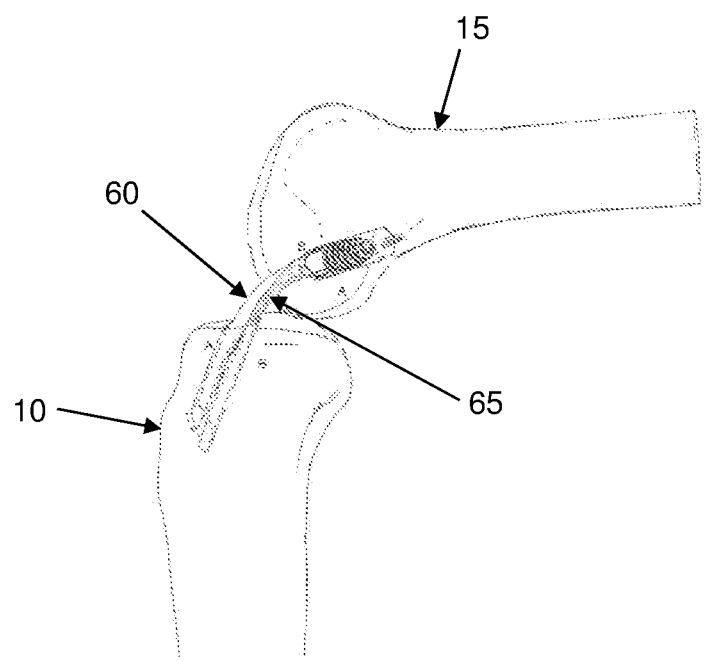
Figure 119C:
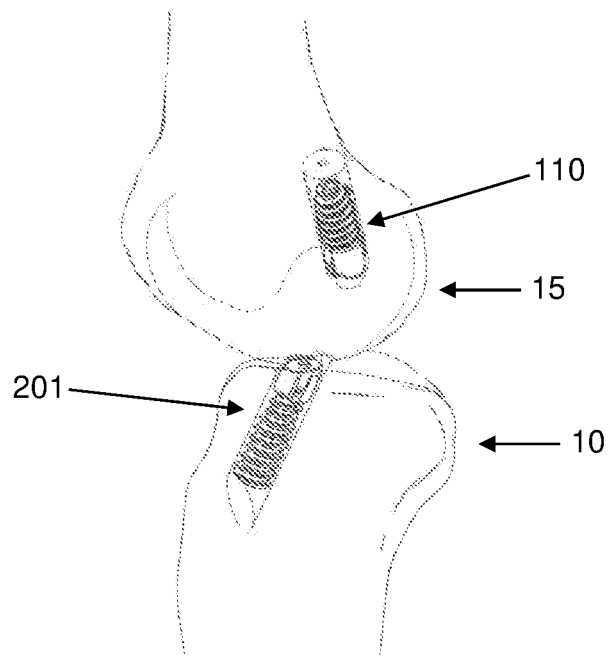
Figure 119D:
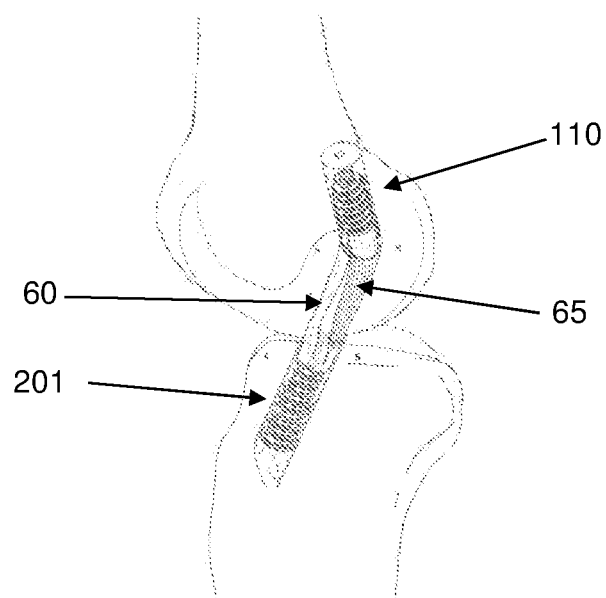
Figure 120A:
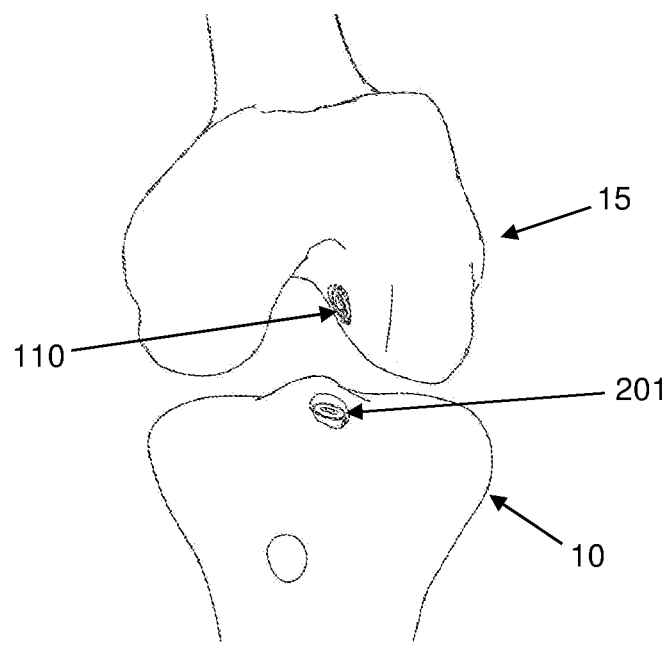
Figure 120B:
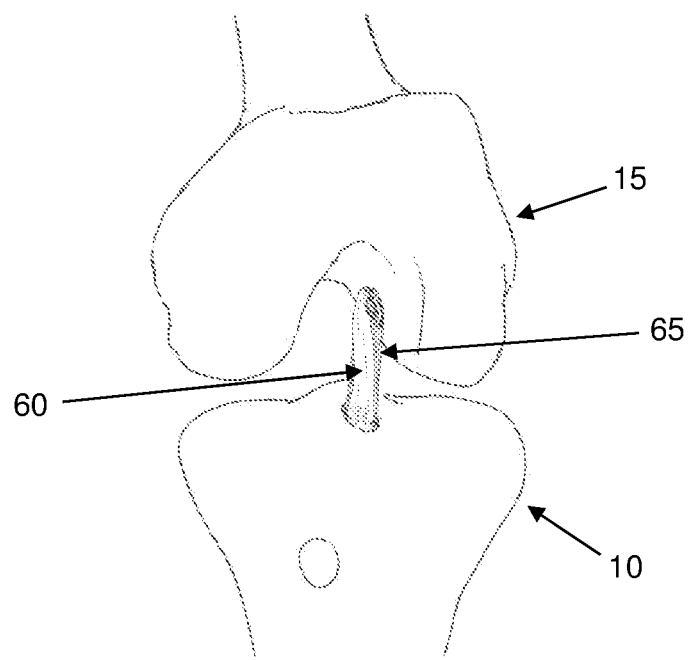
Figure 121A:
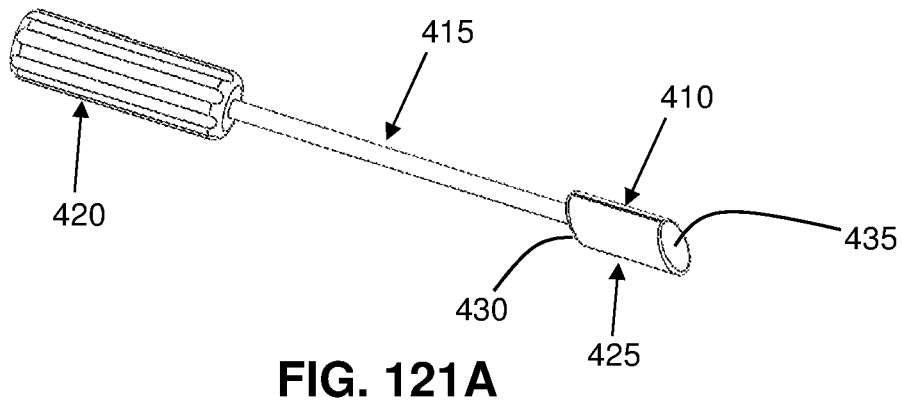
Figure 121B:
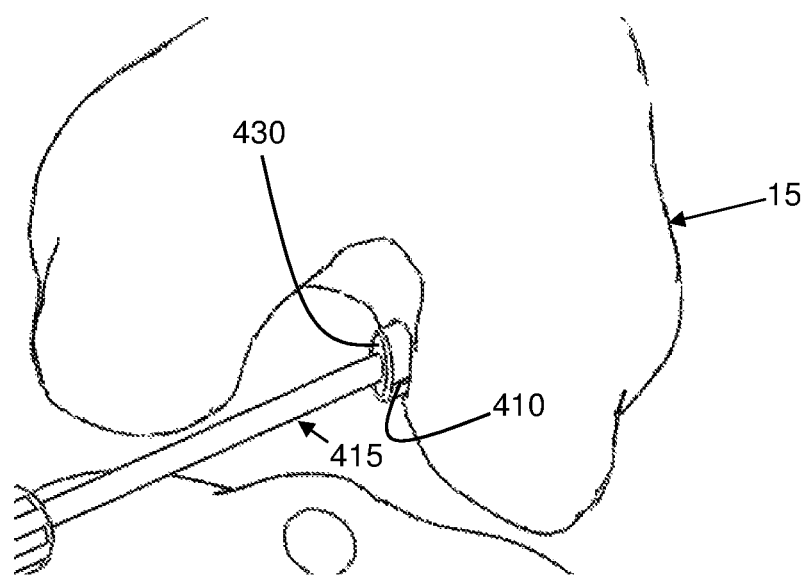
Figure 122:
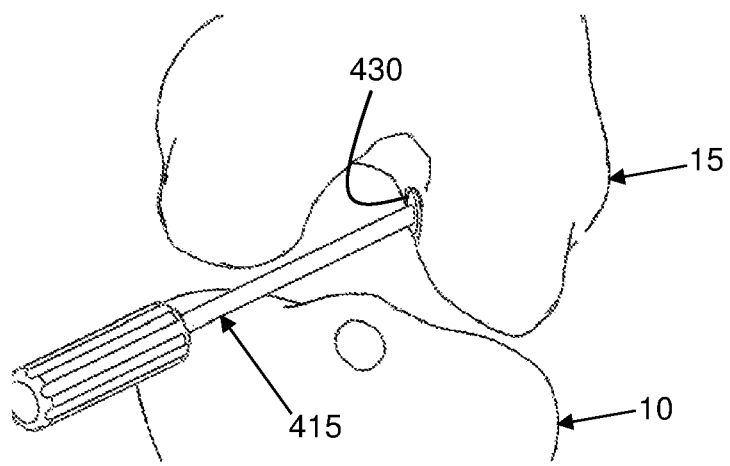
Figure 123:
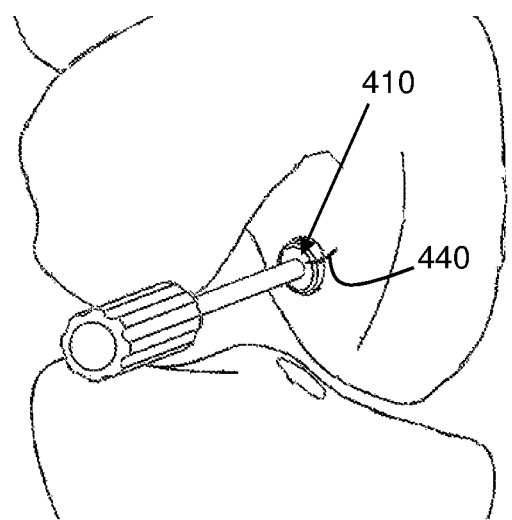
Figure 124A:
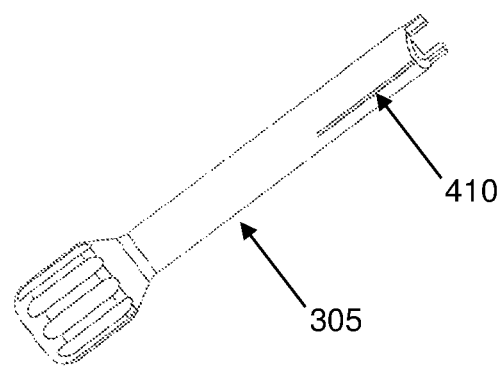
Figure 124B:
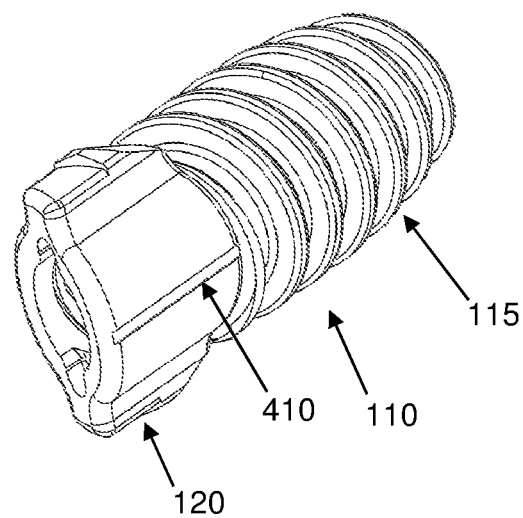
Figure 125:
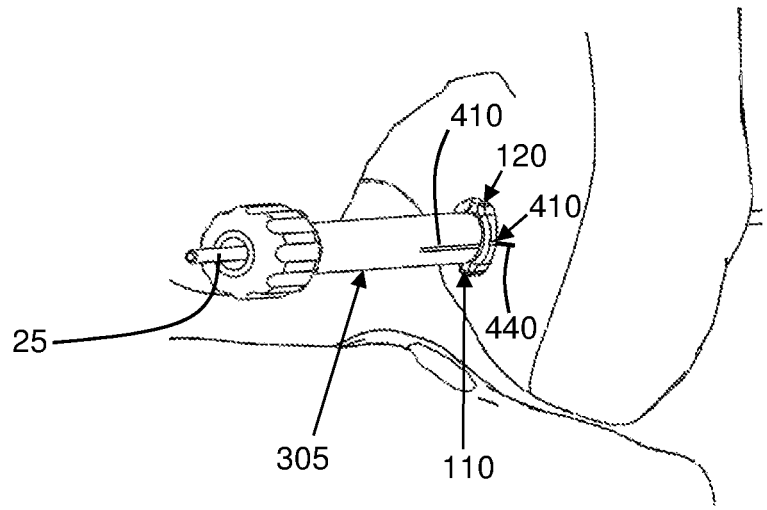
Figure 126:
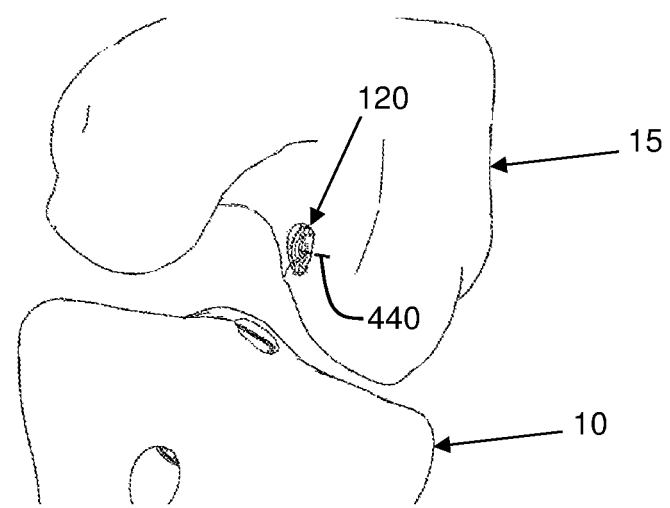
Figure 127:
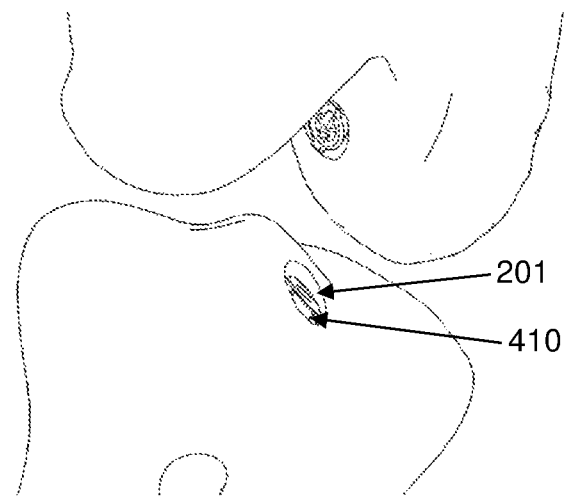
Figure 128:
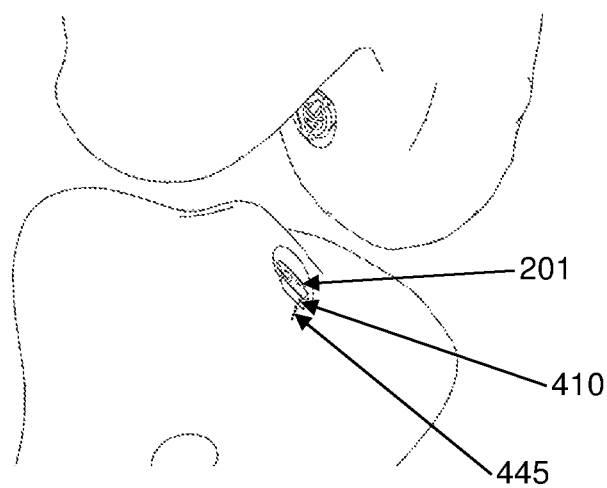
Figure 129:
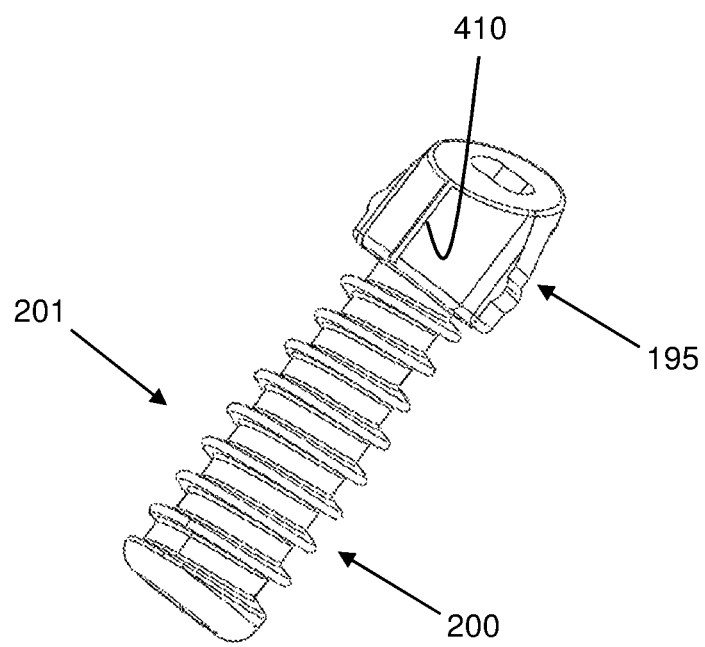
Figure 130:
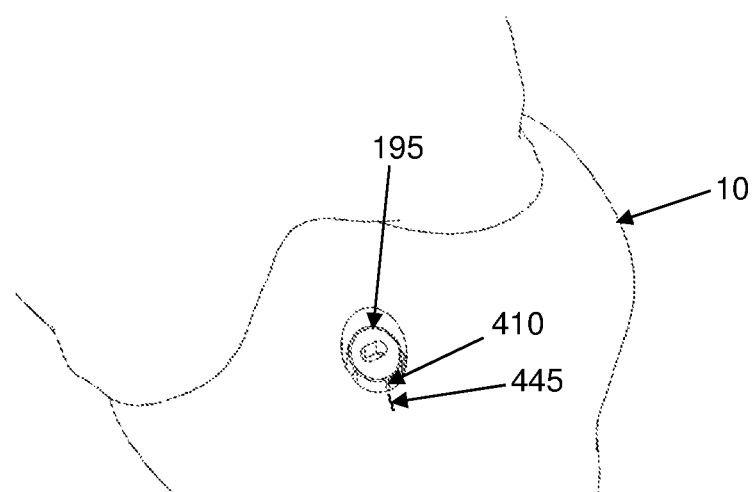
Figure 131:
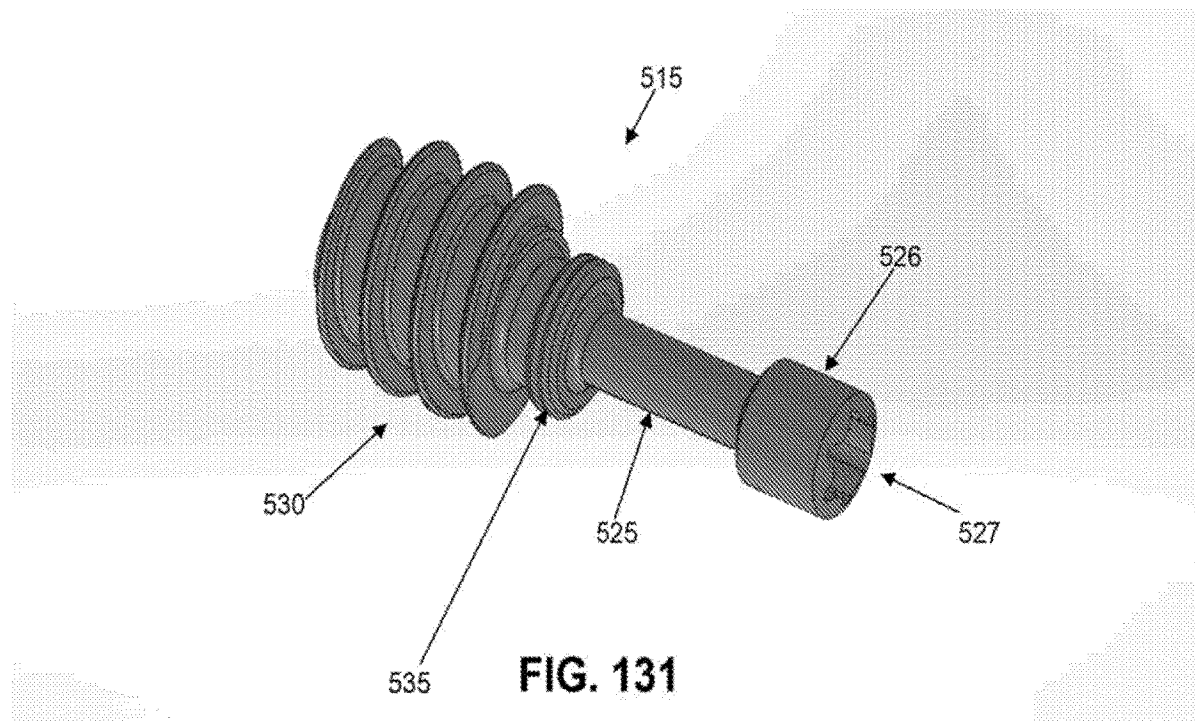
Figure 132:
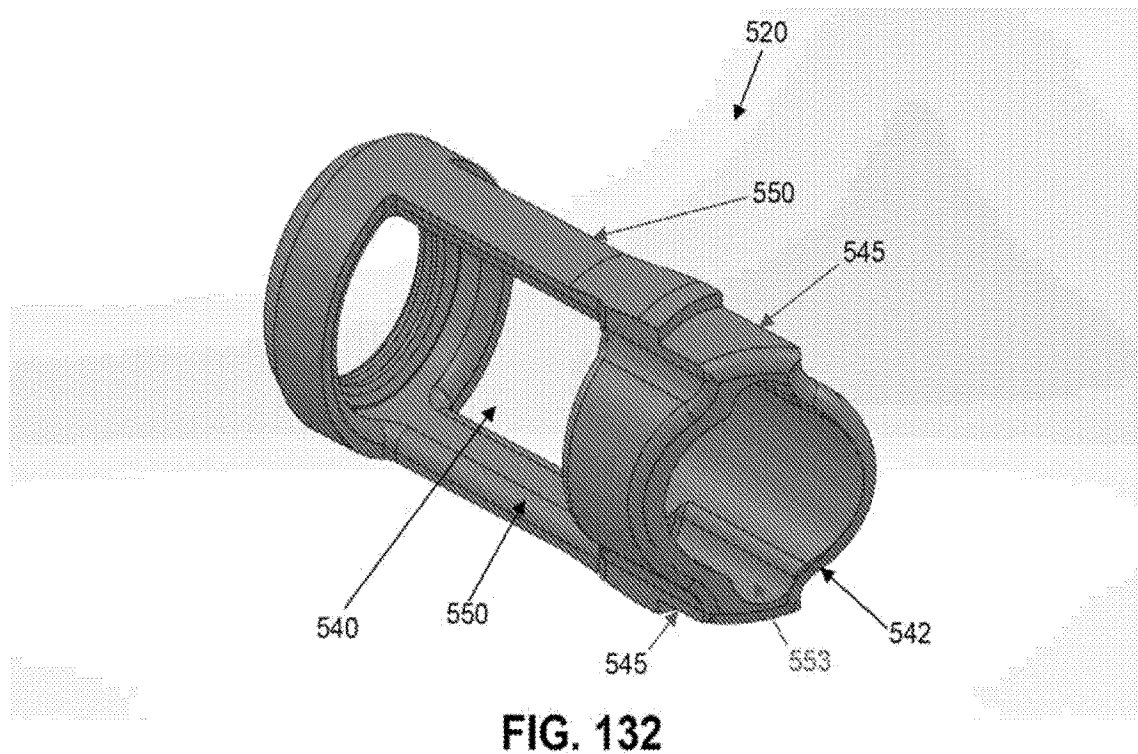
Figure 133:
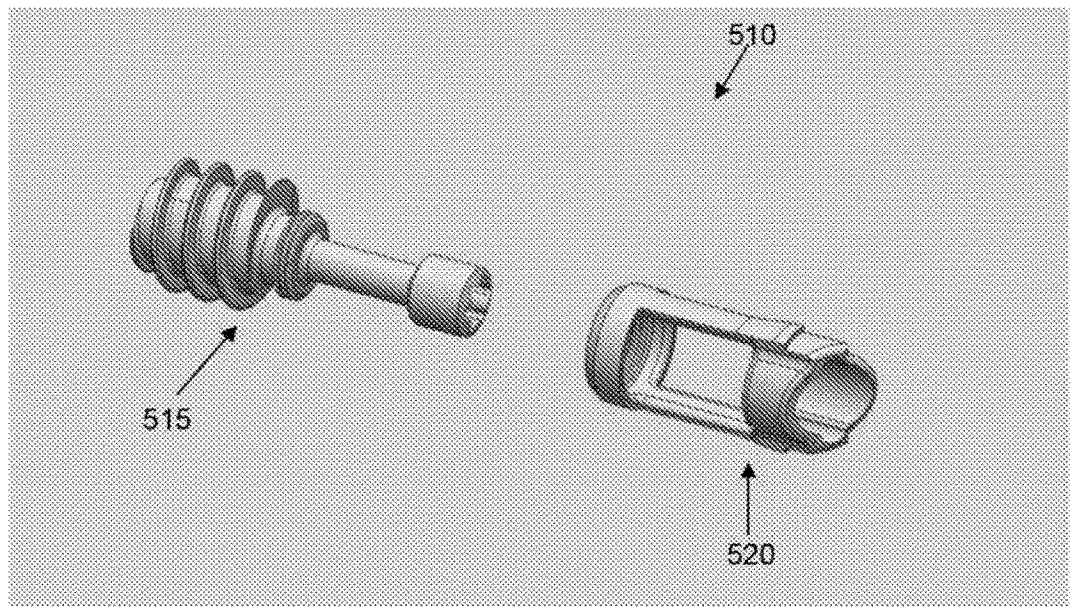
Figure 134A:
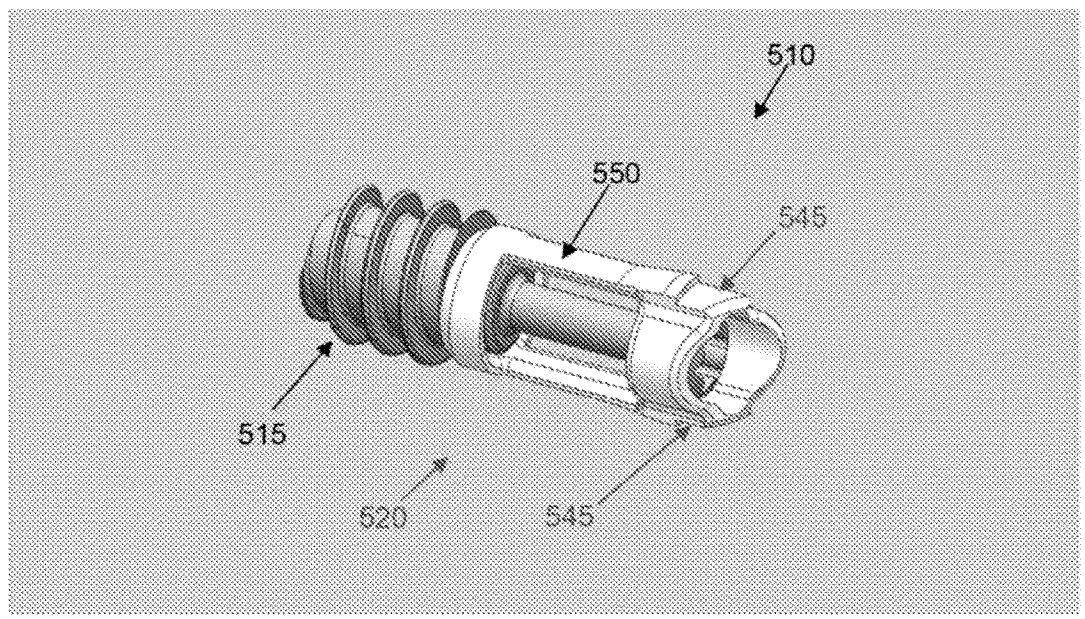
Figure 134B:
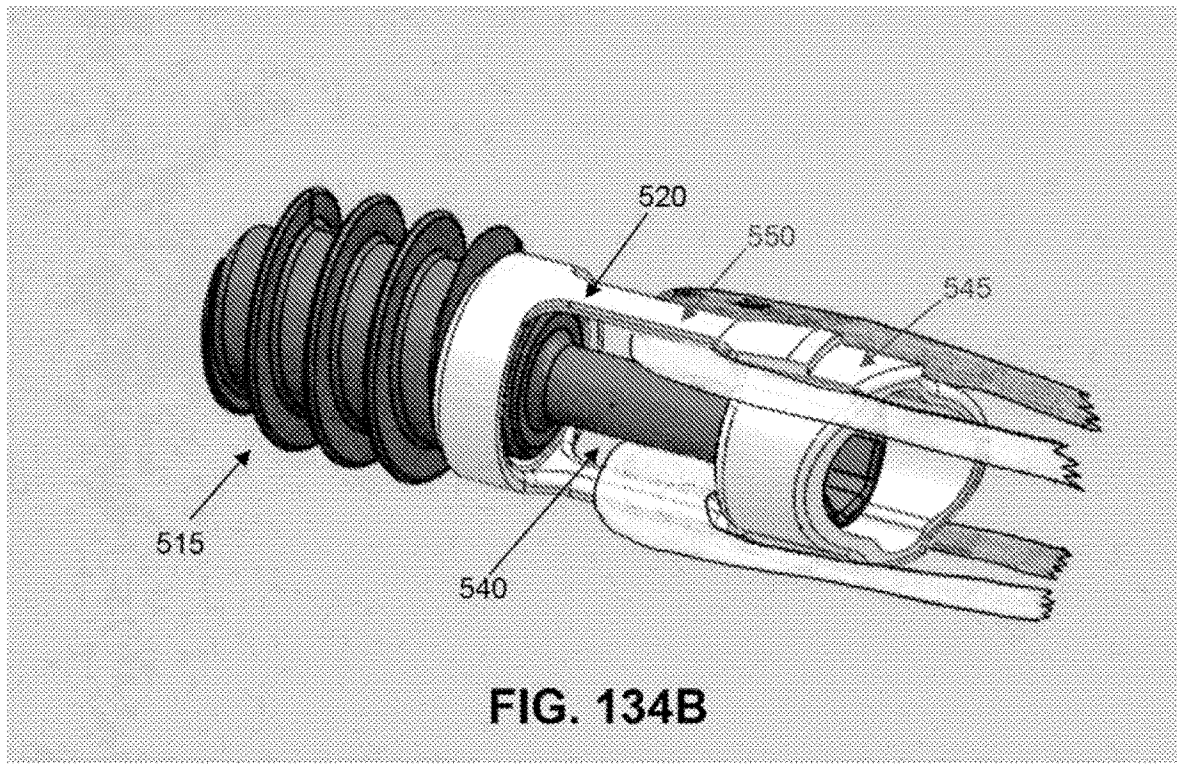
Figure 134C:
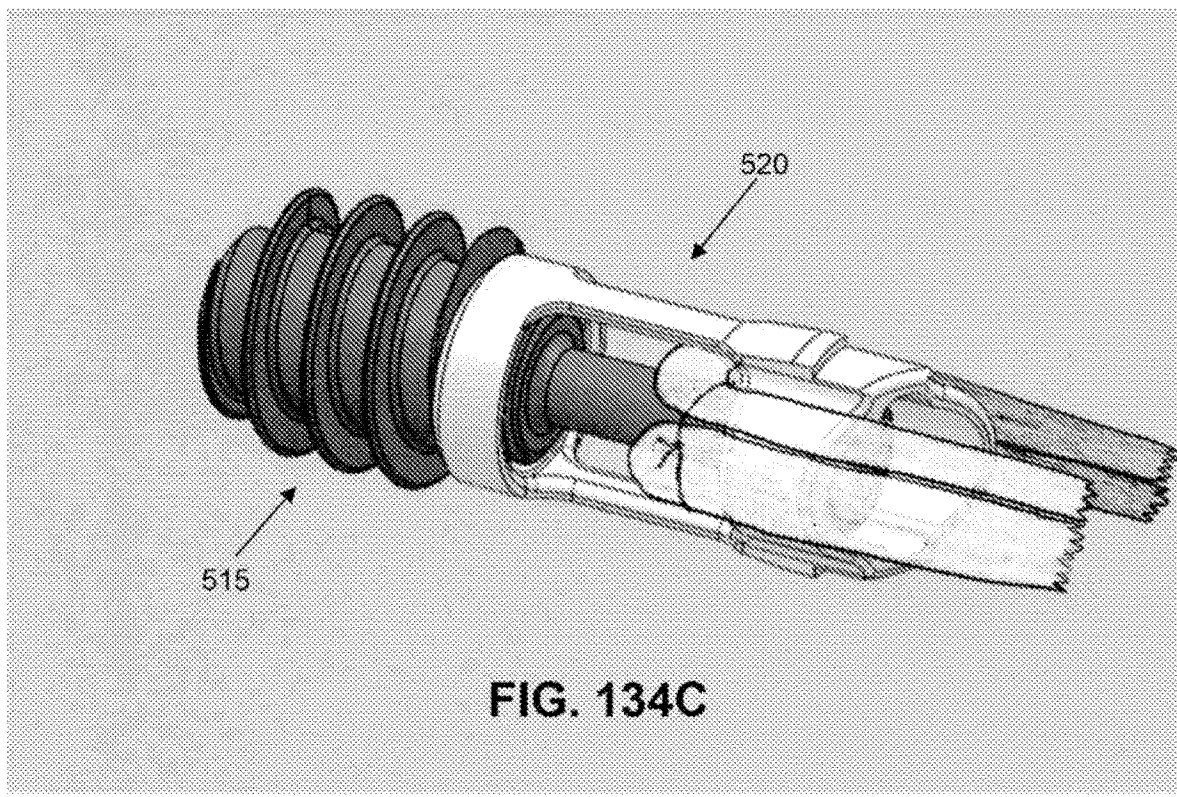
Figure 135:
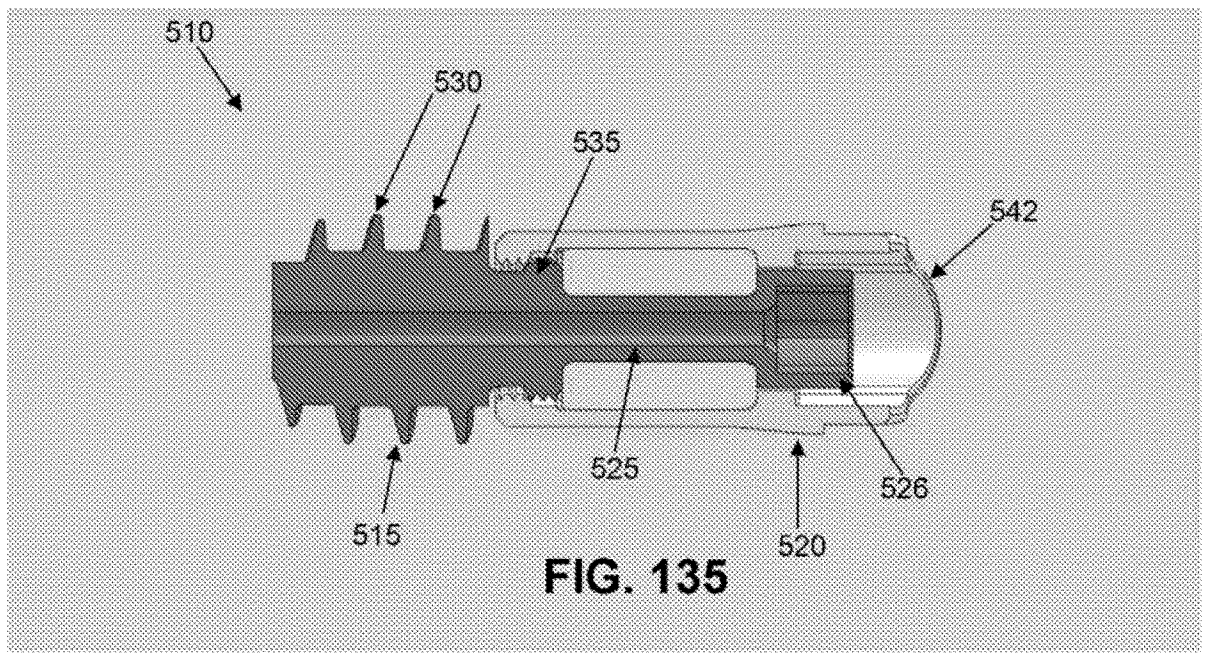
Figure 136A:
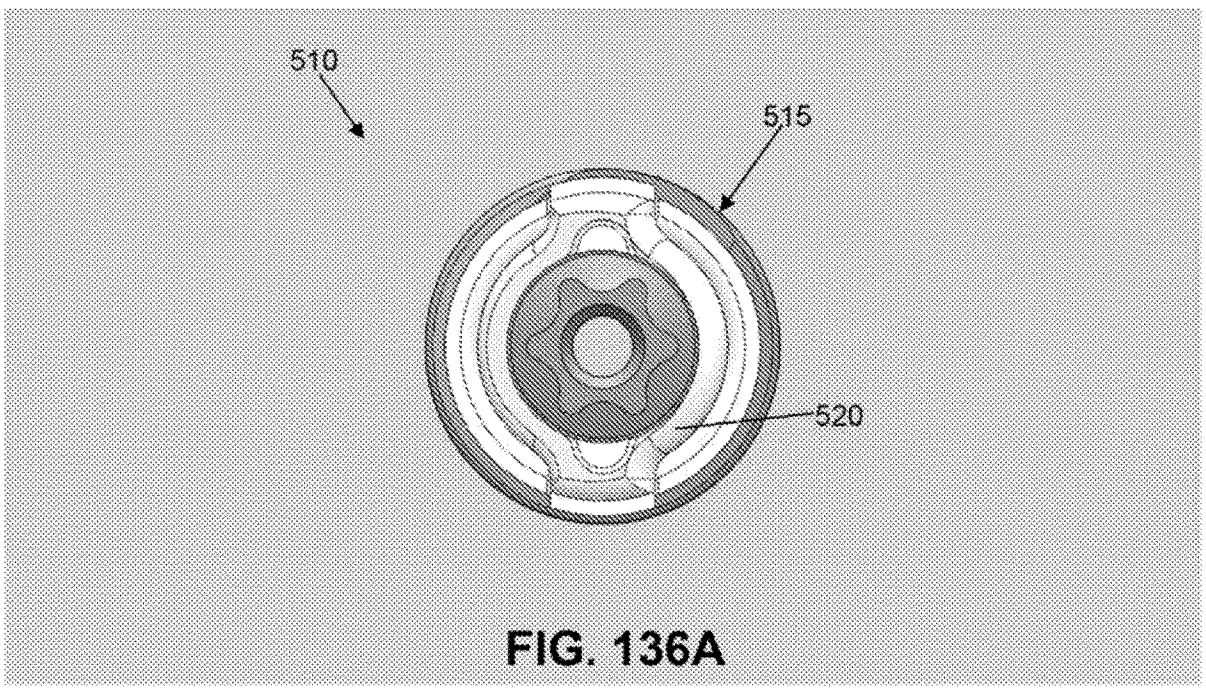
Figure 136B:
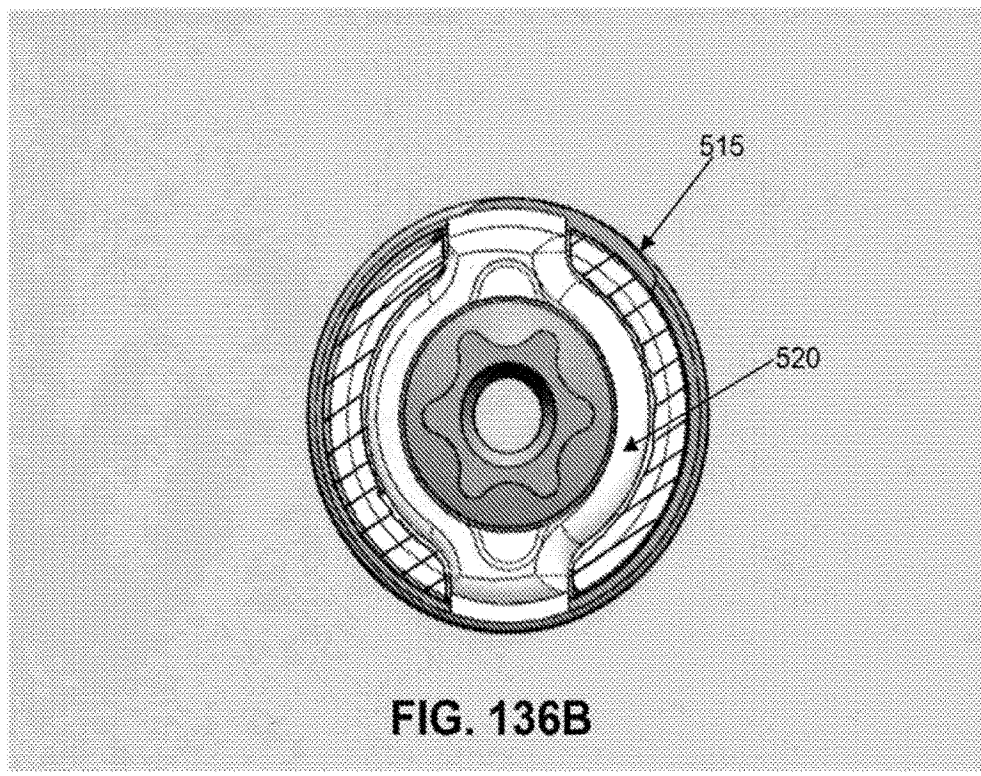
Figure 137:
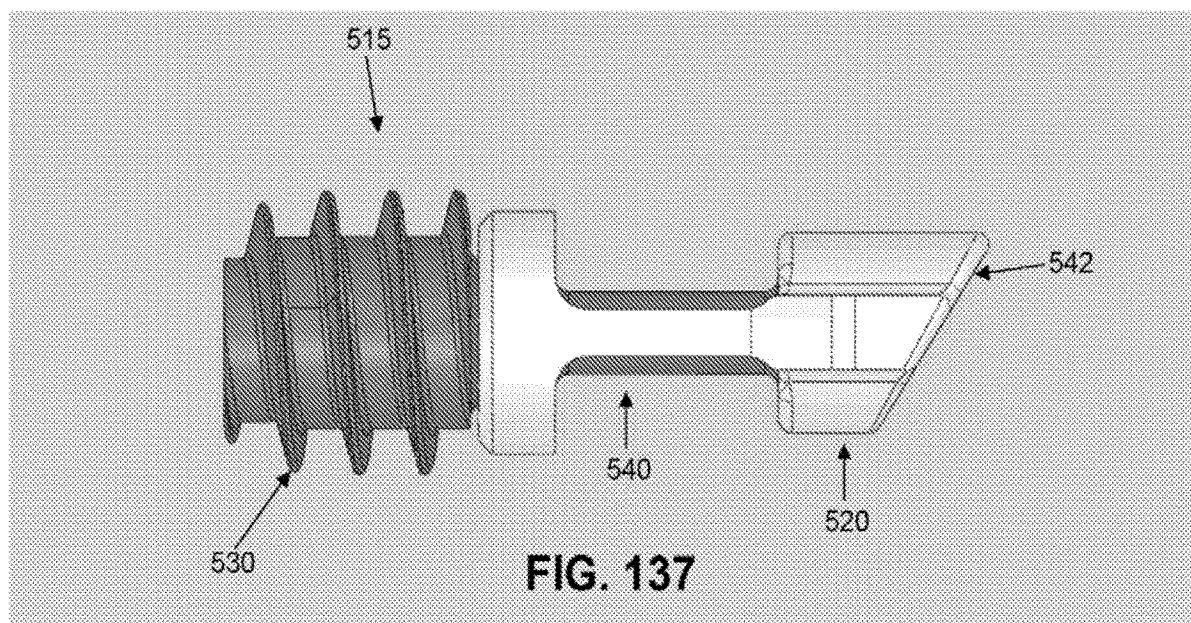
Figure 141A:
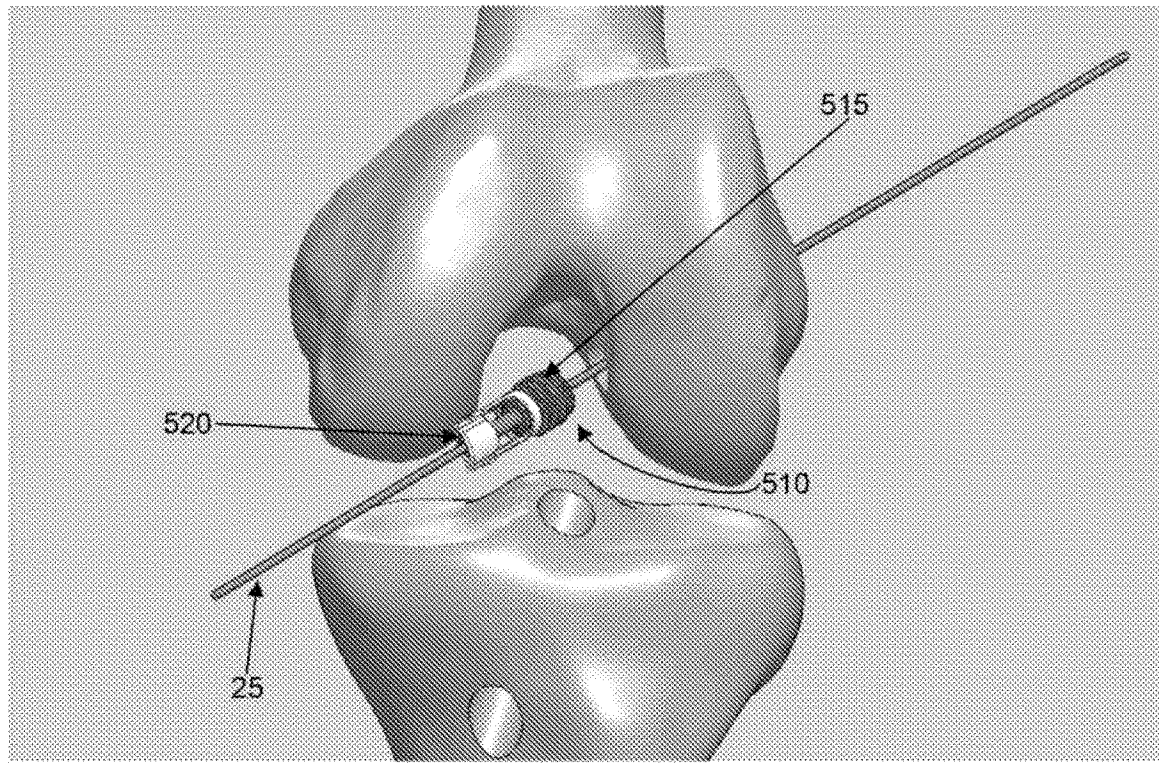
Figure 141B:
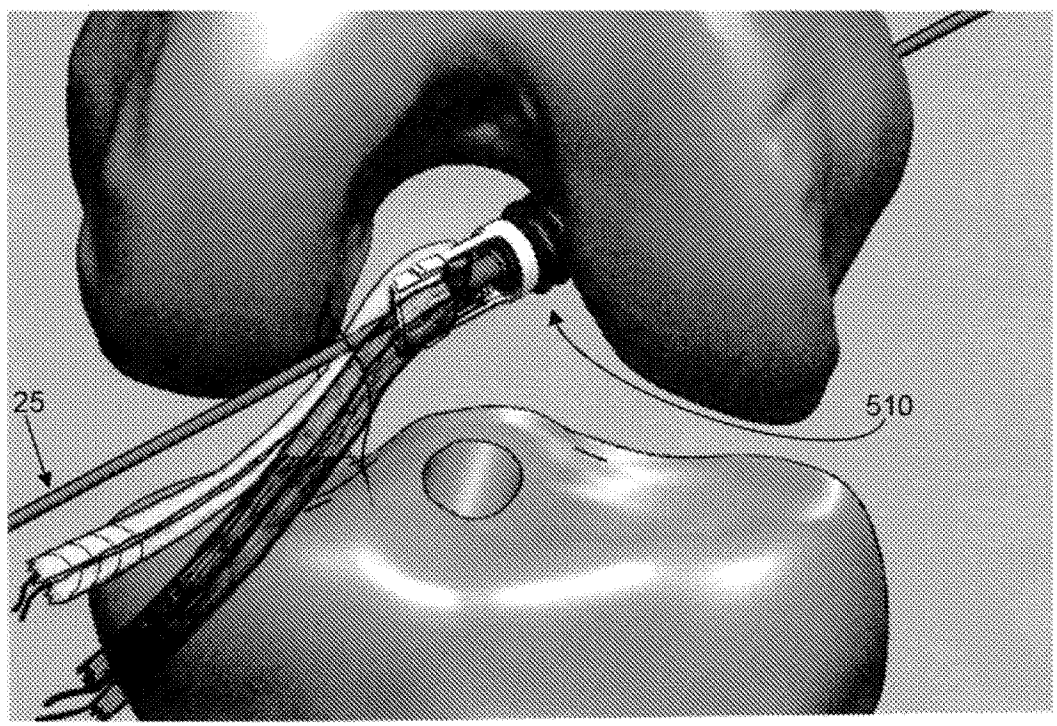
Figure 142:
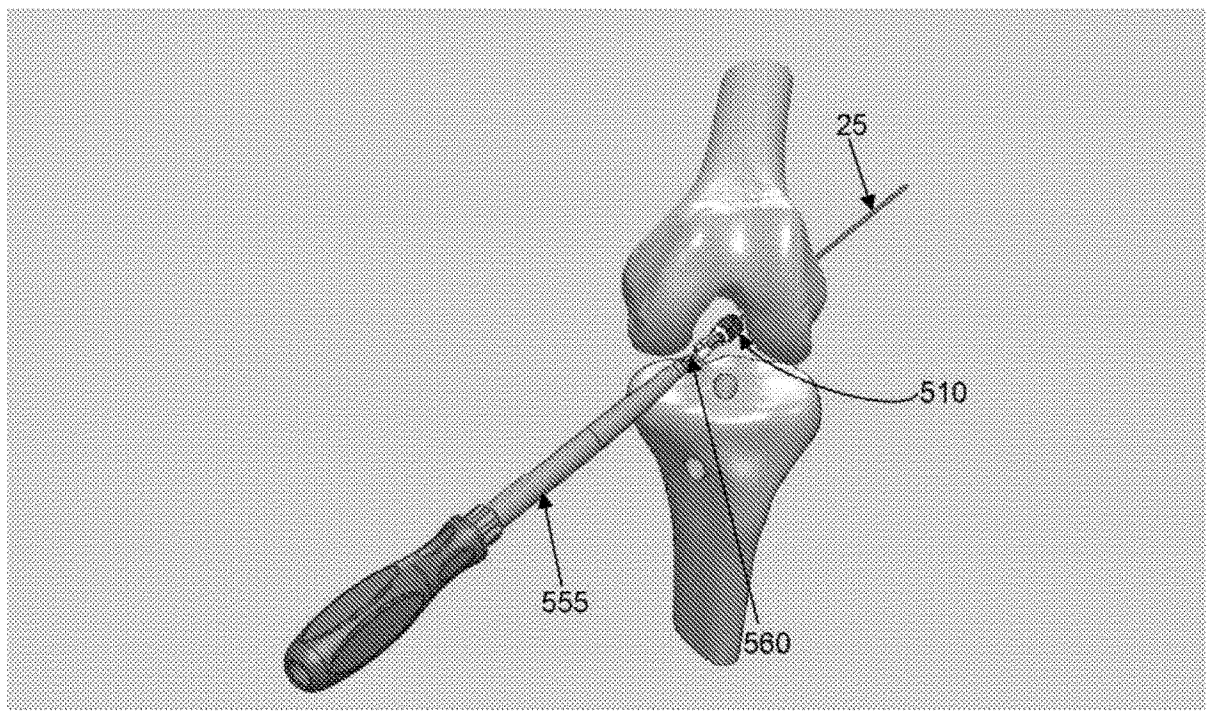
Figure 143:
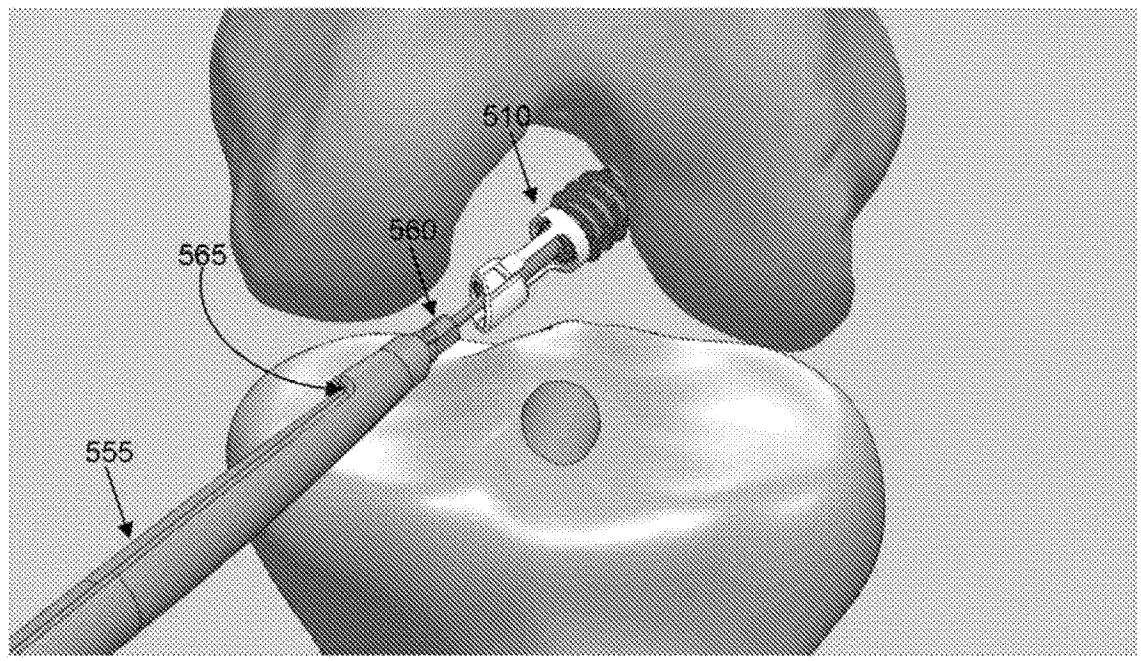
Figure 144:
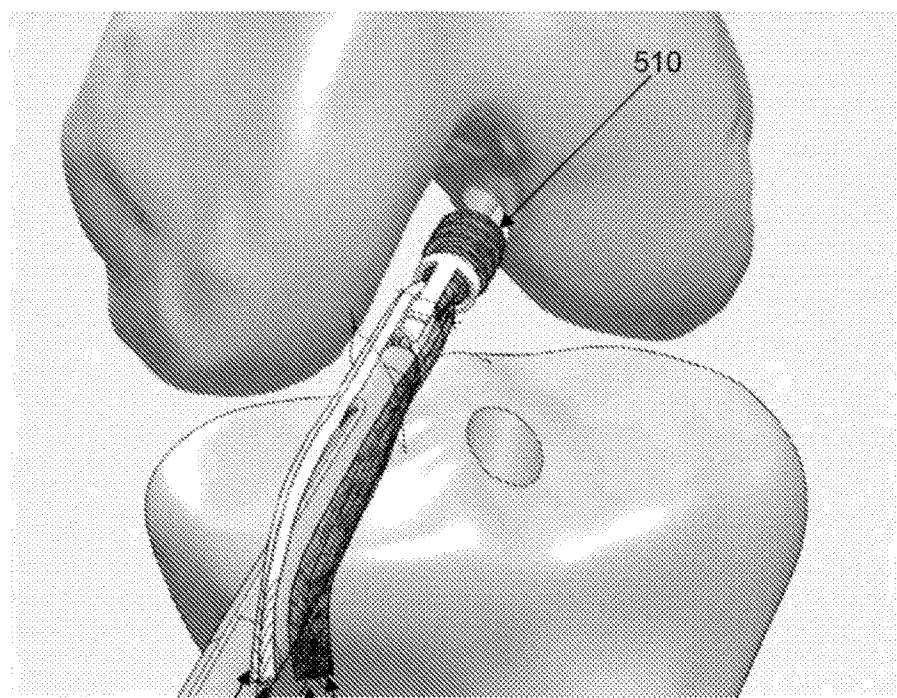
Figure 145A:
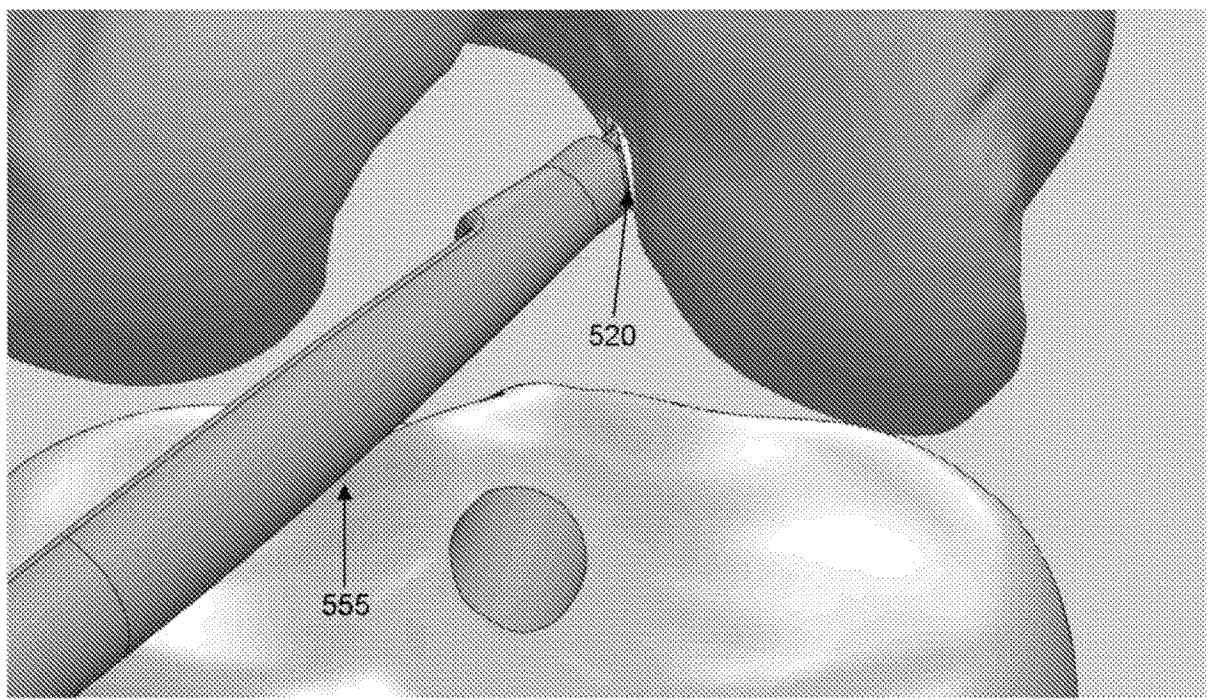
Figure 145B:
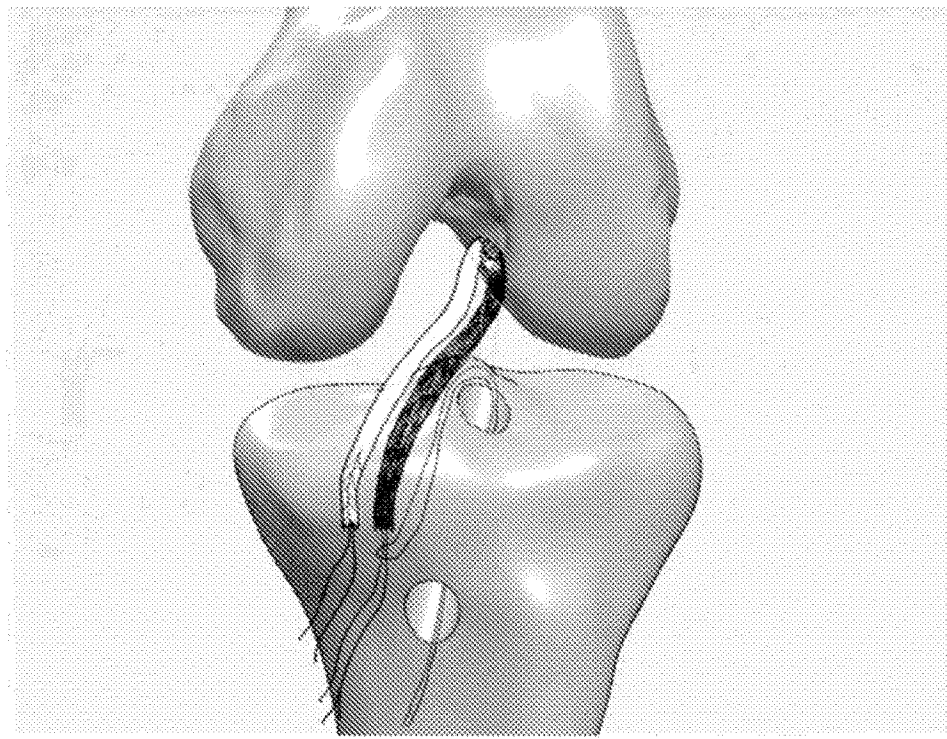
Figure 146:
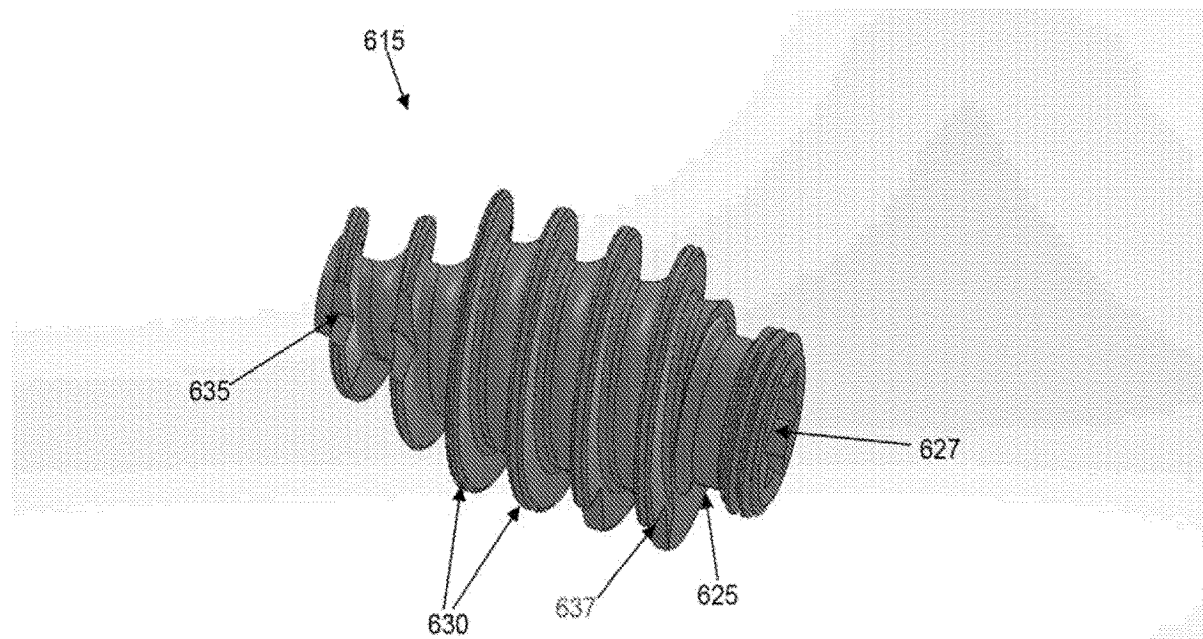
Figure 147:
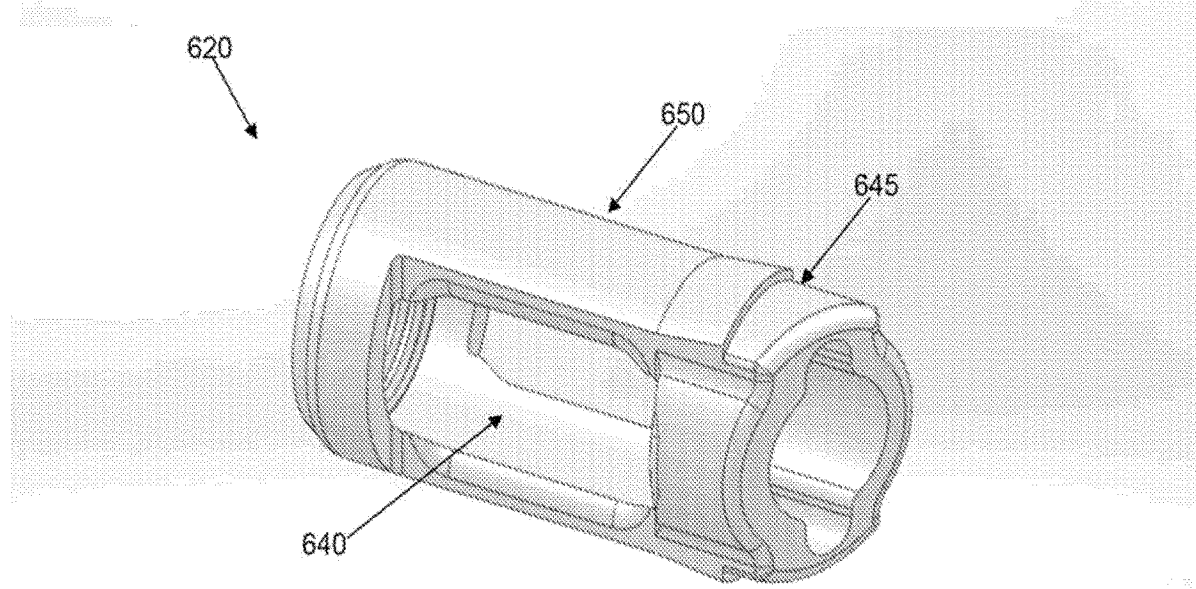
Figure 148:
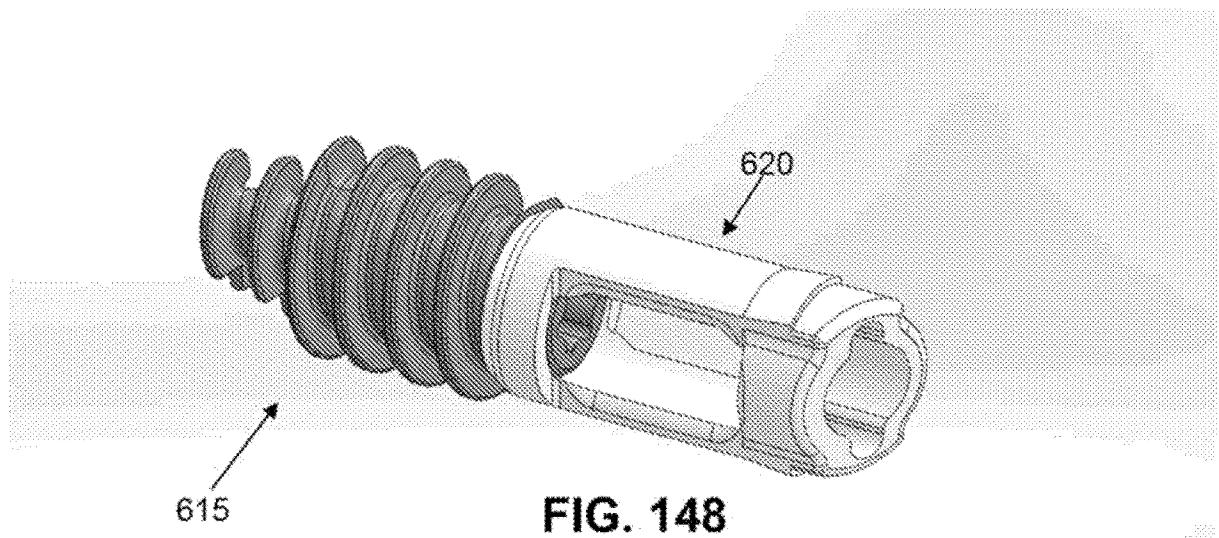
Figure 149:
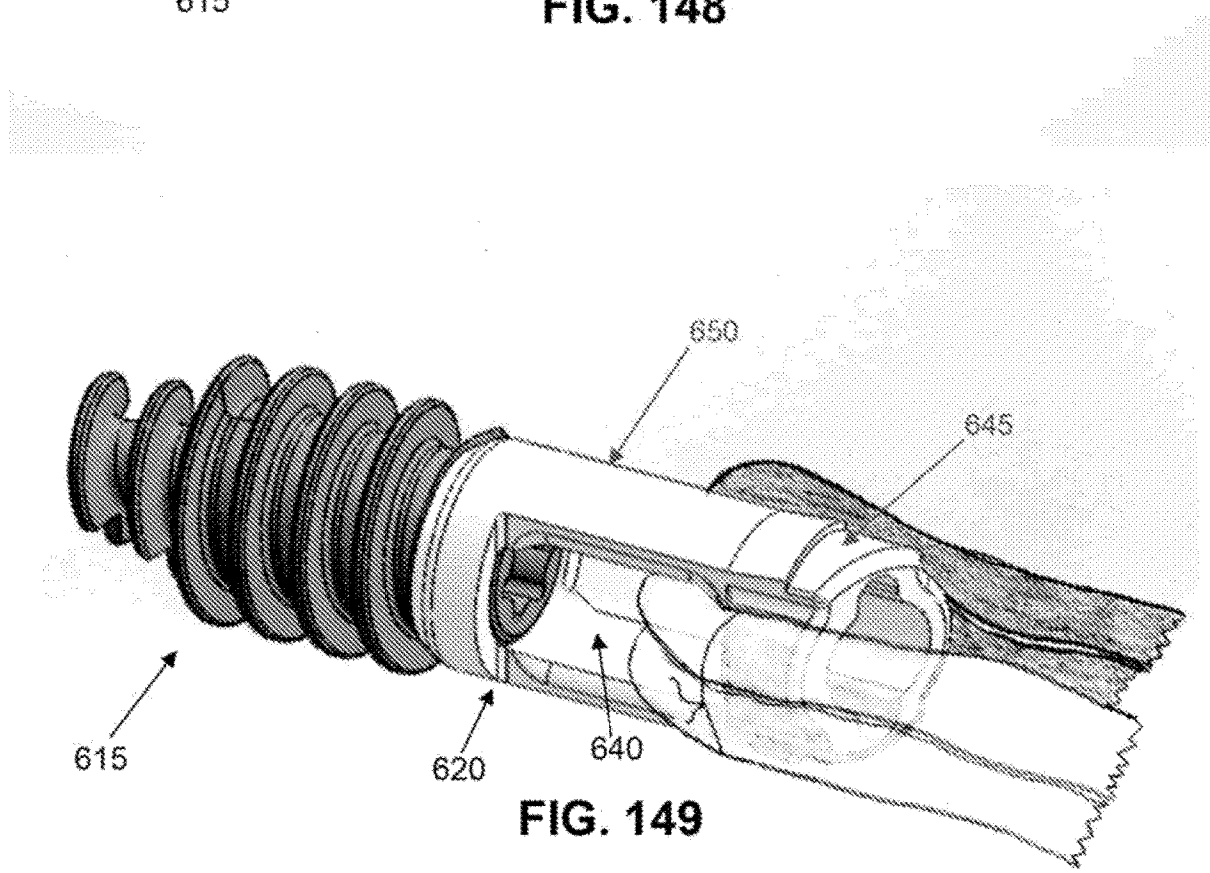
Figure 150:
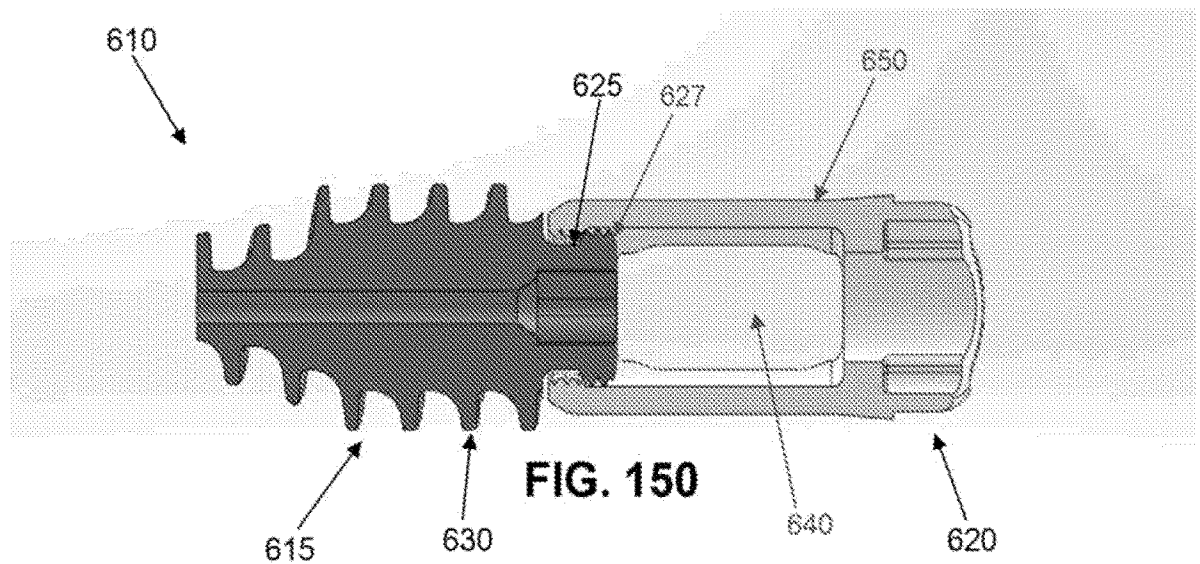
Figure 151A:
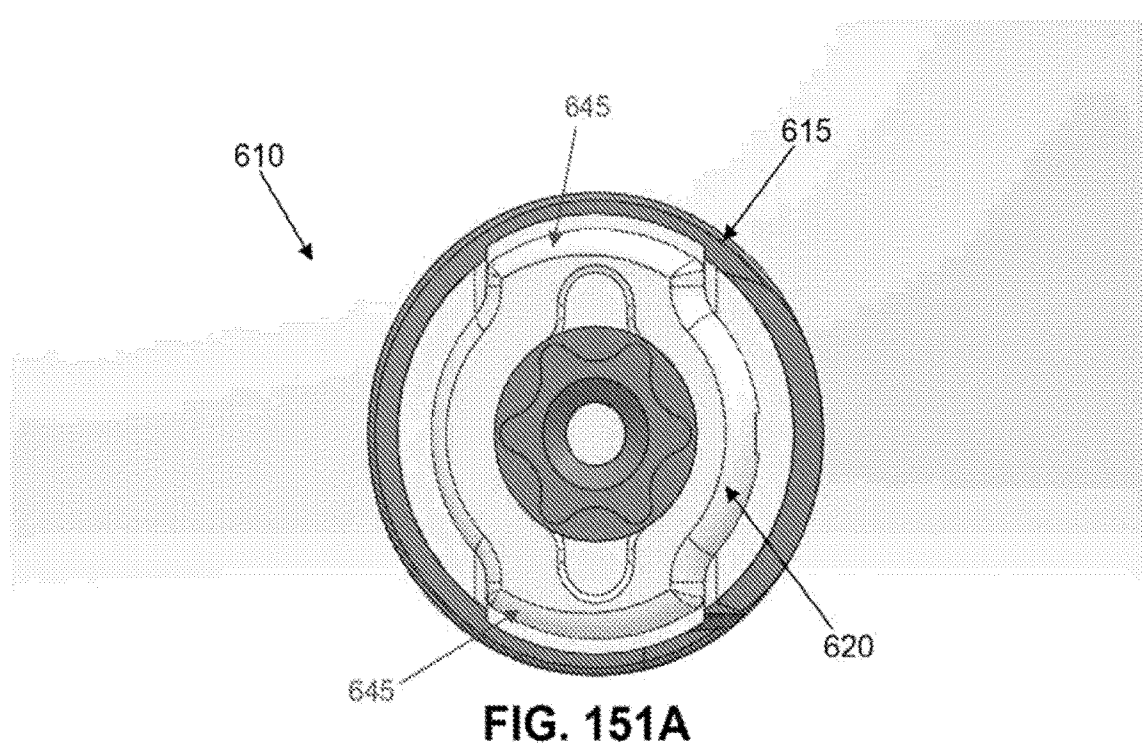
Figure 151B:
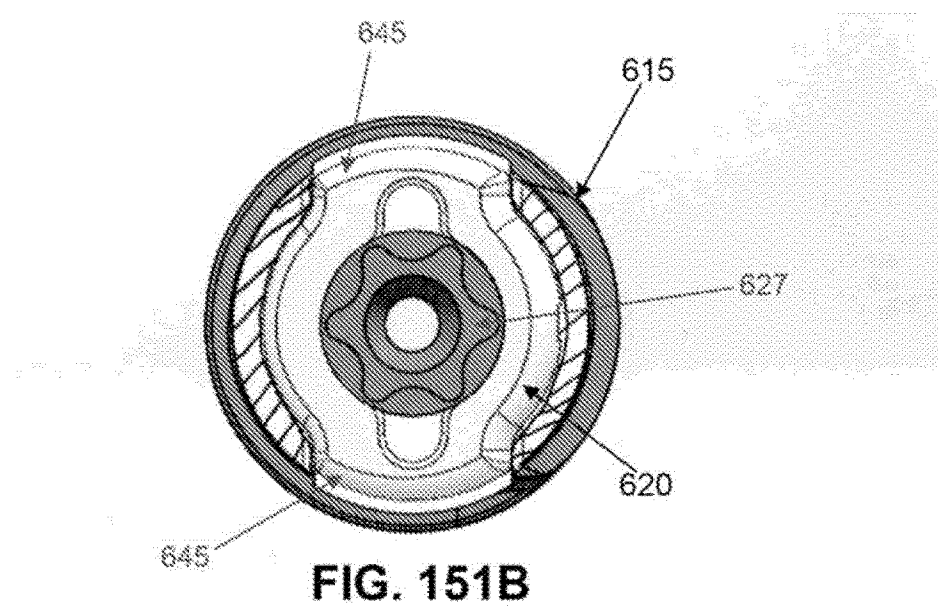
Figure 152:
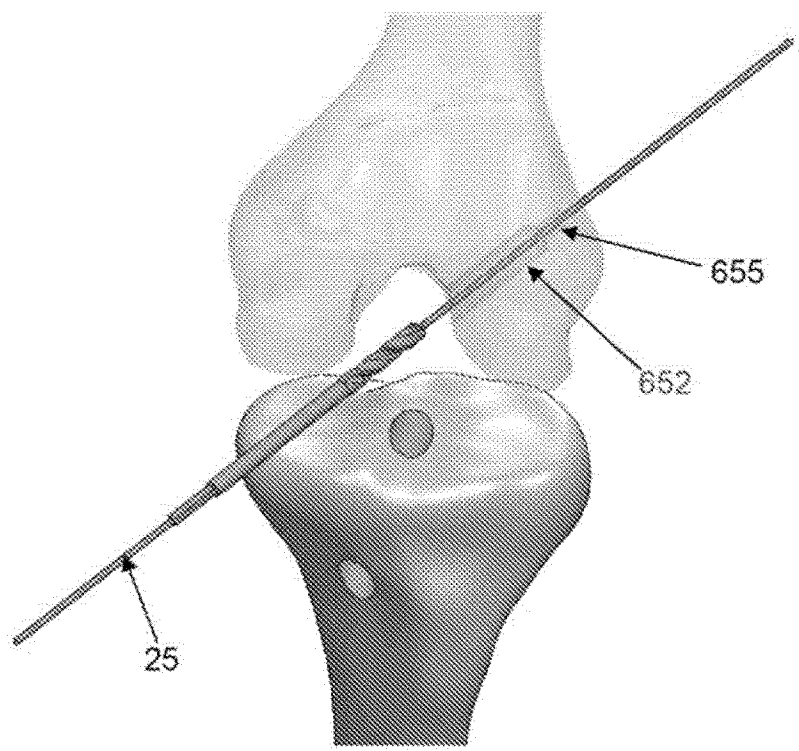
Figure 153:
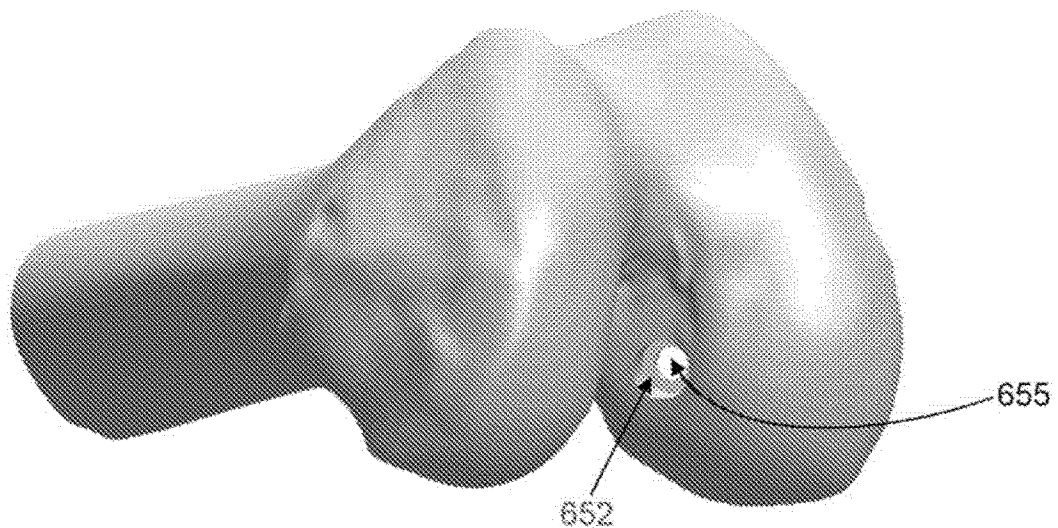
Figure 154:
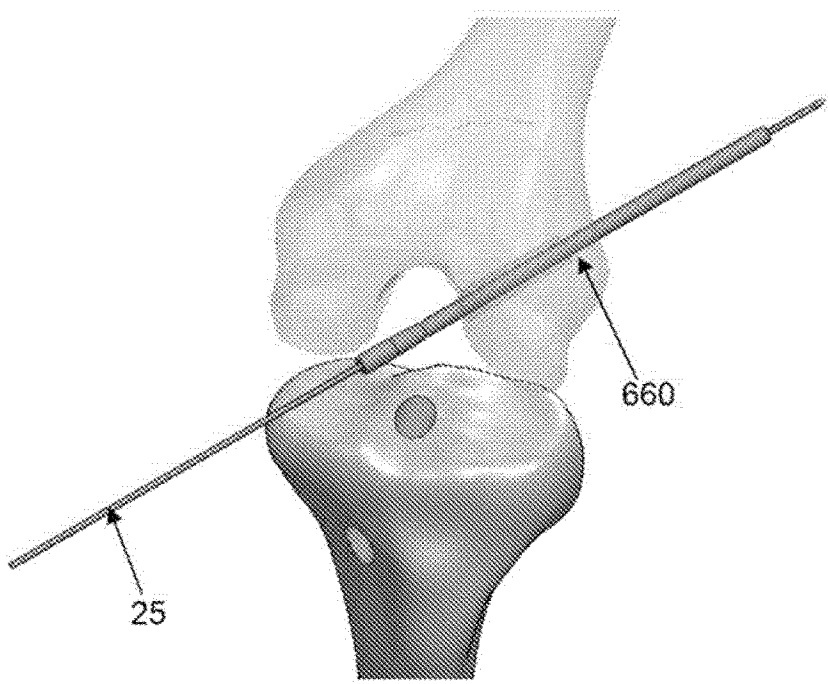
Figure 155:
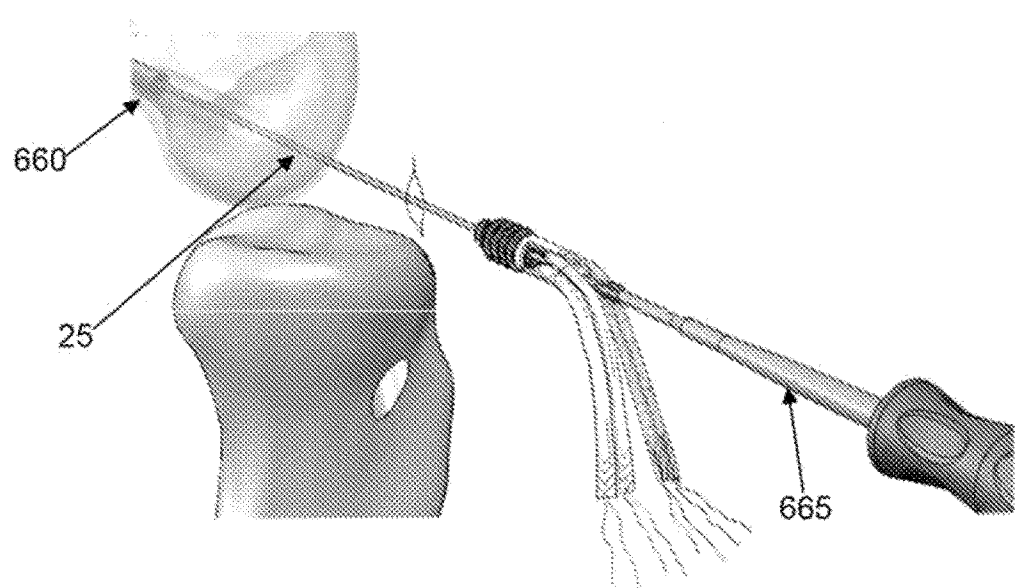
Figure 156:
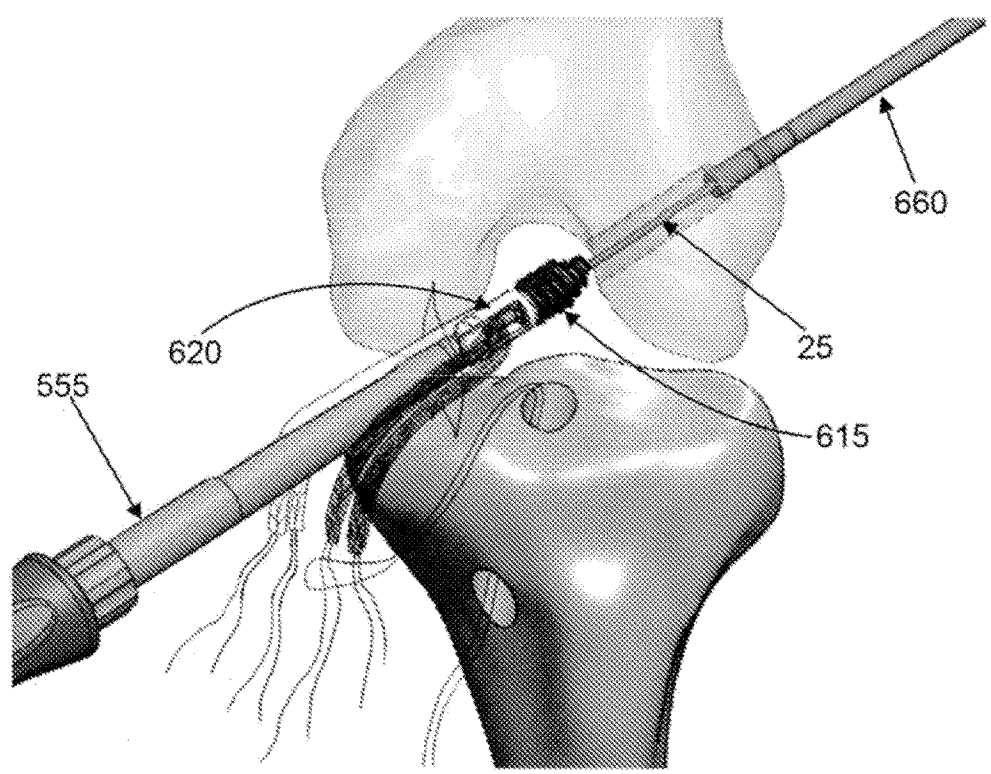
Figure 157A:
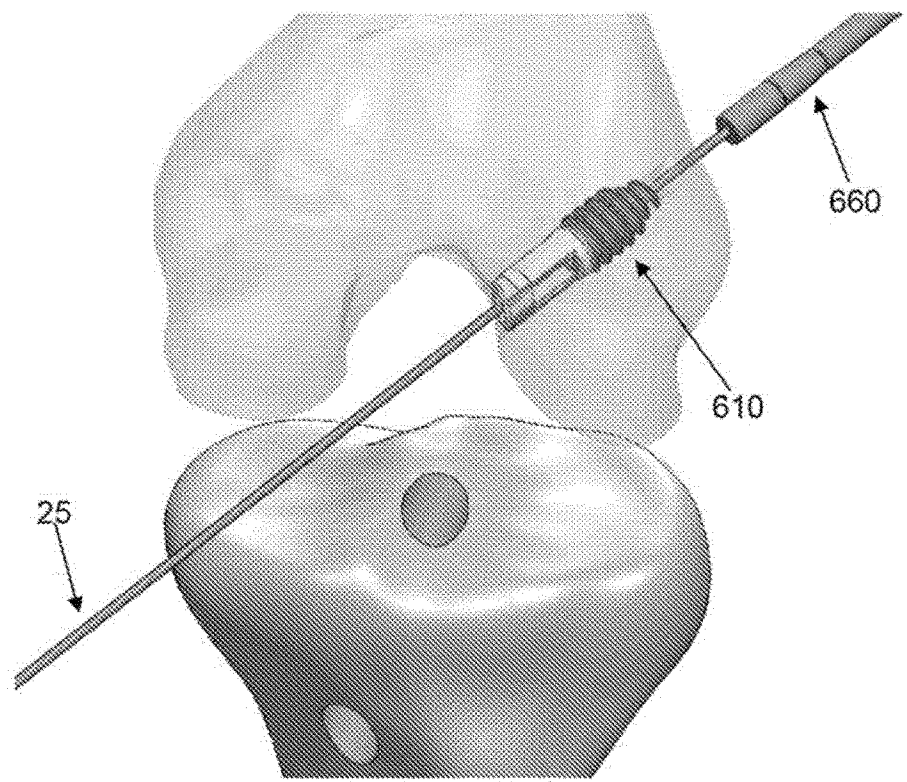
Figure 157B:
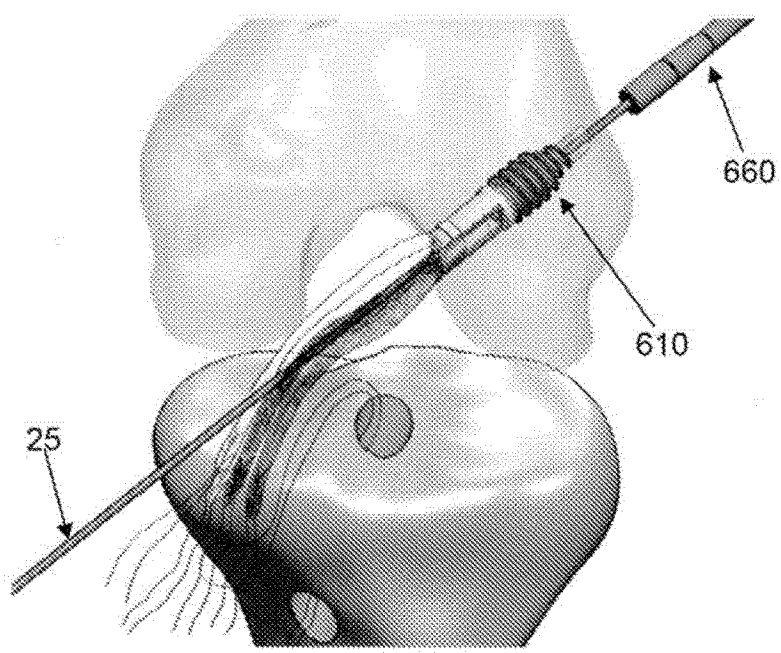
Figure 158A:
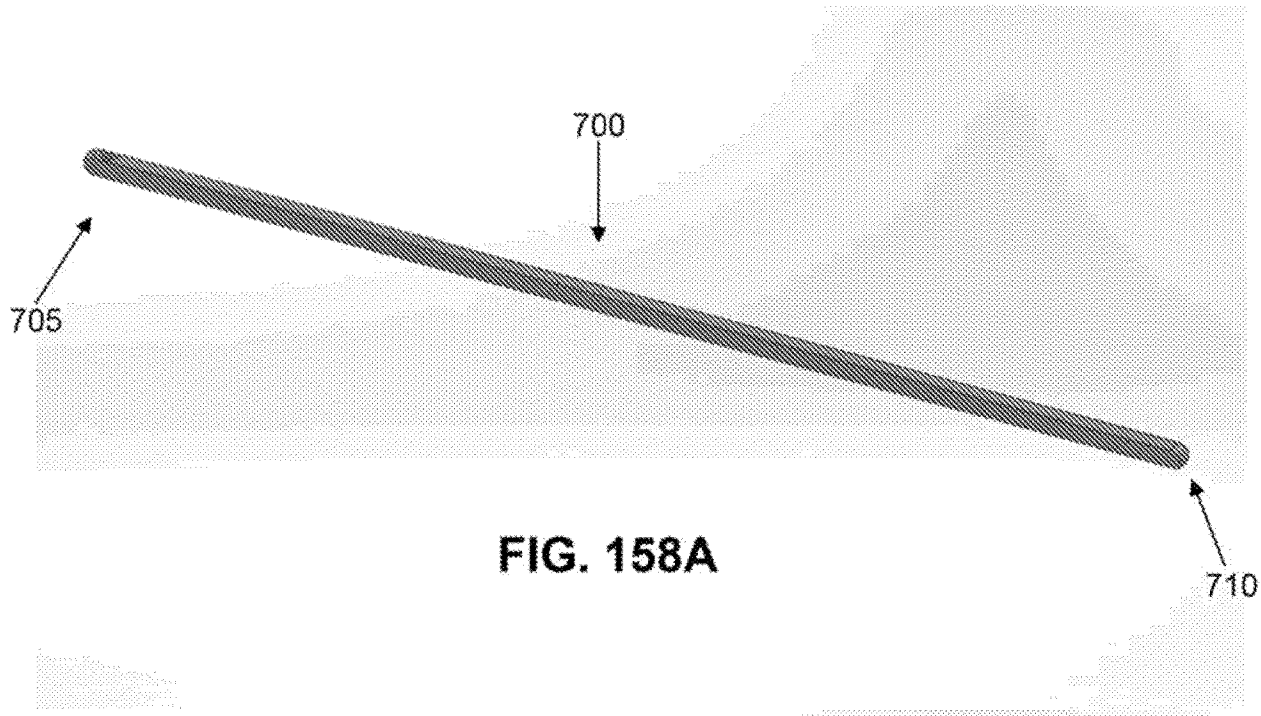
Figure 158B:
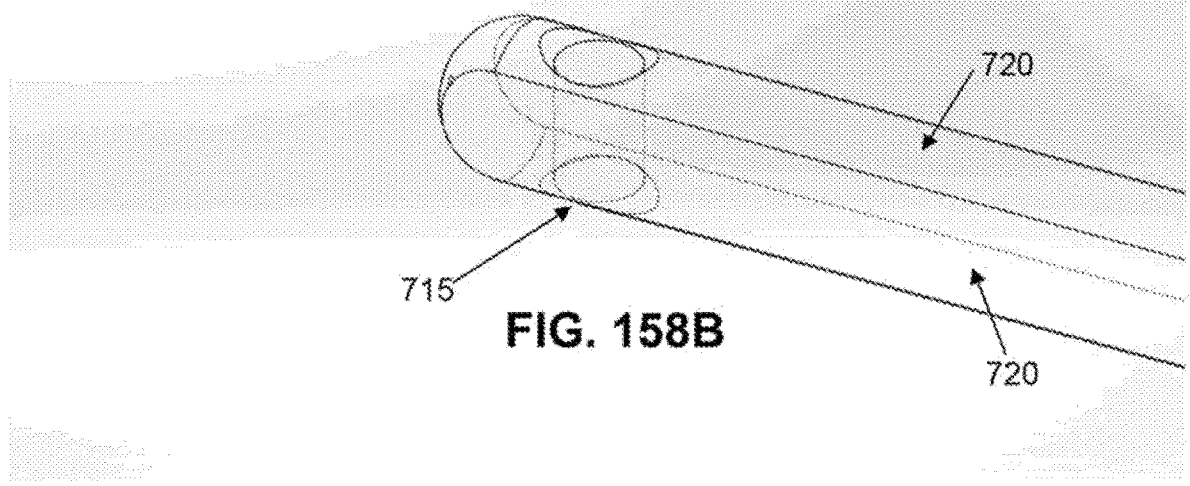
Figure 159A:
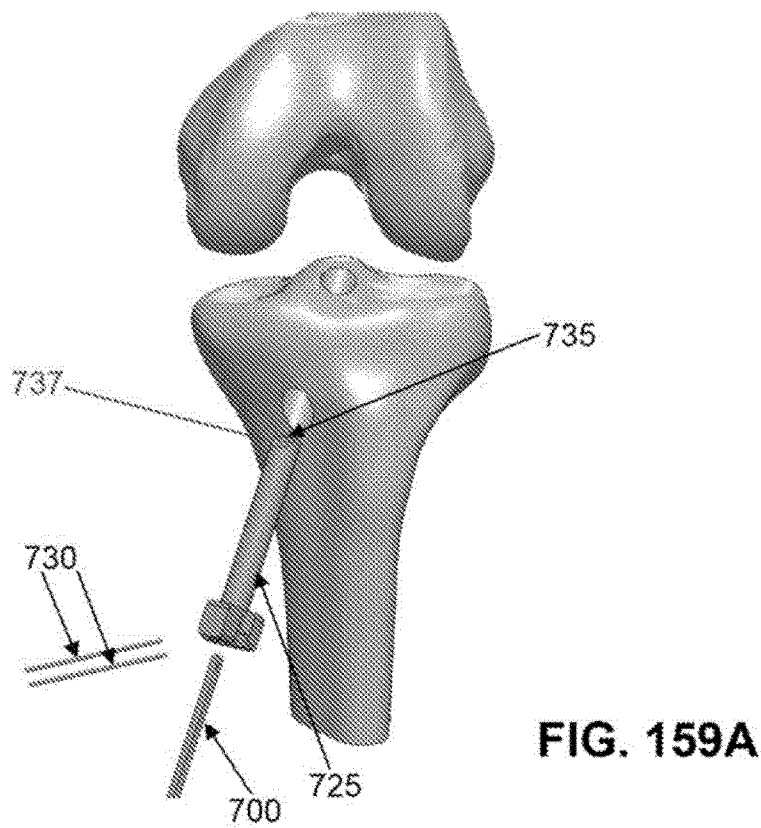
Figure 159B:
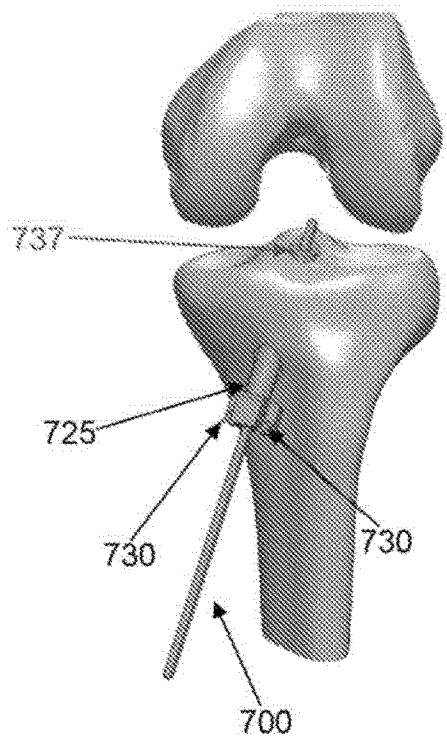
Figure 160A:
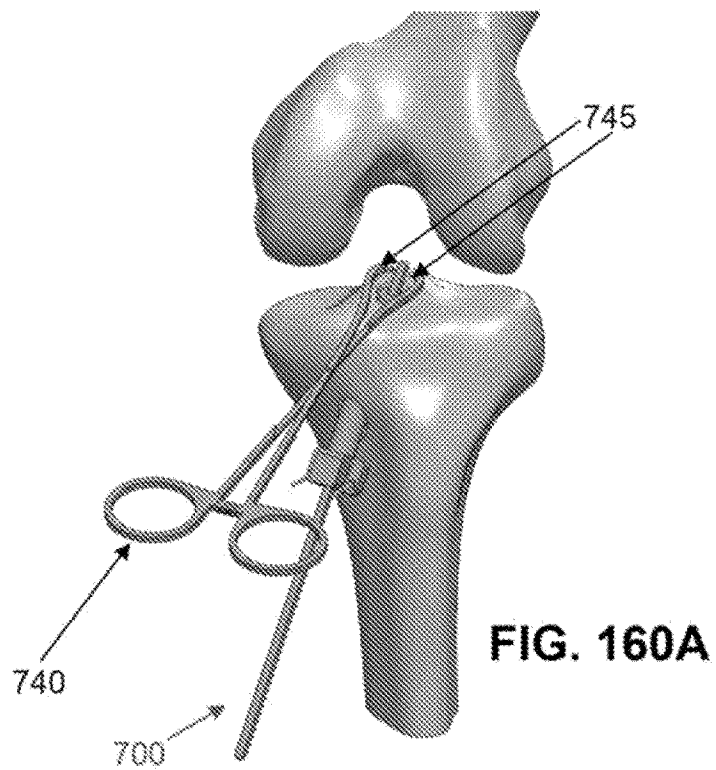
Figure 160B:
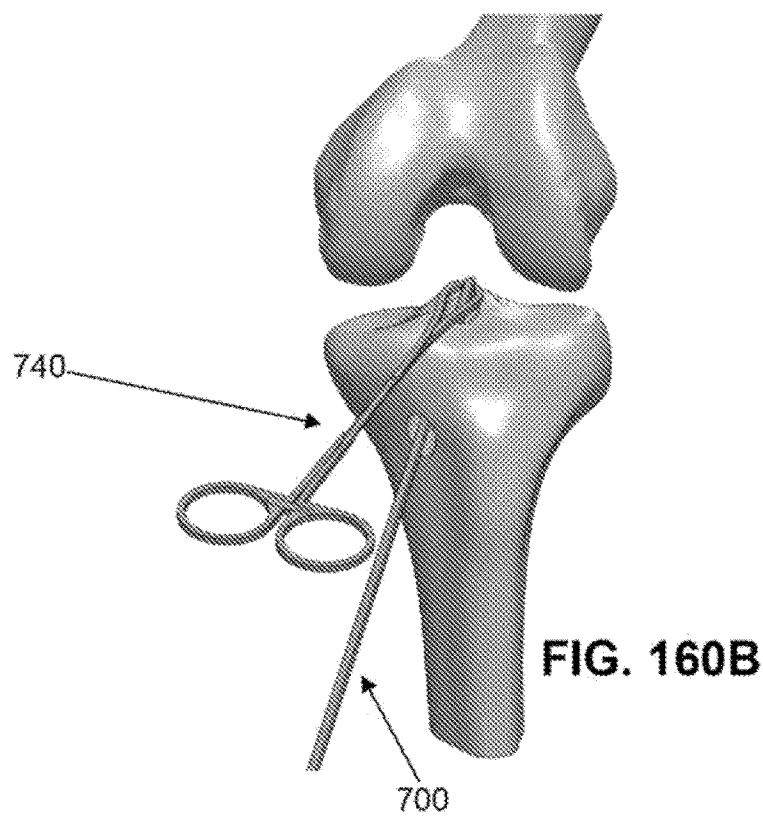
Figure 161A:
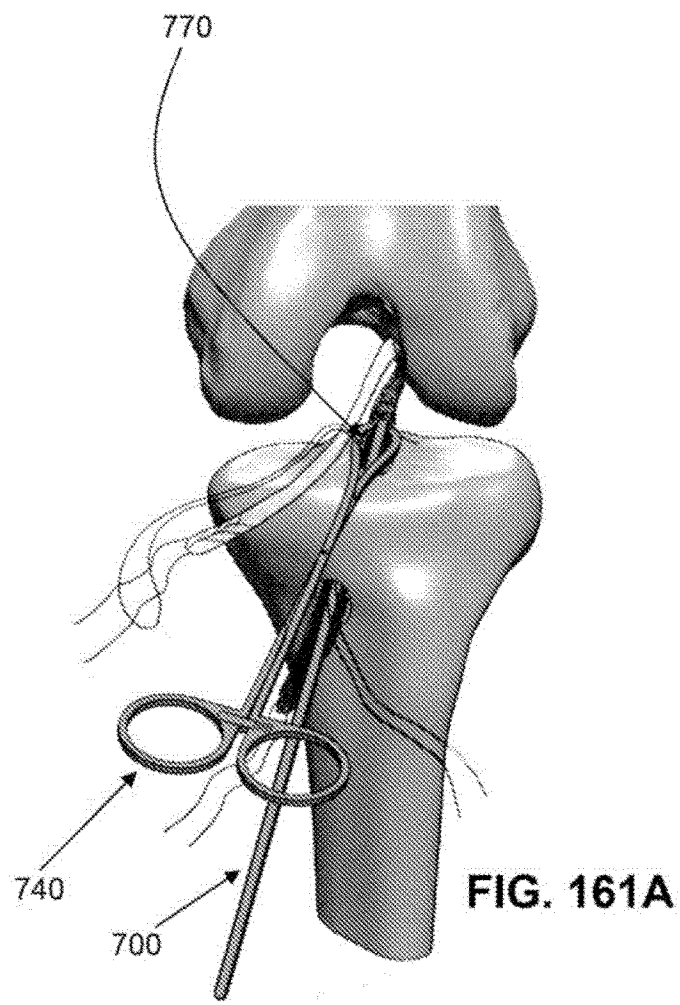
Figure 161B:
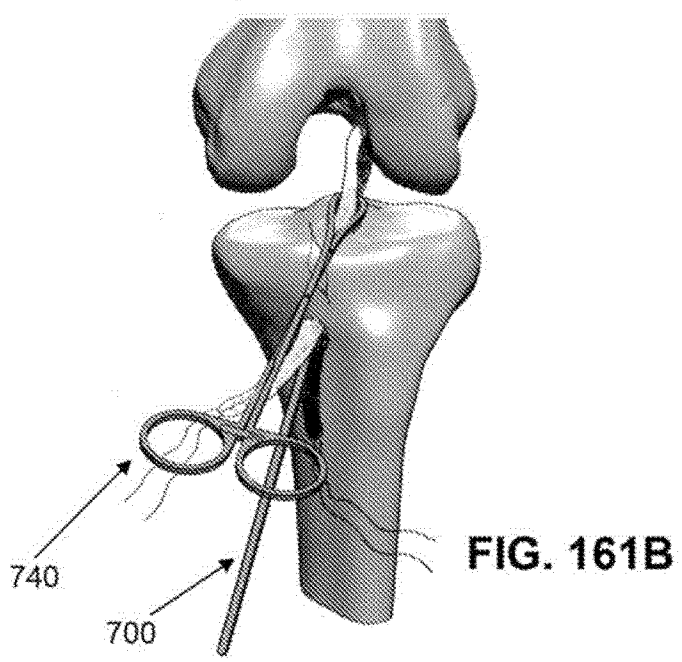
Figure 162:
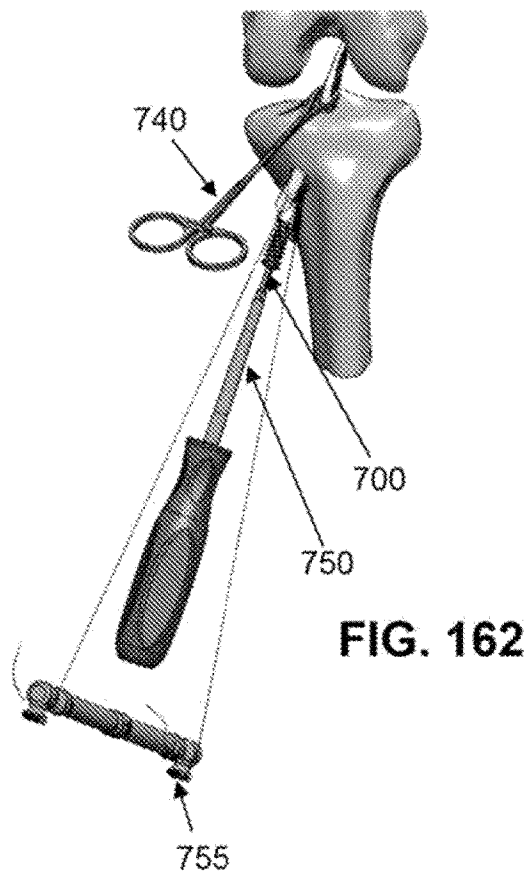
Figure 163:
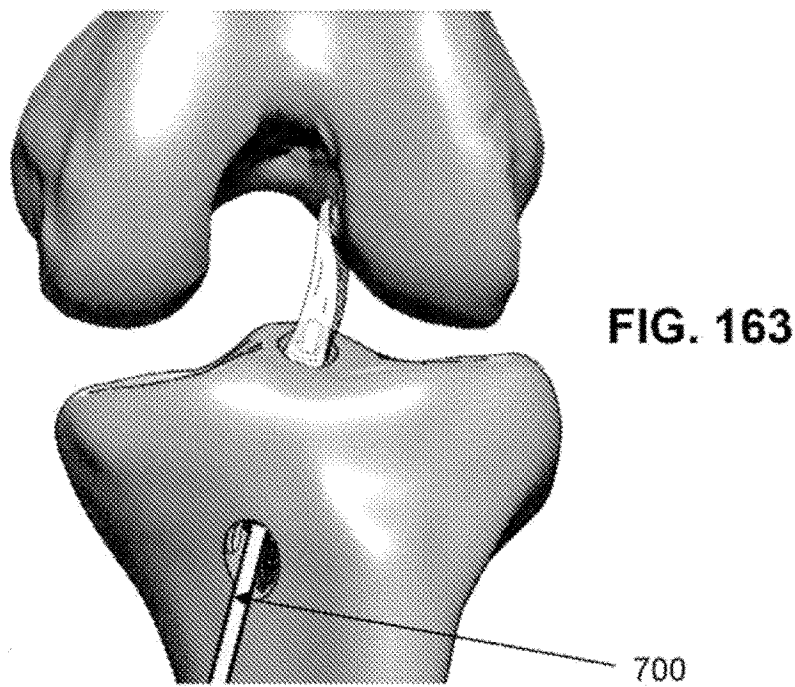
Figure 164:
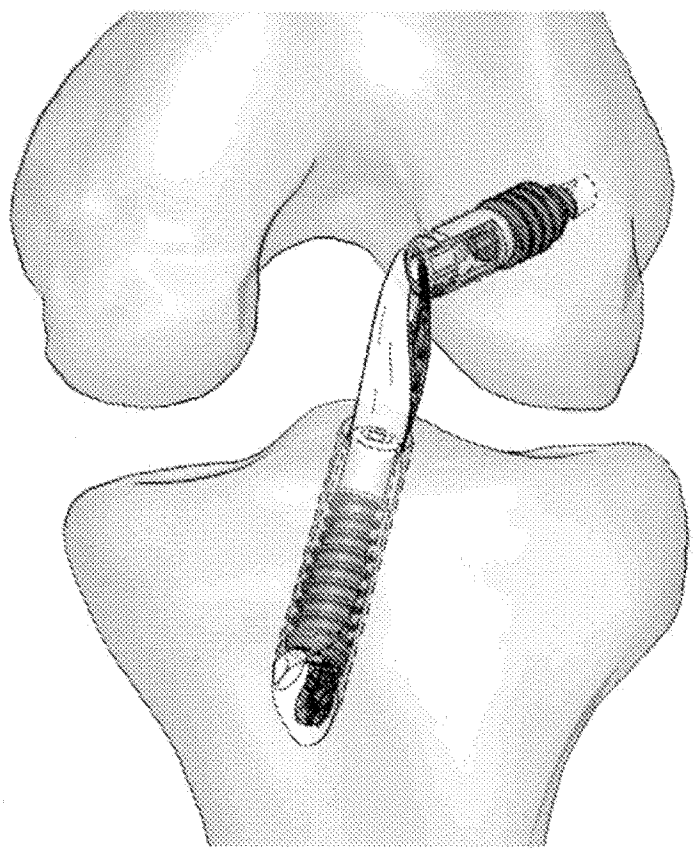

FIG. 111B is a schematic view showing a tibial fixation device and a wrench disposed over a guide pin, and showing ligament graft;

FIG. 112 is a schematic view showing a wrench engaged with a tibial fixation screw;

FIG. 113A is a schematic view showing the overall tibial system;

FIG. 113B is a schematic view showing the overall tibial system, with ligament graft and sutures;

FIG. 114 is a schematic view showing the overall tibial system;

FIG. 115 is a schematic view showing a wrench tightening the tibial fixation device into position;

FIG. 116 is a schematic view showing a tibial fixation device in position;

FIG. 117 is a schematic view showing instrumentation disengaged from the tibial fixation device;

FIG. 118 is a schematic view showing tibial and femoral fixation devices in place;

FIG. 119A is a schematic view showing tibial and femoral fixation devices in place;

FIG. 119B is a schematic view showing tibial and femoral fixation devices in place, with graft ligaments;

FIG. 119C is a schematic view showing tibial and femoral fixation devices in position;

FIG. 119D is a schematic view showing tibial and femoral fixation devices in position, with graft ligament;

FIG. 120A is a schematic view showing tibial and femoral fixation devices in position;

FIG. 120B is a schematic view showing tibial and femoral fixation devices in position, with graft ligament;

FIG. 121A is a schematic view showing a spacer orientation guide;

FIG. 121B is a schematic view showing insertion of a spacer orientation guide into the femoral tunnel;

FIG. 122 is a schematic view showing a spacer orientation guide fully inserted into the femoral tunnel and aligned with the bone surface;

FIG. 123 is a schematic view showing a bone marked in the same location as the guide alignment mark;

FIG. 124A is a schematic view showing a spacer alignment tool with alignment marking;

FIG. 124B is a schematic view showing a femoral ligament spacer having an alignment marking;

FIG. 125 is a schematic view showing an FLS tightened, with its marking aligned with a marking on the bone;

FIG. 126 is a schematic view showing an FLS in place and aligned with a bone mark;

FIG. 127 is a schematic view showing a spacer orientation guide aligned with a tibial surface;

FIG. 128 is a schematic view showing an alignment marking on a tibia;

FIG. 129 is a schematic view showing an alignment marking on a tibial ligament spacer;

FIG. 130 is a schematic view showing a TLS inserted and aligned with a marking on the tibial surface;

FIG. 131 is a schematic view showing a femoral fixation screw;

FIG. 132 is a schematic view showing a femoral ligament spacer;

FIG. 133 is a schematic view showing a femoral fixation screw aligned with a femoral ligament spacer;

FIG. 134A is a schematic view showing an assembled femoral fixation device;

FIGS. 134B and 134C are schematic views showing the assembled femoral fixation device with ligament grafts;

FIG. 135 is a schematic view showing a cross-sectional view of the femoral fixation device;

FIG. 136A is a schematic view showing the femoral fixation device;

FIG. 136B is a schematic view showing the femoral fixation device with ligament grafts;

FIGS. 137-140 are schematic views showing the femoral fixation device;

FIG. 141A is a schematic view showing a guide pin and a femoral fixation device;

FIG. 141B is a schematic view showing a femoral fixation device, a guide pin and ligament grafts;

FIG. 142 is a schematic view showing a femoral fixation device, a guide pin, a ligament spacer alignment tool and a hex wrench;

FIG. 143 is a schematic view showing a femoral fixation device, a ligament spacer alignment tool and a hex wrench;

FIG. 144 is a schematic view showing a femoral fixation device, a ligament spacer alignment tool, a hex wrench and ligament grafts;

FIG. 145A is a schematic view showing a femoral fixation device and a ligament spacer alignment tool;

FIG. 145B is a schematic view showing a femoral fixation device seated in the femur, with ligament grafts being shown;

FIG. 146 is a schematic view showing a femoral fixation screw;

FIG. 147 is a schematic view showing a femoral ligament spacer;

FIG. 148 is a schematic view showing an assembled femoral fixation device;

FIG. 149 is a schematic view showing the assembled femoral fixation device with ligament grafts;

FIG. 150 is a schematic view showing a cross-sectional view of the femoral fixation device;

FIG. 151A is a schematic view showing the femoral fixation device;

FIG. 151B is a schematic view showing the femoral fixation device with ligament grafts;

FIG. 152 a schematic view showing a guide pin and a drill bit;

FIG. 153 is a schematic view showing a femoral tunnel;

FIG. 154 is a schematic view showing a guide pin and a coaxial spacer;

FIGS. 155 and 156 are schematic views showing a guide pin, a coaxial spacer, a femoral fixation device carrying ligament grafts and a hexalobe drive tool;

FIG. 157A is a schematic view showing a guide pin, a femoral fixation device and a coaxial spacer;

FIG. 157B is a schematic view showing a guide pin, a femoral fixation device carrying ligament grafts and a coaxial spacer;

FIGS. 158A and 158B are schematic views of a tibial alignment pin;

FIGS. 159A and 159B are schematic views of a tibial alignment pin, a tibial alignment pin guide and two fixation wires;

FIG. 160A is a schematic view of a tibial alignment pin, a tibial alignment pin guide and a pin retaining clamp;

FIG. 160B is a schematic view of a tibial alignment pin and a pin retaining clamp;

FIGS. 161A and 161B are schematic views of a tibial alignment pin, a pin retaining clamp and ligament grafts;

FIG. 162 is a schematic view of a tibial alignment pin, a tibial fixation device, a pin retaining clamp, a hex wrench and a tensioning bar;

FIG. 163 is a schematic view showing a femoral fixation device with ligament grafts and a tibial alignment pin; and FIG. 164 is a schematic view showing femoral and tibial fixation devices in the final construct.

DETAILED DESCRIPTION OF THE INVENTION

As noted above, the present invention provides new apparatus and method for fixation of the ACL which addresses deficiencies in the prior art. The new apparatus secures the graft ligament along the entire periphery of the elliptical bone tunnel entrance so as to provide complete fixation of the ligament graft and to spread the ligament graft over the natural anatomic footprint of the ACL insertions of both the tibia and femur. As an additional benefit, the new apparatus substantially completely fills the bony defect resulting from the drilling process. The elliptical opening of the bone tunnel no longer becomes a detriment, but rather an asset, towards achieving a more accurate anatomic reconstruction.

First Preferred Construction and Method of Use

Figure 17A:
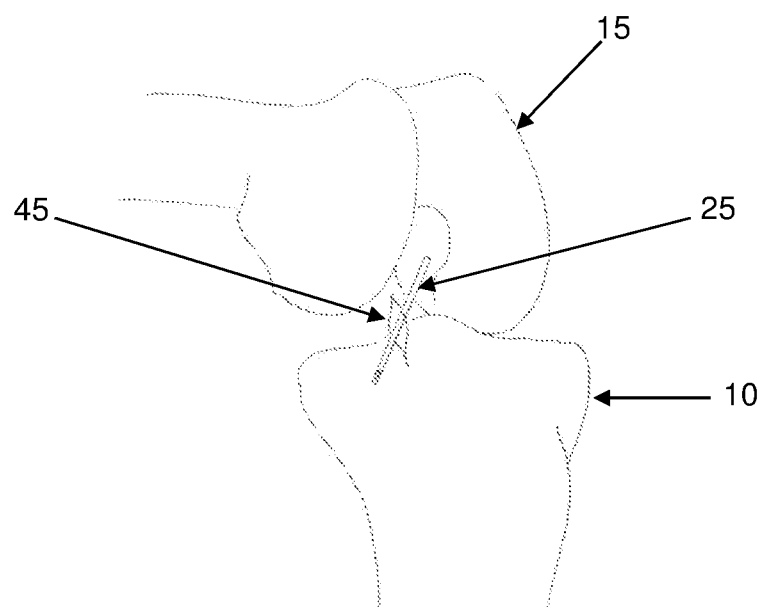
FIG. 17A is a schematic view showing a guide pin through the AM portal which is centered on the femoral ACL footprint in the left knee.
Figure 17B:
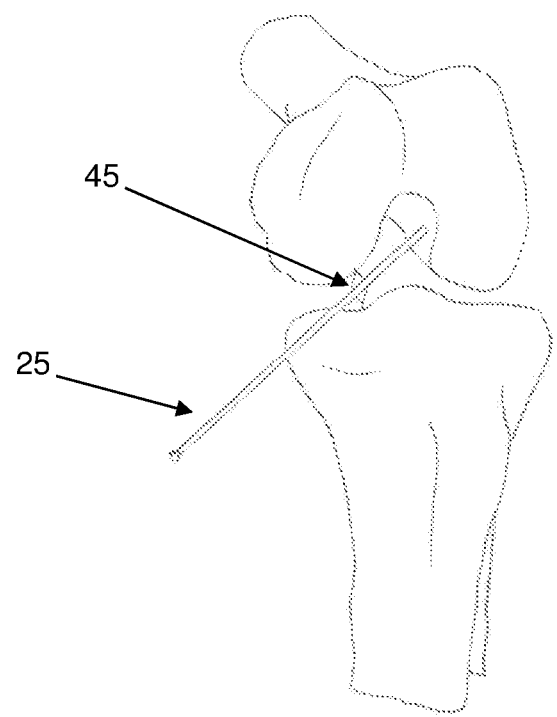
FIG. 17B is a schematic view showing the placement of a guide pin through the AM portal.

In accordance with the present invention, and looking now at FIGS. 17A and 17B (which show the left knee), the femoral tunnel is prepared by first placing a guide pin 25 into the anatomic location of the femoral ACL insertion. It is desirable for the guide pin 25 to enter the intercondylar notch at an angle to avoid the adjacent medial condyle as well as the tibial plateau. As noted above, this angle of approach results in the formation of the aforementioned elliptical femoral tunnel entrance.

Figure 17C:
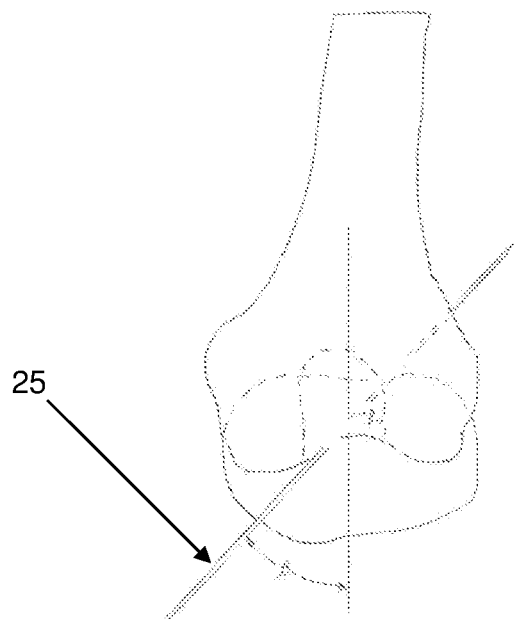
FIG. 17C is a schematic view showing the knee in 90° flexion and showing insertion of a guide pin through the AM portal at an angle β.

From a top view (FIG. 17C), with the knee in 90° flexion, the path of the guide pin 25 is shown as it passes the medial condyle and enters the medial aspect of the intercondylar notch. The guide pin 25 enters at an angle $\beta$ from the sagittal plane. The angle $\beta$ is significant, in order to clear the adjacent medial condyle and to create the elliptical tunnel entrance.

Figure 18:
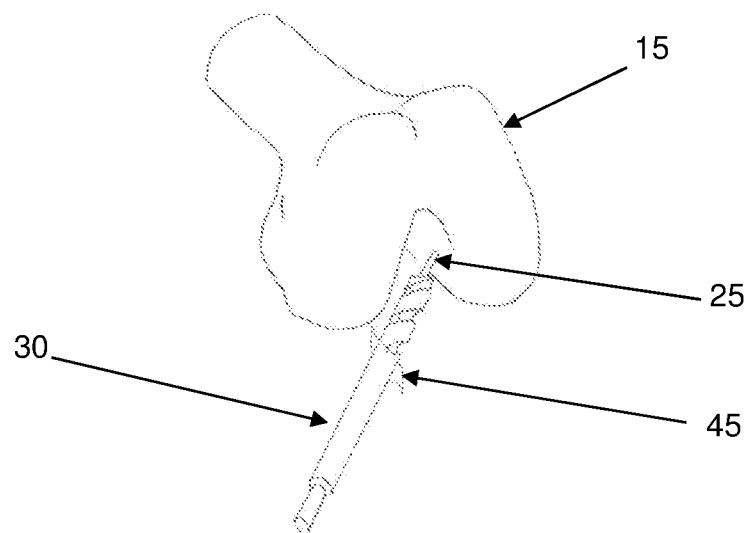
FIG. 18 is a schematic view showing a cannulated drill disposed over the guide pin.

Placement of the guide pin 25 in this manner allows access to the anatomic femoral insertion of the ACL. The drill 30 is then slid over the guide pin 25 (FIG. 18), through the anteromedial portal 45, past the medial condyle and tibial plateau, and into the anatomic location of the femoral ACL insertion.

Figure 19A:
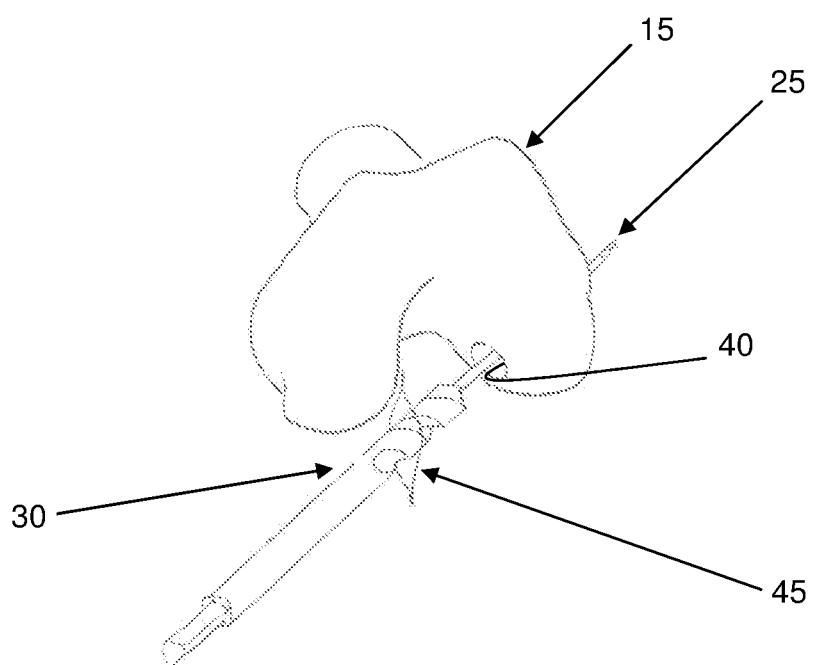
FIG. 19A is a schematic view showing the femoral tunnel drilled and having an elliptical entrance.

The femoral tunnel 40 (FIG. 19A) is then drilled, and the result is a circular bore hole with an elliptical tunnel entrance. This portion of the technique is similar to that which was presented earlier, except that it is completed with the understanding that the angled entrance to the femoral tunnel contributes in a positive manner to creating a more anatomic tunnel entrance. As such, the surgeon does not try to "straighten" out the tunnel to achieve a circular entrance, but rather may slightly increase the angle $\beta$ to achieve the more anatomic elliptical entrance. This is a significant advantage over the prior art.

Figure 19B:
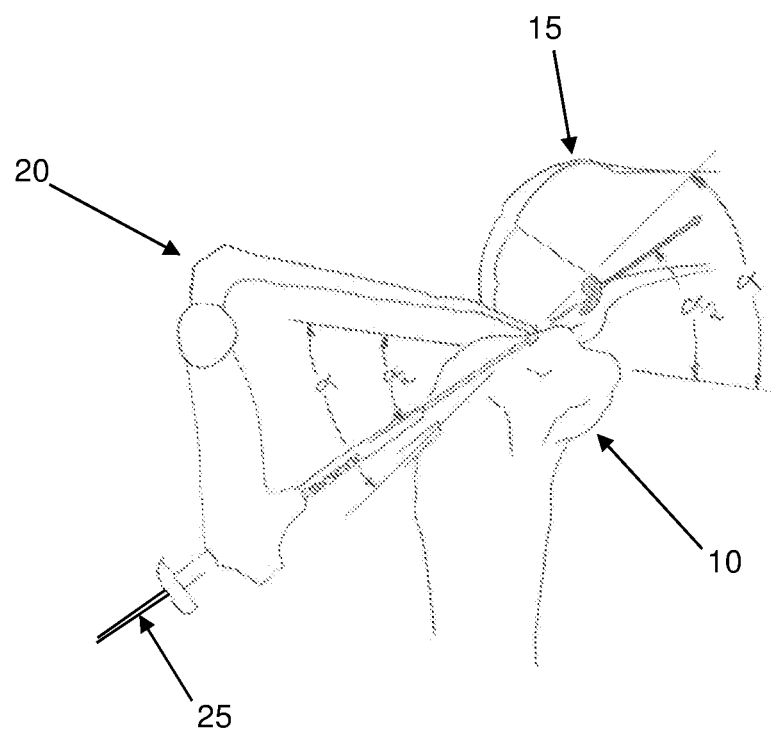
FIG. 19B is a schematic view showing the angle $\alpha_2$ reduced from the original angle α.
Figure 19C:
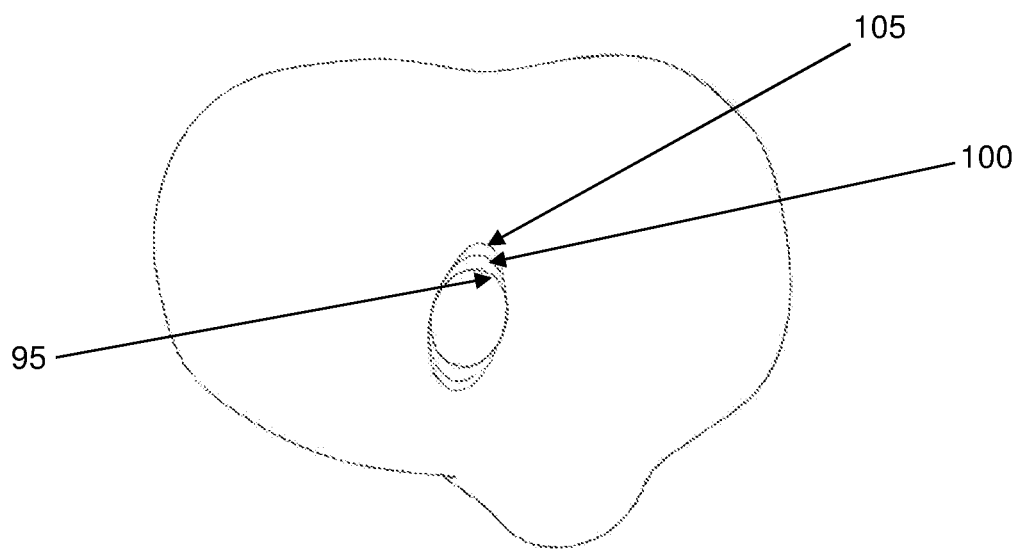
FIG. 19C is a schematic view showing the tibial tunnel "mouth", or entrance, to the joint space.
Figure 20:
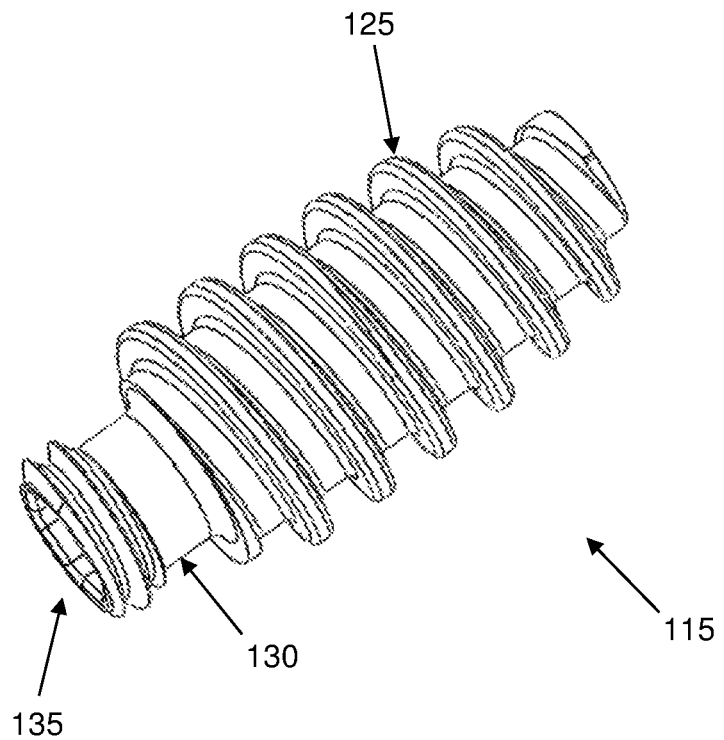
FIG. 20 is a schematic view showing the femoral fixation screw (FFS)
Figure 21:
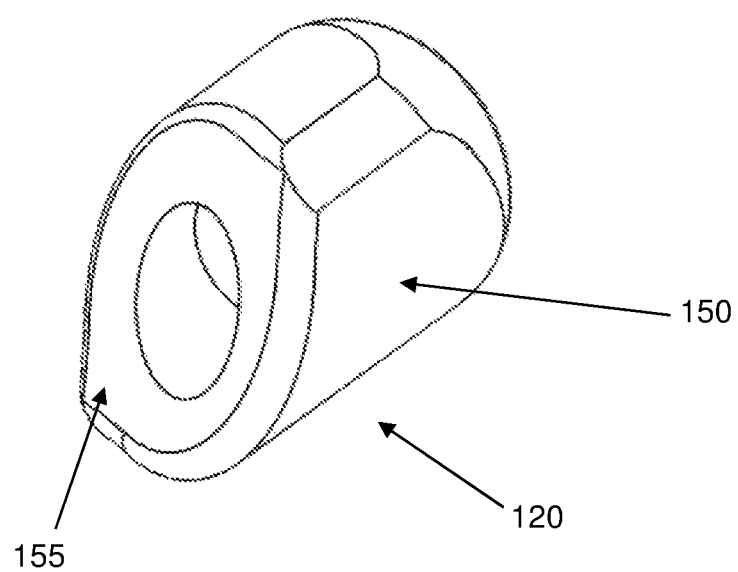
FIG. 21 is a schematic view showing the femoral ligament spacer (FLS)

Similarly, the tibial tunnel (FIG. 19B) is prepared by first drilling a guide pin 25 (with the aid of a drill guide 20) through the anteromedial surface of the tibia 10, exiting through the anatomic center of the ACL insertion on the tibial plateau (as previously described). The angle $\alpha_2$ of the tibial tunnel can be smaller than the original angle $\alpha$ in a typical reconstruction, because the elliptical/oval nature of the tibial tunnel exit into the joint space contributes to the anatomic reconstruction due to the novel aspects of the present invention. This can be a significant advantage over the prior art, since a shorter tunnel means less trauma to the tibia and more space on the bone surface below the tibial tunnel for other surgical procedures, if needed. The drill guide 20 is removed, and the cannulated drill is placed over the guide pin 25. The cannulated drill is then drilled from the outside of the tibia through to the tibial plateau, exiting the tibia at the anatomic footprint of the ACL insertion. FIG. 19C illustrates the effect of the angle $\alpha_2$ on the tunnel entrance into the joint space (i.e., FIG. 19C shows a circular section 95 for reference, a conventional ellipse 100 formed by a bone tunnel drilled at angle α, and the elongated ellipse 105 formed by a bone tunnel drilled at angle $α_2$ in accordance with the present invention). As seen in FIG. 19C, the tibial tunnel entrance into the joint space becomes a more elongated ellipse, increasing the footprint of the ACL graft insertion and contributing to a more anatomic reconstruction.

Figure 1:
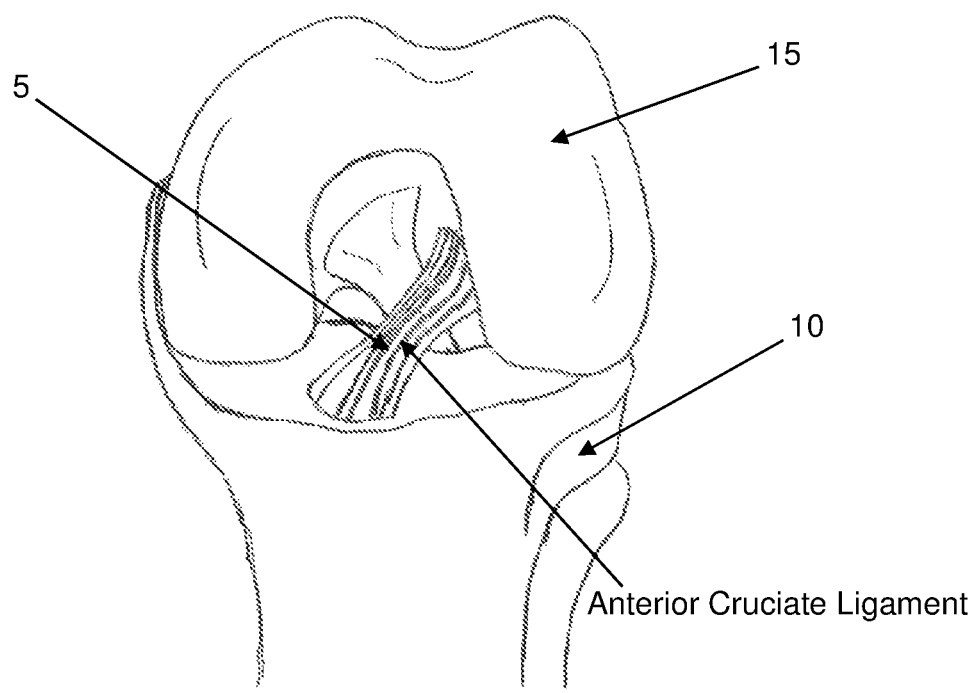
FIG. 1 is a schematic view showing the femur, the tibia and the anterior cruciate ligament of the left knee.
Figure 2:
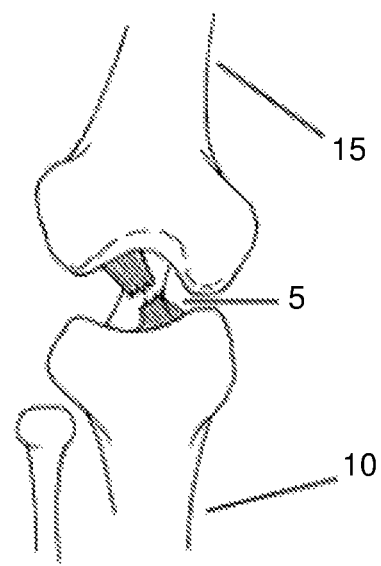
FIG. 2 is a schematic view showing a torn ACL in the right knee.
Figure 3:
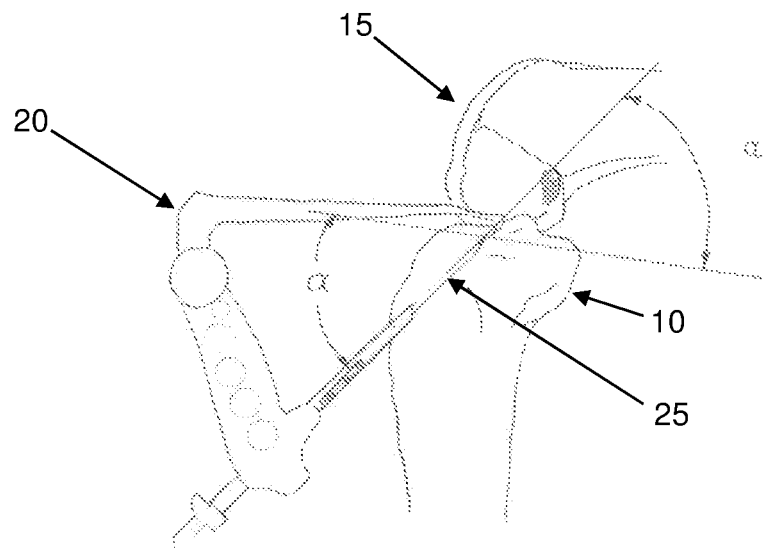
FIG. 3 is a schematic view showing an aiming device and a guide wire.
Figure 4:
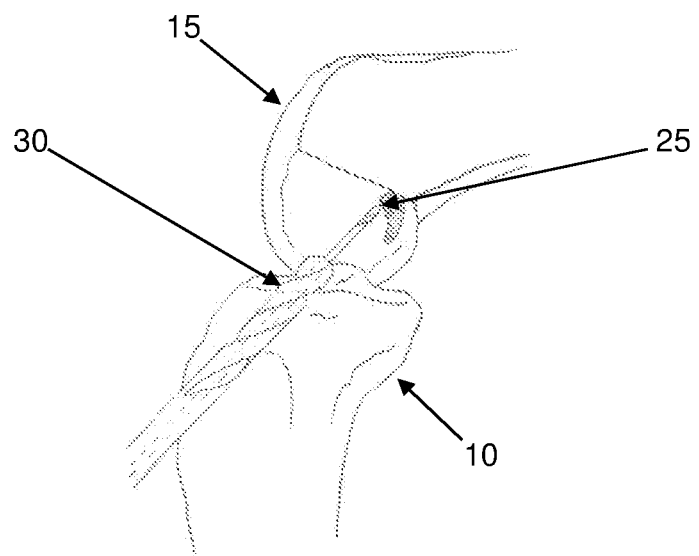
FIG. 4 is a schematic view showing a guide pin and a cannulated drill entering the joint space of the knee.
Figure 5:
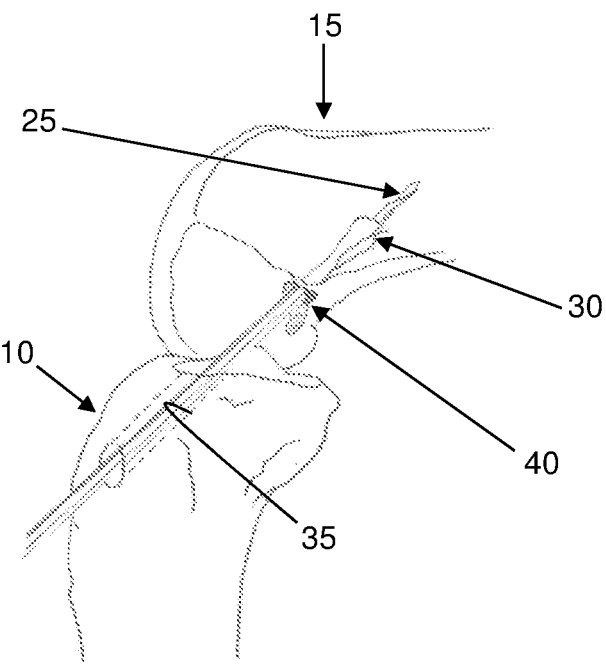
FIG. 5 is a schematic view showing a femoral tunnel, a guide pin and a cannulated drill.
Figure 6:
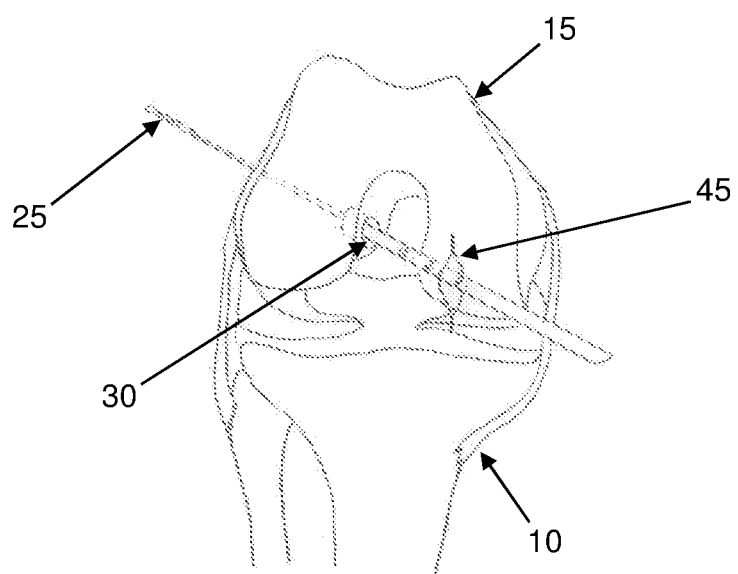
FIG. 6 is a schematic view showing drilling through the AM portal in the right knee.
Figure 7A:
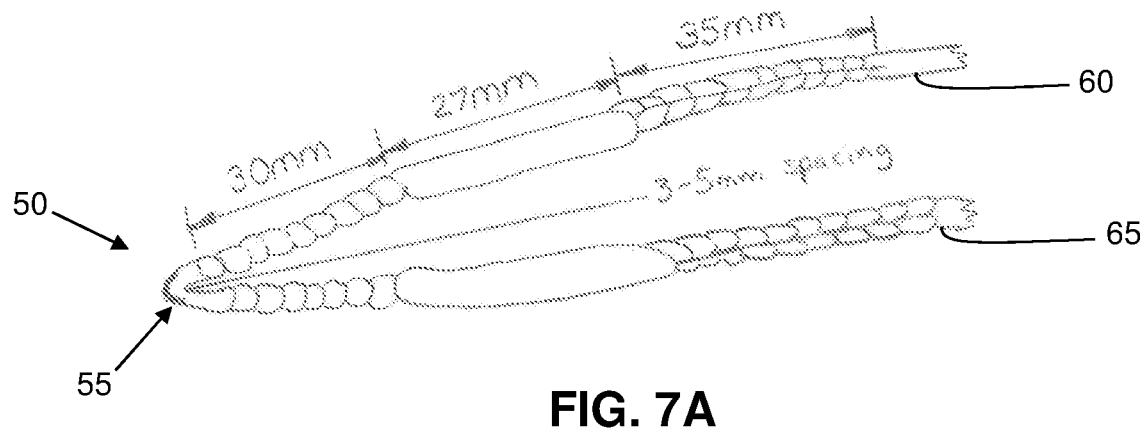
FIG. 7A is a schematic view showing a prepared tissue graft.
Figure 7B:
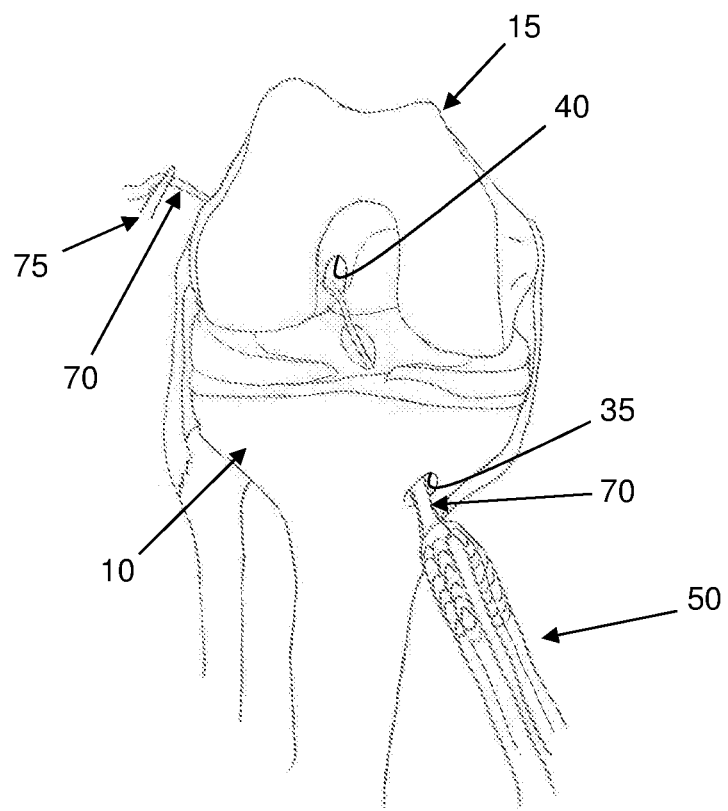
FIG. 7B is a schematic view showing a tissue graft insertion into the tibial and the femoral tunnels.
Figure 8:
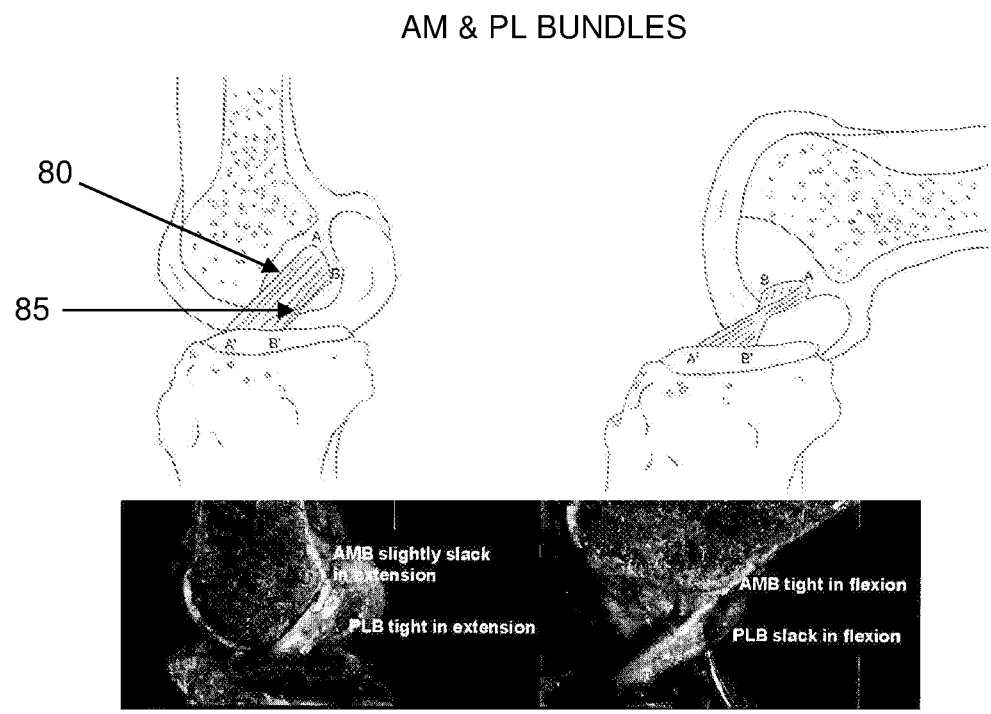
FIG. 8 is a schematic view showing the AM and PL bundles of the ACL.
Figure 9:
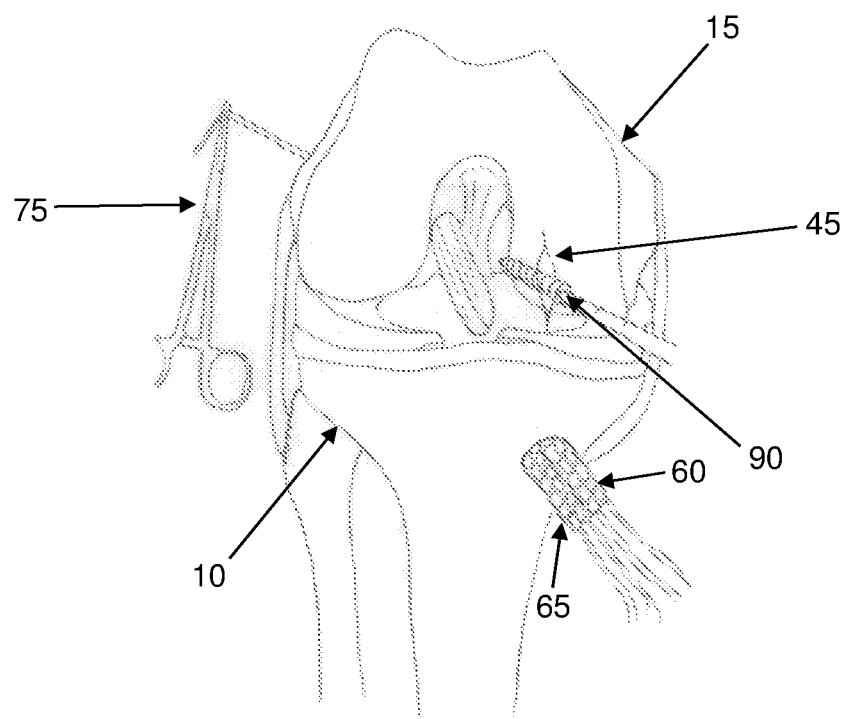
FIG. 9 is a schematic view showing the insertion of an interference screw into the femoral tunnel of the right knee.
Figure 10:
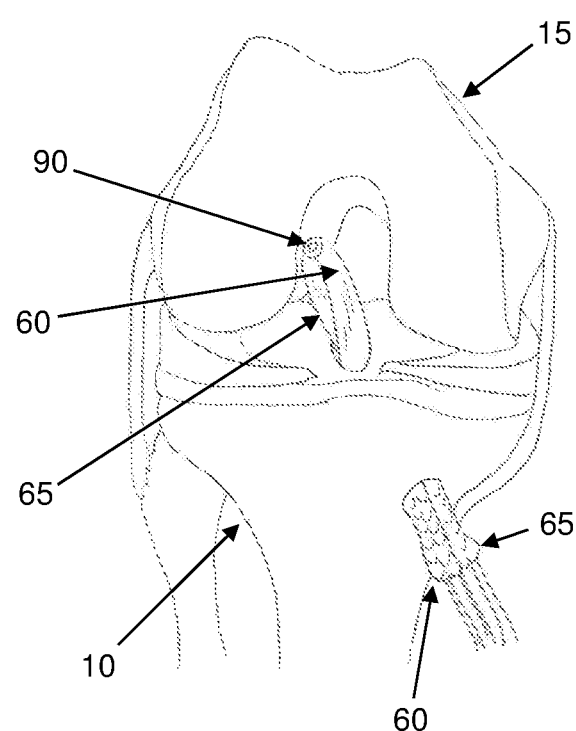
FIG. 10 is a schematic view showing an interference screw in place in the right knee.
Figure 11:
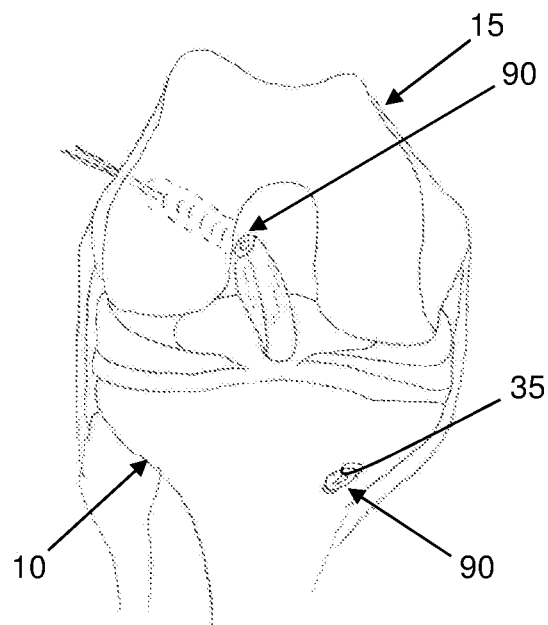
FIG. 11 is a schematic view showing a completed ACL reconstruction in the right knee.
Figure 12:
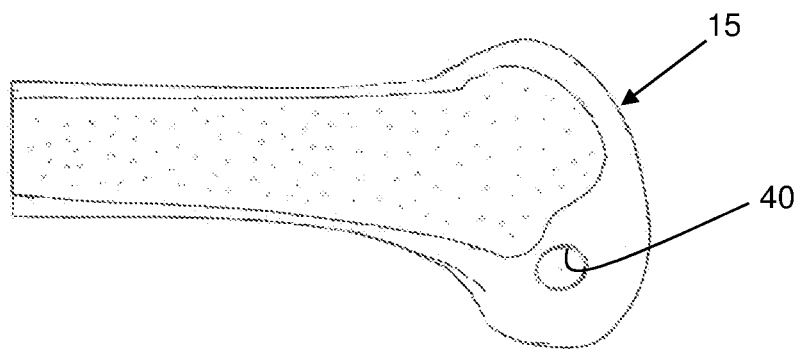
FIG. 12 is a schematic view showing the resulting elliptical/oval tunnel entrance of the bone hole on the femur.
Figure 13:
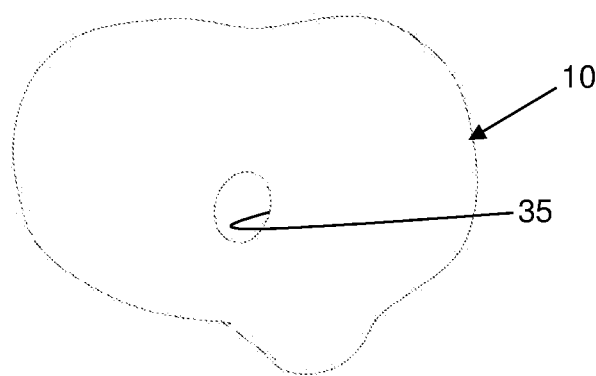
FIG. 13 is a schematic view showing the resulting elliptical/oval tunnel exit formed on the tibial plateau.
Figure 14:
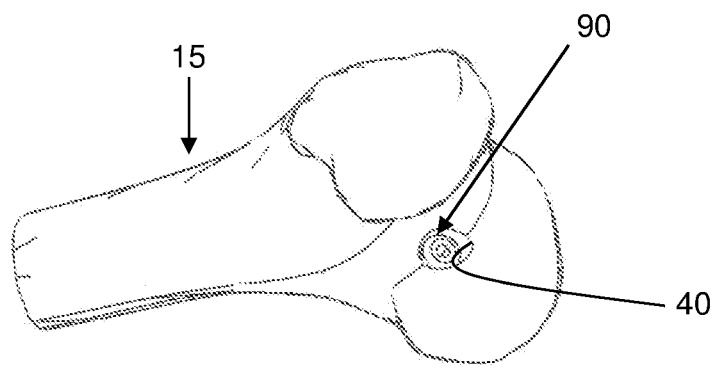
FIG. 14 is a schematic view showing the femur and a normal tunnel entrance and standard fixation.
Figure 15:
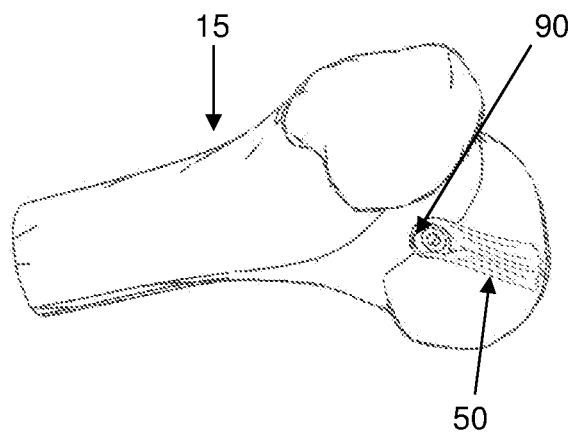
FIG. 15 is a schematic view showing the femur and a standard fixation and ligament grafts.
Figure 16:
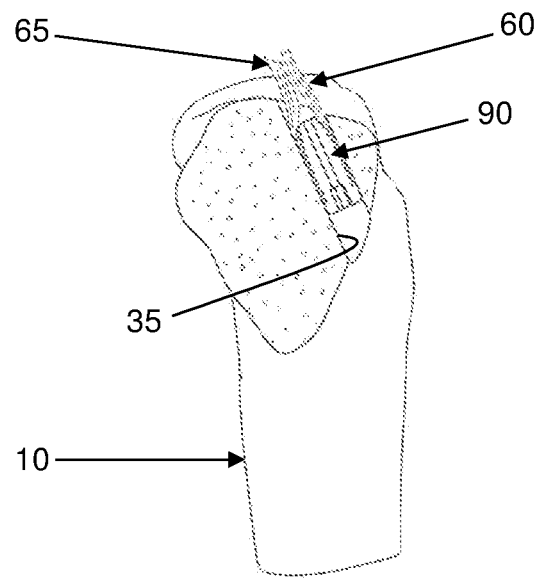
FIG. 16 is a schematic view showing the interference screw and the ligament graft disposed in the tibial tunnel.

The prepared graft ligament 50 is then inserted through the tibial tunnel and into the femoral tunnel. This is done in a manner similar to the method described earlier, i.e., the graft ligament 50 is folded over at 55 such that there are two graft bundles 60, 65 that make up the aggregate ligament graft (FIG. 7A). Sutures are looped around the graft at the area 55 where the graft is folded over. A guide pin (not shown), with an eyelet for passing the sutures, is inserted through the tibial tunnel 35, through the joint space and through the femoral tunnel 40. The guide pin exits through the skin opposite the femoral tunnel. The sutures are then grasped (e.g., with a clamp) and the graft is pulled through the tibial tunnel, through the joint space and into the femoral tunnel. The AM and PL graft bundles (i.e., the graft bundles 60, 65) are manipulated into their approximate anatomic locations.

Next, and looking at FIGS. 20-23, a new femoral fixation device 110, comprising a femoral fixation screw (FFS) 115 and a femoral ligament spacer (FLS) 120, is introduced into the femoral tunnel 40 so as to fixate the graft ligament into place within the femoral tunnel.

More particularly, femoral fixation screw (FFS) 115 comprises a screw body 125 with a necked down region 130 and a head 135. The body 125 of femoral fixation screw (FFS) 115 provides aperture ligament fixation as it is screwed into the femoral tunnel. The fixation screw 115 tapers or curves to a narrow distal end to allow easy starting and insertion into the femoral tunnel. Also, the femoral fixation screw 115 is cannulated at 140 to allow the use of a guide pin to guide the femoral fixation screw straight into the femoral tunnel. A hex socket 145 (or hexalobe socket, square socket or other shaped socket) resides at the near end of the femoral fixation screw to engage with an insertion (tightening) tool.

The femoral ligament spacer (FLS) 120 comprises a substantially tubular body 150 which is cut off at an angle to form an elliptical face 155. The tubular body 150 has in internal diameter 160 that is opened up at 165 to receive and capture the screw head 135 of FFS 115, as will hereinafter be discussed. The femoral ligament spacer 120 spreads the AM and PL bundles as the femoral fixation screw 115 is tightened into place. The femoral ligament spacer 120 can rotate freely on the femoral fixation screw 115, thus allowing the desired alignment of the ligaments. Furthermore, the angled surface 155 of the femoral ligament spacer 120 aligns to the bony surface of the femur such that the bony defect (i.e., the elliptical entrance to the femoral tunnel) is completely filled, and the ligament graft fully supported, about the entire elliptical mouth of the bone tunnel. The angled surface 155 of the FLS 120 may be formed or manufactured in a variety of angles or shapes to best match the mouth of the femoral tunnel. The angled surface 155 corresponds to the angle β (FIG. 17C) and closely approximates the contour of the mouth of the femoral tunnel.

Figure 22:
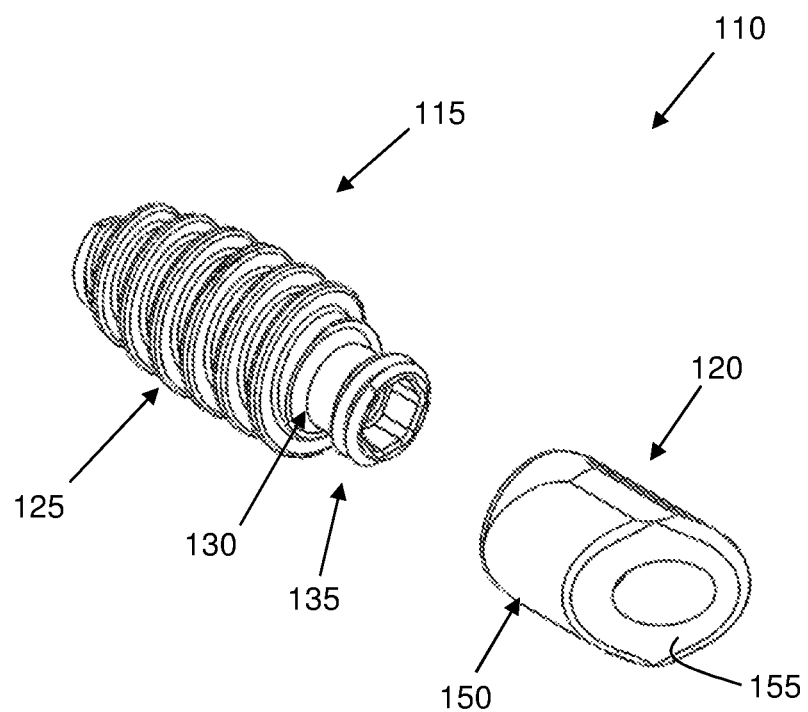
FIG. 22 is a schematic view showing the femoral fixation device.
Figure 23:
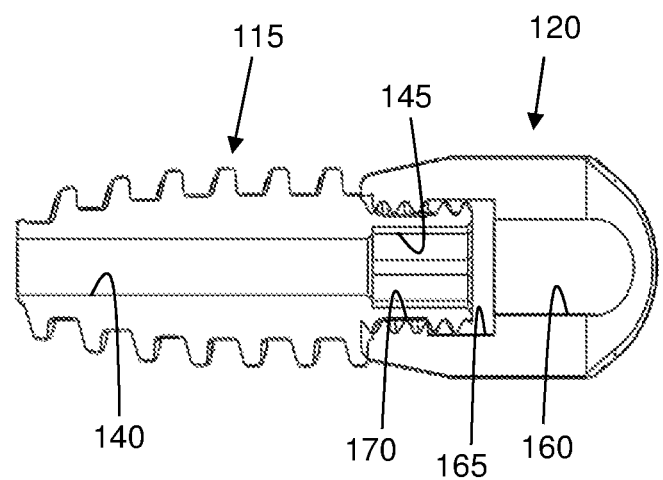
FIG. 23 is a schematic view showing a cross-section of the femoral fixation device.

As seen in FIG. 23, the femoral ligament spacer 120 is captured onto the femoral fixation screw 115 by means of a reversed external thread formed on the head 135 of the screw 115 and a reversed internal thread 170 formed on the distal end of femoral ligament spacer 120. To assemble FLS 120 on FFS 115, the FLS 120 is aligned with the FFS 115 as shown in FIG. 22, and the two parts are screwed together as shown in FIG. 23 until head 135 of FFS 115 is rotatably received in the enlarged diameter 165 of FLS 120. In essence, the "necked down" region of FLS 120 which resides distal to enlarged diameter 165 of FLS 120, and which carries internal thread 170 thereon, rotatably captures the FLS 120 to FFS 115.

Once assembled in this manner, the femoral ligament spacer 120 rotates freely around the groove 130 in the femoral fixation screw 115. The cross-sectional view in FIG. 23 illustrates how the FLS 120 is rotatably retained onto the FFS 115. It should be appreciated that this method of attachment is meant merely as an example of a preferred construction; other means may be used for rotatably capturing the FLS 120 onto the FFS 115, such as a separate screw fastener to hold the FLS to the FFS, or a pressed-in stake with a head to capture the FLS to the FFS, etc. Note that the femoral ligament spacer 120 provides access to the drive channel of the femoral fixation screw 115 via the axial opening 160 extending through the femoral ligament spacer (FIG. 23). The reverse threads 170 inside the FLS 120 are completely disengaged from the threads on the head 135 of the FFS 115 after assembly. This allows the FLS 120 to rotate freely about the head 135 of the FFS 115.

Figure 24:
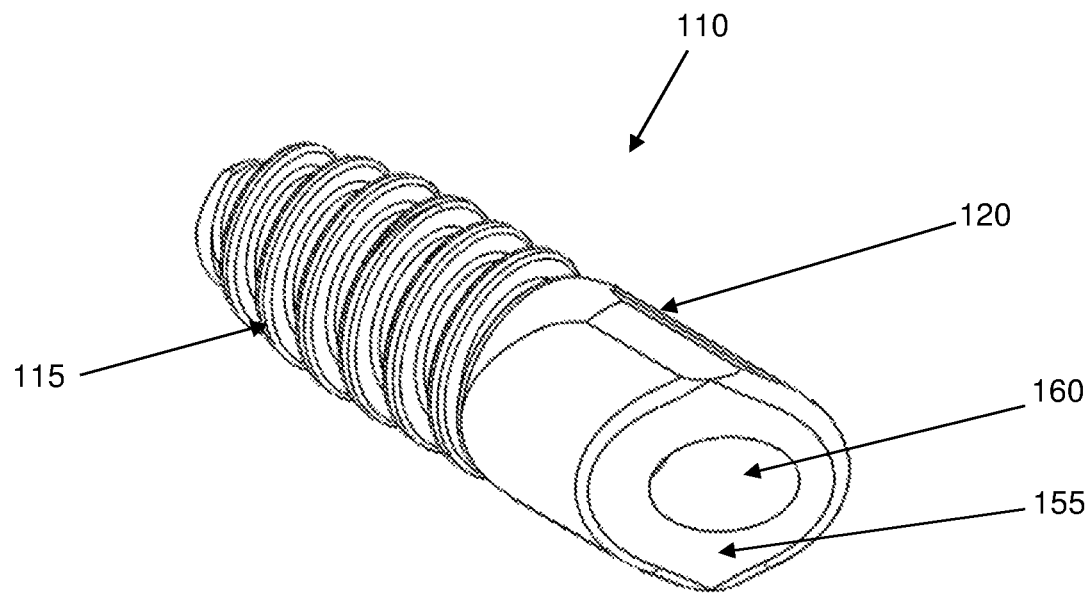
FIG. 24 is a schematic view showing the femoral fixation device.

The femoral ligament spacer 120 functions as a means to align graft ligament strands into the mouth of the femoral tunnel and to completely fill the bony defect at the mouth of the femoral tunnel. The femoral ligament spacer 120 can be positioned so as to spread the ligaments into their anatomic position, regardless of the rotational position of the femoral fixation screw 115 within the femoral tunnel. Thus, the construction of femoral fixation device 110 allows the rotational position of femoral ligament spacer 120 to be optimized for ligament position and ligament support, since it is independent of the rotational position of femoral fixation screw 115. Furthermore, femoral fixation device 110 may function as a "strain relief", allowing the tension in the ligament graft to spread over the length of the femoral fixation device. The components of the femoral fixation device 110 may be made from metal, plastic or bioabsorbable material. The femoral fixation device is inserted into the femoral tunnel as an assembled unit. See FIG. 24.

Figure 25:
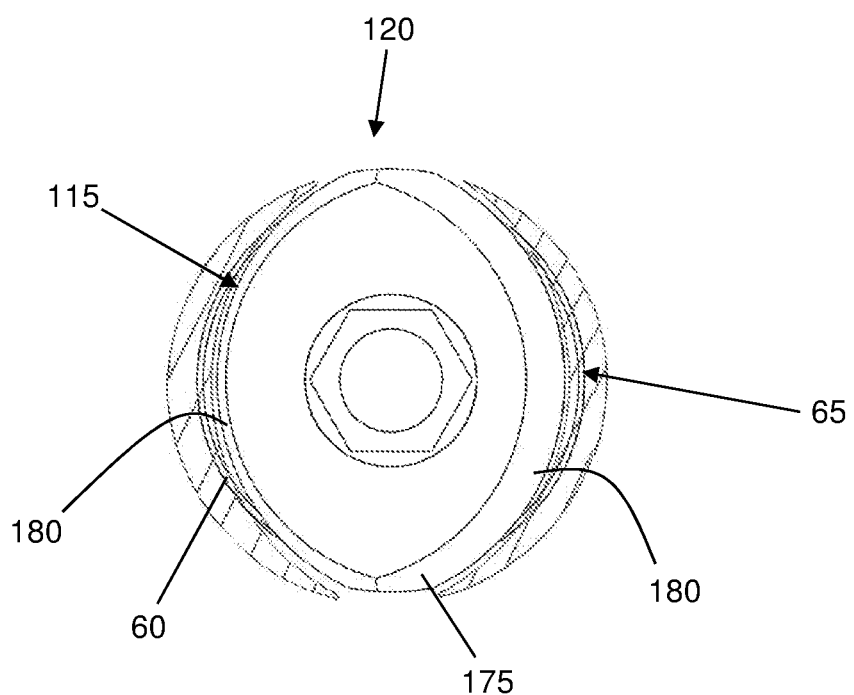
FIG. 25 is a schematic view showing the femoral fixation device.

The end view shown in FIG. 25 illustrates the contours on the sides of the FLS 120 for ligament alignment. The outer wall 175 of FLS 120 is shaped with ligament recesses 180 to further engage with, and provide alignment of, the graft ligament strands 60, 65. The shape of the ligament spacer recesses 180 may comprise a variety of shapes to allow space for the ligament graft strands 60, 65.

The particular ligament recesses 180 shown are provided for example only and may consist of other shapes such as flats, concave surfaces, corrugated surfaces, etc. The hole 160 through the center of the FLS 120 is for the insertion tool to pass through the FLS 120 and access FFS 115, thereby allowing the entire assembly to be tightened into place. The FLS 120 has smooth radii around critical corners to ensure strain relieved fixation of the ligament graft bundles.

The FLS 120 is sized relative to the diameter of the FFS 115. The larger outer portion of the FLS 120 may be larger than the diameter of FFS 115 to create an interference fit with the bone tunnel and to further spread the ligament graft strands apart and to secure the FLS 120 into the bone. This larger FLS diameter, nestled between the graft recesses, has a self-aligning capability. As the femoral fixation device 110 is tightened into place, the larger outer portions of FLS 120 glide on the bone surface, centering the spacer onto the elliptical entrance of the femoral bone tunnel, and thus separating the ligament strands 60, 65 into their AM and PL anatomic location.

Figure 26A:
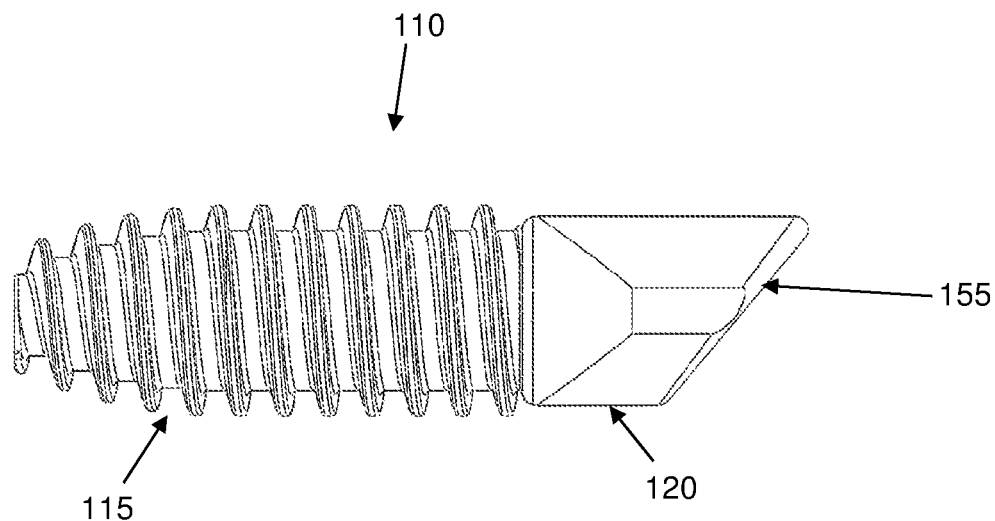
FIG. 26A is a schematic view showing the femoral fixation device.
Figure 26B:
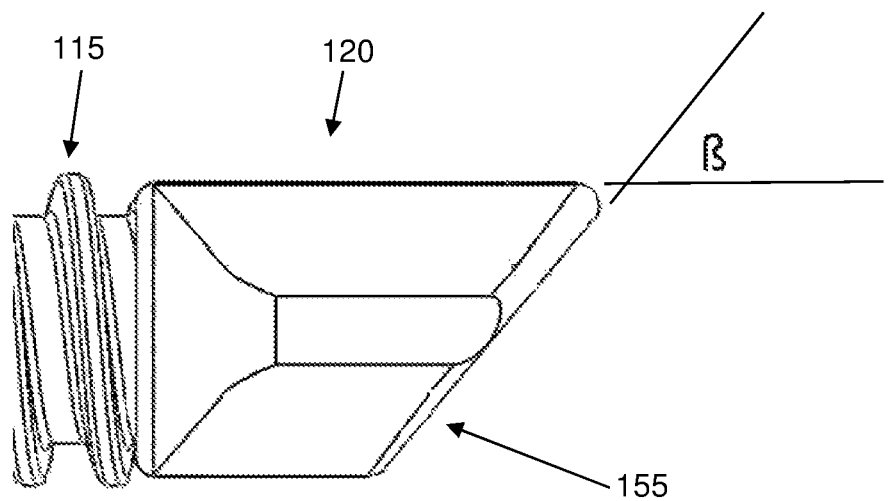
FIG. 26B is a schematic view showing the femoral fixation device and showing the angle β.

The end 155 of the FLS 120 is angled (approximately equal to β) to create the mating elliptical, oval shape to fill the elliptical, oval-shaped entrance of the femoral tunnel. The angled shape of the femoral ligament spacer 120 fills the bone tunnel entrance and urges the ligament graft up against the tunnel entrance to mimic the wider anatomic footprint of the natural femoral insertion. The interference portion of the femoral ligament spacer 120 (i.e., the tips of FLS 120 that engage tightly with the bone) guides the femoral ligament spacer into the proper orientation on the bone. A side view of the femoral fixation device 110 is shown in FIG. 26A. The aforementioned angle β is illustrated in FIG. 26B.

Figure 27:
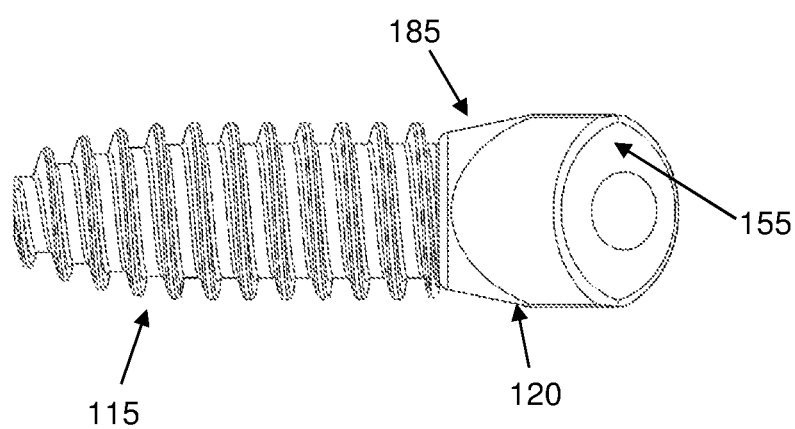
FIG. 27 is a schematic view showing the lead-in and canted face of the femoral fixation device.

In the bottom view of femoral ligament spacer 120 (FIG. 27), the FLS 120 is shown with a lead-in surface 185 that helps start the FLS into the femoral tunnel. The canted surface 155 is shown on the right portion of the image.

It will be appreciated that rotation of the femoral fixation screw 115 seats the femoral ligament spacer 120 into the bone, thus securing the ligaments into their anatomic position (i.e., via an interference fit effected by femoral fixation screw 115 along the more distal portion of the femoral fixation device 110 and via an interference fit effected by the femoral ligament spacer 120 along the more proximal portion of the femoral fixation device 110).

Figure 28:
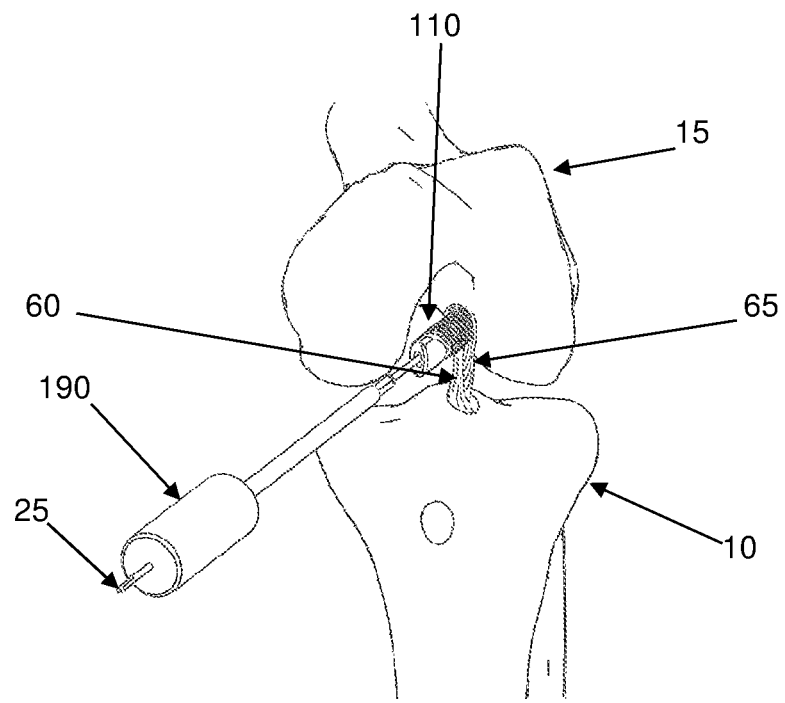
FIG. 28 is a schematic view showing insertion of the femoral fixation device.

Returning now to the preferred method of use, and looking now at FIG. 28, the guide pin 25 is pulled back or re-inserted through the ligament graft. The femoral fixation device 110 (i.e., FFS 115 and FLS 120, with FLS 120 being rotatably captured on FFS 115) are inserted over the guide pin. The femoral fixation device 110 is screwed into the femoral tunnel with the hex tool 190 (which passes through FLS 120 to engage the hex drive 145 on FFS 115) and with the ligament grafts 60, 65 positioned into their approximate anatomic locations. The femoral fixation device 110 is preferably introduced into the femoral tunnel with the use of the guide pin 25, as shown in FIG. 28.

Figure 29:
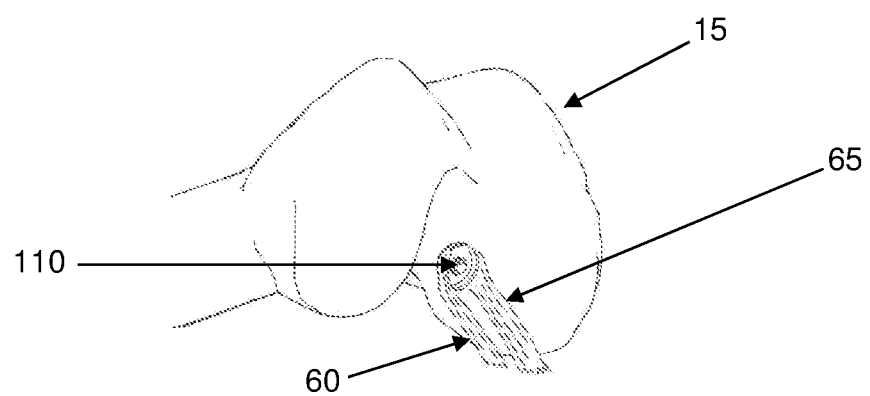
FIG. 29 is a schematic view showing the femoral fixation device and ligament graft in position.

The AM bundle 60 and PL bundle 65 separate from each other onto the opposite sides of the FLS 120 as the FLS begins to engage with the mouth of the bone tunnel. The AM bundle 60 and PL bundle 65 may be manipulated to spread out, with one bundle on each side of the FLS. The ligament graft bundles 60, 65 then align with, and fit in between, the recesses 180 on the FLS and the periphery of the bone tunnel. As the femoral ligament spacer 120 begins to engage with the bone surface, the surface of the FLS adjusts its rotational position (or may be manipulated into the desired rotational position) urging the ligament graft strands 60, 65 into their respective AM and PL bundle locations. See FIGS. 29 and 30.

The femoral fixation device 110 provides at least the following useful functions in ligament fixation:

(1) The final reconstructed ligament more closely imitates the natural anatomic footprint of the femoral ACL insertion, resulting in a biomechanically superior reconstruction. The AM and PL bundles are spread out over the elliptical anatomic footprint at the mouth of the femoral tunnel, with the femoral ligament spacer 120 holding the graft ligament to the rim of the bone tunnel about the periphery of the elliptical mouth of the bone tunnel.

(2) The ligament is secured through the entire periphery of the bone tunnel, eliminating the possible "windshield wiper" action of the graft ligament over the bone surface. This "windshield wiper" action can lead to wear of the ligament, wear of the bone surface, widening of the bone tunnel, and potentially a failed reconstruction.

(3) In the event that the graft ligament needs to be revised at a later date, the entire construct can be easily removed, simply by loosening the interference screw (i.e., the femoral fixation screw 115) from the femur. The femoral ligament spacer 120 and the femoral fixation screw 115 (i.e., the interference screw) will remove as a single assembly, aiding in the revision process. Again, the opening in the FLS 120 allows access to the drive socket 145 in FFS 115 so as to allow removal of FFS 115 (and hence the complete femoral fixation device 110) from the femur.

(4) The femoral ligament spacer 120 also provides strain relief. The strain on the ligament graft is spread over the length of the femoral ligament spacer, rather than the abrupt strain resulting from the transition of a highly compressed ligament graft emerging from a standard interference screw/bone interface.

(5) Inasmuch as the present invention makes the formation of an elliptical femoral bone tunnel opening an asset rather than a liability, the motivation for drilling the femoral tunnel with the knee in deep flexion is significantly reduced, which can reduce trauma to the patient's knee during the surgical procedure.

Figure 32:
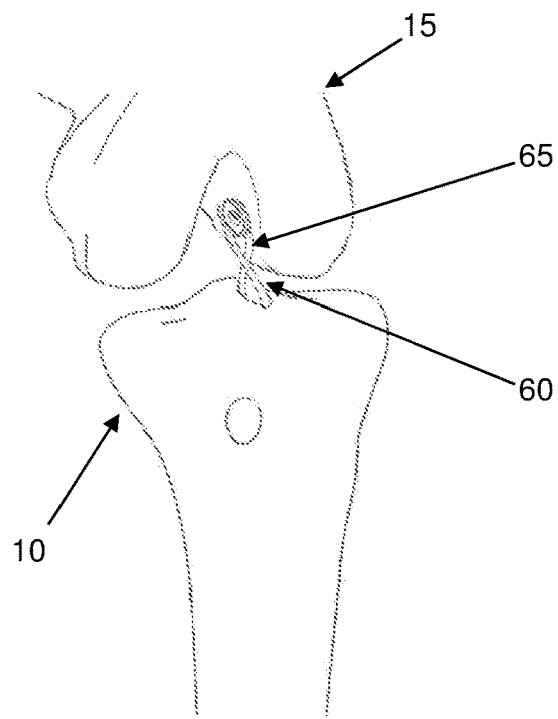
FIG. 32 is a schematic view showing the femur and tibia, femoral fixation and the graft bundles.

See also FIGS. 31A, 31B and 32.

Figure 33:
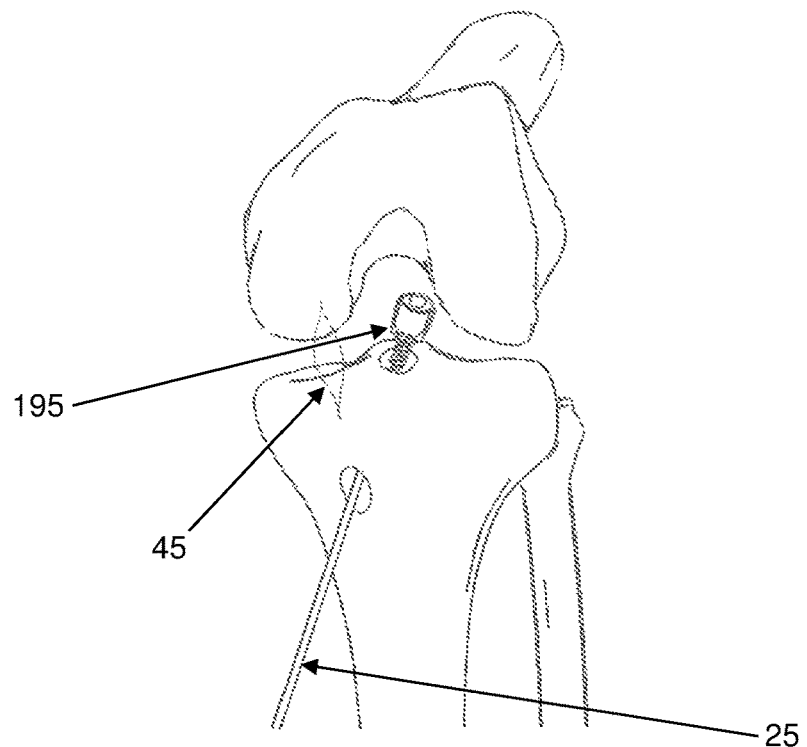
FIG. 33 is a schematic view showing the tibial ligament spacer and guide pin, but without ligament grafts in order to facilitate viewing.

A similar ligament spacer is utilized for tibial fixation. However, in this version of the invention, and looking now at FIGS. 33-37A, the tibial ligament spacer (TLS) 195 is introduced first, and independently from, the tibial fixation screw (TFS) 200. The TLS 195 and the TFS 200 together form the complete tibial fixation device 201. The TLS 195 is introduced through the accessory anteromedial portal 45. It may be introduced with a clamp or a special tool (not shown) that clips over the TLS. See FIG. 33.

Figure 34:
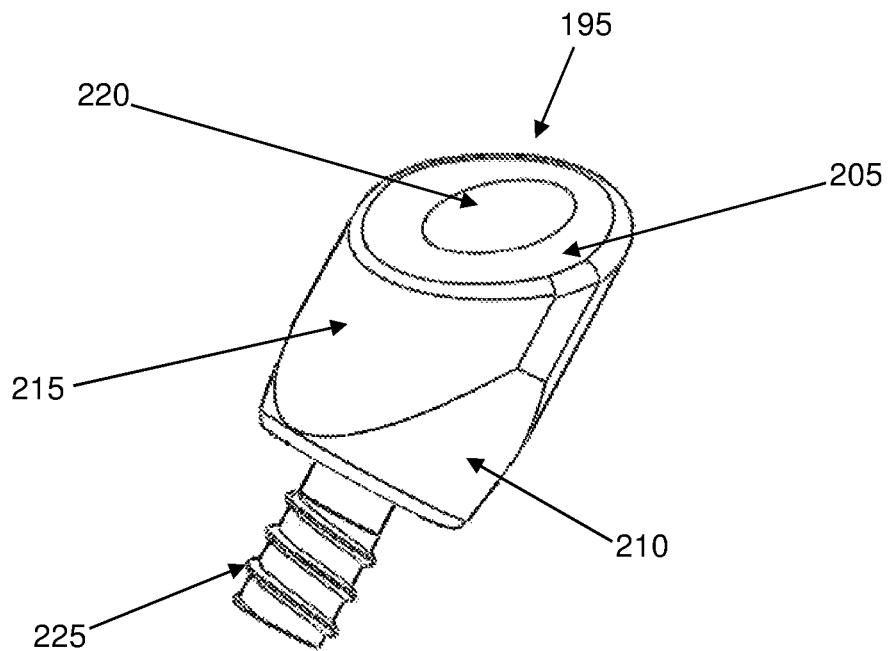
FIG. 34 is a schematic view showing the tibial ligament spacer (TLS)
Figure 37A:
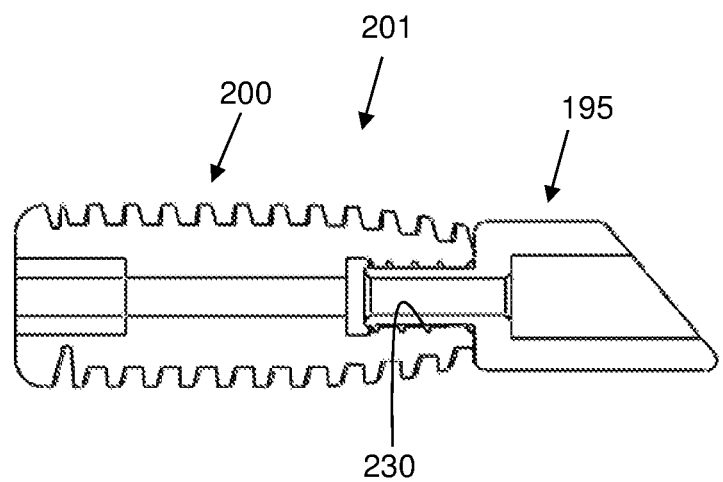
FIG. 37A is a schematic view showing the tibial fixation device.

The TLS 195 is shown in detail in FIG. 34. There are similar features on the TLS 195 as on the FLS 120. The features include the canted surface 205 to form the elliptical shape, the lead-in 210 to aid insertion into the bone tunnel, the recessed surfaces 215 for fixating the ligament in the bone tunnel, and the cannulation 220 through the center of the TLS 195 to receive a guide wire 25. The primary difference between the tibial ligament spacer 195 and the aforementioned femoral ligament spacer 120 is that the tibial ligament spacer 195 has an extension 225 from the body of the spacer that is threaded (FIG. 34). This threaded extension 225 engages with the tibial fixation screw 200 (e.g., as shown in FIG. 37A) during the installation of the tibial fixation screw so that TLS 195 is connected to TFS 200, as will hereinafter be discussed. The threaded extension 225 of TLS 195 is initially used during the installation of the TLS in order to secure the TLS into place. The threaded extension 225 is also cannulated, allowing a guide pin 25 to pass through its center. The threaded extension 225 has a thread pitch that is specifically formed to reduce, or compress, the construct (i.e., the complete tibial fixation device 201, consisting of the united TLS 195 and TFS 200) during final installation (discussed below). The angled face 205 on TLS 195 may be formed, or manufactured, in a variety of angles to match various tibial surfaces.

Figure 35:
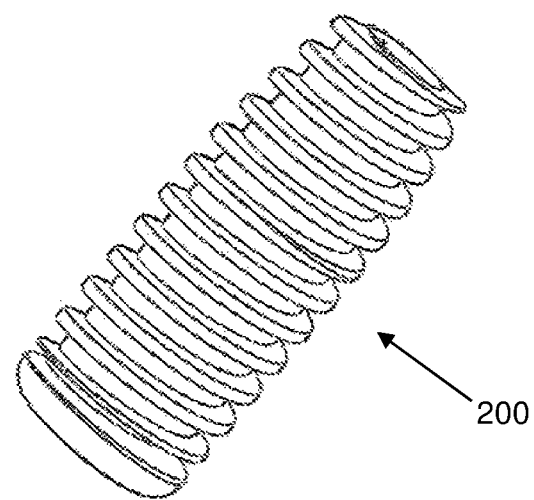
FIG. 35 is a schematic view showing the tibial fixation screw (TFS)
Figure 36:
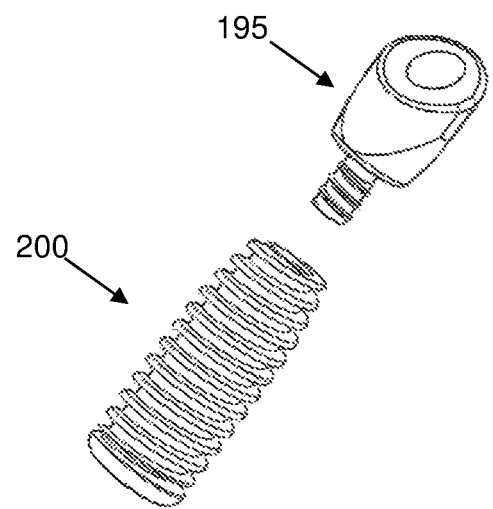
FIG. 36 is a schematic view showing the tibial fixation screw and tibial ligament spacer, in unassembled condition.

The tibial fixation screw (TFS) 200 is shown in FIGS. 35, 36 and 37A. The tibial fixation screw 200 consists of a body of threads for fixating the ligament graft against the bone tunnel wall via an interference fit. The distal end of tibial fixation screw 200 has a counterbore 230 that is threaded to engage with the threaded extension 225 of the TLS 195 (see FIGS. 36 and 37A). Alternatively, the TFS 200 may be made of plastic and the counterbore 230 may be self-tapping or self-thread-forming as it engages with the TLS 195. The tibial fixation screw 200 is cannulated throughout its length. The tibial fixation screw 200 is preferably tapered toward its distal end to help with starting the tibial fixation screw 200 into the tibial bone tunnel.

FIG. 36 illustrates the TFS 200 and the TLS 195 in unassembled form. The external threads on the TLS 195 may have a pitch equal to the tibial fixation screw threads, or slightly less. A slightly smaller pitch will result in additional reduction (compression) during final tightening of the TFS 200 to the TLS 195. In other words, as the tibial fixation screw (TFS) 200 is tightened to the tibial ligament spacer (TLS) 195, the external threads on the TLS extension 225 may advance slightly faster into the TFS 200 than the TFS 200 advances into the bone tunnel, thus compressing the TFS and the TLS together as the TFS is tightened into the bone tunnel.

In the final assembly of the TLS and the TFS (FIG. 37A), the tibial fixation screw 200 tightens up against, or very near to, the proximal surface of the TLS 195.

Figure 37B:
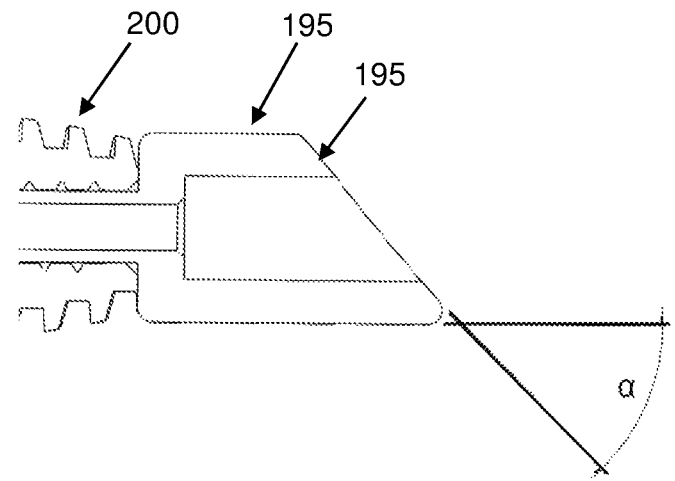
FIG. 37B is a schematic view showing the tibial fixation device and the angle α.

FIG. 37b illustrates the correspondence of angle α from the tunnel drilling technique to the canted surface 205 of the tibial ligament spacer 195. The angled surface 205 at angle α creates a close anatomic alignment between the bone surface and the tibial fixation device 201, and also secures the ligament grafts into their anatomic positions.

Similar to the femoral fixation device 110, the tibial fixation device 201 has graft recesses 215 on the top and bottom side of the tibial ligament spacer 195 to urge the ligaments into their anatomic positions. See FIG. 38. The recesses 215 shown are again crescent-shaped (like the recesses for the femoral ligament spacer), but could be in some other form if desired.

Figure 38:
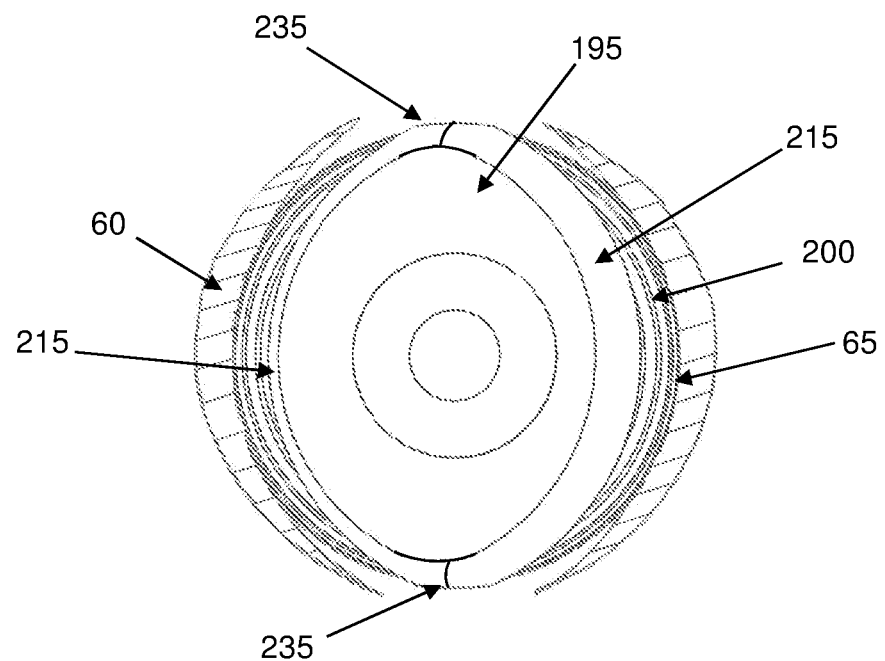
FIG. 38 is a schematic view showing the tibial fixation device.

The TLS 195 is sized relative to the tibial fixation screw 200. In this design, the graft recesses 215 are smaller in size than the diameter of tibial fixation screw 200 (FIG. 38). The interference portions 235 of TLS 195 are larger than the screw diameter for alignment and ligament separation.

Figure 39:
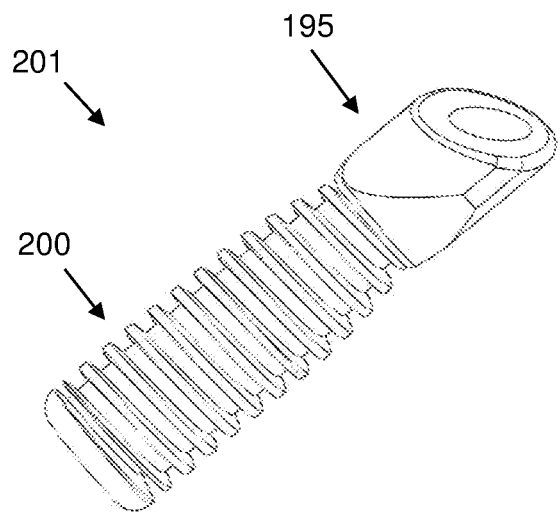
FIG. 39 is a schematic view showing the tibial fixation device.

The tibial ligament spacer 195 functions as a means to align the ligament strands 60, 65 into the bone tunnel and to fill the bony defect at the mouth of the bone tunnel. The tibial ligament spacer 195 can be positioned to spread the ligament strands 60, 65 into their anatomic position, regardless of the rotational position of the tibial fixation screw 200. The components of tibial fixation device 201 may be made from metal, plastic or bioabsorbable material. The tibial fixation device 201 is advanced into the tibia as separate pieces, with the TLS 195 being advanced from the joint side (e.g., through AM portal 45) and the TFS 200 being advanced from the exterior tibial surface (i.e., through the tibial tunnel), and thereafter joined together in situ (see below). FIG. 39 shows the assembled tibial fixation device 201 in an isometric view.

Figure 40:
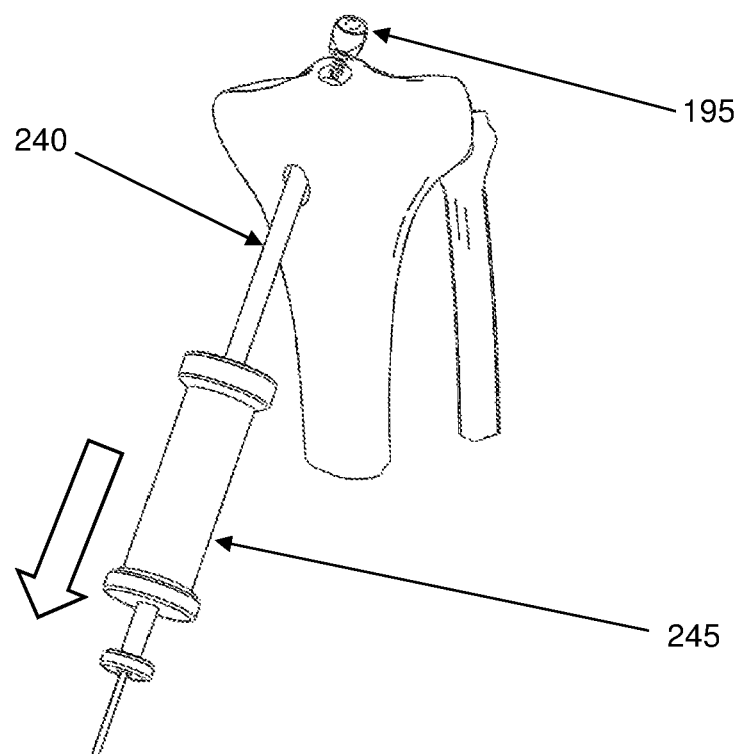
FIG. 40 is a schematic view showing the impactor introduced and aligned with the TLS.
Figure 41:
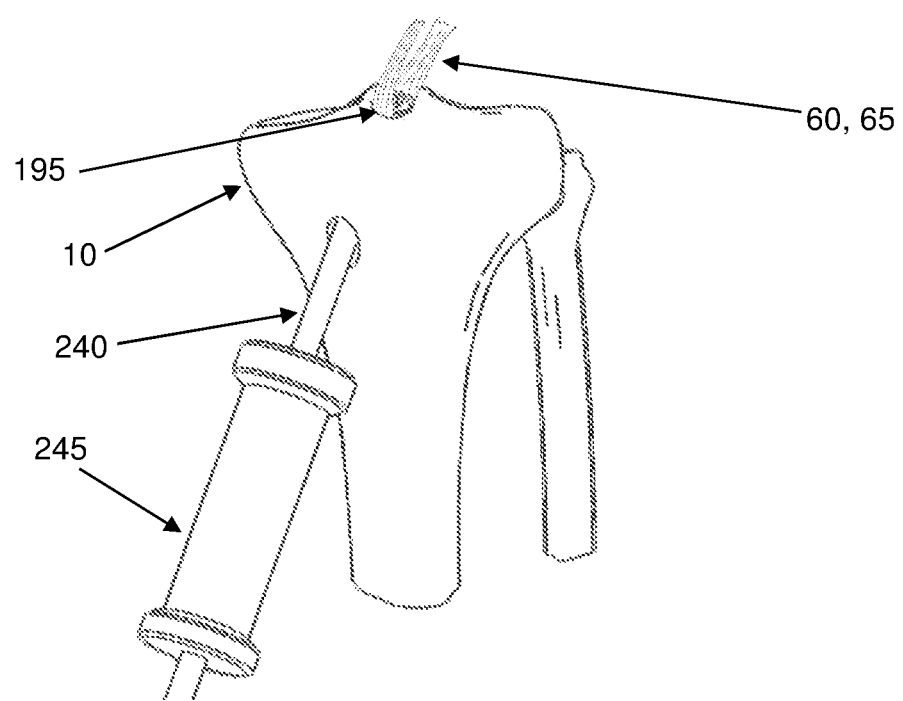
FIG. 41 is a schematic view showing the TLS seated into tibia, and the AM and PL bundles.

Returning now to the discussion of the surgical technique for effecting tibial fixation of the graft ligament using tibial fixation device 201, a long cannulated positioning device 240 is introduced through the tibial tunnel (FIG. 40), between the strands of the ligament graft. The positioning device 240 is tightened onto the threaded portion of the tibial ligament spacer (TLS) 195. The positioning device 240 has a slidable impactor, or slap hammer 245, at the proximal end of the positioning device. The positioning device 240 is used to orient the TLS 195 to fill the mouth of the elliptical bone tunnel. The slidable impactor 245 is then used to seat the TLS 195 into the tibial tunnel, with the ligaments spread appropriately (AM bundle on the anteromedial side and PL bundle on the posterolateral side) of the bone tunnel. A unique aspect of the TLS 195 is that it provides ligament tensioning during its insertion. See FIG. 41.

Figure 42:
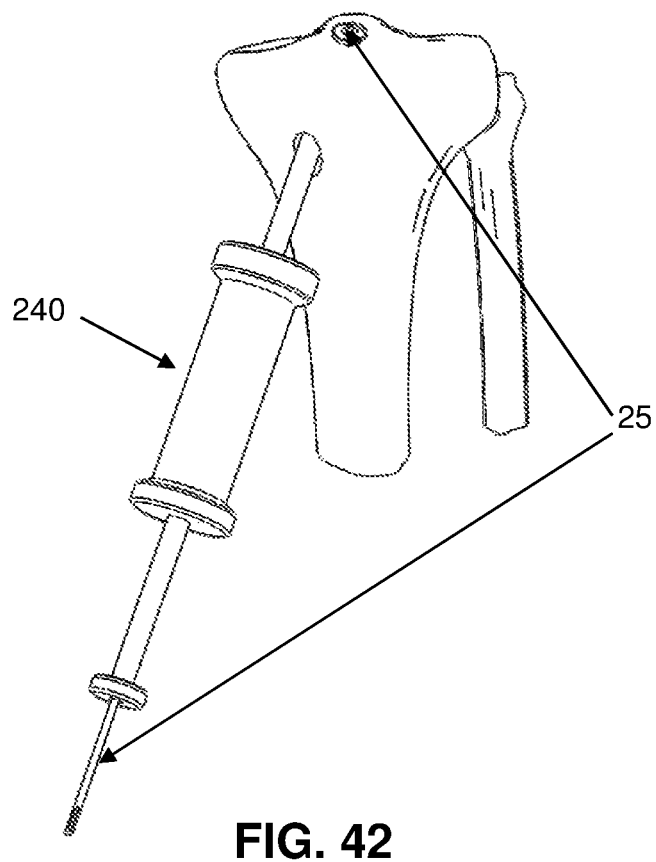
FIG. 42 is a schematic view showing the guide wire inserted into the tibia.

Next, a guide pin 25 is inserted through the cannulated positioning device 240 and through the TLS 195, as shown in FIG. 42.

Figure 43:
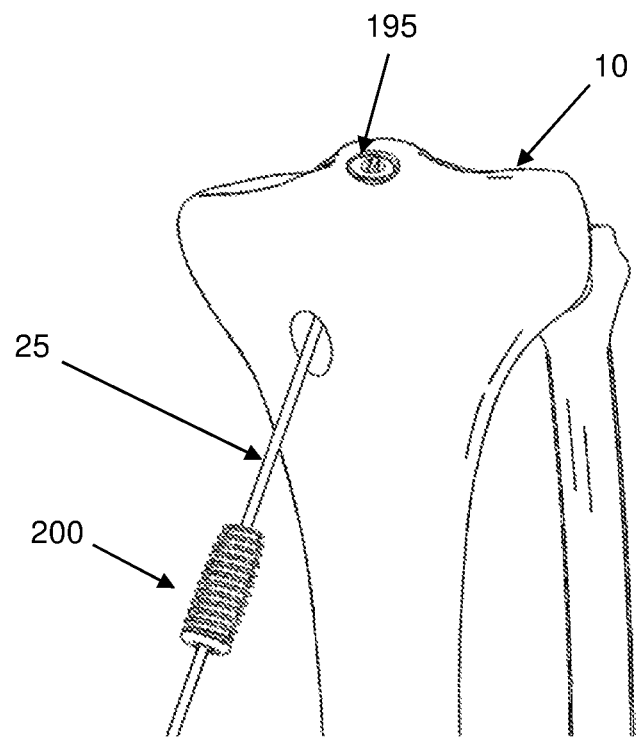
FIG. 43 is a schematic view showing the TFS advancing over the guide wire to engage with the TLS.

The cannulated positioning device 240 is then removed, leaving the guide wire 25, the TLS 195 and the partially fixated ligaments (not shown) in the tibial tunnel. The tibial fixation screw 200 is then inserted over the guide wire 25. See FIG. 43.

Figure 44:
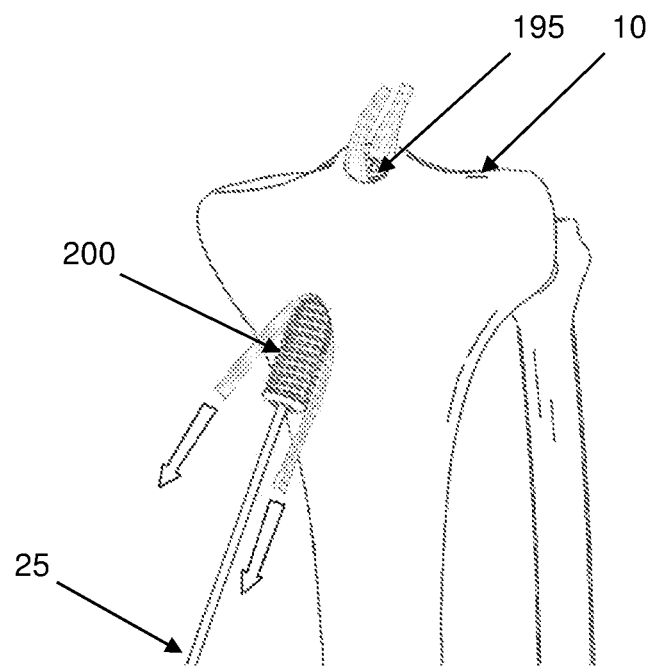
FIG. 44 is a schematic view showing the tibial fixation screw partially inserted.

With tension applied to the ligament strands (FIG. 44), the tibial fixation screw 200 is advanced into place (including into engagement with the tibial ligament spacer 195) with a cannulated hex (or other socket configuration) wrench. TFS 200 compresses the ligament strands 60, 65 against the wall of the bone tunnel as it advances up the bone tunnel, thereby effecting an interference fixation of the graft ligament with the tibia. See FIG. 44, which shows the ligament strands with external tension, the partially inserted tibial fixation screw 200, the guide pin 25 and the tibial ligament spacer 195.

Figure 45:
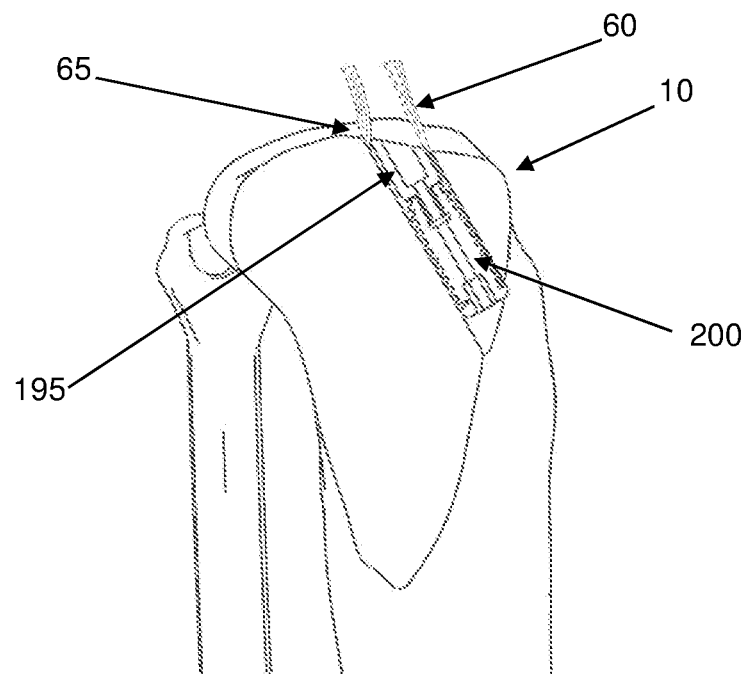
FIG. 45 is a schematic view showing the tibial fixation device and ligaments.

The tibial fixation screw 200 may be tightened until it is flush with the tibia (i.e., with the proximal entrance of the bone tunnel) or until it bottoms out onto the TLS 195. As described earlier, the thread pitches may be designed specifically to compress or reduce the construct as the tibial fixation screw 200 is tightened into place. After the tibial fixation screw 200 has engaged with the tibial ligament spacer 195, the tibial fixation screw 200 is completely tightened into place against the tibial ligament spacer 195. The guide wire 25 is then removed and the external ligament strands 60, 65 are trimmed up to the external surface of the tibia 10. FIG. 45 is a cross-sectional view showing engagement of the TLS 195 with the TFS 200.

Figure 46:
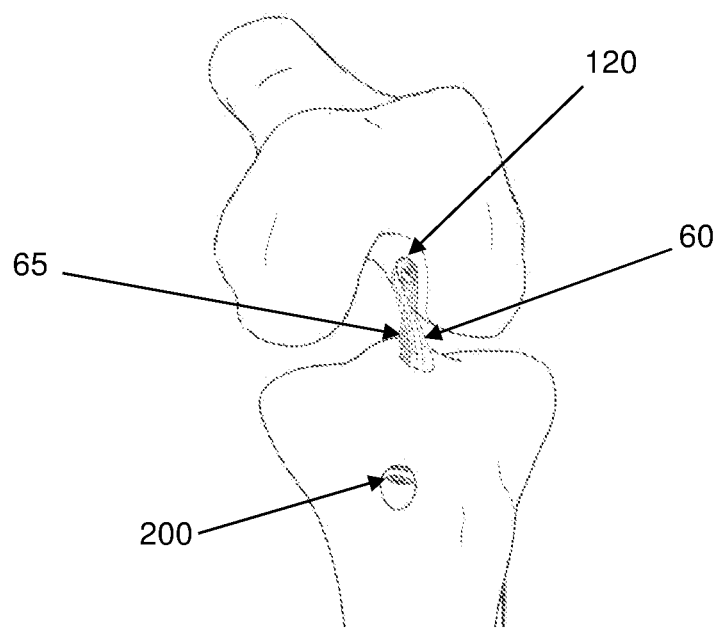
FIG. 46 is a schematic view showing completed anatomic ACL reconstruction.
Figure 47:
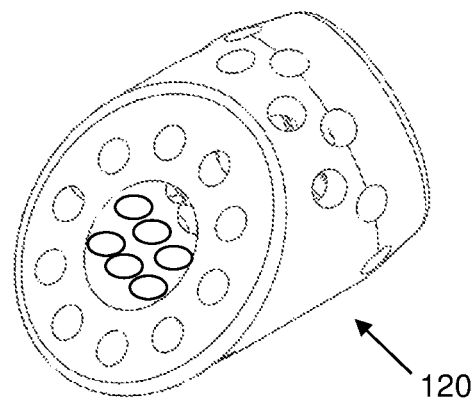
FIG. 47 is a schematic view showing holes or fenestrations through the FLS.
Figure 48:
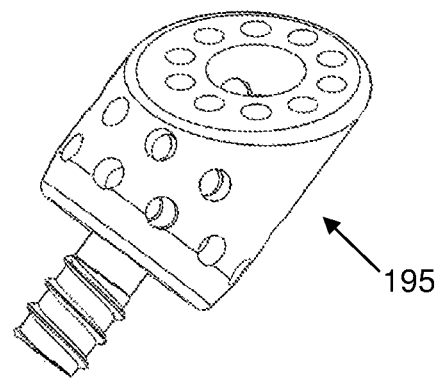
FIG. 48 is a schematic view showing fenestrations through the TLS.
Figure 49:
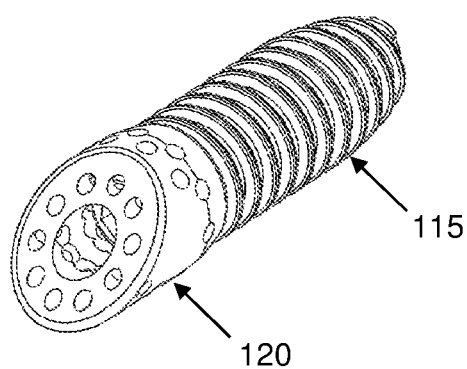
FIG. 49 is a schematic view showing a fenestrated femoral ligament spacer.
Figure 50:
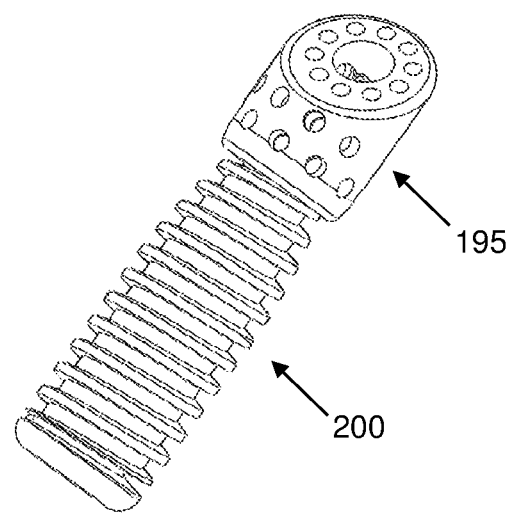
FIG. 50 is a schematic view showing a fenestrated tibial ligament spacer.
Figure 51:
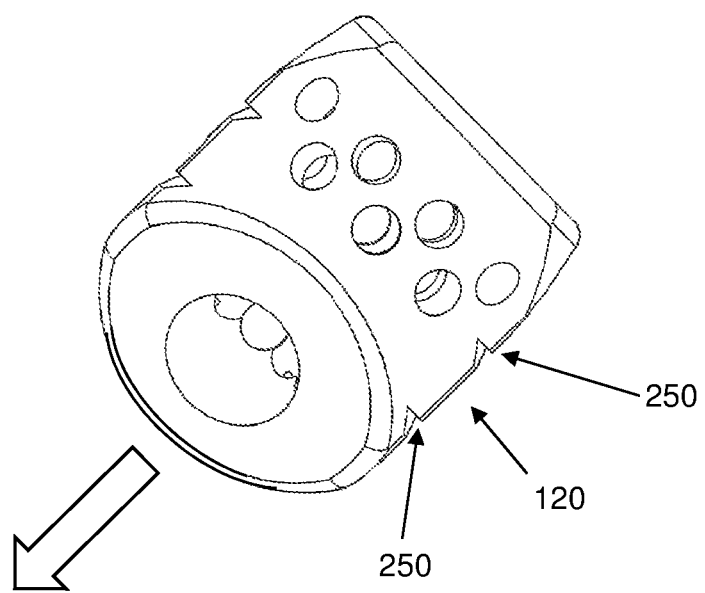
FIG. 51 is a schematic view showing an FLS with retaining barbs.
Figure 52:
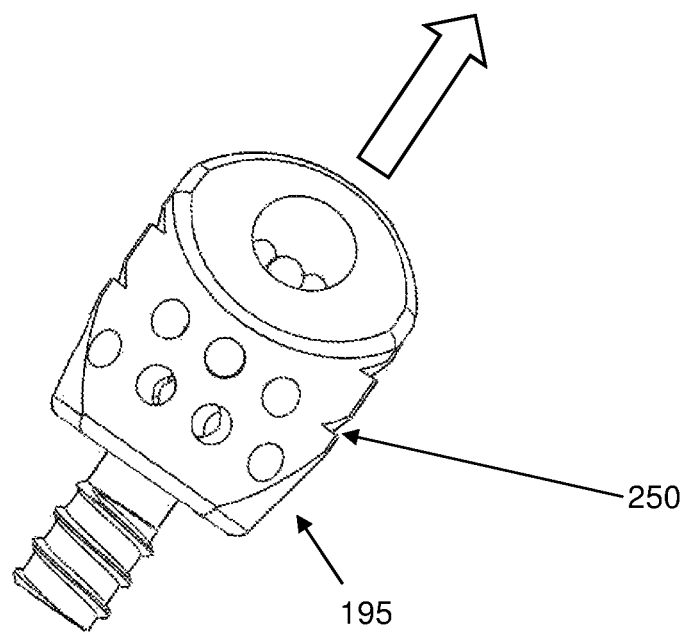
FIG. 52 is a schematic view showing a TLS with retaining barbs.
Figure 53:
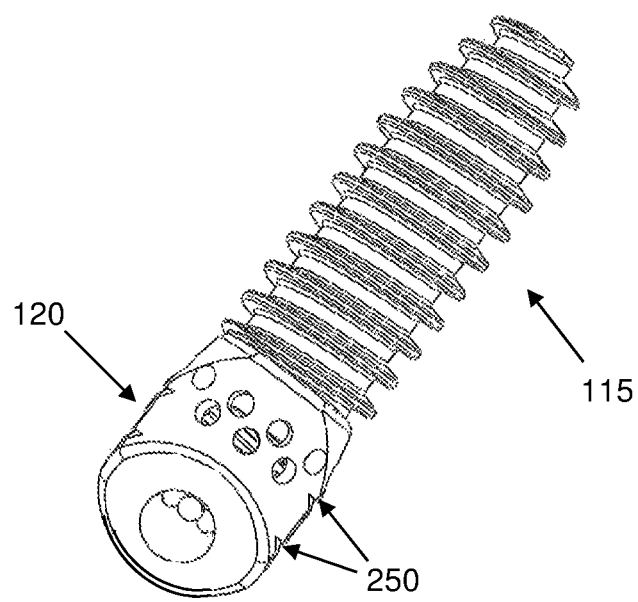
FIG. 53 is a schematic view showing a femoral fixation device with fenestrations, recesses and barbs.
Figure 54:
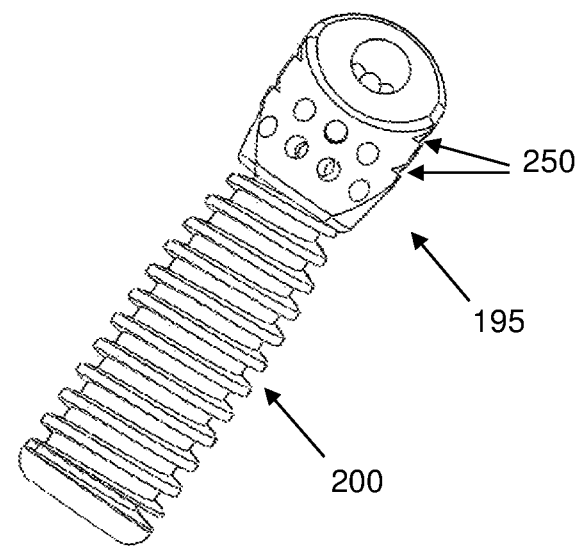
FIG. 54 is a schematic view showing a tibial fixation device, with fenestrations, recesses and barbs.

See FIG. 46 for the completed reconstructed anatomic ACL using the femoral fixation device 110 and tibial fixation device 201. With this reconstruction, the AM and PL bundles 60, 65 are tensioned and fixated into their anatomic positions on both the femur and the tibia.

The tibial fixation device 201 provides at least the following useful functions in ligament fixation:

(1) The final reconstructed ligament more closely imitates the natural anatomic footprint of the tibial ligament insertion, resulting in a biomechanically improved reconstruction. The AM and PL bundles are spread out over the elliptical anatomic footprint at the joint-side mouth of the tibial tunnel.

(2) The ligament is secured over the entire perimeter of the tibial tunnel, eliminating the "windshield wiper" action of the graft ligament over the tunnel entrance at the bone surface. This "windshield wiper" action can lead to wear of the ligament, wear of the bone surface, widening of the bone tunnel, and potentially a failed reconstruction.

(3) The bony defect from the drilling process is substantially completely filled by the tibial fixation device.

(4) The action of inserting the TLS 195 into the tunnel provides tensioning of the ligament graft for easy insertion, ensuring tension to the graft bundles.

(5) The action of rotating the interference screw (i.e., TFS 200) into place further fixates the ligament graft bundles, and may be used to draw the TLS 195 slightly deeper into the tibial bone tunnel for additional security of the fixation.

(6) In the event that the ligament needs to be revised at a later date, the tibial fixation screw 200 is removed by unscrewing the interference screw from the tibia. The tibial ligament spacer 195 is then grasped again with the positioning device 240 and then pulled completely through the tibial tunnel for removal.

(7) The tibial ligament spacer 195 provides a strain relief to distribute the stress over the face of the device to create a smooth and gradual transition from the compression of the tibial fixation screw 200.

Alternatives for the First Preferred Construction and Method of Use

Alternative designs are envisioned for the femoral ligament spacer (FLS) 120 and/or the tibial ligament spacer (TLS) 195.

The femoral ligament spacer (FLS) 120 and/or the tibial ligament spacer (TLS) 195 have been described above as a solid shape with a hole through the center. However, it may be desirable to have a porous version of the FLS 120 and/or the TLS 195. Porosity or larger fenestrations would allow bone to grow into, or through, the spacers. In addition to enhancing the fixation of the devices, this allows bone and ligament growth and regeneration along the surface of the FLS 120 and/or along the surface of the TLS 195, further enhancing the anatomic footprint of the reconstruction. The porosity may be formed into the spacer material itself, or it may be in the form of holes or penetrations extending through the spacer body, e.g., as exemplified in FIGS. 47-50. These fenestrations may extend radially ("side holes") and/or longitudinally ("end holes"), etc. The fenestrations may be configured such that the side holes and end holes are interconnected, providing a biologic communication between the fenestrations.

In other versions of the devices, there may be graft recesses, fenestrations (or a porous material) and small barbed features 250 (FIGS. 51-54) on the interference portion of the femoral ligament spacer 120 and/or on the interference portion of the tibial ligament spacer 195 to resist graft migration. These features may be directed such that they do not substantially resist the insertion of the ligament spacer into bone, but the barbed feature provides significant resistance to ligament movement as a result of the tension imposed on the ligament.

Figure 55:
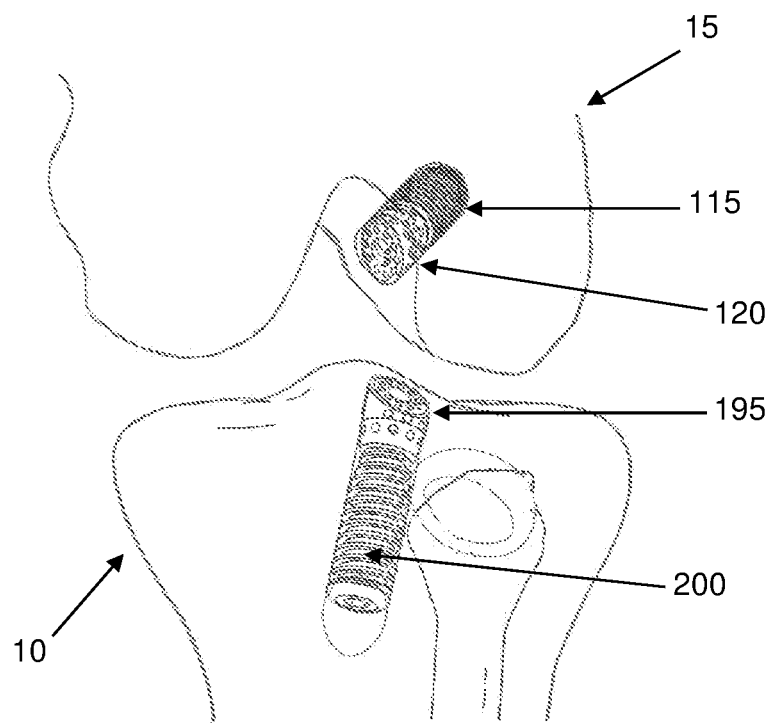
FIG. 55 is a schematic view showing femoral and tibial fixation device (with fenestrations) in place.
Figure 56:
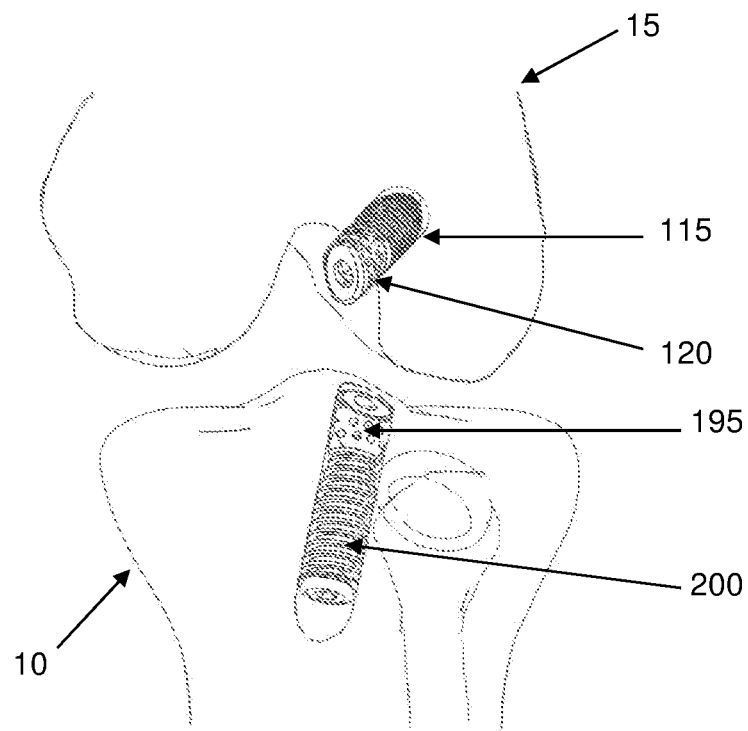
FIG. 56 is a schematic view showing femoral and tibial fixation devices in the final construct.
Figure 57:
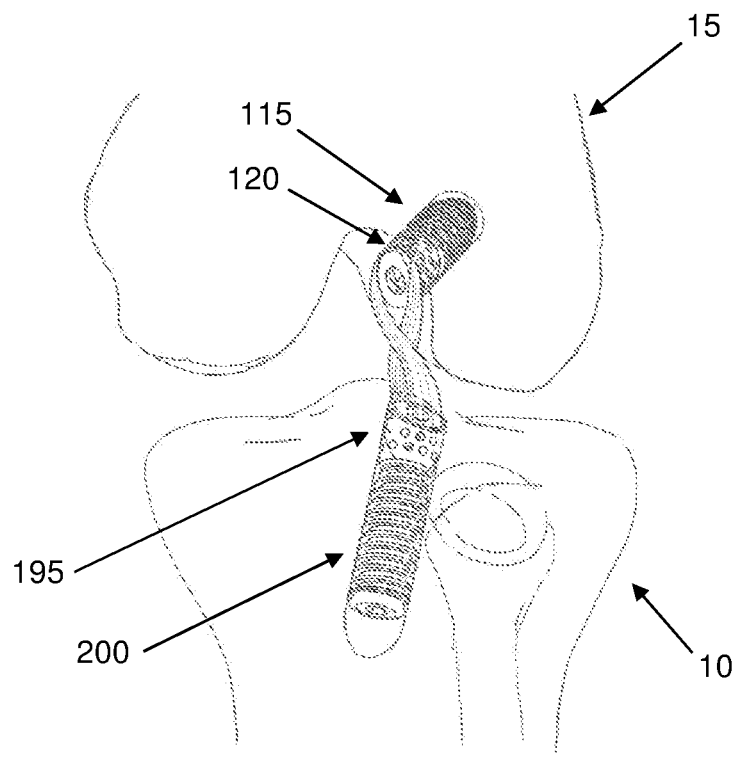
FIG. 57 is a schematic view showing femoral and tibial fixation devices and ligament grafts.

FIGS. 55-57 show fenestrated femoral ligament spacers 120 and fenestrated tibial ligament spacers 195 deployed in bone.

Figure 58:
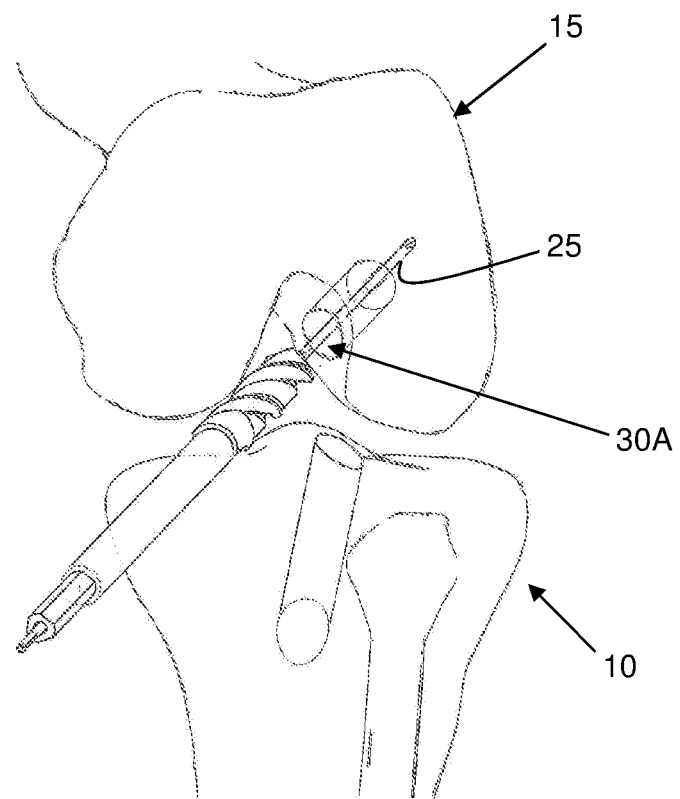
FIG. 58 is a schematic view showing a fixation where a first tunnel is drilled slightly smaller, e.g., 9 mm.
Figure 59:
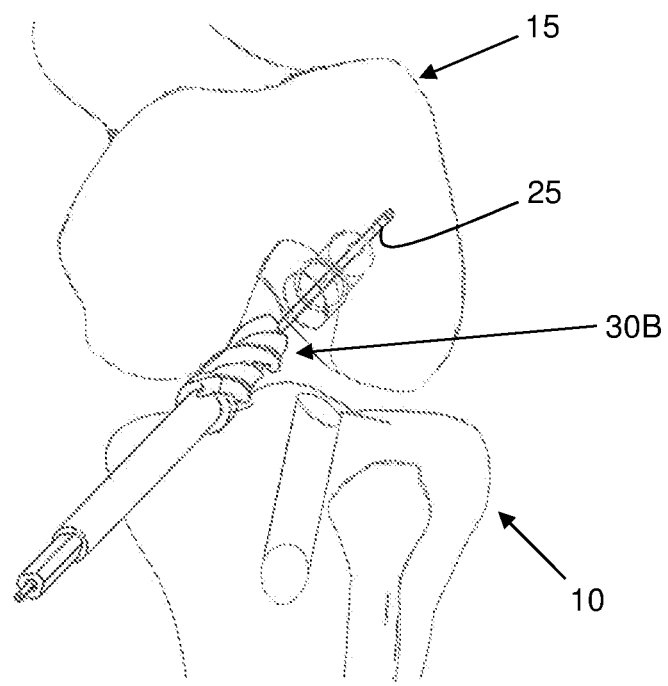
FIG. 59 is a schematic view showing a counterbore being drilled somewhat larger, e.g., 11 mm.

In another version of the invention, the femoral tunnel is drilled in a different manner and the femoral ligament spacer 120 is configured differently to further expand the anatomic footprint. More particularly, and looking now at FIGS. 58 and 59, the femoral bone tunnel is drilled with a counterbore at the mouth of the tunnel (i.e., at the entrance into the joint space). This may be accomplished by first placing the guide pin 25 as before, drilling the smaller tunnel using a cannulated drill 30A of the first diameter, and then drilling the larger tunnel (i.e., the counterbore) using a cannulated drill 30B of a second, larger diameter. The guide pin 25, the smaller tunnel, and the larger tunnel are all aligned on the same centerline, i.e., they are co-axial.

Figure 60:
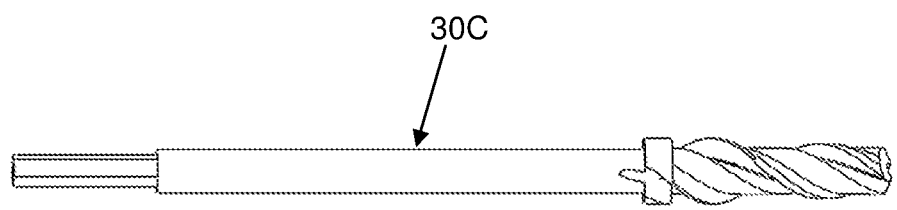
FIG. 60 is a schematic view showing a stepped drill bit.

Or the tunnels may be drilled in a single drilling step with the use of a cannulated stepped drill 30C as shown in FIG. 60. The cannulated stepped drill 30C starts with a smaller diameter, and then steps up to a larger diameter for the counterbore portion of the drilling process.

Figure 61:
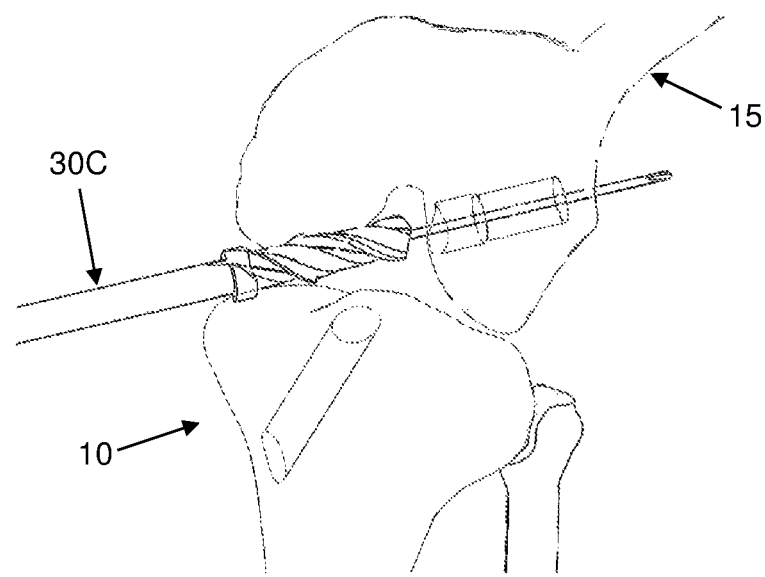
FIG. 61 is a schematic view showing the bore/counterbore hole being drilled with the stepped drill bit.

Drilling the smaller and larger counterbored holes with the stepped drill bit is shown in FIG. 61.

Figure 62:
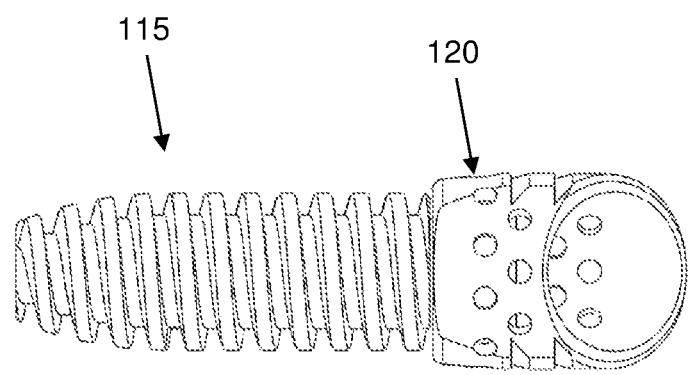
FIG. 62 is a schematic view showing an alternative femoral fixation device with larger FLS.

With this arrangement of bore and counterbore, the FLS 120 is of a larger size and shape than that of the femoral fixation screw 115 (FIG. 62). The advantage of this arrangement is to further spread the ligaments over a larger elliptical anatomic footprint relative to the smaller tunnel diameter, thereby allowing the reconstruction to match with larger natural anatomic footprints. This may also have the advantage of using a smaller femoral interference screw 115 and a smaller distal bone tunnel, thereby reducing the size of the distal femoral tunnel and reducing the amount of bone material removed.

Figure 63:
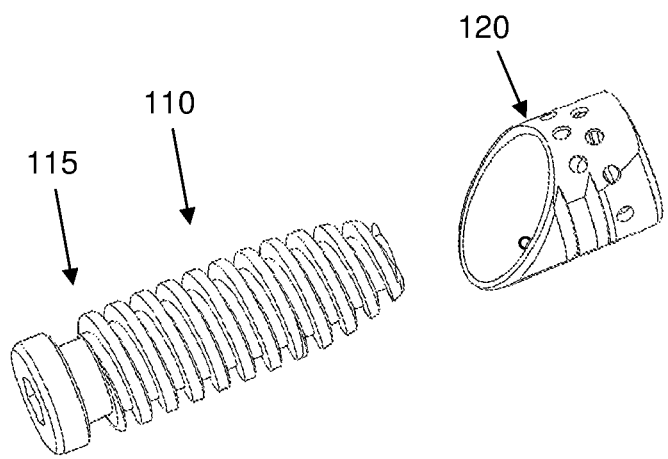
FIG. 63 is a schematic view showing an expanded femoral fixation device with a larger FLS.
Figure 64:
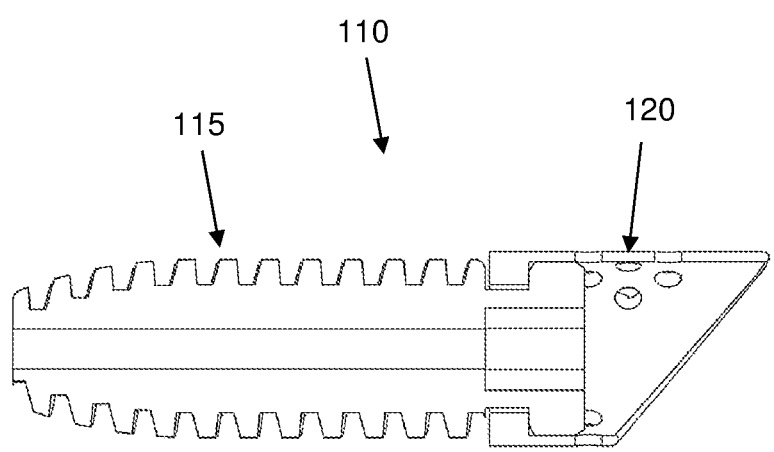
FIG. 64 is a schematic view showing a femoral fixation device.

Other details of this configuration of the femoral fixation device 110 may also be different from the previously described femoral fixation device 110. With the larger FLS 120 and smaller FFS 115, the FLS 120 can now be assembled from the other end of the FFS 115. FIGS. 63 and 64 show the exploded view, and the subsequent cross-sectional view, after assembly of the components to form the complete femoral fixation device 110. In this form of the invention, the FFS 115 is assembled through the FLS 120 by passage of the FLS 120 over the FFS threads. The head of the FFS 115 then stops on the inside face of the FLS 120. This arrangement has the advantage of a simplified manufacturing technique, eliminating the need for the reverse threads on the head of the FFS 115 (or other means for FLS retention, such as a bonded head to capture the FLS 120 to the FFS 115). The other features of the femoral ligament spacer 120 preferably remain similar to the previously described FLS, such as the ligament recesses, the fenestrations and the retaining barbs. The reverse thread 170 is not utilized in this version of the FLS 120 because of the different assembly process and the head features.

Figure 65:
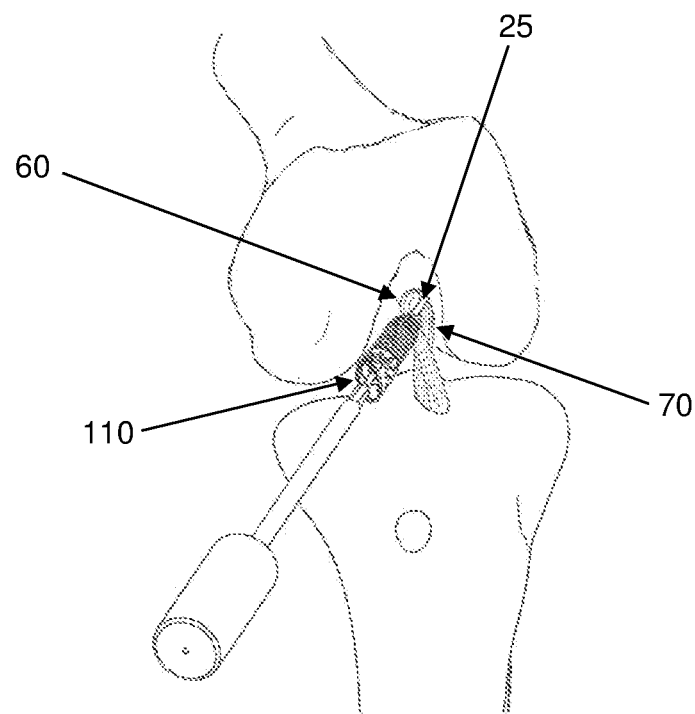
FIG. 65 is a schematic view showing an expanded femoral fixation (larger FLS) insertion.
Figure 66:
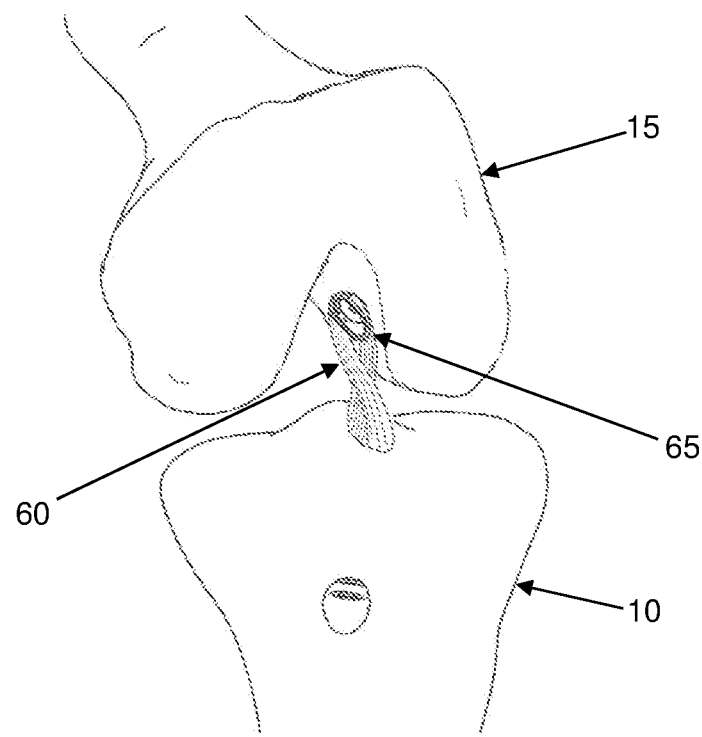
FIG. 66 is a schematic view showing an expanded femoral fixation.

The expanded femoral fixation device 110 is then installed (FIGS. 65 and 66). The expanded femoral fixation device 110 is slid over the guide wire 25, introduced through the AM portal and brought into proximity of the femoral tunnel. The ligaments are then manipulated to their approximate anatomic positions and the femoral fixation device 110 is tightened into place. As the device is tightened, FFS 115 binds the ligament bundles to the femur with an interference fit and FLS 120 binds the ligament bundles to the femur with an interference fit. As the device is tightened into the femur, the AM and PL bundles 60, 65 are further separated by the FLS 120.

Figure 67:
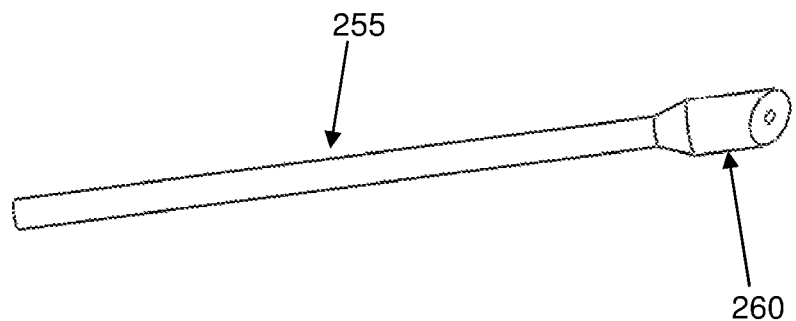
FIG. 67 is a schematic view showing a femoral guide wire aimer.
Figure 68:
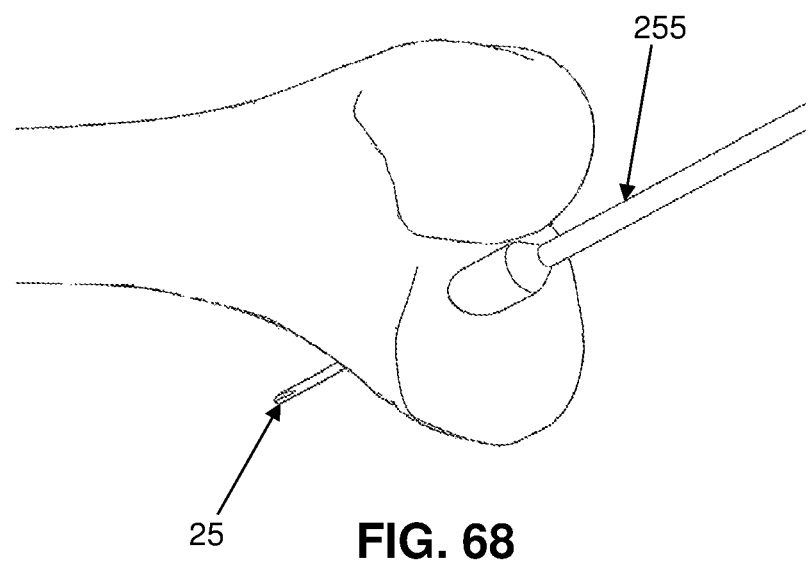
FIG. 68 is a schematic view showing a femoral guide wire aimer and guide wire.

In another version of the instrumentation, a specially shaped guide wire aimer 255 (FIG. 67) can be used to show the anticipated footprint of the femoral and tibial ACL reconstruction. The aimer 255 is constructed as a cannulated tube that guides the wire, but with an elliptical face 260 on the distal end of the tube to align with the femoral surface. The aimer 255 can be rotated and moved to closely approximate the femoral ACL insertion (FIG. 68). The femoral aimer 255 may also have a one or more prongs (not shown) protruding from its face 260 to register onto the bone surface. The aimer 255 (and the FLS 120 and TLS 195) may be manufactured with various degrees of angled faces (i.e., at different angles) that allow the devices to be aligned to individual patient anatomy.

Figure 69:
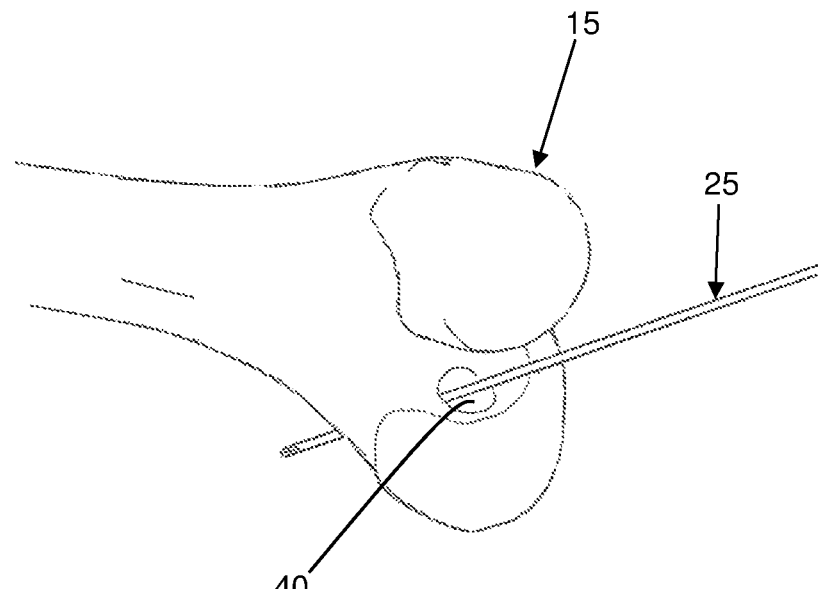
FIG. 69 is a schematic view showing a tunnel entrance with guide wire.

The tunnel is then drilled with the cannulated drill and the slanted, elliptical shape of the femoral tunnel exit approximates the outline of the femoral guide wire aimer 255, as shown in FIG. 69.

Figure 70:
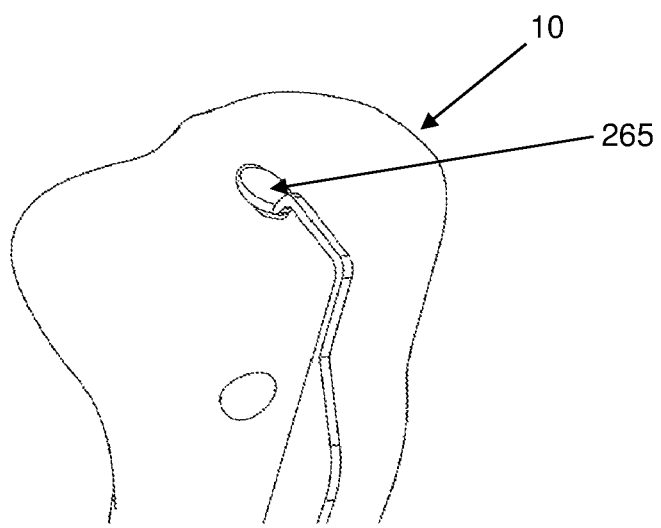
FIG. 70 is a schematic view showing an elliptical tibial aimer for assessing footprint and aiming the guide wire.

Similarly, on the tibial side, a pointer 265 with an elliptical shape can be used to visualize the tibial tunnel as it appears in the joint space. See FIG. 70.

Figure 71:
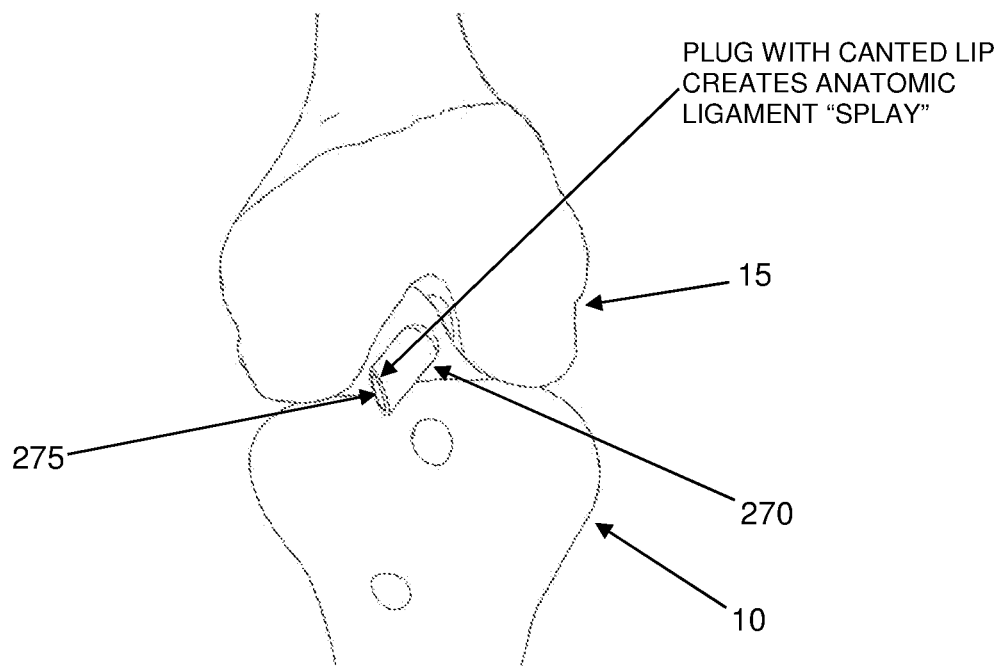
FIG. 71 is a schematic view showing a plug with a canted tip to achieve an anatomic footprint and "splay" the ligament grafts.

In another version of the invention, the femoral fixation device comprises a simple plug 270 with a canted surface 275. See FIG. 71.

Figure 72:
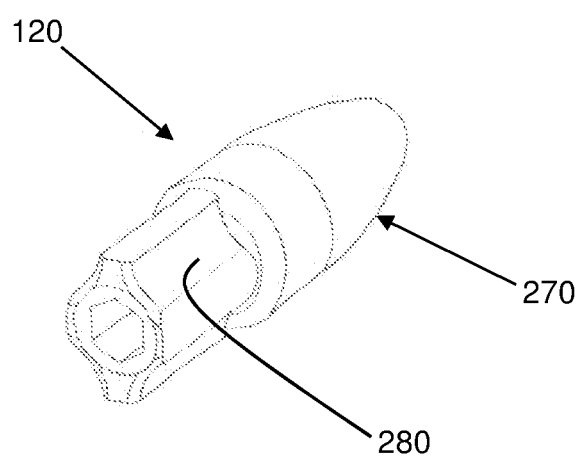
FIG. 72 is a schematic view showing an example of an alternatively shaped FLS (or TLS)

In another version of the invention, the FLS 120 (and TLS 195) may have a different shape than that disclosed above, e.g., the spacers may have a shape such as the exemplary FLS 120 shown in FIG. 72. In this form of the invention, there are indentations 280 in the ligament spacer to provide more space for the graft to reside. The near end of the spacer may be canted or flat (in the preferred form of the FLS 120, the proximal end of the FLS is canted, in the preferred form of the TLS 195, the proximal end of the TLS is flat). Also, instead of mating with a threaded fixation screw, a bullet shaped interference fixation plug 270 may form the distal end of the femoral fixation device. The bullet shaped device may have other features such as barbs, ribs, fenestrations and recesses for providing additional fixation and ligament alignment.

Figure 73:
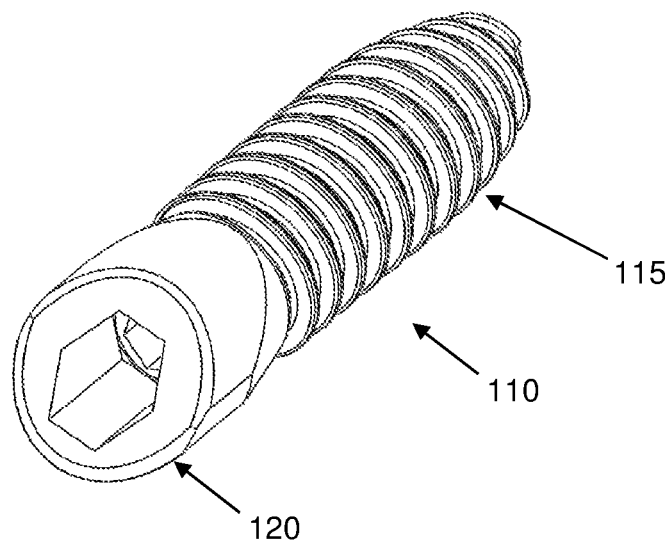
FIG. 73 is a schematic view showing a femoral fixation device.

In another version of the femoral ligament spacer 120 (FIG. 73), the hole through the spacer has additional features, such as a hexagonal-shaped bore for engagement with a hex tool (Allen wrench) to help rotate the FLS 120 to ensure full perimeter filling of the bone defect. Rotation of the FLS may also be desirable prior to fully tightening the FLS 120 into place in order to position the AM and PL bundles into their correct anatomic positions. The tool features could take on alternate forms such as a slot or spanner wrench, as long as the size of the central bore in the FLS is adequately maintained to get a smaller wrench through the femoral ligament spacer to engage with the femoral fixation screw, whereby to tighten the assembly into place. FIG. 73 shows the femoral ligament spacer 120 with engagement tool features (hex shape) through the center for rotating the FLS 120 relative to the FFS 115.

Second Preferred Construction and Method of Use

The pages that follow describe alternative, and in some cases preferred, embodiments for the femoral fixation device 110 and the tibial fixation device 201 that make up the complete anatomic ACL reconstruction system. The alternative version of the femoral fixation device 110 is described first, followed by the description of the alternative version of the tibial fixation device 201.

Figure 74:
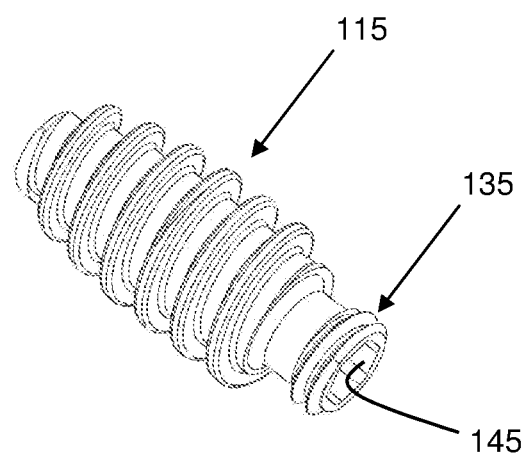
FIG. 74 is a schematic view showing a femoral fixation screw.
Figure 75:
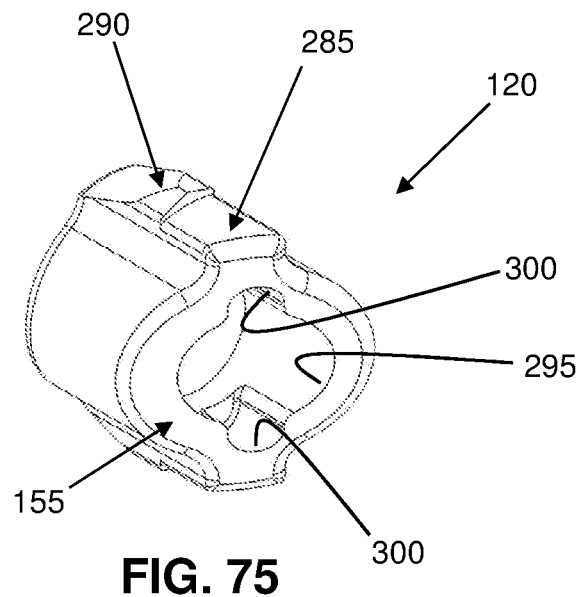
FIG. 75 is a schematic view showing a femoral ligament spacer.

The alternative femoral fixation device 110 consists of a femoral fixation screw 115 (FIG. 74) and a femoral ligament spacer 120 (FIG. 75).

Looking now at FIG. 74, the femoral fixation screw 115 includes a tapered threaded body that presses the graft ligament against the tunnel drilled into the bone so as to make an interference fit. It also has a cannulation through its length in order to slide along a guide pin 25 as it is tightened into place. The head of the screw consists of a reverse thread 135 for retaining the femoral ligament spacer 120, and a hex socket 145 in the head for tightening FFS 115 into bone.

Looking now at FIG. 75, the femoral ligament spacer 120 rotates freely after assembled onto the femoral fixation screw 115. The femoral ligament spacer 120 is made from biocompatible metal, plastic, absorbable ceramic, bone graft material or a combination of these materials. The FLS 120 has two or more tab-like features 285 extending from the sides to separate the two or more bundles of the ligament graft. Each tab 285 has one (shown) or more teeth (or barbs) 290 protruding from the side. The teeth 290 are oriented to provide resistance to being pulled out of the bone tunnel. The front face 155 of the FLS 120 is canted, or sloped, to approximately match the surface of the bone at the mouth of the bone tunnel, i.e., at approximately the angle β. A socket 295 is formed into the canted face 155 to permit insertion of tooling through FLS 120 to tighten the FFS 115, and also indentations 300 are formed into canted face 155 for receiving a separate tool to rotate and align the FLS 120 to its most anatomic position, or the position where the canted surface is most congruent to the adjacent bone surface. This device 120 may vary by having additional barbs, holes (fenestrations) throughout the device, and/or various shaped recesses for the graft.

Figure 76:
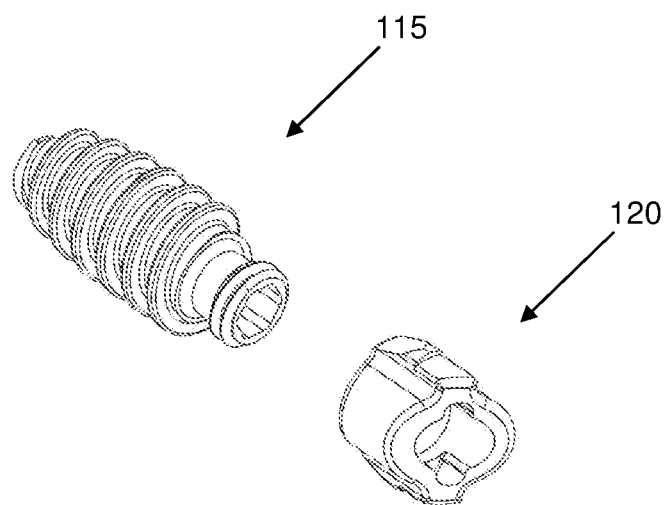
FIG. 76 is a schematic view showing a femoral fixation screw aligned with a femoral ligament spacer.

The two components (i.e., the FFS 115 and the FLS 120) are brought into axial alignment as shown in FIG. 76. The two components are assembled together by use of a reverse (left hand) thread (preferred) or, alternatively, another mechanism such as a right hand thread or a retaining ring or other feature, etc. The left hand thread is advantageous because there is minimal risk of the FLS 120 coming free of the FFS 115 as the device is tightened into place.

Figure 77:
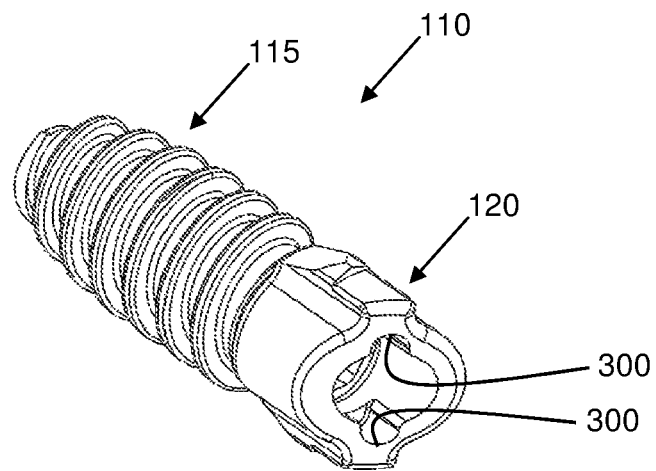
FIG. 77 is a schematic view showing an assembled femoral fixation device.
Figure 78:
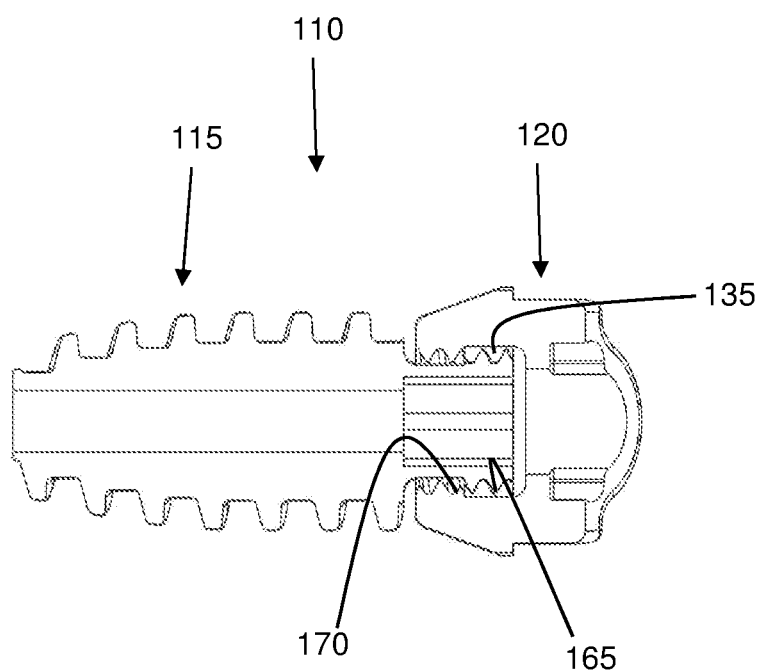
FIG. 78 is a schematic view showing a femoral fixation device.

FIG. 77 shows the two components 115 and 120 fastened together by use of the left hand thread so as to form the complete femoral fixation device 110. The threads 135 of the FFS 115 and the threads 170 of the FLS 120 are short so that the threads disengage from one another when the FLS 120 is fully assembled onto the FFS 115 (FIG. 78), whereupon the threads 135 of FFS 115 are rotatably received in enlarged diameter 165 of FLS 120. This allows the FLS 120 to spin freely relative to the FFS 115. Thus, the connection between FFS 115 and FLS 120 is similar to the connection discussed above with respect to the first preferred construction of the apparatus.

A cross-sectional view of the assembled femoral fixation device 110 (FIG. 78) further illustrates the assembly of the two components 115, 120 together. The thread length is short enough so that the threads 135, 170 completely disengage when the two pieces are assembled together. The threads 135, 170 then form a retaining feature to hold the two components together, while allowing the femoral ligament spacer 120 to spin freely on the femoral fixation screw 115.

Figure 79A:
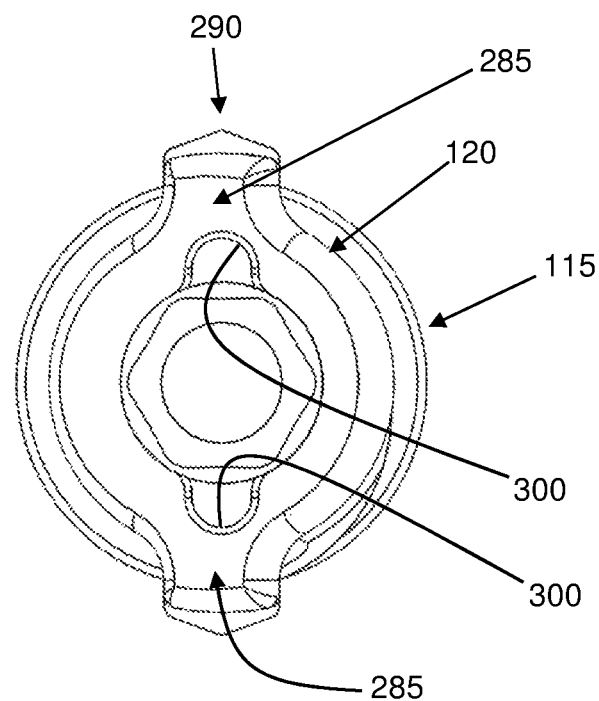
FIG. 79A is a schematic view showing a femoral fixation device.

In an end view (FIG. 79A) the relationship between the femoral fixation screw 115 and the femoral ligament spacer 120 is shown. The ligament graft is tightly pressed up against the bone tunnel in the area of the FFS 115. The bone tunnel is usually similar to, or just slightly larger than, the diameter of the FFS 115. The tabs 285 of FLS 120 are at a diameter that is equal to the bone tunnel. The teeth 290 are slightly larger than the bone tunnel, allowing them to grip into the bone. The side recesses 180 of FLS 120 are smaller than the bone tunnel and smaller than the FFS 115 diameter. This allows space for the ligament to reside and be aligned into its desired anatomic position. It also provides an area for the pressure on the ligament to be reduced, thus acting as a stress relief. FIG. 79A shows a femoral ligament spacer 120 that is divided into two sections, separated by the tabs 285. In another version of the invention, the spacer could be divided into 3 or more sections to further split and locate the ligament graft, especially for those cases where a four-stranded ligament graft may be used.

Figure 79B:
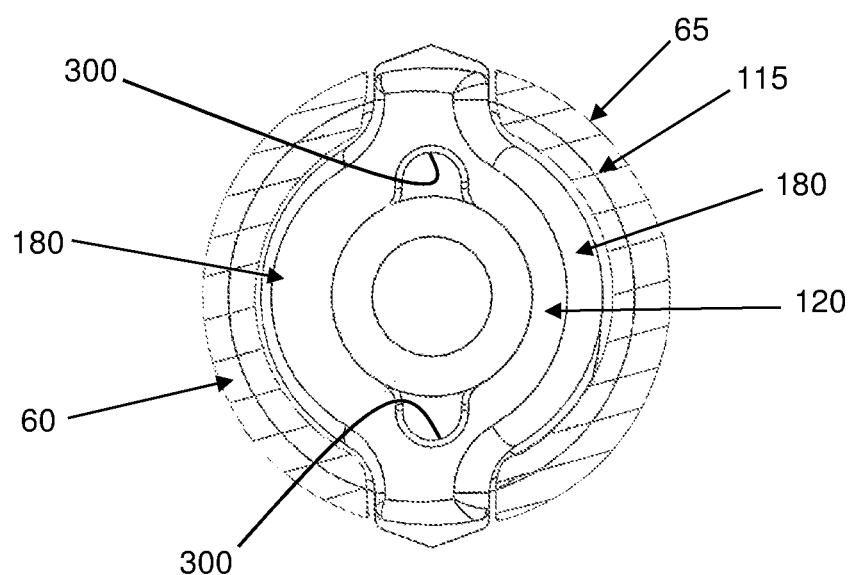
FIG. 79B is a schematic view showing femoral fixation with tissue graft.

FIG. 79B illustrates the area where the ligament resides between the bone tunnel and the FFS 115 and FLS 120. The cross-hatched area represents the ligament graft.

Figure 80:
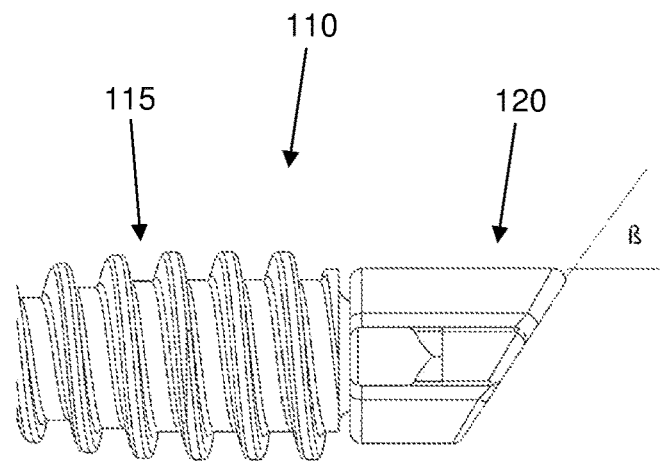
FIG. 80 is a schematic view showing a femoral fixation device.
Figure 81:
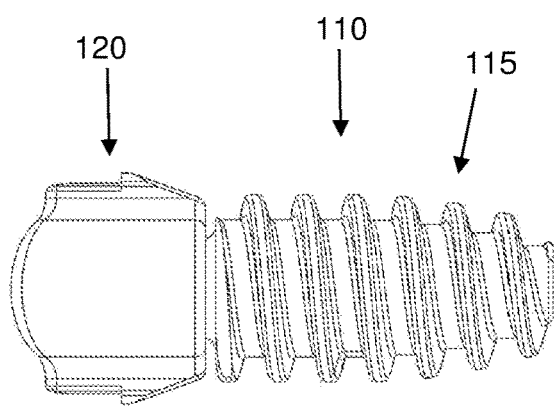
FIG. 81 is a schematic view showing a femoral fixation device.
Figure 82:
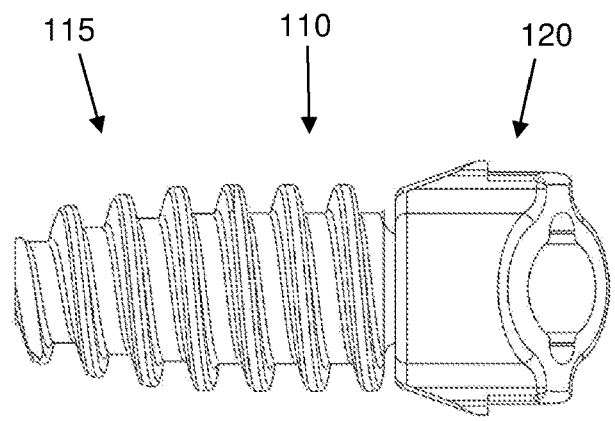
FIG. 82 is a schematic view showing a femoral fixation device.

FIGS. 80-82 are additional views which depict the femoral fixation device 110 in additional orthogonal views.

Figure 83:
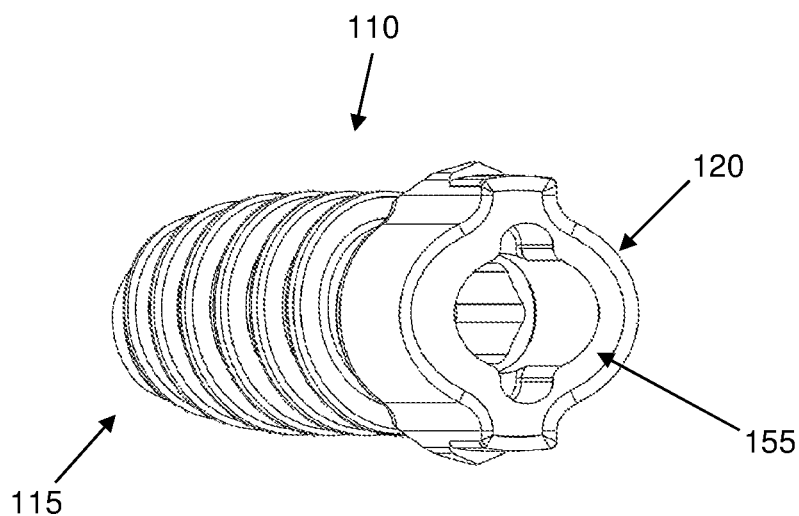
FIG. 83 is a schematic view showing a femoral fixation device.

FIG. 83 is an oblique view of the femoral fixation device 110, looking directly into the angled surface 155.

Figure 84A:
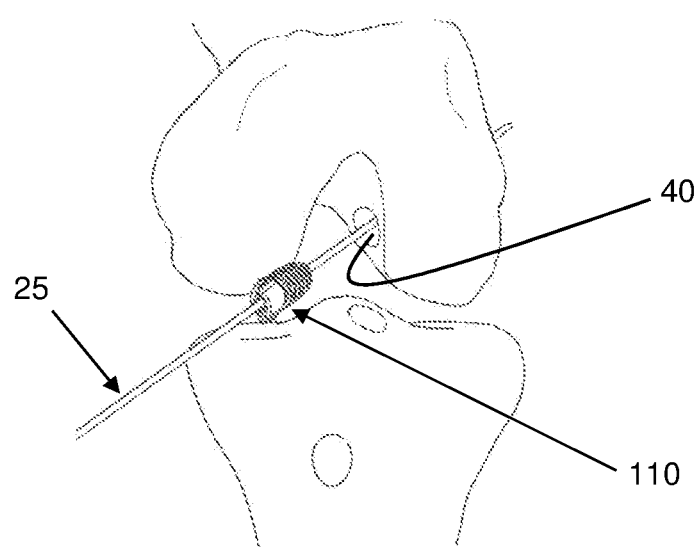
FIG. 84A is a schematic view showing a guide pin and a femoral fixation device.

Looking now at FIG. 84A, after placement of the guide pin 25 through the AM portal at the angle β, the femoral fixation device 110 is introduced onto the guide pin 25 to the proximity of the femoral tunnel 40.

Figure 84B:
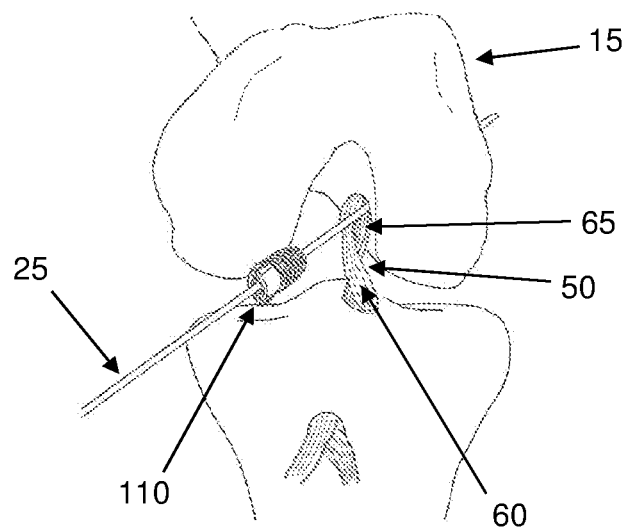
FIG. 84B is a schematic view showing a femoral fixation device, a guide pin and ligament grafts.

FIG. 84B is the same as FIG. 84A, except showing the graft ligament in place. The portion of the graft ligament entering the tibial tunnel from the joint space and located nearest the front (anterior) portion of the tibia (and slightly medial) is the graft replacement for the anteromedial (AM) bundle 60. The portion of the graft entering the tibial tunnel from the joint space and located slightly posterior (and lateral) is the graft replacement for the posterolateral (PL) bundle 65.

Figure 85:
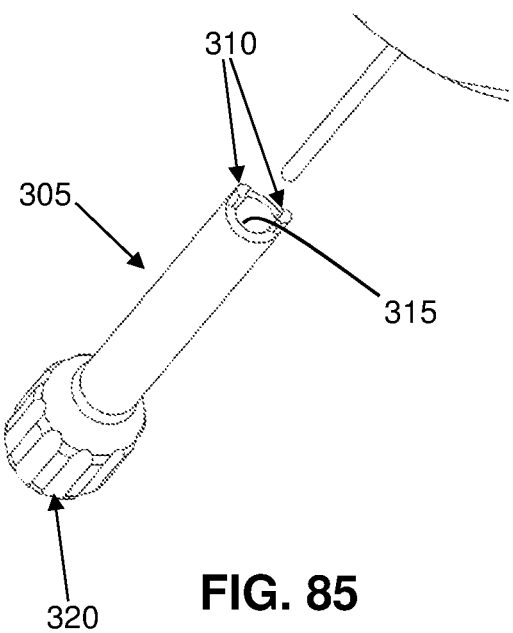
FIG. 85 is a schematic view showing a ligament spacer alignment tool.

A ligament spacer alignment tool 305 is shown in FIG. 85. Two prongs 310 protrude from the distal end to engage with the indentations 300 of FLS 120, so that ligament spacer alignment tool 305 can be used to turn FLS 120 to the appropriate radial position, whereby to align the canted surface 155 of FLS 120 with the adjacent bone and whereby to appropriately position graft ligament strands 60, 65 as they emerge from the femoral bone tunnel. A through hole 315 is formed through the tool 305 for a hex wrench (see below) to pass through. A hub 320 at the proximal end of the tool (shown with scallops) can be turned to rotate the FLS 120 into desired positions, as will hereinafter be discussed.

Figure 86:
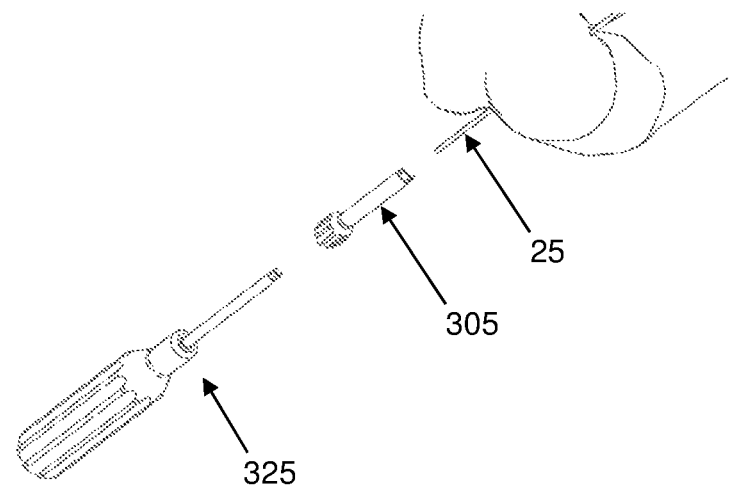
FIG. 86 is a schematic view showing a hex wrench and ligament spacer alignment tool.

In FIG. 86, the ligament spacer alignment tool 305 is shown aligned with the hex wrench 325. The hex wrench 325 could also be some other profile to mate with the FFS 115, such as a square head, or hexalobular head.

Figure 87:
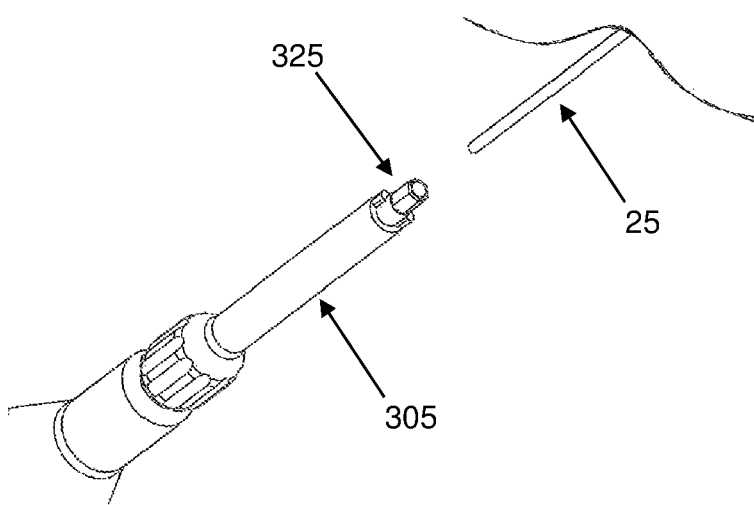
FIG. 87 is a schematic view showing a hex wrench extending through a ligament spacer alignment tool.

The hex wrench 325 slides through the ligament spacer alignment tool 305 as shown in FIG. 87. This allows simultaneous, and independent, rotation and adjustment of the FFS 115 and FLS 120, as will hereinafter be discussed.

Figure 88A:
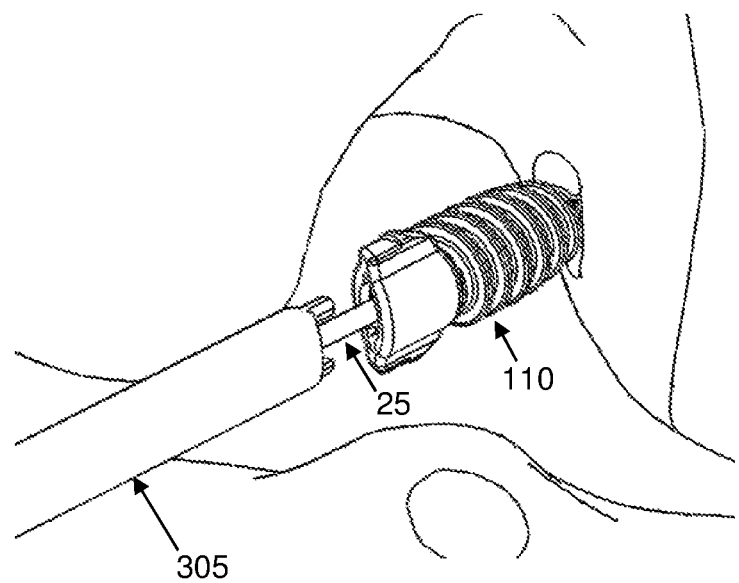
FIG. 88A is a schematic view showing a ligament spacer alignment tool over a guide pin.

More particularly, in FIG. 88A, the instruments are brought into the proximity of the femoral fixation device 110 by sliding them over the guide pin 25.

Figure 88B:
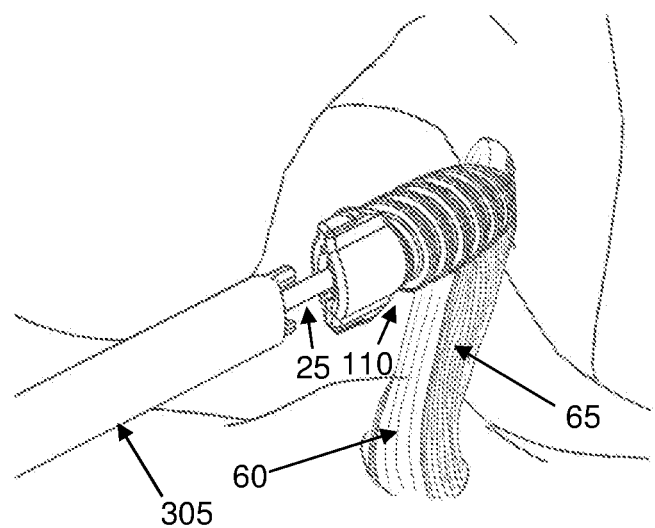
FIG. 88B is a schematic view showing a ligament spacer alignment tool, femoral fixation device and ligament grafts.

The femoral fixation device 110 is approximately between the two strands 60, 65 of the ligament graft as shown in FIG. 88B.

Figure 89A:
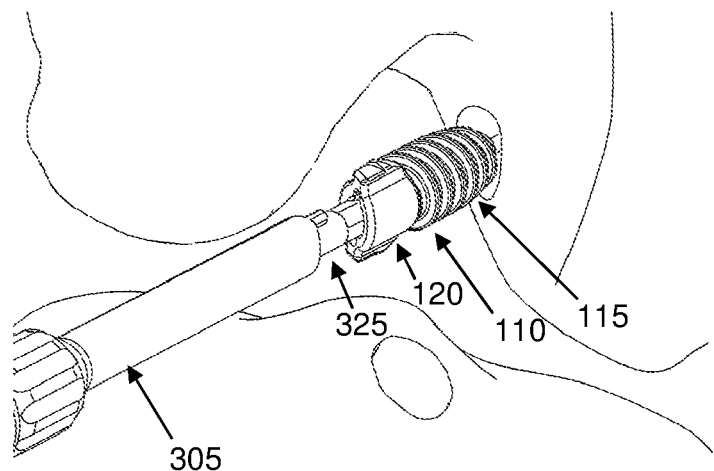
FIG. 89A is a schematic view showing a hex wrench about to engage a femoral fixation screw.
Figure 89B:
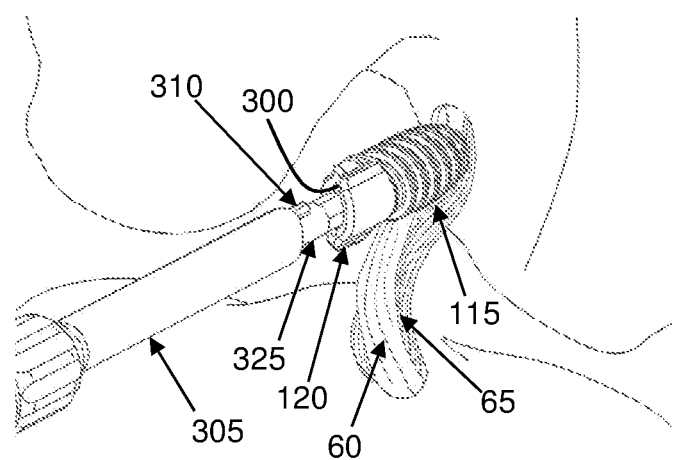
FIG. 89B is a schematic view like that of FIG. 89A, except also showing a tissue graft.

The hex wrench 325 (FIGS. 89A and 89B) is advanced closer to the femoral fixation screw 115. Again, from the attachment point into the tibia, the AM bundle 60 is front (anterior) and medial, and the PL bundle 65 is back (posterior) and lateral.

Figure 90:
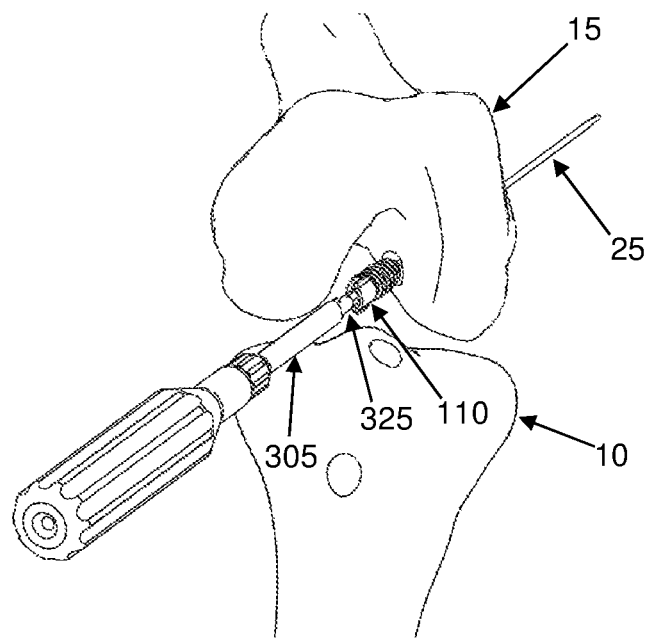
FIG. 90 is a schematic view showing a femoral fixation device.

FIG. 90 is an overall view showing the insertion of the femoral fixation device 110 (i.e., showing the guide pin 25, the hex wrench 325, the FLS alignment tool 305 and the femoral fixation device 110.

Figure 91A:
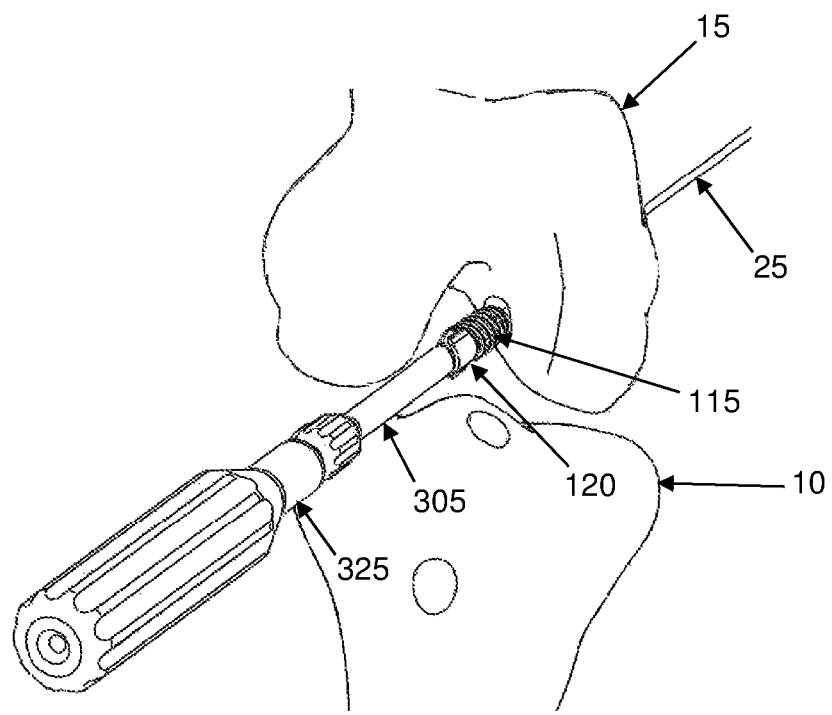
FIG. 91A is a schematic view showing tools engaged with a femoral fixation device.
Figure 91B:
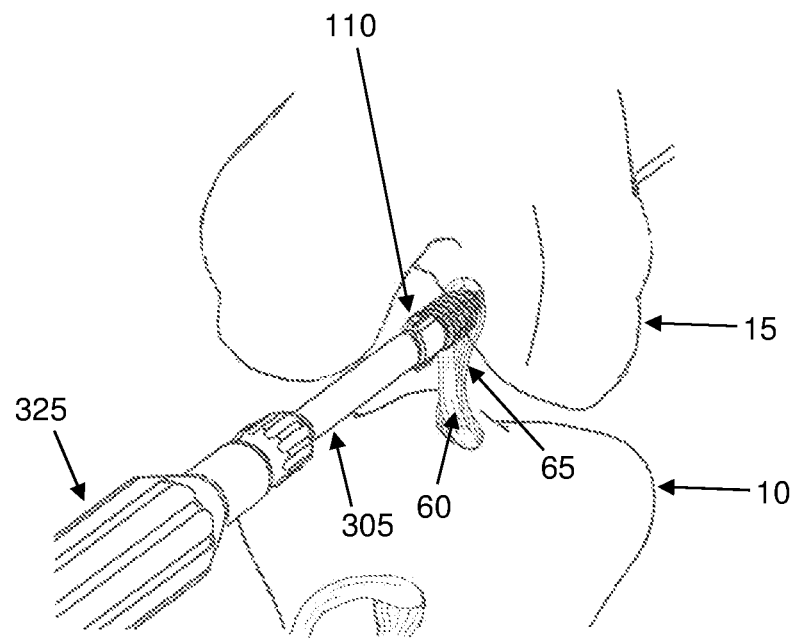
FIG. 91B is a schematic view showing tools engaged with a femoral fixation device, and showing ligament grafts.

FIGS. 91A and 91B show the hex wrench 325 and the FLS alignment tool 305 engaged with the FFS 115 and the FLS 120, respectively. The FLS 120 can be held steady with FLS alignment tool 305 (by virtue of prongs 310 of FLS alignment tool 305 being disposed in indentations 300 in FLS 120) while the FFS 115 is rotated by turning the hex wrench 325 (which is an engagement with hex socket 145 of femoral fixation screw 115).

Figure 92:
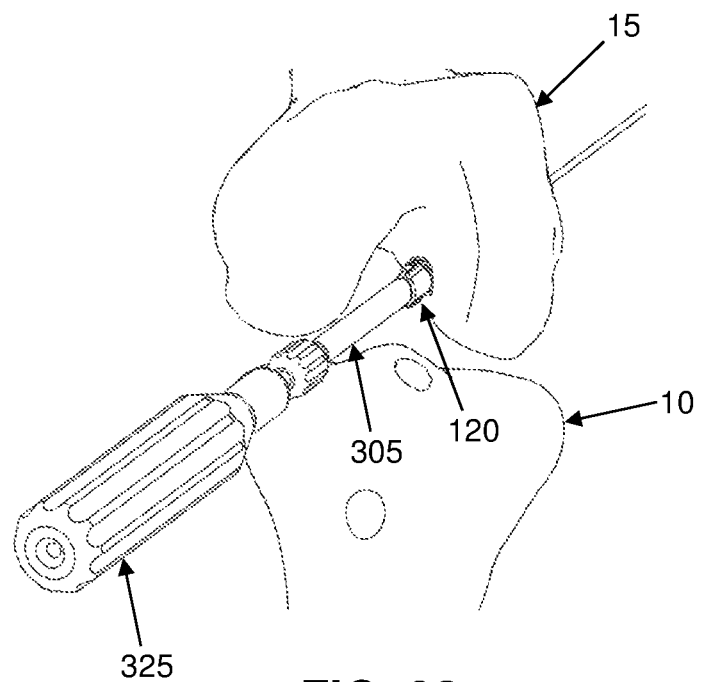
FIG. 92 is a schematic view showing insertion of the femoral fixation device.

As the FLS 120 gets closer to the femoral tunnel entrance (FIG. 92), it can be rotated with the FLS alignment tool 305 to appropriately align it with the bony surface. It is also rotated to position, or urge, the ligament graft bundles 60, 65 into their desired anatomic positions.

Figure 93A:
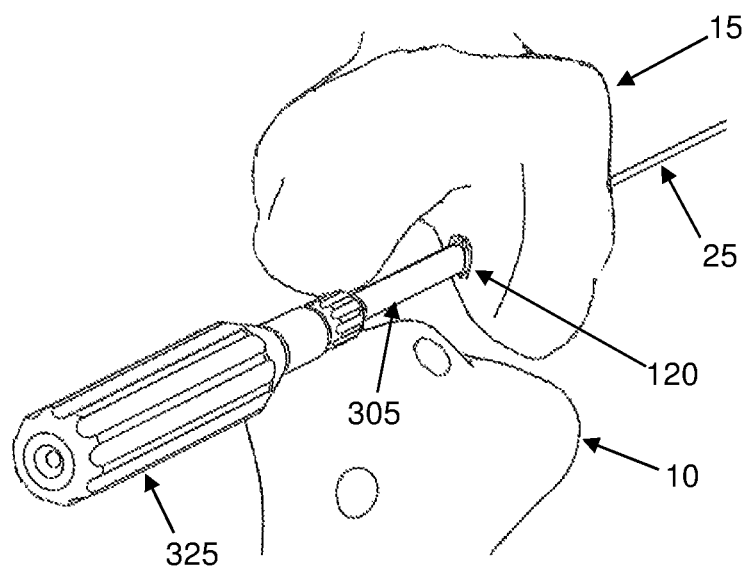
FIG. 93A is a schematic view showing a femoral fixation device seated in the femur.
Figure 93B:
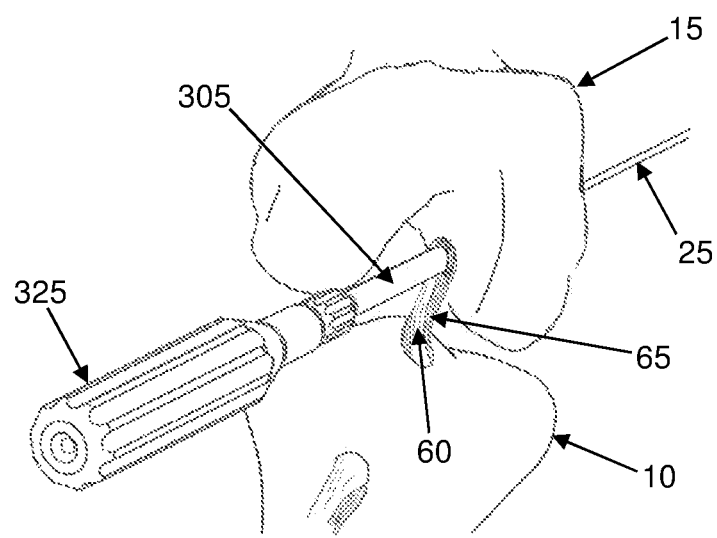
FIG. 93B is a schematic view showing a femoral fixation device seated in the femur, with ligament grafts being shown.

FIGS. 93A and 93B show the femoral fixation device 110 as it is completely seated into the femoral tunnel. The ligament graft is completely fixated to the femur, with the ligament graft bundles 60,65 located in their proper anatomic positions.

Figure 94A:
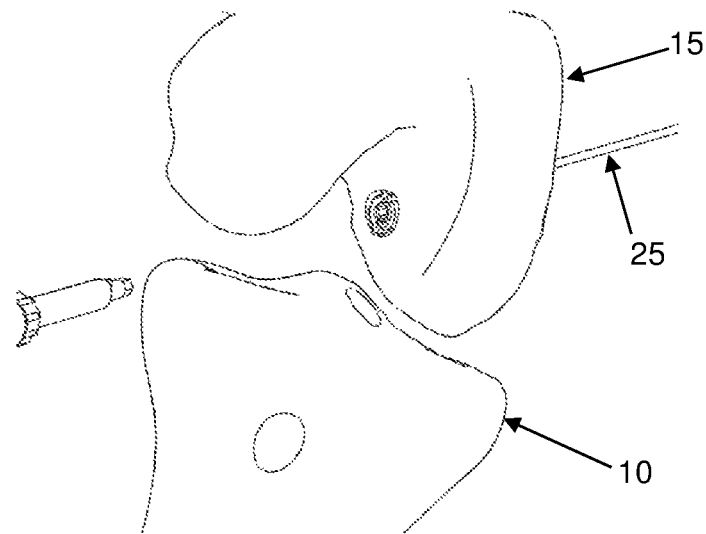
FIG. 94A is a schematic view showing a final femoral construct.
Figure 94B:
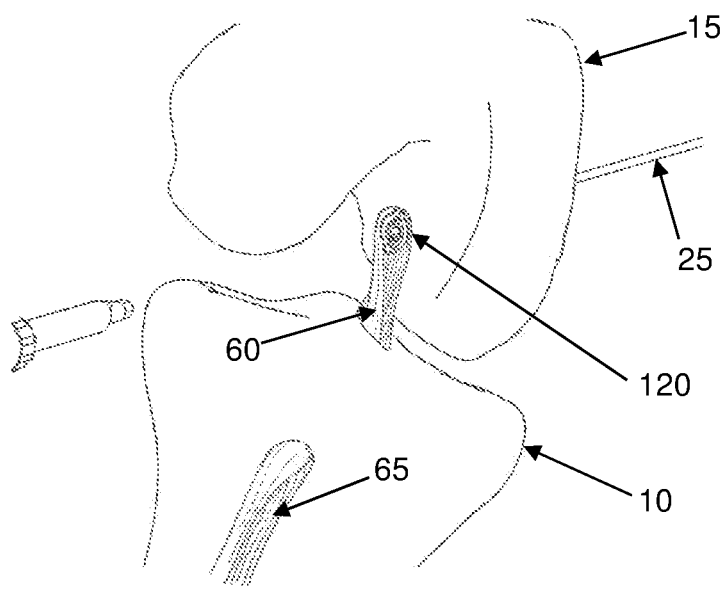
FIG. 94B is a schematic view showing a final femoral construct, with ligament graft.

FIGS. 94A and 94B show the final femoral construct with the ligament bundles 60, 65 placed in their proper anatomic locations. The instrumentation is thereafter retracted from the AM portal.

Figure 95A:
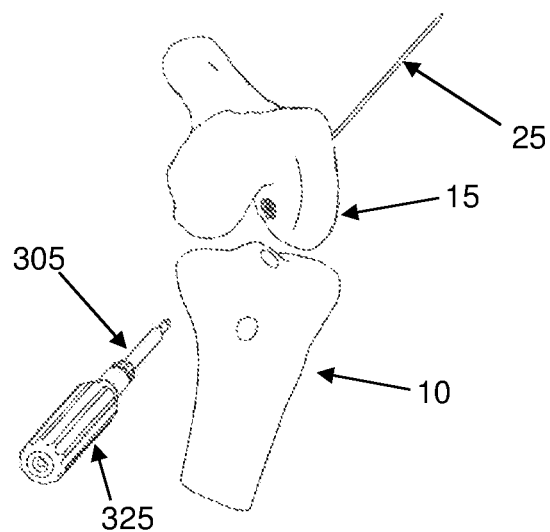
FIG. 95A is a schematic view showing a final femoral construct.
Figure 95B:
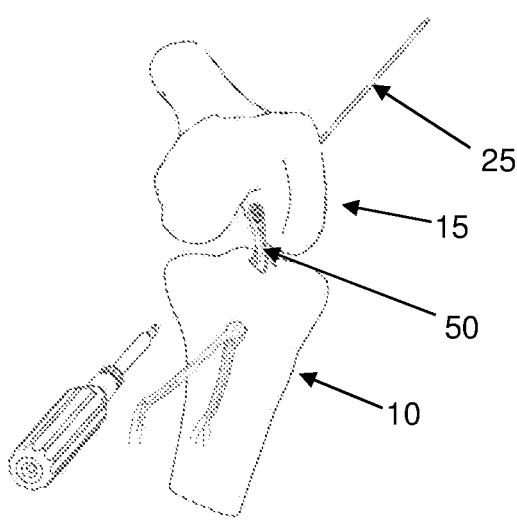
FIG. 95B is a schematic view showing a final femoral construct, with ligament graft.

FIGS. 95A and 95B show a larger perspective view of the final construct. The instrumentation is pulled away. The ligament graft bundles are also shown traversing the tibial tunnel with sutures extending from both ligament bundles.

In addition to the advantages previously stated, the alternative femoral fixation device described immediately above provides at least the following useful functions in ligament fixation:

(1) Controlled and careful alignment of the tibial ligament spacer 120 using the TLS alignment tool 305 to independently control the orientation of the TLS 120, and thus the alignment of the ligament graft, for an improved anatomic reconstruction.

(2) Barbed features 290 on the sides of the TLS 120 enhance the pullout strength of the TLS and the overall femoral fixation construct.

(3) More clearly defined ligament recesses in the TLS to provide a more anatomic reconstruction.

The alternative tibial fixation device 201 (FIGS. 96-101B) is described below. In this version of the invention, the tibial ligament spacer 195 is assembled onto the tibial fixation screw 200 in a manner similar to that of the femoral fixation device 110. However, in the case of the tibial fixation device 201, the TLS 195 is assembled to the leading end of the tibial fixation screw 200 first, and then they are introduced into the tibial tunnel as a unit.

Figure 96:
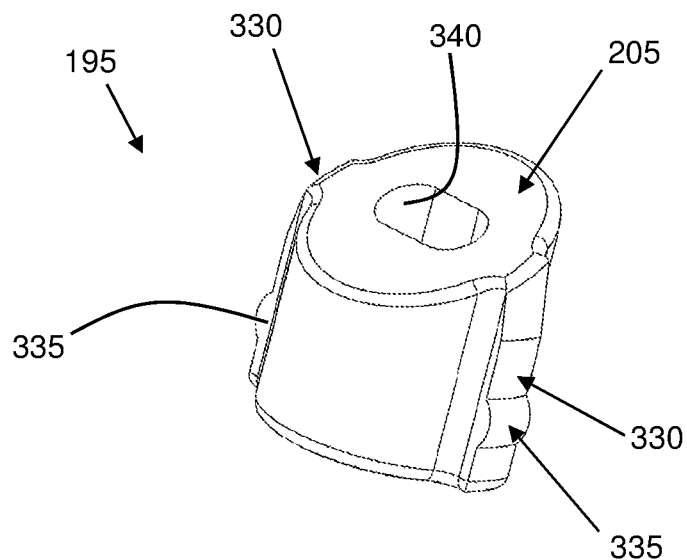
FIG. 96 is a schematic view showing a tibial ligament spacer.

FIG. 96 is an upper isometric view of the tibial ligament spacer 195. TLS 195 is made from biocompatible metal, plastic, absorbable ceramic, bone graft material or a combination of these materials. The outside portion of the spacer 195 consists of a body with the two or more tab features 330 protruding from the sides of TLS 195, the angled surface 205 at the distal end, one or more bumps 335 formed on the periphery of the tabs 330, and a slotted feature 340 for permitting alignment of the TLS 195 within the tibial bone tunnel. The bumps 335 are not the same as the barbs 250 discussed above, which resist motion primarily in one direction. The bumps 335 of this construction allow insertion of the device through the bone tunnel, but resist passing the device all the way through the bone tunnel as they come into proximity with the cortical layer of bone near the top end of the tibia, near the inside of the knee joint.

Figure 97:
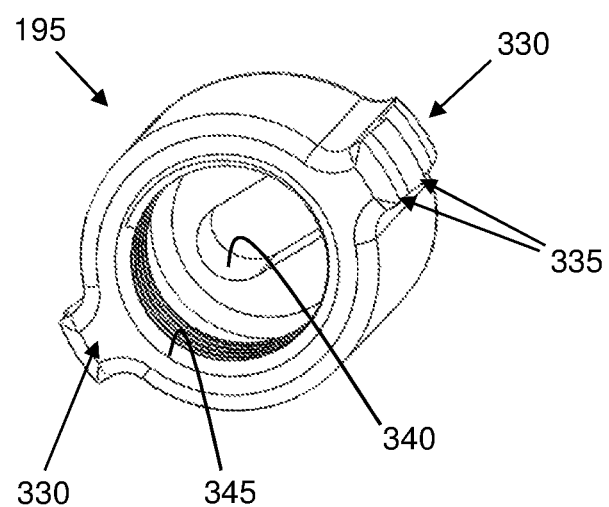
FIG. 97 is a schematic view showing a tibial ligament spacer.

FIG. 97 is a lower isometric view of the tibial ligament spacer 195. Threads 345 are formed on the inside of the component. The alignment slot 340 is accessible from the inside of the part. The corners of TLS 195 are carefully rounded to permit easy insertion and protection of the soft tissue ligament graft.

Figure 98:
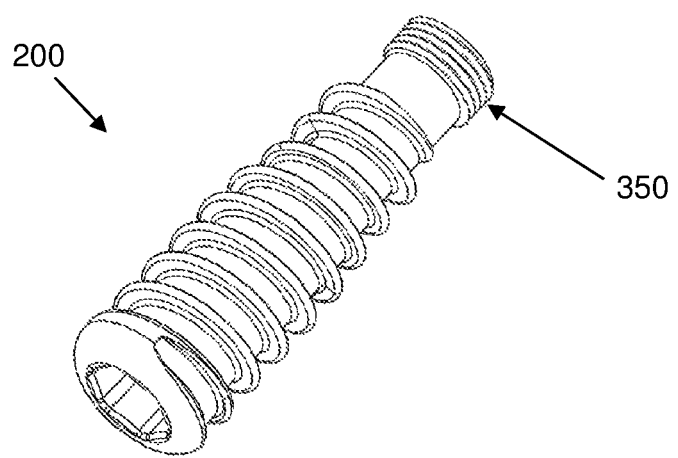
FIG. 98 is a schematic view showing a tibial fixation screw.

The tibial fixation screw 200 is shown in FIG. 98. The tibial fixation screw (TFS) 200 may also be made from a variety of materials but, in the preferred embodiment, comprise a biocompatible metal such as stainless steel, cobalt chrome or titanium (the same is true for other fixation screw components described herein). The distal tip of the TFS 200 has a fine pitch thread 350 that engages with thread 345 of the TLS 195. The fine pitch thread 350 of TFS 200 allows a larger minor thread diameter, permitting a larger cannulation through the body of the TFS 200. The body of the tibial fixation screw 200 has larger smooth threads for compressing the ligament up against the bone tunnel wall. A hole 355 passes through the TFS 200, and may be slightly larger than the hole in the FFS 115. The larger hole (e.g., 3-4 mm diameter) in TFS 200 accommodates a special alignment pin (see below) for rotating the TLS 195 into the proper orientation while the TLS 195 is disposed in the tibial tunnel.

Figure 99:
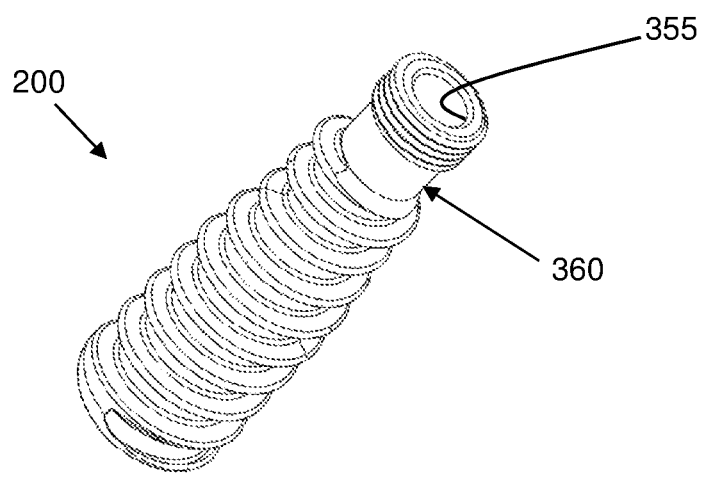
FIG. 99 is a schematic view showing a tibial fixation screw.

FIG. 99 is another isometric view of the tibial fixation screw 200. The hole 355 shown on the distal end of TFS 200 passes all the way through the body of the screw. A "relief" area 360 exists between the larger ligament-compressing threads formed on the proximal portion of TFS 200 (for engaging the ligament) and the fine pitched threads 350 (for engaging the TLS 195). This clearance allows the threads of the TFS 200 to disengage from the threads of the TLS 195 (FIG. 101A) so that the TLS 195 can rotate freely on TFS 200 after assembly.

Figure 100:
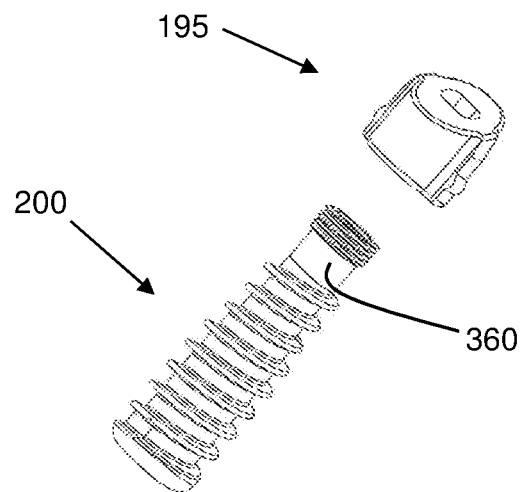
FIG. 100 is a schematic view showing a tibial ligament spacer aligned with a tibial fixation screw.

FIG. 100 shows the tibial fixation screw 200 and the tibial ligament spacer 195 aligned for assembly to each other.

Figure 101A:
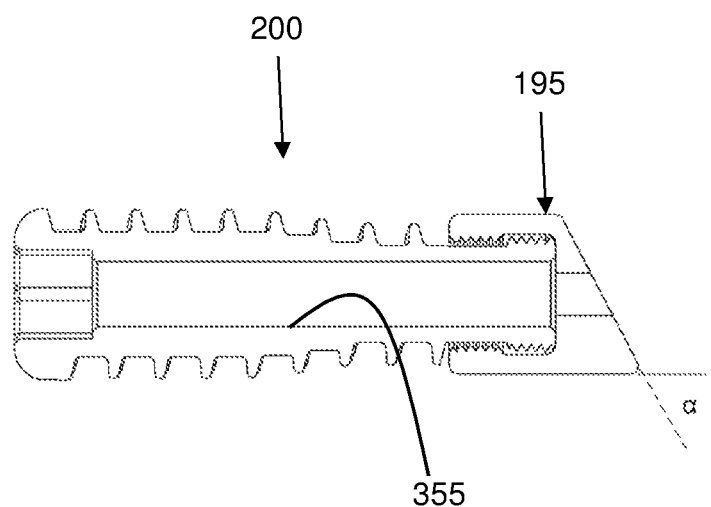
FIG. 101A is a schematic view showing a tibial ligament spacer assembled to a tibial fixation screw.
Figure 101B:
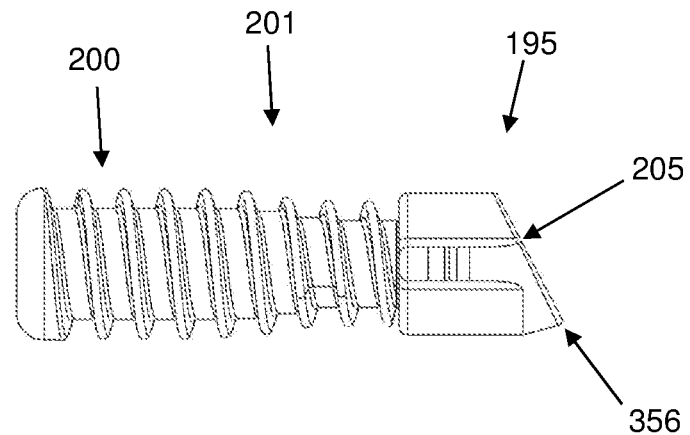

The two units (i.e., TLS 195 and TFS 200) are assembled together as shown in FIG. 101A. The threads between the TFS 200 and the TLS 195 may be left hand or right hand thread. Right handed threads are preferred so that there is no chance of the TLS 195 disengaging from the TFS 200 during the rotational insertion of the TFS 200. After final assembly, there is a clearance between the two components such that the TLS 195 can rotate freely on the tip of the TFS 195 without engagement with the fine pitch threads 350 of the TFS 200, thus allowing anatomic adjustment and placement of the TLS with the tibia. The angle $\alpha_2$ (hereafter referred to simply as a in the context describing the TLS) corresponds to the angle of the mouth of the tibial tunnel at the top surface of the tibia. The canted surface 205 of TLS 195 at angle $\alpha$ permits a relatively congruent and continuous surface to the tibia. FIG. 101B shows a version with a conical or wedge-shaped angled surface 356 on the TLS 195 to allow the TLS 195 to be inserted between the ligament grafts more easily and subsequently engage the threads of the TFS 200 to the ligament graft.

Figure 102A:
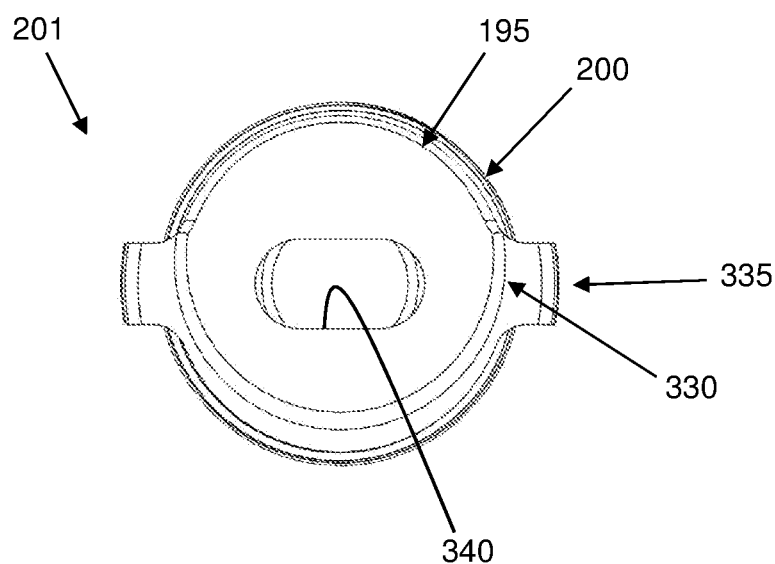

The distal end view of the tibial fixation device 201 is shown in FIG. 102A. The relationship between the diameters of the device is illustrated. The features that protrude furthest out from the center of the device are the retaining bumps 335. The outer surfaces of the tabs 330 are approximately the same dimension as the tunnel diameter, thus creating a definitive separation of the ligaments. The outer diameter of the tibial fixation screw 200 is just slightly less (e.g., 0-1 mm less) than the tunnel diameter to tightly compress the ligament against the walls of the bone tunnel. The recessed portion of the TLS 195 provides a space for the ligament strands to reside in the final placement. By appropriately rotating the TLS 195 (see below), the canted face 205 of TLS 195 is aligned with the tibial plateau and the ligament strands are directed to their proper anatomic locations. The slot 340 in the TLS 195 is used to rotationally position the TLS 195 with the tibial alignment pin (see below).

Figure 102B:
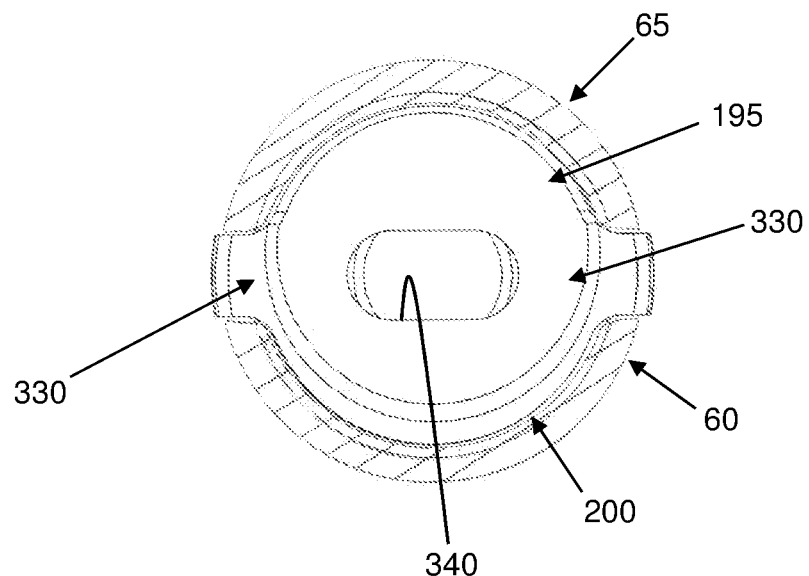

FIG. 102B illustrates what the graft strands 60, 65 look like in an end view cross-section. The graft strands 60, 65 are bound on the outside of the tibial fixation device 201 by the bone tunnel diameter. The graft strands 60, 65 are squeezed between the TFS 200 and the bone tunnel, and are directed into position by the tabs 330 and recesses of the TLS 195. The preferred embodiment comprises two tabs 330, but the TLS 195 might be further subdivided into three or four sections to further differentiate the fibers of the ACL reconstruction.

In the associated surgical procedure, the tibial tunnel is drilled with normal technique, giving consideration to the angles $\alpha$. The smaller angle $\alpha$ creates a more elliptical tunnel exit at the top of the tibia.

In order to understand the overall system for tibial fixation, several of the component interfaces are illustrated first.

Figure 103:
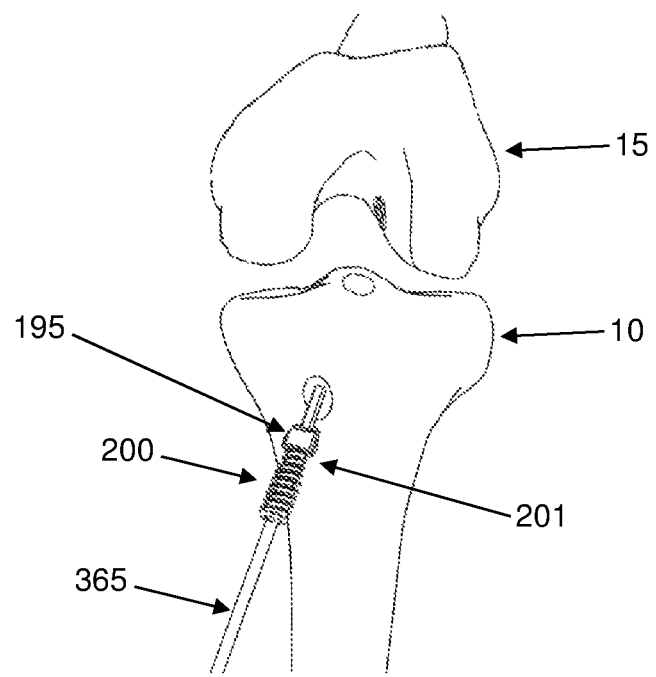
Figure 105:
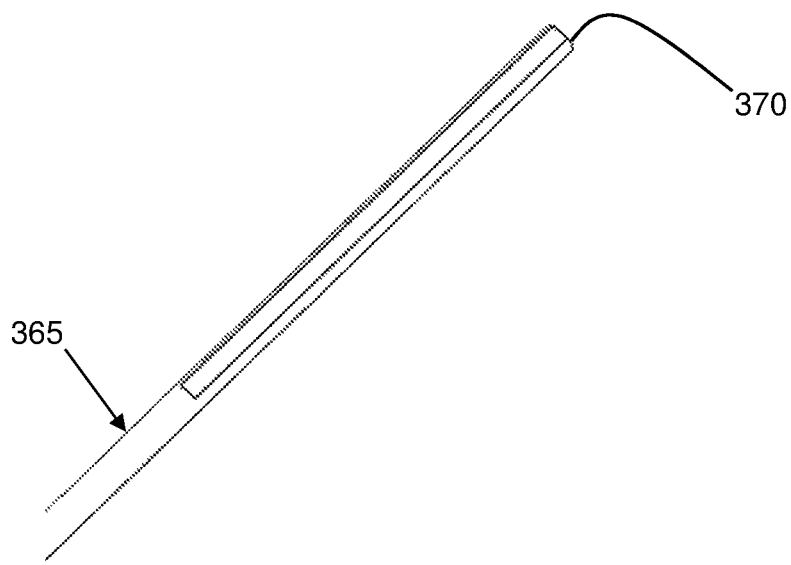

The tibial fixation device 201 fits over the tibial alignment pin 365 (FIG. 103). The slot 340 in the tibial ligament spacer 195 aligns with the end 370 of the tibial alignment pin 365 (FIG. 105).

Figure 104:
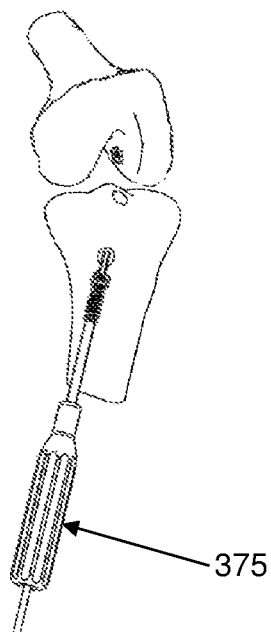

The hex wrench 375 (FIG. 104) fits over the tibial alignment pin 365 and can rotate freely around the pin diameter. Both the hex wrench 375 and the tibial fixation screw 200 can rotate freely over the tibial guide pin 365.

Figure 106:
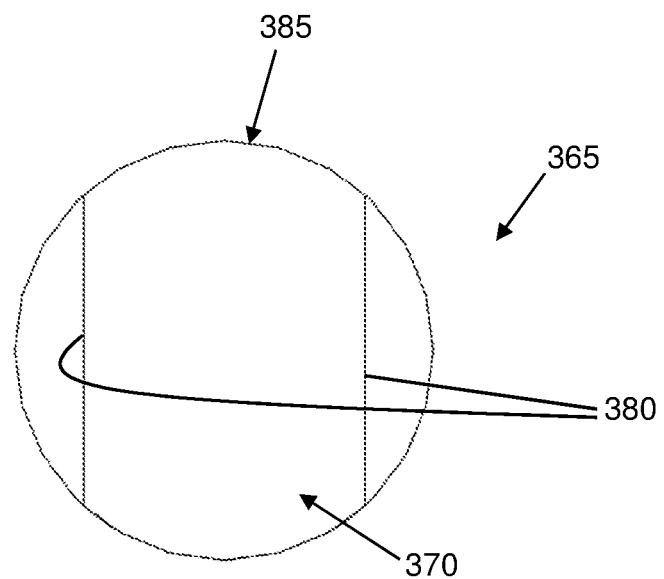

The end 370 of the tibial alignment pin 365 (FIG. 106) that engages with the tibial ligament spacer 195 has two flats 380 on opposing sides of the pin 365, forming a tab 385 that fits into the slot 340 of the tibial ligament spacer 195, whereby to permit tibial alignment pin 365 to turn tibial ligament spacer 195 as desired.

Figure 107:
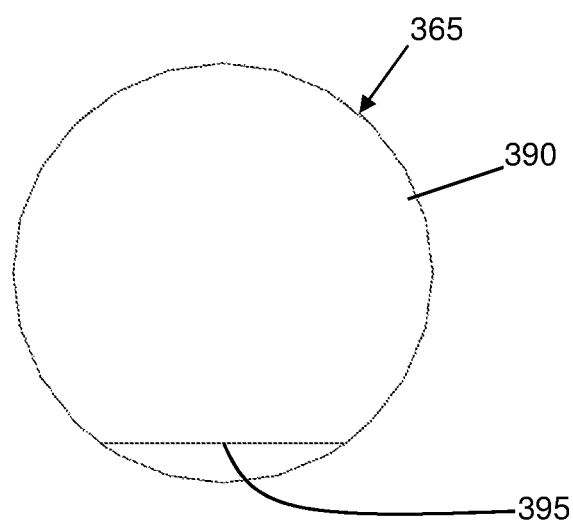

The opposite end 390 (FIG. 107) of the tibial alignment pin 365 preferably has at least one flat 395 (and may have more) for aligning with additional instrumentation, e.g., as discussed below.

Figure 108:
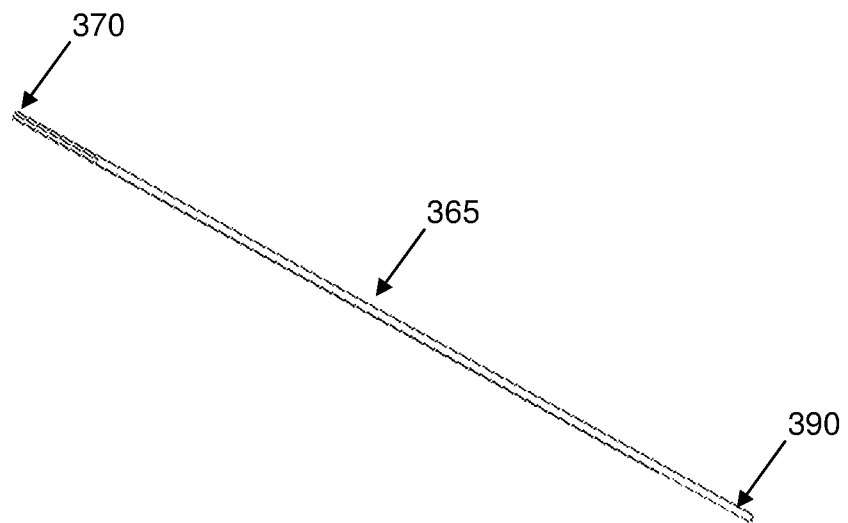

The overall tibial alignment pin 365 is shown in FIG. 108. The end 370 is the tab side that engages with the tibial fixation device 201 (in particular, with the slot 340 of the TLS 195). The opposite end 390 engages with additional instrumentation (see below).

Figure 109A:
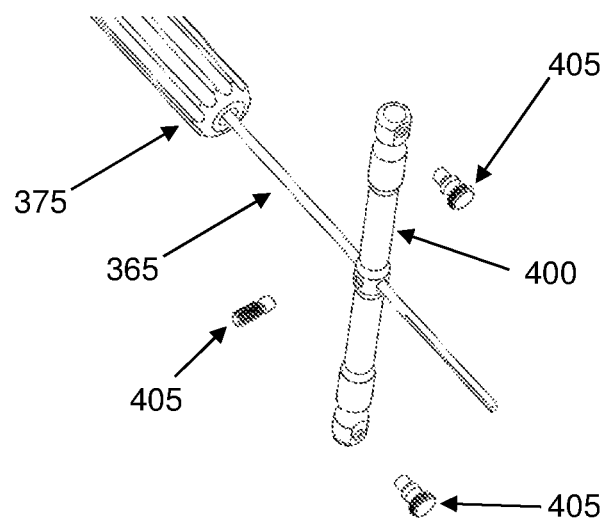
Figure 109B:
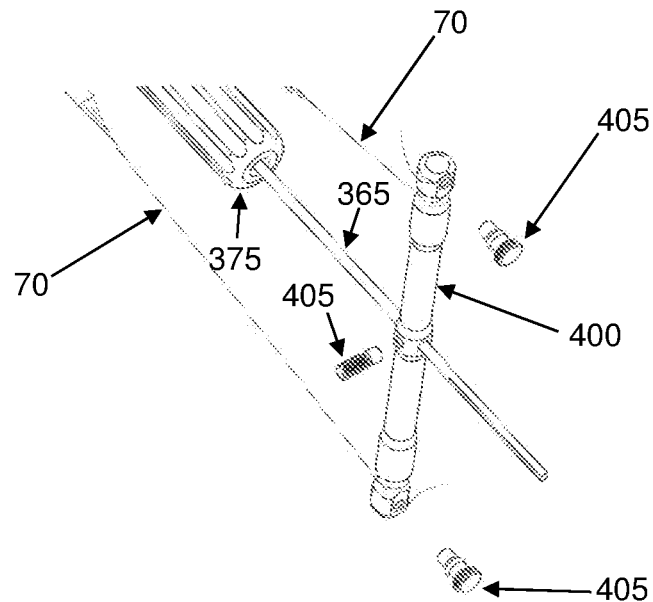

Looking now at FIGS. 109A and 109B, the aforementioned additional instrumentation preferably comprises the ligament tensioning bar 400. The ligament tensioning bar 400 includes fasteners 405 (shown as thumbscrews in FIGS. 109A and 109B). The fasteners 405 are used to tighten down and secure sutures 70 coming from the ligament graft. Grooves at each end of the bar 400 may be used to wrap the sutures 70 prior to tightening with the fasteners 405, e.g., for additional fixation. The fastener 405 in the middle of the ligament tensioning bar 400 tightens down onto the flat 395 on the tibial alignment pin 365, rotationally fixing the tibial tensioning bar 400 to the tibial alignment pin 365. The handle end of the hex wrench 375 is shown in FIGS. 109A and 109B.

The set-up of ligament graft sutures 70 and the ligament tension bar 400 is shown in FIG. 109B. The sutures 70 are secured to the ends of the ligament graft and wrapped in the grooves on the ligament tensioning bar 400. The fasteners 405 are then tightened into place.

Figure 110:
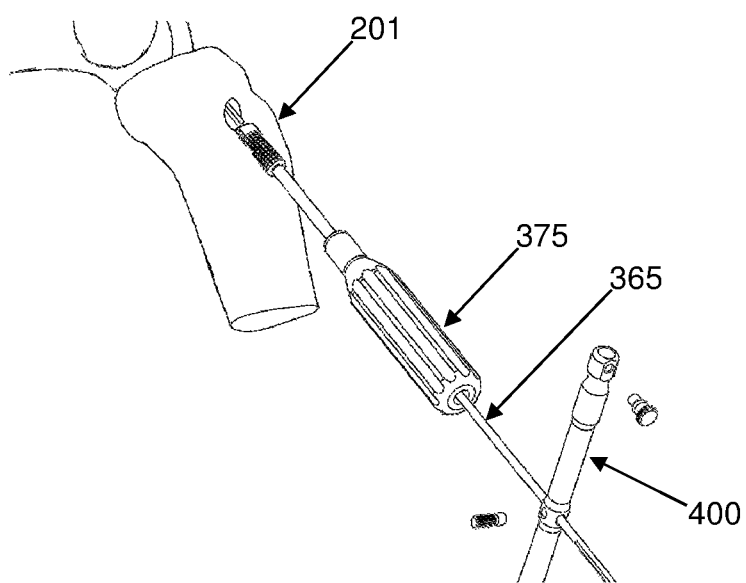

FIG. 110 shows the relationship of the tibial fixation device 201, the tibial alignment pin 365, the hex wrench 375 and the ligament tensioning bar 400.

In more detail, FIG. 111A shows the tip of the hex wrench 375 about to engage with the tibial fixation device 201. The ligament graft and sutures are not shown in FIG. 111A for clarity of illustration. The end of the tibial alignment pin 365 is shown engaged with the TLS 195. The TLS 195 is constrained to rotate only as the tibial alignment pin 365 is rotated, inasmuch as the tibial alignment pin 365 comprises a tab with flats 380 that fits into the slot 340 in the TLS 195. The tibial fixation screw 200 and the hex wrench 375 are free to rotate on the tibial guide pin 365.

FIG. 111B illustrates how the tibial ligament spacer 195 is pushed (using hex wrench 375 to push TFS 200 and hence TLS 195 distally on the tibial alignment pin 365) between the strands 60, 65 of the graft ligament (the strands 60, 65 are shown without tension in the strands for visualization purposes).

Looking now at FIG. 112, hex wrench 375 can engage with the tibial fixation screw 200. The tibial fixation screw 200 then rotates as the hex wrench 375 is rotated.

The overall system is shown in FIG. 113A (but without the ligament graft or sutures for clarity of illustration).

Looking now at FIG. 113B, the ligament strands 60, 65 and sutures 70 are added to the drawing, illustrating the overall functional construct. To summarize the method, ligament graft sutures 70 are fastened to the ligament tensioning bar 400 with the fasteners 405. The tibial alignment pin 365 is passed through the center hole of the ligament tensioning bar 400. The hex wrench 375 and the tibial fixation device 201 are slid over the tibial alignment pin 365. The tibial alignment pin 365 is then loosened from the ligament tensioning bar 400 and extended into the tibial tunnel for the length of the tunnel. The tibial alignment pin 365 may have markings on its outer surface to indicate the depth that it has traveled into the tibial tunnel. When the tibial alignment pin 365 has been appropriately inserted into the tibial tunnel, the middle fastener 405 on the ligament tensioning bar 400 is tightened so as to secure the tibial alignment pin 365 to the ligament tensioning bar 400. At this point, the orientation of the tibial ligament spacer 195, the tibial guide pin 365, and the ligament tensioning bar 400 are rotationally fixed together, and the orientation of the tibial ligament spacer 195 can be rotationally adjusted by rotating the ligament tensioning bar 400 about the axis of the tibial guide pin 365. When tension is applied to the ligament tensioning bar 400, the bar can then be rotated to align the tibial ligament spacer 195 into the desired orientation. Specifically, the recesses between the tabs 330 on the tibial ligament spacer 195 are then adjusted so as to place the ligament strands into their anatomic AM and PL locations. The length of the ligament tensioning bar 400 may be varied as desired so as to space the suture lines to the desired extent and allow more space for the user to grip the handle of hex wrench 375.

FIG. 114 shows another view of the system, without the ligament graft 60, 65 and the sutures 70 being shown.

Next, and looking now at FIG. 115, as tension is applied to the ligament tensioning bar 400, the hex wrench 375 is turned to advance the tibial fixation device 201 into the tibial tunnel.

FIG. 116 illustrates the final position of the tibial fixation device 201 in the tibial tunnel. As discussed above, the ligament graft recesses are positioned for anatomic location of the AM and PL bundles.

The instrumentation is then disengaged from the tibial fixation device 201 as shown in FIG. 117.

The reconstructed ligament construct is then complete. FIG. 118 shows a top view of the ligament construct with the knee in 90 degrees flexion. The top of the tibial fixation device 201 (i.e., the tibial ligament spacer 195) is shown, as is the tibial fixation screw 200. The recesses between the tabs 330 are located so as to properly position the AM and PL bundles. FIG. 118 also shows the femoral fixation device 110.

FIG. 119A is a side view of the tibial and femoral fixation discussed above. The ligament graft is omitted from this view for clarity of illustration.

FIG. 119B is a view like that of FIG. 119A, except that it also shows the graft ligament strands 60, 65. The knee is shown in 90 degrees of flexion. The AM bundle 60 (A-A) crosses the PL bundle 65 (B-B) in the same way as the natural ACL.

FIG. 119C is another view showing the femoral fixation device 110 and the tibial fixation device 201. In this view the knee is in full extension.

FIG. 119D is a side view which illustrates how the AM graft 60 (A-A) is roughly parallel to the PL graft 65 (B-B) when the knee is in full extension, in the same way as the natural ACL.

FIG. 120A is a front view of the completed construct discussed above.

FIG. 120B is a view like that of FIG. 120A, except showing graft ligament strands 60, 65. The AM bundle 60 appears near the front of the tibia at the tibial tunnel. The PL bundle 65 is posterolateral to the AM bundle 60 at the tibial tunnel exit. The construct therefore more closely replicates the nominal location and approximate shape of the natural ACL.

In addition to the advantages listed earlier for the tibial fixation device, the present version of the invention includes at least the following advantages and benefits:

(1) An integrated, assembled tibial fixation device, with the tibial fixation screw 200 and the tibial ligament spacer 195 being assembled together prior to insertion in the tibia.

(2) An added slot alignment feature in the tibial ligament spacer 195 for remote orientation of the TLS 195 into the desired anatomic position.

(3) Small bumps 335 on both sides of the TLS ligament separation tabs 330 allow the assembly into the tibial tunnel, but resist pull through as the bumps reach the harder tibial cortex at the mouth of the tibial tunnel.

(4) A system of instruments that allows orientation of the TLS, tensioning of the ligaments and tightening of the tibial fixation device 201 into its final position, all introduced and fixed into place from the outside of the tibia (antegrade), rather than from the inside of the joint (retrograde).

Alternatives for the Second Preferred Construction and Method of Use

In another embodiment of the invention, and looking now at FIG. 121A, alignment markings 410 are formed on a new device, the spacer orientation guide 415, as well as the ligament spacer alignment tool 305, the femoral ligament spacer 120 and the tibial spacer 195. The alignment markings 410 are placed in a location that is visible and non-ambiguous in order to create the most flush or even fit with the native bone surface.

In this form of the invention, after the bone tunnels are drilled into the femur, the specially shaped spacer orientation guide 415 is inserted into the femoral tunnel. The spacer orientation guide 415 has a handle 420 at one end and a plug 425 at the other end. The plug 425 has two angled surfaces, one (430) as a guide for the femoral tunnel (the near surface) and one (435) as a guide for the tibial tunnel (the far surface). Alignment marking 410 extends along the plug 425, and this alignment marking is aligned with the tips, or extreme points, of the elliptical faces 430, 435. The marking location at the extreme points is an example. Other marking locations around the plug 425 may also be used.

Looking now at FIG. 121B, the spacer orientation guide 415 has its plug 425 inserted first into the femoral tunnel. The elliptical surface 430 of the guide is aligned such that it is approximately even with, or flush with, the femoral tunnel entrance.

The fully inserted spacer orientation guide 415 is shown in FIG. 122. The guide is rotated until the near surface 430 of the plug 425 at the end of the guide is best aligned with the bone surface.

Then the mark 410 on the spacer orientation guide 415 is visualized. A corresponding mark 440 is made on the adjacent bone surface with a sterile, surgical pen or a small awl or pick. See FIG. 123.

In this form of the invention, femoral spacer alignment tool 305 includes a corresponding "line" or "marking" 410 corresponding to the tips, or extreme points, or other marked locations, of the ellipse. See FIG. 124A. Similarly, the femoral ligament spacer 120 includes an alignment marking 410 on its surface as well. See FIG. 124B.

While the guide pin 25 is still in place, the femoral fixation device 110 is inserted into the femoral tunnel. The femoral alignment tool 305 engages the FLS 120 and rotates the FLS 120 into alignment (i.e., so that the marking 410 on FLS 120 is aligned with the marking 440 made on the adjacent bone). Then FLS 120 is tightened into position. See FIG. 125.

The aligned FLS 120 is shown in FIG. 126.

In a similar fashion, the tibial fixation device 201 is placed utilizing a mark 445 on the tibial surface. See FIGS. 127-130.

The use of the spacer orientation tool 415, the spacer alignment tool 305 and the marked ligament spacers 115, 195 allows an improved fit between the ligament graft spacers and the bone surfaces. The resulting location of the ligament spacers, both femoral (115) and tibial (195), creates a reconstruction that is closely aligned with the native bone surfaces. This alignment contributes to anatomic fixation of the ligament grafts by giving the surgeon a target to align to when tightening the fixation devices into place.

The benefits of the aligned ligament graft spacers 115, 195 include:

(1) Both the femoral and tibial ligament spacers 115, 195, respectively, are inserted such that they are aligned with the bone surface. This allows more natural movement of the ligament, as if bone had already filled in the space around the ligament graft.

(2) The aligned ligament graft spacers 115, 195 help to ensure an anatomic construction, separating the AM bundle 60 and PL bundle 65 and positioning them into their correct anatomic positions.

(3) The aligned ligament graft spacers 115, 195 provide a clear target for aligning the ligament spacers.

Third Preferred Construction and Method of Use

The following pages describe improvements to the anatomic single tunnel femoral and tibial fixation.

The alternative version of the femoral fixation device 510 consists of a femoral fixation screw (FFS) 515 (FIG. 131) and a femoral ligament spacer (FLS) 520 (FIG. 132).

In this embodiment, femoral fixation device 510 (i.e., both femoral fixation screw 515 and femoral ligament spacer 520) may be made from biocompatible metal, plastic, absorbable ceramic, bone graft material or a combination of these materials.

Looking now at FIG. 131, femoral fixation screw (FFS) 515 includes an elongated neck 525 for receiving femoral ligament spacer 520. In this embodiment, the tapered threaded portion or bone tunnel thread 530 of FFS 515 engages directly with a bone tunnel, rather than pressing the ligament grafts against the wall of the bone tunnel. The smaller retaining threads 535 (between bone tunnel threads 530 and elongated neck 525) are utilized for retaining femoral ligament spacer 520. The bone tunnel threads 530 are located further away from the head of the screw, as compared to the earlier embodiments. The smaller retaining threads 535 are preferably left hand threads for retaining femoral ligament spacer 520 during tightening of femoral fixation screw 515, such that femoral ligament spacer 520 does not loosen from femoral fixation screw 515 during tightening of the right handed bone tunnel threads 530 into the bone tunnel. Also, femoral fixation screw 515 has a cannulation through its length to slide along an alignment pin as it is tightened into the bone tunnel.

Looking now at FIG. 132, femoral ligament spacer (FLS) 520 is lengthened in this embodiment to span a longer length of the bone tunnel. One, two, three or more windows 540 are formed through femoral ligament spacer 520. In the embodiment shown in FIG. 132, femoral ligament spacer 520 has two windows, one on each side of the femoral ligament spacer. Windows 540 are bounded by tension members 550 that extend off the end of the FLS tabs 545 and connect the two ends of the FLS. Windows 540 are used to pass the ligament grafts directly through FLS 520, and around tension members 550, rather than passing the ligament grafts over and around the threads of the FFS.

Similar to the previous embodiments, FFS 515 and FLS 520 are assembled by bringing the two components into axial alignment as shown in FIG. 133. The components are assembled together with the small left hand retaining threads. As in the earlier embodiments, FLS 520 disengages from the retaining threads 535 of FFS 515 after sufficient rotation, and can then freely rotate about FFS 515.

The assembled femoral fixation device 510 is shown in FIG. 134A. Windows 540 in the middle of femoral fixation device 510 are used to pass the ligament grafts through and to allow the ligament grafts to be pulled into the femoral tunnel as the FFS 515 is screwed into the femoral tunnel.

FIG. 134B shows the assembled femoral fixation device 510 with the ligament grafts passed through graft windows 540. In this configuration, two soft tissue grafts are harvested from the patient or obtained from a tissue bank; typically the gracilis and semitendinosus. Each of the two ligament grafts is looped around one of each of the tension bars 550 of femoral ligament spacer 520.

The ligament grafts near the top of FIG. 134B are comprised of either of the soft tissue grafts (gracilis or semitendinosus). The ligament grafts near FIG. 134B are comprised of the other graft strand (gracilis or semitendinosus). Then, one strand of the gracilis and one strand of the semitendinosus are brought into close proximity to one another to form the AM bundle. The opposite strands of the gracilis and semitendinosus form the PL bundle. The bundles may be sutured together near graft windows 540 through the femoral ligament spacer 520 to further organize the grafts into the AM and PL bundles as shown in FIG. 134C.

A cross-sectional view of the assembled femoral fixation device 510 (FIG. 135) further illustrates how the femoral fixation device functions. Retaining threads 535 and FLS 520 function in much the same way as the previous embodiments. However, the length of femoral fixation device 510 is increased such that retaining threads 535 are close to bone tunnel threads 530 and the head 526 of FFS 515 and the oblique face 542 OF FLS 520 are near the bone tunnel entrance. As stated above, an elongated neck 525 exists between retaining threads 535 and head 526. The femoral fixation screw head 526 provides circumferential support to FLS 520. Also, elongated neck 525 places head 526 and the hexalobe drive socket 527 (FIG. 131) near the proximal portion of the device and therefore provides easy access for a hex wrench.

Graft windows 540 are formed into the sides of FLS 520 to allow the ligament grafts to be looped through, past neck 525 of FFS 515 and back out of the device and into the bone tunnel entrance. Therefore, in this version of the device, the ligament grafts are not pressed between bone tunnel threads 530 and the bone tunnel. In this improved embodiment, rotation of FFS 515 is completely independent of the ligament grafts. Thus, rotation of the ligament grafts, or the tendency for rotation, is eliminated.

Since bone tunnel threads 530 of FFS 515 do not compress the ligament grafts against the bone tunnel wall, the threads can be enlarged slightly (about 5% to 15% larger than the bone tunnel) to cut into the bone tunnel and further increase the pullout strength of the construct. As can be seen in an end view of the assembled femoral fixation device 510 (FIG. 136A), FFS 515 forms the larger outer diameter of the femoral fixation device 510.

As the device is inserted into the bone tunnel, the ligament grafts (as shown by cross-hatching in FIG. 136B) are spread and compressed into graft windows 540. Note that the outside diameter represents the diameter of FFS 515. The thread diameter of the FFS 515 is slightly larger than the tunnel diameter to form threads in the bone tunnel and to increase the pullout strength of the construct.

An additional view (FIG. 137) of the femoral fixation device shows the relationship between threads 530 of FFS 515, and the graft windows 540 and oblique face 542 of FLS 520. The angle of oblique face 542 can be produced in various degrees of steepness or flatness to match the unique angle of the varied bone surfaces and surgical bone tunnel placement.

Figure 138:
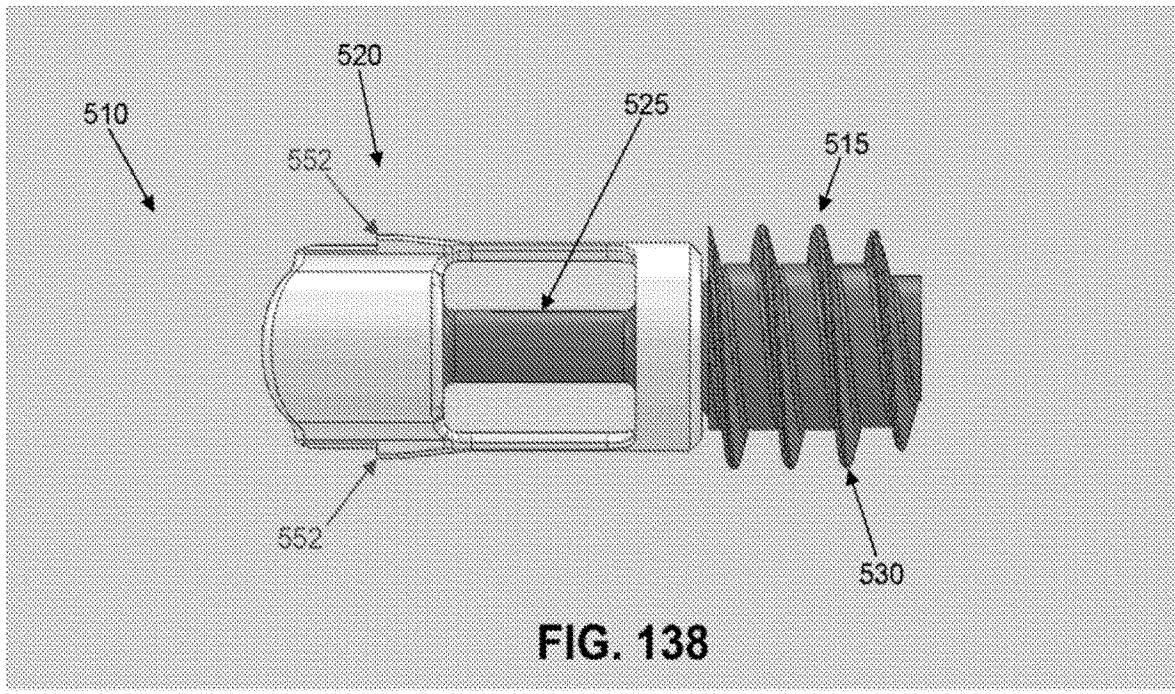

FIG. 138 shows the front side of femoral fixation device 510 (the side facing more toward the front of the patient, or anteriorly). The small barbs 552 protruding from the sides and the windows through the FLS 520 are shown. Neck 525 and threads 530 of the FFS 515 are also shown.

Figure 139:
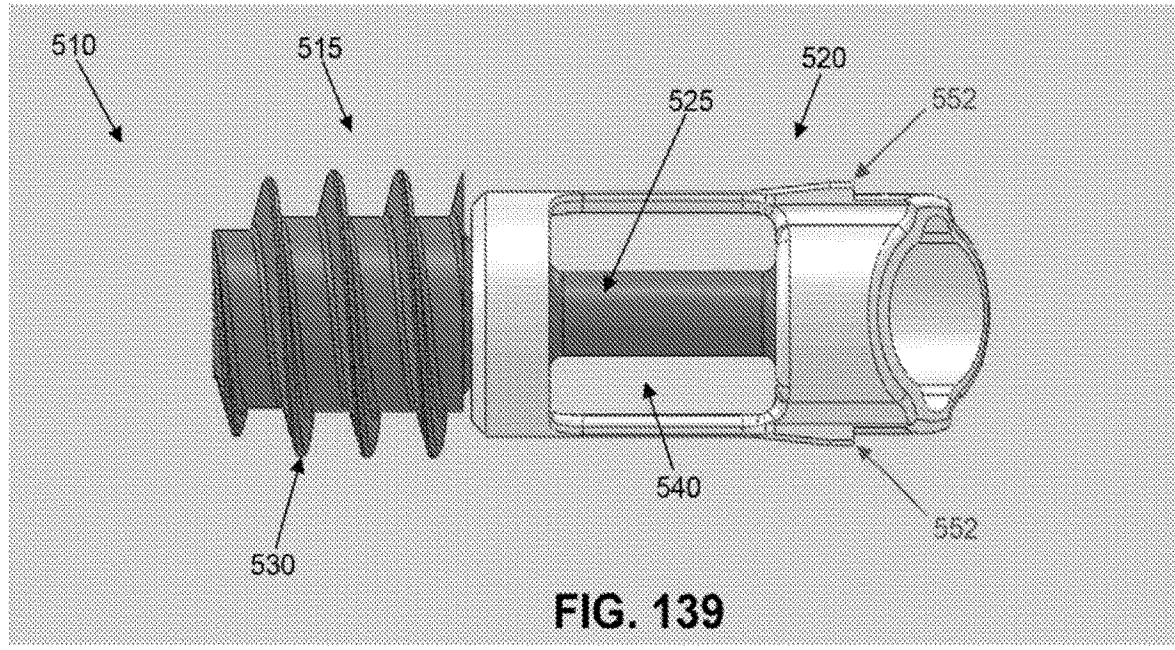

FIG. 139 shows a back side of femoral fixation device 510 (the side facing more toward the back of the patient, or posteriorly). FIG. 139 shows threads 530 and neck 525 of FFS 515 and windows 540, barbs 552 and oblique face 542 of the FLS 520.

Figure 140:
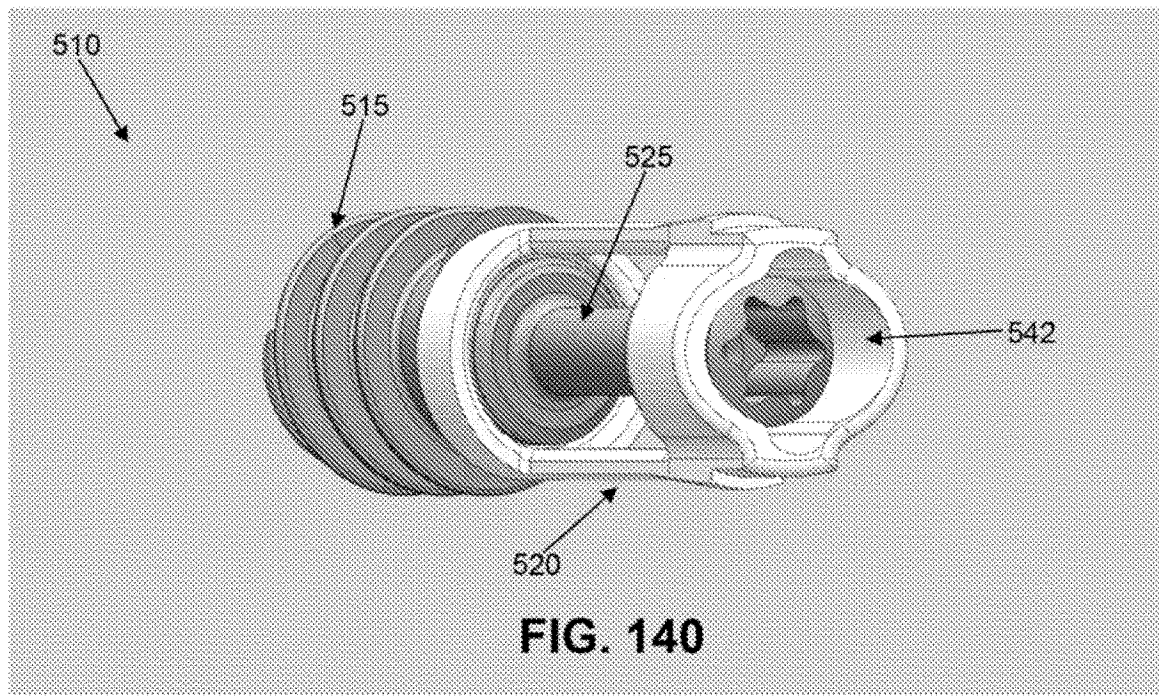

An additional view, shown in FIG. 140, is a view looking directly into oblique face 542 of FLS 520.

Looking now at FIG. 141A, after guide pin 25 has been placed and the bone tunnel has been drilled to the proper depth, femoral fixation device 510, with the ligament grafts properly assembled to the femoral fixation device, is placed over guide pin 25 and inserted through the anteromedial or accessory medial (AM) portal. FIG. 141A shows femoral fixation device 510 over guide pin 25, about to enter the femoral tunnel. It is shown without the ligament grafts for clarity.

In another view, FIG. 141B, femoral fixation device 510 is shown partially inserted with the ligament grafts looped through the FLS 520 as described earlier. The AM bundle is in its anatomic position behind femoral fixation device 510 and the PL bundle is in front of femoral fixation device 510. Guide pin 25, femoral fixation device 510 and the ligament grafts are all inserted through the AM portal. This ensures easy passage of the femoral device fixation and ligament grafts directly into the femoral bone tunnel with an arthroscopic technique.

FIG. 142 shows femoral fixation device 510, sliding over guide pin 25, with a ligament spacer alignment tool 555 and a hex wrench 560 being positioned to insert the device and to align FLS 520. The ligament grafts are not shown. Both ligament spacer alignment tool 555 and FLS 520 can freely rotate independently of hex wrench 560 and FFS 515, respectively. Using ligament spacer alignment tool 555, a user orients FLS 520 into the approximate anatomic position, such that oblique surface 542 of FLS 520 is approximately parallel to the mating bone surface.

FIG. 143 is an overall view of the knee joint, femoral fixation device 510, ligament spacer alignment tool 555 and hex wrench 560. Again the ligament grafts are not shown for clarity of the devices. In a preferred embodiment, ligament spacer alignment tool 555 comprises an opening 565 which provides clearance for ligament spacer alignment tool 555 to pass by the adjacent femoral condyle. Opening 565 also provides the surgeon with a reference feature to visually check the alignment of ligament spacer alignment tool 555. Hex wrench 560 is then engaged with FFS 515. Ligament spacer alignment tool 555 is engaged with FLS 520, by virtue of the small tabs protruding from the tip of the tool into the slots 553 formed in FLS 520 (FIG. 132).

FIG. 144 shows femoral fixation device 510 entering the bone tunnel with the ligament grafts. As FFS 515 is rotated into place with hex wrench 560, FLS 520 stays in position (with the use of ligament spacer alignment tool 555) and the ligament grafts are gently pulled into the femoral tunnel through the AM portal. FFS 515 engages directly with the bone tunnel, so there is no injurious abrasion or cutting of the ligament grafts during insertion. Also, there is more efficient use of the ligament graft tissue since the ligament grafts do not need to travel over the end of FFS 515, but instead through graft windows 540 in FLS 520.

As femoral fixation device 510 is inserted, tension bars 550 and tabs 545 on FLS 520 separate the two graft ligament bundles into their anatomic position. This is especially important since in practice, the ligament grafts quite often obscure the view of a fixation screw. By using ligament spacer alignment tool 555, the user can be assured that femoral fixation device 510 is inserted properly, the ligament grafts are separated and the ligament grafts are not twisting around FLS 520.

The notations at the bottom of FIG. 144 are S, G, G', and S'. For clarity, S to S' is one continuous ligament graft and G to G' is one continuous ligament graft. The AM bundle is formed by combining the S and G ligament grafts and the PL bundle is formed by combining the G' and S' ligament grafts.

FIG. 145A shows femoral fixation device 510 fully inserted into the femur and approximately congruent to the bone surface. Ligament spacer alignment tool 555 is shown engaged with FLS 520. The ligament grafts are left out to illustrate the devices.

FIG. 145B shows femoral fixation device 510 fully inserted into the femur with the ligament grafts extending therefrom. Sutures are looped around the ligament grafts. Sutures may then be looped around the sutures which have been looped around the ligament grafts and fed through the AM portal. The sutures are retrieved with a suture hook or grasper and pulled through the tibial tunnel.

In another improved and preferred embodiment of the femoral fixation device, the femoral fixation screw (FFS) may be configured with a short neck such that the graft windows extending through the femoral ligament spacer (FLS) are not obstructed by the neck of the FFS.

In this embodiment, and looking now at FIGS. 146-148, femoral fixation device 610 comprises a femoral fixation screw 615 (FIG. 146) and a femoral ligament spacer 620 (FIG. 147). FFS 615 has a shortened neck 525 with a hexalobe-type wrench socket 627. FFS 615 is slightly longer, allowing more threads 630 to engage with bone. By shortening neck 625 of FFS 615 and recessing wrench socket 627, the ligament grafts have more room to pass through the graft windows of FLS 620. This allows FLS 620 to be slightly shorter than the previous embodiment. Near the distal tip of FFS 615, there is a small groove 635 formed into threads 630 for thread cutting during insertion in the cortical bone. At the proximal end of FFS 615 (i.e., the larger diameter end), there is a small groove 637 formed into threads 630 for thread cutting during removal of femoral fixation device 610 from the bone tunnel. Smaller grooves 635 and 637 are useful in the event of a later surgical revision, or if FFS 615 were to be removed.

FFS 615 and FLS 620 are assembled in the same fashion as the earlier embodiments and are shown in their assembled state in FIG. 148. Again, the tapered threaded portion or bone tunnel threads 630 of FFS 615 engage directly with the bone tunnel, rather than pressing the ligament grafts against the wall of the bone tunnel. However, in this embodiment, threaded portion 630 of FFS 615 narrows to a much smaller thread diameter. The smaller thread diameter facilitates driving FFS 615 into the distal cortex of the femur, thereby further enhancing the pullout strength. Also, as discussed above, the first one or two threads of FFS 615 have a small cut-out feature or groove 635 for cutting the threads into the distal cortical bone.

As also discussed above, by shortening neck 625 of FFS 615, graft windows 640 of FLS 620 have a larger area for the graft ligaments to pass through. The increased window space allows easier passage of the ligament grafts therethrough. As a result, tension members 650 can be manufactured to a wider dimension, strengthening FLS 620 and increasing its tension loading capability.

In the previous embodiment, head 526 of FFS 515 supports FLS 520 in the area of graft windows 540, where FLS 520 supports the ligament grafts against the bone wall. This forces the small barbs 552 on the outside of FLS 520 to dig more deeply into bone. Head 526 may also provide more support of the ligament grafts against the bone tunnel. Alternately, with the neck eliminated and the screw head positioned away from the proximal portion of FLS 620 (as in the current embodiment), FLS 620 has more flexibility to squeeze into the bone tunnel permitting a larger variation of ligament graft sizes and densities.

In use, and looking now at FIG. 149, the ligament grafts are passed through windows 640 of femoral fixation device 610. Femoral fixation device 610 has the advantage over the previous embodiments in that graft windows 640 are clear of any device features that could possibly interfere with the passage of the graft ligaments through the windows. Tension members 650 and tabs 645 align the ligament grafts such that the ligament grafts rest in the graft windows 640. A suture may be added to further secure the ligament grafts together. Another advantage of this embodiment is that the graft ligaments do not need to be split into two or more strands. This may allow greater utility for securing other graft types such as the quadriceps tendon graft. This embodiment may also be suitable for more allograft (graft from a donor) types such as Achilles tendon graft or anterior tibialis tendon.

The cross-sectional view of femoral fixation device 610 in FIG. 150 further illustrates how femoral fixation device 610 functions. In this embodiment, the retaining threads on neck 625 and hexalobe drive socket 627 of FFS 615 are both close to bone tunnel threads 630, making clear and open graft windows 640 through FLS 620. Again in this embodiment, ligament grafts are not pressed between bone tunnel threads 630 of FFS 615 and the bone tunnel. Since the ligament grafts are looped through FLS 620 only, any rotation of the ligament grafts is eliminated during the tightening of the FFS 615.

In an end view of femoral fixation device 610 (FIG. 151A), it can be seen that the femoral fixation device 610 provides wider ligament separation tabs 645. The wider ligament separation tabs 645 further separate the AM and PL bundles of the ligament grafts as shown in FIG. 151B, where cross-hatching is drawn to show the ligament grafts. Also, tension members 650, behind tabs 645, are wider which strengthens the overall construct. The center hole through FLS 620 serves the unique purpose of aligning and passing a hex wrench into hexalobe socket 627 of FFS 615.

Now, returning again to the surgical technique, an additional drilling step is used to create an approximately 4 mm to an approximately 5 mm hole through the distal cortex of the femur. The additional hole is drilled by placing a drill bit over guide pin 25, which is centered in the femoral tunnel after drilling the larger femoral tunnel. See FIG. 152.

The newly drilled femoral tunnel then consists of a regularly-sized bone tunnel 652 (e.g., typically 7 mm to 10 mm in diameter) through most of the femur and a smaller-sized bone tunnel 655 (e.g., approximately 4 mm to 5 mm) through the distal cortex. FIG. 153 shows the femoral tunnel as viewed from the tunnel entrance. The addition of a smaller sized bone tunnel 655 is a commonly practiced step when button-type fixation is passed through the smaller bone tunnel. In this case, instead of using the smaller sized bone tunnel 655 for button fixation, the smaller threads 635 at the tip of FFS 615 will engage into the femoral cortex for improved stability and fixation strength.

After drilling the smaller 4 mm to 5 mm hole 655, the drill bit is removed and guide pin 25 is left in place. A coaxial spacer 660 is introduced and slid over guide pin 25 to center guide pin 25 into the bone tunnel and into the smaller drilled hole 655. See FIG. 154. Coaxial spacer 660 tapers outward slightly at the proximal end in order to fit closely into the smaller hole through the cortex. The coaxial spacer 660 may fit tightly, or even with a slight press fit, in order to keep coaxial spacer 660 aligned and fixed in the smaller hole. From the position shown in FIG. 154, coaxial spacer 660 is pushed almost through the distal cortex so that it locates guide pin 25 in the center of the hole, but does not occupy a significant portion of the larger portion of the bone tunnel.

Then, a hex wrench or hexalobe drive tool 665 is brought into alignment with guide pin 25 and femoral fixation device 610 carrying the ligament grafts. A side view of the knee is shown in FIG. 155. Hexalobe drive tool 665 is inserted into the proximal end of femoral fixation device 610, past the ligament grafts and into hexalobe drive socket 627 in FFS 615. The ligament spacer alignment tool 555 is not shown in FIG. 155 for clarity.

In the far upper left portion of FIG. 155, coaxial spacer 660 is shown holding guide pin 25 in the center of the femoral tunnel. Guide pin 25 traverses through the accessory medial (AM) portal.

Ligament spacer alignment tool 555 is added and hexalobe drive tool 665 is manipulated through the ligament grafts to reach hexalobe drive socket 627. Femoral fixation device 610 is then inserted into the joint through the AM portal along guide pin 25. See FIG. 156. Coaxial spacer 660 is shown at the distal end of the femoral tunnel. Coaxial spacer 660 centers guide pin 25 to ensure that FFS 615 tightens into the bone tunnel, in coaxial alignment with the bone tunnel.

As FFS 615 is tightened into the femoral tunnel, ligament spacer alignment tool 555 is used to rotate FLS 620 into a position in which canted surface 642 of FLS 620 is roughly parallel to the bone surrounding the aperture of the bone tunnel. As FFS 615 is further tightened, it pulls FLS 620 and the ligament grafts into the femoral tunnel with it. The ligament grafts spread out into graft windows 640, between tabs 645, as FLS 620 is pulled into the bone tunnel. As FFS 615 is tightened into the bone tunnel, guide pin 25 guides FFS 615 into the smaller drilled hole 655 such that the small threaded tip 635 of FFS 615 engages with smaller drilled hole 655. FFS 615 is tightened until FLS 620 is approximately coincident, or recessed slightly inside the aperture of the bone tunnel. In this way, threads 630 of FFS 615 are engaged with the bone tunnel as well as the distal cortical bone. Hexalobe drive tool 665 and ligament spacer alignment tool 555 are removed. Coaxial spacer 660 is pushed through the femoral tunnel by FFS 615 and then coaxial spacer 660 is removed by hand. See FIG. 157A.

FIG. 157B shows the same view as FIG. 157A with the ligament grafts attached to femoral fixation device 610. The AM and PL bundles are now in their anatomic positions on the femoral side. A suture has been passed through the tibial tunnel and looped around the PL bundle sutures for retrieval later.

Improvements to the tibial fixation are described below.

FIGS. 158A and 158B show an improved tibial alignment pin 700. Tibial alignment pin 700 comprises a distal end 705 and a proximal end 710 with a hole 715 extending through distal end 705. Hole 715 may be used to grasp and orient tibial alignment pin 700. Tibial alignment pin 700 further comprises alignment flats 720. Tibial alignment pin 700 is shorter than tibial alignment pin 365 depicted in the previous embodiment, and flats 720 traverse the entire length of tibial alignment pin 700. FIG. 158B shows a close up of distal end 705 illustrating hole 715 extending through the distal end of tibial alignment pin 700.

FIG. 159A shows tibial alignment pin 700, a tibial alignment pin guide 725 and two small fixation wires 730.

The purpose of alignment pin guide 725 is to hold tibial alignment pin 700 in proper position for subsequent steps. Alignment pin guide 725 slides into the tibial tunnel. Alignment pin guide 725 has a canted distal tip 735 that corresponds to the anatomic surface of the tibia. Alignment pin guide 725 also has a slot 737 at the very tip of the distal end to orient tibial alignment pin 700. Alignment pin guide 725 is inserted into the tibial tunnel and the two small fixation pins 730 are placed to secure alignment pin guide 725 into position. There is a friction element, such as an O-ring, a thumb screw or some other element assembled inside alignment pin guide 725 to hold tibial alignment pin 700 into position.

FIG. 159B illustrates alignment pin guide 725, fixation pins 730 and tibial alignment pin 700 placed into position. Alignment pin guide 725 mimics tibial ligament spacer 195 discussed above in that alignment pin guide 725 has a canted surface 735 to align with the tibial plateau and alignment pin guide 725 has a slotted tip 737 to orient tibial alignment pin 700. When positioning alignment pin guide 725, a surgeon is careful to align canted surface 735 with the surface of the tibial plateau. FIG. 159B is shown with two fixation pins drilled into the bone to hold alignment pin guide 725 in position. However, it may only be necessary to use one of fixation pins 730 to properly secure alignment pin guide 725. The use of the alignment pin guide 725 also allows the surgeon to check the positioning of alignment pin guide 725 and tibal alignment pin 700 with viewing equipment such as an arthroscope.

Now with tibial alignment pin 700 in its proper position, a pin retaining clamp 740 is inserted, preferably through the AM portal. The AM Portal is approximately aligned anteromedially to the tibial tunnel. Insertion of pin retaining clamp 740 from the AM portal will align with the anteromedial and posterolateral separation of the tibial tunnel. FIG. 160A shows pin retaining clamp 740 inserted into the AM portal and prepared to engage with tibial alignment pin 700. Pin retaining clamp 740 has two small pin-like posts 745 at each tip to engage into side holes in tibial alignment pin 700. Pin retaining clamp 740 is lockable, so that once tibial alignment pin 700 is engaged with pin retaining clamp 740, the pin retaining clamp can be released from a user's hand and tibial alignment pin 700 may remain in place.

FIG. 160B shows pin retaining clamp 740 secured to tibial alignment pin 700. Alignment pin guide 725 has been removed. With pin retaining clamp 740 in place, tibial alignment pin 700 is sufficiently secured and oriented such that tibial alignment pin 700 splits the boundary between the AM and PL bundles. Pin retaining clamp 740 is held into position by the accessory medial (AM) portal, and can be further adjusted and held by the surgeon to further define the anatomic location.

The AM bundle and the PL bundle are now integral ligament graft bundles. Sutures may be looped around each of the AM bundle suture tails, and the PL bundle suture tails may be grasped with a suture grasper. The PL bundle sutures are grasped and pulled posterior to (behind) tibial alignment pin 700 and pin retaining clamp 740. The PL Bundle is pulled through the tibial tunnel into the PL position (its anatomic position). FIG. 161A shows the PL bundle after being pulled through the tibial tunnel. This is the desired location of the PL bundle. The position of the PL bundle is posterior and slightly lateral to the center of the tibial tunnel, similar to the anatomic ACL insertion on the surface of the tibia.

The AM bundle suture tails are captured by another suture. This suture is passed through the inside of the window 770 formed by pin retaining clamp 740. The sutures are pulled and the AM bundle is pulled into window 770 formed by pin retaining clamp 740 and then through the tibial tunnel. FIG. 161B shows the AM bundle also in its anatomic position. Now both the AM and PL bundles are in their anatomic locations. The suture tails are available for tensioning the ligament graft. Tibial alignment pin 700 and pin retaining clamp 740 remain in position and separate the graft ligament bundles. The next step is the insertion of the tibial fixation device.

FIG. 162 shows a tibial fixation device over tibial alignment pin 700. Careful attention is paid to locating the canted surface of the tibial ligament spacer such that it will be approximately parallel to the tibial plateau. A hex wrench 750 is also slipped over tibial alignment pin 700. The ligament graft suture tails are attached to a tensioning bar 755. In this embodiment, tensioning bar 755 does not need to be secured to tibial alignment pin 700, because the tibial alignment pin is secured with pin retaining clamp 740. Tension is applied to tensioning bar 755 and the tibial fixation device is driven forward with hex wrench 750. The positions of the ligament grafts, both the AM and PL bundles, are maintained by pin retaining clamp 740 and tibial alignment pin 700. The ligament grafts are spread and separated by the tibial ligament spacer while the tibial fixation screw is tightened into place. The tibial fixation device is advanced until the tibial ligament spacer is approximately coincident with, or slightly recessed from the tibial plateau.

After the tibial fixation device is tightened into place, the instrumentaton is removed and the ligament grafts are trimmed down to the bone surface. Tibial alignment pin 700 is the last piece of instrumentation to be removed and is still shown in place with the final ligament construct in FIG. 163.

During the fixation of the ligament grafts in the tibial tunnel, tibial alignment pin 700 is important for separating the AM and PL bundles and guiding the tibial fixation device into position. Firstly, tibial alignment pin 700 is aligned with alignment pin guide 725 to replicate the split between the AM and PL bundles. Secondly, tibial alignment pin 700 aligns the tibial ligament spacer to position the ligament grafts into their anatomic locations. The improvements described in this embodiment ensure that tibial alignment pin 700 is secured during insertion of the ligament grafts as well as during the tightening of the tibial fixation device.

The final construct is shown in FIG. 164 with both the femoral fixation device and the tibial fixation device visible through the bones. The AM bundle is positioned anterior, and medially in the bone tunnel (i.e., in front of and toward the inner side of the tibial fixation device) and the PL bundle is positioned posterior, and laterally in the bone tunnel (i.e., behind and to the outside of the tibial fixation device). The final positioning of the AM and PL bundles closely replicates the normal anatomy of the anterior cruciate ligament.

In addition to the advantages previously stated, the alternative femoral fixation device and the improvements to the instrumentation for positioning the tibial fixation device in the tibial tunnel provide at least the following useful functions in ligament fixation:

(1) The ligament grafts are captured in the graft windows of the femoral ligament spacer and do not rotate as the femoral fixation screw is rotated, eliminating the potential for ligament graft rotation during insertion of the femoral fixation device. The graft windows also eliminate the possibility of cutting the ligament grafts with the threads of the femoral fixation screw since the ligament grafts are not in contact with the threads of the femoral fixation screw.

(2) The femoral fixation screw has a thread diameter that is larger than the bone tunnel diameter, i.e., the femoral fixation screw cuts its own threads into the bone, thereby increasing the pull-out strength of the femoral fixation device.

(3) The smaller distal thread of the femoral fixation screw engages with the distal cortex, further increasing the ability of the femoral fixation device to resist pullout.

(4) The tension on the ligament grafts can be slightly adjusted after the reconstruction is completed. More particularly, the adjustment of the reconstruction is accomplished by tightening the femoral fixation device (i.e., turning the femoral fixation device clockwise) so as to move the femoral fixation device further into the bone tunnel to add tension on the ligament grafts, or by loosening the device (i.e., turning the femoral fixation device counter-clockwise) so as to move the femoral fixation device proximally in the bone tunnel so as to reduce tension on the ligament grafts. Adjusting the tension on the ligament grafts provides a means to more closely match normal ligament mechanics.

(5) The ligament graft construct requires shorter ligament grafts since the ligament graft are passed through the opening in the femoral ligament spacer, rather than over the end of an interference screw. This allows more flexibility in ligament grafts dimensions and preparation.

In addition, the same overall advantages described above in connection with the earlier embodiments also apply to the femoral fixation device described immediately above, including but not limited to the anatomic footprint of the graft ligaments in the bone tunnel, the biomechanical advantages of the anatomic double bundle reconstruction, aperture fixation of the ligament grafts to the bony tunnel wall, potential reduction in tunnel widening, whether biological or mechanical, and potential reduction in bone wear due to the windshield wiper effect.

Furthermore, the same overall advantages described above in connection with the earlier embodiments also apply to the improved instrumentation and techniques for the tibial fixation described immediately above, including but not limited to ensuring that the tibial ligament spacer maintains proper orientation relative to the AM and PL bundles and anatomic separation between the ligament graft bundles.

In addition to ACL reconstruction, the femoral fixation device described above may have utility in other surgical procedures including but not limited to posterior cruciate ligament reconstruction (PCL), biceps tenodesis and lateral knee ligament reconstruction.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

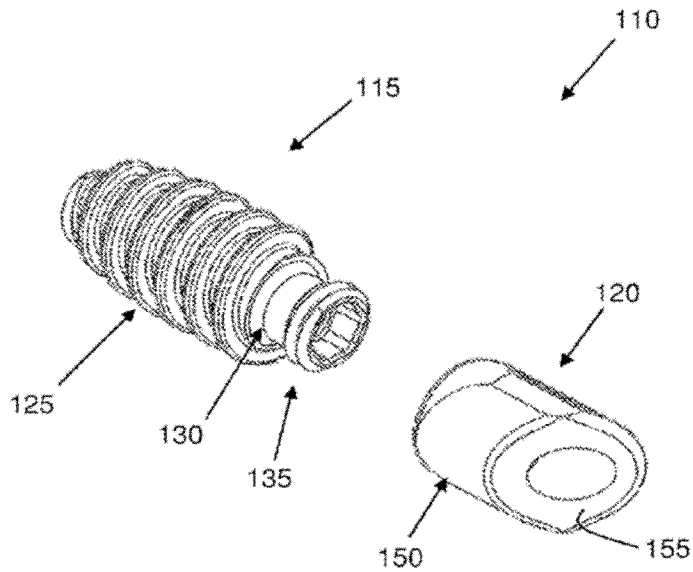

What is claimed is:

1. An apparatus for reconstructing a ligament, the apparatus comprising:
   a fixation device for maintaining a graft ligament in a bone hole formed in a bone, the fixation device comprising:
      a fixation screw having a distal end and a proximal end, the fixation screw comprising:
         a threaded body having a distal end and a proximal end;
         a reduced-diameter threaded portion extending proximally from the proximal end of the threaded body;
         a reduced-diameter neck extending proximally from the reduced-diameter threaded portion; and
         a head extending proximally from the reduced-diameter neck, wherein the head comprises a drive element for driving the fixation screw into the bone hole from the proximal end of the fixation screw; and
      a ligament spacer comprising a distal end, a proximal end, a canted face disposed at the proximal end of the ligament spacer and at least one opening between the distal end and the proximal end of the ligament spacer for receiving the graft ligament,
      wherein the ligament spacer is configured to be coaxially mounted to the fixation screw, with the distal end of the ligament spacer being retained proximal to the threaded body of the fixation screw by the reduced-diameter threaded portion of the fixation screw;
      wherein the fixation device is configured to be advanced into the bone hole with the fixation screw preceding the ligament spacer and with the graft ligament disposed within the at least one opening in the ligament spacer, such that the threaded body of the fixation screw engages a wall of the bone hole, the ligament spacer retains the graft ligament in the at least one opening of the ligament spacer and the canted face of the ligament spacer is aligned with an adjacent surface of the bone.

2. The apparatus according to claim 1 wherein the ligament spacer is rotatably mounted to the fixation screw.

3. The apparatus according to claim 2 wherein the ligament spacer comprises a bore extending from the distal end to the proximal end and internal screw threads disposed on the bore at the distal end of the ligament spacer, the reduced-diameter threaded portion of the fixation screw being sized to make threaded engagement with the internal screw threads of the ligament spacer, such that the distal end of the ligament spacer is configured to be screwed over the reduced-diameter threaded portion of the fixation screw, whereby to rotatably mount the ligament spacer to the proximal end of the fixation screw with the neck of the fixation device extending through the bore of the ligament spacer.

4. The apparatus according to claim 3 wherein the drive element of the fixation screw is accessed through the bore of the ligament spacer when the ligament spacer is rotatably mounted to the fixation screw.

5. The apparatus according to claim 4 wherein the drive element comprises a hex recess.

6. The apparatus according to claim 1 wherein the graft ligament comprises a plurality of graft strands, and further wherein the ligament spacer comprises a peripheral geometry configured to separate the plurality of graft strands within the bone hole.

7. The apparatus according to claim 6 wherein the ligament spacer comprises at least one pair of diametrically opposed tabs, and further wherein each of the plurality of graft strands is separated by the pair of diametrically opposed tabs.

8. The apparatus according to claim 1 wherein the fixation screw further comprises at least one small groove formed in a screw thread of the threaded body.

9. The apparatus according to claim 1 wherein the ligament spacer comprises a bore extending from the distal end to the proximal end and internal screw threads disposed on the bore at the distal end of the ligament spacer, the reduced-diameter threaded portion of the fixation screw being sized to make threaded engagement with the internal screw threads of the ligament spacer, such that the distal end of the ligament spacer is configured to be screwed over the reduced-diameter threaded portion of the fixation screw, whereby to rotatably mount the ligament spacer to the reduced-diameter threaded portion of the fixation screw.

10. An apparatus for reconstructing a ligament, the apparatus comprising:
a first fixation device for maintaining a graft ligament in a first bone hole formed in a first bone, the first fixation device comprising:
a first fixation screw having a distal end and a proximal end, the first fixation screw comprising;
a threaded body having a distal end and a proximal end;
a reduced-diameter threaded portion extending proximally from the proximal end of the threaded body;
a reduced-diameter neck extending proximally from the reduced-diameter threaded portion; and
a head extending proximally from the reduced-diameter neck, wherein the head comprises a drive element for driving the first fixation screw into the first bone hole from the proximal end of the first fixation screw; and
a first ligament spacer comprising a distal end, a proximal end, a canted face disposed at the proximal end of the first ligament spacer and at least one opening between the distal end and the proximal end of the first ligament spacer for receiving the graft ligament,
wherein the first ligament spacer is configured to be coaxially mounted to the first fixation screw, with the distal end of the first ligament spacer being retained proximal to the threaded body of the first fixation screw by the reduced-diameter threaded portion of the first fixation screw;
wherein the first fixation device is configured to be advanced into the first bone hole with the first fixation screw preceding the first ligament spacer and with the graft ligament disposed within the at least one opening in the first ligament spacer, such that the threaded body of the first fixation screw engages a wall of the first bone hole, the first ligament spacer retains the graft ligament in the at least one opening of the first ligament spacer and the first canted face of the first ligament spacer is aligned with an adjacent surface of the first bone; and
a second fixation device for maintaining the graft ligament in a second bone hole formed in a second bone, the second fixation device comprising:
a second fixation screw comprising a body having screw threads formed thereon; and
a second ligament spacer mounted to the second fixation screw, the second ligament spacer comprising a distal end and a proximal end, the distal end of the second ligament spacer being mounted to the second fixation screw and the proximal end of the second ligament spacer having a canted face, the second ligament spacer comprising at least one opening formed between the distal end and the proximal end for receiving the graft ligament;
wherein when the second fixation screw and the second ligament spacer are advanced into the second bone hole, the screw threads of the second fixation screw engage a wall of the second bone hole and the canted face of the second ligament spacer is aligned with an adjacent surface of the second bone.

11. The apparatus according to claim 10 wherein the second fixation device is configured to be advanced into the second bone hole with the second fixation screw preceding the second ligament spacer into the second bone hole.

12. An apparatus for reconstructing a ligament, the apparatus comprising:
a fixation device for maintaining a graft ligament in a bone hole formed in a bone, the fixation device comprising:
a fixation screw having a distal end and a proximal end, the fixation screw comprising:
a threaded body having a distal end and a proximal end;
a reduced-diameter threaded portion extending proximally from the proximal end of the threaded body;
a reduced-diameter neck extending proximally from the reduced-diameter threaded portion; and
a head extending proximally from the reduced-diameter neck, wherein the head comprises a drive element for driving the fixation screw into the bone hole from the proximal end of the fixation screw; and
a ligament spacer coaxially mounted to the reduced-diameter threaded portion of the fixation screw proximal to the threaded body of the fixation screw, the ligament spacer comprising a canted face disposed opposite the fixation screw;
wherein the fixation device is configured to be advanced into the bone hole with the fixation screw preceding the ligament spacer and with the graft ligament so that the fixation screw and the ligament spacer maintain the graft ligament within the bone hole and the canted face of the ligament spacer is aligned with an adjacent surface of the bone.

13. A method for reconstructing a ligament, the method comprising:
forming a bone hole in a bone;

providing a fixation device for maintaining a graft ligament in the bone hole, the fixation device comprising:
   a fixation screw having a distal end and a proximal end, the fixation screw comprising:
      a threaded body having a distal end and a proximal end;
      a reduced-diameter threaded portion extending proximally from the proximal end of the threaded body;
      a reduced-diameter neck extending proximally from the reduced-diameter threaded portion; and
      a head extending proximally from the reduced-diameter neck, wherein the head comprises a drive element for driving the fixation screw into the bone hole from the proximal end of the fixation screw; and
   a ligament spacer coaxially mounted to the reduced-diameter threaded portion of the fixation screw proximal to the threaded body of the fixation screw, the ligament spacer comprising a canted face disposed opposite the fixation screw;
advancing the fixation screw and the ligament spacer into the bone hole with the fixation screw preceding the ligament spacer and with the graft ligament so as to maintain the graft ligament in the bone hole and so that the canted face of the ligament spacer is aligned with an adjacent surface of the bone.

14. The method according to claim 13 wherein the ligament comprises an anterior cruciate ligament (ACL), the bone hole is formed in a femur, and the fixation device comprises a femoral fixation device.

* * * * *

UNITED STATES PATENT AND TRADEMARK OFFICE
CERTIFICATE OF CORRECTION

| | | |
|---|---|---|
| PATENT NO. | : 10,939,992 B2 | |
| APPLICATION NO. | : 14/397370 | |
| DATED | : March 9, 2021 | |
| INVENTOR(S) | : Kelly G. Ammann | |

It is certified that error appears in the above-identified patent and that said Letters Patent is hereby corrected as shown below:

On the Title Page

Please delete the Title page and insert the corrected Title page as shown on the attached page.

In the Drawings

Please insert FIGS. 131-164 as shown on the attached pages.

Signed and Sealed this
Twenty-fourth Day of October, 2023

Katherine Kelly Vidal
*Director of the United States Patent and Trademark Office*

(12) United States Patent
Ammann

(10) Patent No.: US 10,939,992 B2
(45) Date of Patent: *Mar. 9, 2021

(54) APPARATUS AND METHOD FOR LIGAMENT RECONSTRUCTION

(71) Applicant: AnatomACL, LLC, Boulder, CO (US)

(72) Inventor: Kelly G. Ammann, Boulder, CO (US)

(73) Assignee: AnatomACL, LLC, Boulder, CO (US)

(*) Notice: Subject to any disclaimer, the term of this patent is extended or adjusted under 35 U.S.C. 154(b) by 504 days.

This patent is subject to a terminal disclaimer.

(21) Appl. No.: 14/397,370

(22) PCT Filed: Jan. 31, 2013

(86) PCT No.: PCT/US2013/024145
§ 371 (c)(1),
(2) Date: Oct. 27, 2014

(87) PCT Pub. No.: WO2013/162663
PCT Pub. Date: Oct. 31, 2013

(65) Prior Publication Data
US 2015/0173886 A1    Jun. 25, 2015

Related U.S. Application Data

(63) Continuation-in-part of application No. 13/528,680, filed on Jun. 20, 2012, now Pat. No. 9,089,416.
(Continued)

(51) Int. Cl.
*A61F 2/08*    (2006.01)

(52) U.S. Cl.
CPC ..... *A61F 2/0811* (2013.01); *A61F 2002/0829* (2013.01); *A61F 2002/0858* (2013.01)

(58) Field of Classification Search
CPC .. A61F 2/08; A61F 2/0811; A61F 2002/0858; A61F 2002/0829;
(Continued)

(56) References Cited

U.S. PATENT DOCUMENTS 5,282,802 A    2/1994    Mahony, III
6,123,711 A    9/2000    Winters
(Continued)

FOREIGN PATENT DOCUMENTS

EP    1 297 794    4/2003
WO    WO 2007/109280    9/2007
(Continued)

*Primary Examiner* — Jerrah Edwards
*Assistant Examiner* — Rokhaya Diop
(74) *Attorney, Agent, or Firm* — Pandiscio & Pandiscio

(57) ABSTRACT

Apparatus for reconstructing a ligament, the apparatus comprising a fixation device for maintaining a graft ligament in a bone hole, the fixation device comprising a fixation screw comprising a body having screw threads formed thereon; and a ligament spacer mounted to the fixation screw, the ligament spacer comprising a canted face disposed opposite the fixation screw; such that the fixation screw and ligament spacer may be advanced into the bone hole with the graft ligament so that the fixation screw and the ligament spacer maintain the graft ligament within the bone hole and the canted face of the ligament spacer is aligned with the adjacent surface of the bone.

14 Claims, 99 Drawing Sheets